US007537761B2

(12) United States Patent
Xu et al.

(10) Patent No.: US 7,537,761 B2
(45) Date of Patent: May 26, 2009

(54) ANTI-IL-22RA ANTIBODIES AND BINDING PARTNERS AND METHODS OF USING IN INFLAMMATION

(75) Inventors: Wenfeng Xu, Seattle, WA (US); Wayne R. Kindsvogel, Seattle, WA (US); Yasmin A. Chandrasekher, Saratoga, CA (US); Stacey R. Dillon, Seattle, WA (US); Joyce M. Lehner, Seattle, WA (US); Anthony W. Siadak, Seattle, WA (US); Pallavur V. Sivakumar, Seattle, WA (US); Margaret Dow Moore, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 361 days.

(21) Appl. No.: 11/256,499

(22) Filed: Oct. 21, 2005

(65) Prior Publication Data

US 2006/0141582 A1    Jun. 29, 2006

Related U.S. Application Data

(60) Provisional application No. 60/621,553, filed on Oct. 22, 2004.

(51) Int. Cl.
*A61K 39/395* (2006.01)
(52) U.S. Cl. ............... 424/141.1; 530/388.1; 530/809; 530/350; 435/70.2
(58) Field of Classification Search .................. None
See application file for complete search history.

(56) References Cited

U.S. PATENT DOCUMENTS

| 3,654,090 | A | * | 4/1972 | Hermanus et al. | .......... | 435/7.93 |
|---|---|---|---|---|---|---|
| 4,847,325 | A | * | 7/1989 | Shadle et al. | .............. | 525/54.1 |
| 5,488,032 | A | | 1/1996 | Dower et al. | .................... | 514/2 |
| 5,723,299 | A | | 3/1998 | Bell et al. | ..................... | 435/7.1 |
| 5,789,192 | A | | 8/1998 | Moore et al. | .............. | 435/69.1 |
| 5,843,725 | A | | 12/1998 | Sledziewski et al. | ....... | 435/69.7 |
| 5,945,511 | A | | 8/1999 | Lok et al. | .................. | 530/350 |
| 5,965,704 | A | | 10/1999 | Lok et al. | .................. | 530/350 |
| 5,985,614 | A | | 11/1999 | Rosen et al. | ............. | 435/69.52 |
| 6,020,163 | A | | 2/2000 | Conklin | ...................... | 435/69.1 |
| 6,274,710 | B1 | | 8/2001 | Dumoutier et al. | ....... | 530/387.9 |
| 6,486,301 | B1 | | 11/2002 | Ebner et al. | ................. | 530/351 |
| 6,576,743 | B1 | | 6/2003 | Conklin et al. | ............. | 530/351 |
| 6,610,286 | B2 | | 8/2003 | Thompson et al. | ......... | 424/85.2 |
| 6,875,845 | B2 | | 4/2005 | Presnell et al. | .............. | 530/351 |
| 6,897,292 | B2 | | 5/2005 | Presnell et al. | .............. | 530/350 |
| 2002/0042366 | A1 | | 4/2002 | Thompson et al. | ............ | 514/12 |
| 2002/0085992 | A1 | | 7/2002 | Chandrasekher et al. | ... | 424/85.2 |
| 2003/0022827 | A1 | | 1/2003 | Weiss et al. | .................... | 514/12 |
| 2003/0157096 | A1 | | 8/2003 | Kindsvogel et al. | ...... | 424/143.1 |
| 2004/0209330 | A1 | | 10/2004 | Ku et al. | .................. | 435/70.21 |
| 2005/0136004 | A1 | | 6/2005 | Ku et al. | ..................... | 424/1.49 |

FOREIGN PATENT DOCUMENTS

| WO | WO 94/13801 | 6/1994 |
|---|---|---|
| WO | WO 98/02542 | 1/1998 |
| WO | WO 98/37193 | 8/1998 |
| WO | WO 99/03982 | 1/1999 |
| WO | WO 99/07740 | 2/1999 |
| WO | WO 99/07848 | 2/1999 |
| WO | WO 99/27103 | 6/1999 |
| WO | WO 99/37772 | 7/1999 |
| WO | WO 99/46281 | 9/1999 |
| WO | WO 99/46379 | 9/1999 |
| WO | WO 99/61630 | 12/1999 |
| WO | WO 00/24758 | 5/2000 |
| WO | WO 00/39161 | 7/2000 |
| WO | WO 00/42189 | 7/2000 |
| WO | WO 00/65027 | 11/2000 |
| WO | WO 00/70049 | 11/2000 |
| WO | WO 00/73457 | 12/2000 |
| WO | WO 00/77037 | 12/2000 |
| WO | WO 01/04304 | 1/2001 |
| WO | WO 01/12672 | 2/2001 |
| WO | WO 01/16318 | 3/2001 |
| WO | WO 01/36467 | 5/2001 |
| WO | WO 01/40467 | 6/2001 |

(Continued)

OTHER PUBLICATIONS

Apparailly et al., "Interleukin-22 gene transfer in experimental model of arthritis," *American College of Rheumatology, Abstract Supplement*, S671, Abstract 1755, 2003.
Asadullah et al., "Analysis of Cytokine Expression in Dermatology," *Arch. Dermatol.* 138(9): 1189-1196, Sep. 2002.
Asadullah et al., "Interleukin-10 Therapy—Review of a New Approach," *Pharmacol. Rev.* 55(2): 241-269, 2003.
Baumann and Gauldie, "The acute phase response," *Immunology Today* 15(2): 74-80, 1994.
Blumberg et al., "Interleukin 20: Discovery, Receptor Identification, and Role in Epidermal Function," *Cell* 104: 9-19, Jan. 2001.
Bork et al., "Go hunting in sequence databases but watch out for the traps," *TIG* 12(10): 425-427, 1996.
Bork et al., "Predicting functions from protein sequences—where are the bottlenecks?" *Nature Genetics* 18: 313-318, 1998.

(Continued)

*Primary Examiner*—Dong Jiang
(74) *Attorney, Agent, or Firm*—Aaron A. Schutzer; Shelby J. Walker

(57) ABSTRACT

The present invention relates to blocking, inhibiting, reduceing, antagonizing or neutralizing the activity of IL-22, IL-20, or both IL-20 and IL-22 polypeptide molecules. IL-20 and IL-22 are cytokines that are involved in inflammatory processes and human disease. IL-22RA (zcytor11) is a common receptor for IL-20 and IL-22. The present invention includes anti-IL-22RA antibodies and binding partners, as well as methods for antagonizing IL-22 or both IL-20 and IL-22 using such antibodies and binding partners.

19 Claims, No Drawings

FOREIGN PATENT DOCUMENTS

| WO | WO 01/46232 | 6/2001 |
|---|---|---|
| WO | WO 01/46261 | 6/2001 |
| WO | WO 01/46422 | 6/2001 |
| WO | WO 01/98342 | 12/2001 |
| WO | WO 02/20569 | 3/2002 |
| WO | WO 02/24912 | 3/2002 |
| WO | WO 02/058724 | 8/2002 |
| WO | WO 02/066647 | 8/2002 |
| WO | WO 02/068476 | 9/2002 |
| WO | WO 02/070001 | 9/2002 |
| WO | WO 02/072607 | 9/2002 |
| WO | WO 02/077174 | 10/2002 |
| WO | WO 03/035096 | 5/2003 |
| WO | WO 03/039444 | 5/2003 |
| WO | WO 03/051384 | 6/2003 |
| WO | WO 2004/085475 | 10/2004 |

OTHER PUBLICATIONS

Bork, "Powers and Pitfalls in Sequence Analysis: The 70% Hurdle," *Genome Research 10*: 398-400, 2000.

Cameron et al., "Cytokines and Chemokines—Their Receptors and Their Genes: An Overview," Ch.2 in Cytokines and Chemokines in Autoimmune Disease, pp. 8-32, Plenum Publishers, 2003.

Conti et al., "IL-10 subfamily members: IL-19, IL-20, IL-22, IL-24 and IL-26," *Immunology Letters 88*: 171-174, 2003.

Cosman, D., "The Hematopoietin Receptor Superfamily," *Cytokine 5*(2): 95-106, Mar. 1993.

Cunningham et al., "High-Resolution Epitope Mapping of hGH-Receptor Interactions by Alanine-Scanning Mutagenesis," *Science 244*: 1081-1085, Jun. 1989.

Davis et al., "Isolation of Angiopoietin-1, a Ligand for the TIE2 Receptor, by Secretion-Trap Expression Cloning," *Cell 87*: 1161-1169, Dec. 1996.

de Groot-Kruseman et al., "Expression of the Novel Cytokine Il-21 During Acute Rejection After Clinical Heart Transplantation and the Effect of Immunosuppressive Agents," *J. Interferon & Cytokine Research 22*(Suppl. I): S-97, Abstract P-2-1, 2002.

Dumoutier et al. "Human interleukin-10-related T cell-derived inducible factor: Molecular cloning and functional characterization as an hepatocyte-stimulating factor," *Proc. Natl. Acad. Sci. 97*(18): 10144-10149, Aug. 2000.

Dumoutier et al., "Cloning and Characterization of IL-10-Related T Cell-Derived Inducible Factor (IL-TIF), a Novel Cytokine Structurally Related to IL-10 and Inducible by IL-9," *J. Immunol. 164*: 1814-1819, 2000.

Dumoutier et al., "IL-TIF/IL-22: genomic organization and mapping of the human and mouse genes," *Genes and Immunity. 1*: 488-494, 2000.

Dumoutier et al., "Cloning and Characterization of IL-22 Binding Protein, a Natural Antagonist of IL-10-Related T Cell-Derived Inducible Factor/IL-22," *J. Immunol. 166*: 7090-7095, 2001.

Dumoutier et al., "Cutting Edge: STAT Activation By IL-19, IL-20 and mda-7 Through IL-20 Receptor Complexes of Two Types," *J. Immunol. 167*(7): 3545-3549, 2001.

Dumoutier et al., "Viral and cellular interleukin-10 (IL-10)-related cytokines: from structures to functions," *Eur. Cytokine Netw. 13*(2): 5-15, Mar. 2002.

Dynan et al., "Control of eukaryotic messenger RNA synthesis by sequence-specific DNA-binding proteins," *Nature 316*: 774-778, Aug. 1985.

Fernandez-Botran, R., "Soluble cytokine receptors: novel immunotherapeutic agents," *Exp. Opin. Invest. Drugs 9*(3): 497-514, 2000.

Fickenscher et al., "The interleukin-10 family of cytokines," *TRENDS in Immunology 23*(2): 89-96, Feb. 2002.

George et al., "Current Methods in Sequence Comparison and Analysis," Ch. 12, in Macromolecular Sequencing & Synthesis, pp. 127-149, Alan R. Liss, Inc., 1988.

Gibbs and Pennica, "CRF2-4: isolation of cDNA clones encoding the human and mouse proteins," *Gene 186*: 97-101, 1997.

Gröne, "Keratinocytes and cytokines," *Veterinary Immunol. and Immunopath. 88*: 1-12, 2002.

Gruenberg et al., "A novel, soluble homologue of the human IL-10 receptor with preferential expression in placenta," *Genes and Immunity 2*(6): 329-334, 2001.

Gurney, A., "IL-22, a novel human cytokine that signals through the Interferon receptor related proteins CRF2-4 and IL-22R," *Eur. Cytokine Network 11*: 39, Abstract 05002, Nov. 2000.

Harlow et al., *Antibodies: A Laboratory Manual*, Ch. 5, p. 76, Cold Springs Harbor Laboratory, 1988.

He et al., "Serum Amyloid a Induces IL-8 Secretion Through A G Protein-Coupled Receptor, FPRL1/LXA4R," *J. Interferon & Cytokine Research 22*(Suppl. 1): S-97, Abstract P-1-23, 2002.

Henikoff et al., "Amino acid substitution matrices from protein blocks," *Proc. Natl. Acad. Sci. USA 89*: 10915-10919, Nov. 1992.

Holliger and Hoogenboom, "Antibodies come back from the brink," *Nature Biotech. 16*: 1015-1016, 1998.

Hosoi et al., "Lipolysaccharide induces IL-20 expression in the primary cultured glial cells," *The 75th Annual Meeting, Department of Pharmacology, Kumamoto University*, p. 89P, Abstract P-112, 2002.

Hughes et al., "Induction of T Helper Cell Hyporesponsiveness in an Experimental Model of Autoimmunity by Using Nonmitogenic Anti-CD3 Monoclonal Antibody," *J. Immunol 153*: 3319-3325, 1994.

Huston et al., "Protein engineering of antibody binding sites: Recovery of specific activity in an anti-digoxin single-chain Fv analogue produced in *Escherichia coli*," *Proc. Natl. Acad. Sci. USA 86*: 5879-5883, Aug. 1988.

Kasakura, S., "Novel interleukins: IL-19, IL-20, IL-21, IL-22, IL-23," *Biotherapy* (Tokyo, Japan) 16 (3): 193-203, 2002 (Abstract only).

Kotenko et al., "Jak-Stat signal transduction pathway through the eyes of cytokine class II receptor complexes," *Oncogene 19*: 2557-2565, 2000.

Kotenko et al., "Identification of the Functional Interleukin-22 (IL-22) Receptor Complex," *J. Biochem. 276*(4): 2725-2732, Jan. 2001.

Kotenko et al., "Identification, Cloning, and Characterization of a Novel Soluble Receptor That Binds IL-22 and Neutralizes Its Activity," *J. Immunol. 166*(12): 7096-7013, 2001.

Kotenko, "The family of IL-10-related cytokines and their receptors: related, but to what extent," *Cytokine & Growth Factor Reviews 13*: 223-240, 2002.

Kunz et al., "Immune Cells as Sources and Targets of the Interleukin-10 Family Members?" *J. Interferon & Cytokine Research 22*(Suppl. I): S-97-S-98, Abstract P-2-3, 2002.

Langer et al., "The Class II cytokine receptor (CRF2) family: overview and patterns of receptor-ligand interactions," *Cytokine Growth Factor Rev. 15*(1): 33-48, 2004.

Last et al., "Use of EpiDerm™ as an Inflammatory Model for Preclinical Screening," *J. Investigative Dermatology 119*(1): 325, Abstract 707, Jul. 2002.

Lécart et al., "IL-22, in contrast to IL-10, does not induce Ig production, due to absence of a functional IL-22 receptor on activated human B cells," *Int. Immunol. 14*(11): 1351-1356, 2002.

Lee et al., "Interleukin-20 is up-regulated in psoriasis and responds to conventional and novel biologic therapy," 121(1), Abstract 0664, Jul. 2003.

Li et al., "Temporal associations between IL-22 and the extracellular domains of IL-22R and IL-10R2," Eur. Cytokine Network 14 (suppl.): 91, Abstract 250, Sep. 2003.

Liu et al., "Expression Cloning and Characterization of a Human IL-10 Receptor," *J. Immunol. 152*: 1821-1829, 1994.

Liu et al., "Il-20 Specifically Stimulates the Proliferation of Human and Murine Multipotential Hematopoietic Progenitors," *Blood 100*(11): 189a-190a, Abstract 710, Nov. 2002.

Liu et al., "Selective enhancement of multipotential hematopoietic progenitors in vitro and in vivo by IL-20," *Blood 102*(9): 3206-3209, Nov. 2003.

Logsdon et al., "Comparison of interleukin-22 and interleukin-10 soluble receptor complexes," *J. Interferon Cytokine Res. 22*(11): 1099-1112, 2002.

Lutfalla et al., "A new member of the cytokine receptor gene family maps on chromosome 21 at less than 35kb from IFNAR," *Genomics 16*: 366-373, 1993.

Lutfalla et al., "Structure of human CFRB4 Gene: Comparison with its IFNAR neighbor," *J. Mol. Evolution 41*: 338-344, 1995.

McKinnon et al., "Strategies for the Discovery of Cytokine Receptor Antagonists," *Drug News and Perspectives 9*(7): 389-398, Sep. 1996.

Mohler et al., "Immunotherapeutic Potential of Soluble Cytokine Receptors in Inflammatory Disease," *FASB J. US Fed of American Soc. For Experimental Biology*, 6(4): A1123, Abstract 1086, 1992.

Musso et al., "Role of IL-21 in the Differentiation of Human Dendritic Cells," *J. Interferon & Cytokine Research 22*(Suppl. 1): S-98, Abstract P-2-4, 2002.

Nagalakshmi et al., "Human IL-22 (IL-TIF) is a novel homolog of IL-10 that phosphorylates STAT 3 in colon carcinoma cells expressing the IL-22R1 chain," *FASEB Journal 15*(5): A1052, Mar. 2001.

Nagem et al., "Crystal structure of recombinant human interleukin-22," *Structure 10*(8): 1051-1062, Aug. 2002.

National Center for Biotechnology Information (NCBI) Human Genome Map Viewer, build 35.1. Available online at http://www.ncbi.nlm.nih.gov/projects/genome/guide/_human/ See particularly the region of chromosome 6 between 135 MB and 138 MB, Accessed Oct. 18, 2004.

Ozaki et al., "Cytokine and Cytokine Receptor Pleiotropy and Redundancy," *J. Biol. Chem. 277*(33): 29355-29358, 2002.

Parrish-Novak et al., "Interleukins 19, 20, and 24 Signal through Two Distinct Receptor Complexes," *J. Biol. Chem. 277*(49): 47517-47523, 2002.

Parrish-Novak et al., "Overlapping Ligand Specificities but Divergent Function in the IL-20 Subfamily," *J. Interferon & Cytokine Research 22*(Suppl. 1): S-46, Abstract W-1-5, 2002.

Pirhonen et al., "Regulation of IL-12 and IL-23 Expression in Macrophages During Virus Infection," *J. Interferon & Cytokine Research 22*(Suppl. 1): S-98, Abstract P-2-6, 2002.

Pletnev et al., "Characterization of the recombinant extracellular domains of human interleukin-20 receptors and their complexes with interleukin-19 and interleukin-20," *Biochemistry 42*(43): 12617-12624, 2003.

Ramesh et al., "MDA-7/IL-24 is a Novel Ligand that Regulates Angiogenesis via the IL-22 Receptor," *Cancer Gene Therapy*, S3, Abstract 008, 2002.

Renauld, J.-C., "Class II cytokine receptors and their ligands: key antiviral and inflammatory modulators," *Nat. Rev. Immunol. 3*(8): 667-676, Aug. 2003.

Resmini et al., "An anti-murine IL-22 monoclonal antibody decreases disease severity in a murine model of collagen induced arthritis," *Eur. Cytokine Network 14*(suppl.): 129, Abstract 370, Sep. 2003.

Rich et al., "Cytokines: IL-20—a new effector in skin inflammation," *Curr. Biol. 11*(13): R531-R534, 2001.

Rich, "IL-20: a new target for the treatment of inflammatory skin disease," *Expert Opin. Ther. Targets 7*(2): 165-174, 2003.

Robinson and Sauer, "Optimizing the stability of single-chain proteins by linker length and composition mutagenesis," *Proc. Natl. Acad. Sci. USA 95*: 5929-5934, May 1998.

Rohovsky et al., "Growth factors and angiogenesis in wound healing," Ch. 2 in *Growth Factors and Wound Healing*, pp. 8-26, Springer, NY, 1997.

Rømer et al, "Epidermal overexpression of interleukin-19 and -20 mRNA in psoriatic skin disappears after short-term treatment with cyclosporine a or calcipotriol," *J. Invest. Dermatol. 121*(6): 1306-1311, 2003.

Rose-John, "Interleukin-6 biology is coordinated by membrane bound and soluble receptors," *Acta Biochimica Polonica 50*(3): 603-611, 2003.

Salazar et al., *Eur. J. of Clin. Invest. 31*(12): 1070-1077, 2001.

Sempowski et al., "Subsets of Murine Lung Fibroblasts Express Membrane-Bound and Soluble IL-4 Receptors," *J. Immunol. 152*: 3606-3614, 1994.

Slavin, "Cytokines and tissue repair," *J. Immunol. Immunopharmacol. 17*(1): 25-29, 1997.

Smeets et al., "Interleukin-20 is expressed in inflamed synovium of patients with psoriatic arthritis and rheumatoid arthritis," *American College of Rheumatology, Abstract Supplement*, S57, Abstract 21, 2003.

Smith et al., "Partial TCR Signmals Delivered by FcR-Nonbinding Anti-CD3 Monoclonal Antibodies Differentially Regulate Individual Th Subsets," *J. Immunol. 160*: 4841-4849, 1998.

Spencer et al., "The Orphan Receptor CRF2-4 is an Essential Subunit of the Interleukin 10 Receptor," *J. Exp. Med. 187*(4): 571-578, Feb. 1998.

Stolina et al., "Novel Neurotrophin-1/B Cell Stimulating Factor-3 (NNT-1/BSF-3) Stimulates Osteoblastic Cell Activities In Vitro Including Bone Formation and IL-6 Production," *J. Interferon & Cytokine Research 22*(Suppl. 1): S-98-S-99, Abstract P-2-7, 2002.

Strengell et al., "IL-21 Up-Regulates the Expression of Genes Associated with Innate Immunity and Th1 Response," *J. Interferon & Cytokine Research 22*(Suppl. 1): S-99, Abstract P-2-8, 2002.

Tachiiri et al., "Genomic structure and inducible expression of the IL-22 receptor IL-22 receptor $\alpha$ in mice," *Genes and Immunity 4*: 153-159, 2003.

Tutt et al., "Monoclonal Antibody Therapy of B Cell Lymphoma: Signaling Activity on Tumor Cells Appears More Important Than Recruitment of Effectors," *J. Immunol. 161*: 3176-3185, 1998.

Uhlar et al., "Serum amyloid A, the major vertebrate acute-phase reactant," *Eur. J. Biochem. 265*: 501-523, 1999.

Vandenbroeck et al., "The Conserved Helix C Region in the Superfamily of Interferon-γ/Interleukin-10-related Cytokines Corresponds to a High-affinity Binding Site for the HSP70 Chaperone DnaK," *J. Biol. Chem. 277*(28): 25668-25676, 2002.

Volk et al., "IL-10 and its homologs: important immune mediators and emerging immunotherapeutic agents," *TRENDS in Immunology 22*(8): 414-417, 2001.

Walter, "Structure of Interleukin-10/ Interleukin-10R1 Complex," *Immunologic Res. 26*(1-3): 303-308, 2002.

Wang et al, "IL-20: promoter analysis and characterization of biological function," *International Cytokine Society Annual Meeting*, p. 64, Abstract 174, 2003.

Wei et al., "Cloning and characterization of mouse IL-22 binding protein," *Genes and Immunity 4*(3):204-211, 2003.

Wells, "Additivity of Mutational Effects In Proteins," *Biochemistry 29*(37): 8509-8517, Sep. 1990.

Whitters et al., "Phenotype of IL21R-/-Mice and Gene Expression Analysis Support a Role for Regulation of T and B Cell Responses by Interleukin 21," *J. Interferon & Cytokine Research 22*(Suppl. 1) S-99-S-100, Abstract P-2-11, 2002.

Witek et al., "Primary Macrophages Express IL-21R and Respond to IL-21 By Proliferating and Secreting Increased Levels of Cytokines and Chemokines," *J. Interferon & Cytokine Research 22*(Suppl. 1): S-100, Abstract P-2-12, 2002.

Wolk et al., "Cutting Edge: Immune Cells as Sources and Targets of the IL-10 Family Members," *J. Immunol. 168*(11): 5397-5402, 2002.

Wuyts et al., "Isolation of the CXC chemokines ENA-78, Groα and Groγ from tumor cells and leukocytes reveals NH2-terminal heterogeneity," *Eur. J. Biochem. 260*: 421-429, 1999.

Xie et al., "Interleukin (IL)-22, a Novel Human Cytokine That Signals through the Interferon Receptor-related Proteins CRF2-4 and IL-22R," *J. Biol. Chem. 275*(40): 31335-31339, 2000.

Xu et al., "A soluble class II cytokine receptor, IL-22RA2, is a naturally occurring IL-22 antagonist," *Proc. Nat. Acad. Sci. 98*(17): 9511-9516, Aug. 2001.

Xu et al., "IL-20 and IL-22 in psoriasis," *European Cytokine Network 14*(suppl.): 65, Abstract 177, 2003.

Zhang et al., "Identification, Purification, and Characterization of a Soluble Interleukin (IL)-13-binding Protein," *J. Biochem. 272*(14): 9474-9480, Apr. 1997.

\* cited by examiner

US 7,537,761 B2

ANTI-IL-22RA ANTIBODIES AND BINDING PARTNERS AND METHODS OF USING IN INFLAMMATION

CROSS REFERENCE TO RELATED APPLICATIONS

This application claims the benefit of U.S. Provisional Application Ser. No. 60/621,553, filed Oct. 22, 2004, which is herein incorporated by reference.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783 (1990); Mosmann, *Curr. Opin. Immunol.* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of CD34+ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains. For example, the receptor chains responsible for binding and/or transducing the effect of interferons are members of the class II cytokine receptor family, based upon a characteristic 200 residue extracellular domain.

The demonstrated in vivo activities of cytokines and their receptors illustrate the clinical potential of, and need for, other cytokines, cytokine receptors, cytokine agonists, and cytokine antagonists. For example, demonstrated in vivo activities of the pro-inflammatory cytokine family illustrates the enormous clinical potential of, and need for antagonists of pro-inflammatory molecules. The present invention addresses these needs by providing antagonists to pro-inflammatory cytokines IL-20 and IL-22. Such antagonists of the present invention, which may block, inhibit, reduce, antagonize or neutralize the activity of IL-22, IL-20, or both IL-20 and IL-22, include soluble IL-22RA receptors and neutralizing anti-IL-22RA antibodies. The invention further provides uses therefor in inflammatory disease, as well as related compositions and methods.

DETAILED DESCRIPTION OF THE INVENTION

1. Overview

Amongst other inventions, the present invention provides novel uses for a soluble receptor, designated "Zcytor11" or "IL-22RA" and neutralizing antibodies to IL-22RA cytokine receptors. The present invention also provides soluble IL-22RA polypeptide fragments and fusion proteins, for use in human inflammatory and autoimmune diseases. The anti-IL-22RA antibodies, and soluble IL-22RA receptors of the present invention, including the neutralizing anti-IL-22RA antibodies of the present invention, can be used to block, inhibit, reduce, antagonize or neutralize the activity of either IL-22 or IL-20, or both IL-20 and IL-22 in the treatment of specific human diseases such as psoriasis, psoriatic arthritis, arthritis, endotoxemia, inflammatory bowel disease (IBD), colitis, and other inflammatory conditions disclosed herein.

An illustrative nucleotide sequence that encodes human Zcytor11 (IL-22RA) is provided by SEQ ID NO:1; the encoded polypeptide is shown in SEQ ID NO:2. IL-22RA is a receptor subunit for both IL-20 and IL-22. Zcytor11 (IL-22RA) is disclosed in commonly owned U.S. Pat. No. 5,965,704, commonly owned WIPO publication WO 02/12345, and commonly owned WIPO publication WO 02/072607. Analysis of a human cDNA clone encoding IL-22RA (SEQ ID NO:1) revealed an open reading frame encoding 574 amino acids (SEQ ID NO:2) comprising an extracellular ligand-binding domain of approximately 211 amino acid residues (residues 18-228 of SEQ ID NO:2; SEQ ID NO:3), a transmembrane domain of approximately 23 amino acid residues (residues 229-251 of SEQ ID NO:2), and an intracellular domain of approximately 313 amino acid residues (residues 252 to 574 of SEQ ID NO:2). Thus molecules of the present invention include polypepetides that include a cytokine binding domain comprising amino acids residues 18-228 of SEQ ID NO:2; SEQ ID NO:3. In one embodiment of the soluble receptor of the present invention, the soluble IL-22R is fused to the constant region of the heavy chain (representative shown in SEQ ID NO:4). Those skilled in the art will recognize that these domain boundaries are approximate. Deletion of residues from the ends of the domains is possible.

As described below, the present invention provides isolated polypeptides comprising an amino acid sequence that is at least 70%, at least 80%, or at least 90%, or greater than 95%, such as 96%, 97%, 98%, or greater than 99% or more identical to a reference amino acid sequence of 18-228 of SEQ ID NO:2, which is also shown as SEQ ID NO:3, wherein the isolated polypeptide specifically binds with an antibody that specifically binds with a polypeptide comprising the amino acid sequence of SEQ ID NO:3. Illustrative polypeptides include polypeptides comprising either amino acid residues SEQ ID NO:3 or amino acid residues SEQ ID NO:3. Moreover, the present invention also provides isolated polypeptides as disclosed above that bind IL-22 (e.g., human IL-22 polypeptide sequence as shown in SEQ ID NO:6). The human IL-22 polynucleotide sequence is shown in SEQ ID NO:5. The mouse IL-22 polynucleotide sequence is shown in SEQ ID NO:10, and corresponding polyepeptide is shown in SEQ ID NO:11. The present invention also provides isolated polypeptides as disclosed above that bind IL-20 (e.g., human IL-20 polypeptide sequence as shown in SEQ ID NO:8; WIPO Publication No. WO 99/27103). The human IL-20 polynucleotide sequence is shown in SEQ ID NO:7.

The present invention also provides isolated polypeptides and epitopes comprising at least 15 contiguous amino acid residues of an amino acid sequence of SEQ ID NO:3. Illustrative polypeptides include polypeptides that either comprise, or consist of SEQ ID NO:3, an antigenic epitope thereof, or a functional IL-20 or IL-22 binding fragment thereof. Moreover, the present invention also provides isolated polypeptides as disclosed above that bind to, block, inhibit, reduce, antagonize or neutralize the activity of L-22 or IL-20.

The present invention also includes variant IL-22RA polypeptides, wherein the amino acid sequence of the variant polypeptide shares an identity with the amino acid residues of SEQ ID NO:3 selected from the group consisting of at least 70% identity, at least 80% identity, at least 90% identity, at least 95% identity, or greater than 95% identity, such as 96%, 97%, 98%, or greater than 99% or more identity, and wherein any difference between the amino acid sequence of the variant polypeptide and the corresponding amino acid sequence of SEQ ID NO:3 is due to one or more conservative amino acid substitutions. Such conservative amino acid substitutions are described herein. Moreover, the present invention also provides isolated polypeptides as disclosed above that bind to, block, inhibit, reduce, antagonize or neutralize the activity of IL-22 or IL-20.

The present invention further provides antibodies and antibody fragments that specifically bind with such polypeptides. Exemplary antibodies include neutralizing antibodies, polyclonal antibodies, murine monoclonal antibodies, humanized antibodies derived from murine monoclonal antibodies, and human monoclonal antibodies. Illustrative antibody fragments include F(ab')$_2$, F(ab)$_2$, Fab', Fab, Fv, scFv, and minimal recognition units. Neutralizing antibodies preferably bind IL-22RA such that the interaction of IL-20 and IL-22 with IL-22RA is blocked, inhibited, reduced, antagonized or neutralized; anti-IL-22RA neutralizing antibodies such that the binding of either IL-20 or IL-22 to IL-22RA is blocked, inhibited, reduced, antagonized or neutralized are also encompassed by the present invention. That is, the neutralizing anti-IL-22RA antibodies of the present invention can either bind, block, inhibit, reduce, antagonize or neutralize each of IL-20 or IL-22 singly, or bind, block, inhibit, reduce, antagonize or neutralize IL-20 and IL-22 together. The present invention further includes compositions comprising a carrier and a peptide, polypeptide, or antibody described herein.

In addition, the present invention provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide or antibody described herein.

The present invention also contemplates anti-idiotype antibodies, or anti-idiotype antibody fragments, that specifically bind an antibody or antibody fragment that specifically binds a polypeptide comprising the amino acid sequence of SEQ ID NO:3 or a fragment thereof. An exemplary anti-idiotype antibody binds with an antibody that specifically binds a polypeptide consisting of SEQ ID NO:3.

The present invention also provides fusion proteins, comprising a IL-22RA polypeptide and an immunoglobulin moiety. In such fusion proteins, the immunoglobulin moiety may be an immunoglobulin heavy chain constant region, such as a human F$_C$ fragment. The present invention further includes isolated nucleic acid molecules that encode such fusion proteins.

The present invention also provides polyclonal and monoclonal antibodies that bind to polypeptides comprising an IL-22RA extracellular domain such as monomeric, homodimeric, heterodimeric and multimeric receptors, including soluble receptors. Moreover, such antibodies can be used antagonize the binding of IL-22RA ligands, IL-22 (SEQ ID NO:6), and IL-20 (SEQ ID NO:8), individually or together to the IL-22RA receptor.

Moroever, over expression or upregulation of IL-22 and IL-20 was shown in human psoriatic lesions and human atopic dermatitis skin samples, suggesting that IL-22, like IL-20 is also involved in human psoriasis, atopic dermatitis or other inflammatory diseases of the skin and epithelial tissues. Moreover, as described herein, over expression of IL-20 or IL-22 in transgenic mice showed epidermal thickening and immune cell involvement indicative of a psoriatic phenotype; and in addition injection of IL-22 into normal mice showed epidermal thickening and immune cell involvement indicative of a psoriatic phenotype which was ablated by the soluble receptor antagonist IL-22RA2 (zcytor16; WIPO Publication No. WO 01/40467). Such in vivo data further suggests that the pro-inflammatory IL-22 is involved in psoriasis, atopic dermatitis or other inflammatory diseases of the skin and epithelial tissues. As such, antagonists to IL-22 and IL-20 activity, such as IL-22RA soluble receptors and antibodies thereto including the anti-human-IL-22RA monoclonal and neutralizing antibodies of the present invention, are useful in therapeutic treatment of inflammatory diseases, particularly as antagonists to both IL-22 and IL-20 singly or together in the treatment of psoriasis. Moreover, antagonists to IL-22 activity, such as IL-22RA soluble receptors and antibodies thereto including the anti-human-IL-22RA monoclonal and neutralizing antibodies of the present invention, are useful in therapeutic treatment of other inflammatory diseases for example as bind, block, inhibit, reduce, antagonize or neutralize IL-22 and IL-20 (either individually or together) in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

These and other aspects of the invention will become evident upon reference to the following detailed description. In addition, various references are identified below and are incorporated by reference in their entirety.

2. Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SPI, cAMP response element binding protein (CREB; Loeken, *Gene Expr.* 3:253 (1993)) and octamer factors (see, in general, Watson et al., eds., *Molecular Biology of the Gene,* 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

Heterologous DNA' refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces IL-22RA from an expression vector. In contrast, IL-22RA can be produced by a cell that is a "natural source" of IL-22RA, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a IL-22RA polypeptide fused with a polypeptide that binds an affinity matrix. Such a fusion protein provides a means to isolate large quantities of IL-22RA using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi). Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. Soluble receptors of class I and class II cytokine receptors generally comprise the extracellular cytokine binding domain free of a transmsmbrane domain and intracellular domain. For example, representative soluble receptors include soluble receptors for CRF2-4 (a.k.a., IL-10RB) (Genbank Accession No. Z17227) as shown in SEQ ID NO:44 and SEQ ID NO:45; a soluble receptor for IL-10RA (Genbank Accession No.s U00672 and NM_001558) as shown in SEQ ID NO:46; a soluble receptor for pDIRS 1 (a.k.a., IL-20RB) (Genbank Accession No. AY358305) as shown in SEQ ID NO:47; and a soluble receptor for IL-22RA (U.S. Pat. No. 5,965,704) as shown in SEQ ID NO:3. It is well within the level of one of skill in the art to delineate what sequences of a known class I or class II cytokine sequence comprise the extracellular cytokine binding domain free of a transmsmbrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, an dthe like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-IL-22RA antibody, and thus, an anti-idiotype antibody mimics an epitope of IL-22RA.

An "antibody fragment" is a portion of an antibody such as $F(ab')_2$, $F(ab)_2$, Fab', Fab, and the like. Regardless of structure, an antibody fragment binds with the same antigen that is recognized by the intact antibody. For example, an anti-IL-22RA monoclonal antibody fragment binds with an epitope of IL-22RA.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See, in general, Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a IL-22RA polypeptide component. Examples of an antibody fusion protein include a protein that comprises a IL-22RA extracellular domain, and either an Fc domain or an antigen-binding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for IL-22RA" or a "IL-22RA anti-sense oligonucleotide" is an oligonucleotide having a sequence (a) capable of forming a stable triplex with a portion of the IL-22RA gene, or (b) capable of forming a stable duplex with a portion of an mRNA transcript of the IL-22RA gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant IL-22RA gene" refers to nucleic acid molecules that encode a polypeptide having an amino acid sequence that is a modification of SEQ ID NO:3. Such variants include naturally-occurring polymorphisms of IL-22RA genes, as well as synthetic genes that contain conservative amino acid substitutions of the amino acid sequence of SEQ ID NO:3. Additional variant forms of IL-22RA genes are nucleic acid molecules that contain insertions or deletions of the nucleotide sequences described herein. A variant IL-22RA gene can be identified, for example, by determining whether the gene hybridizes with a nucleic acid molecule having the nucleotide sequence of SEQ ID NO:1, or its complement, under stringent conditions.

Alternatively, variant IL-22RA genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide, sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant IL-22RA gene or variant IL-22RA polypeptide, a variant gene or polypeptide encoded by a variant gene may be functionally characterized the ability to bind specifically to an anti-IL-22RA antibody. A variant IL-22RA gene or variant IL-22RA polypeptide may also be functionally characterized the ability to bind to its ligand, IL-22, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The present invention includes functional fragments of IL-22RA genes. Within the context of this invention, a "functional fragment" of a IL-22RA gene refers to a nucleic acid molecule that encodes a portion of a IL-22RA polypeptide which is a domain described herein or at least specifically binds with an anti-IL-22RA antibody.

Due to the imprecision of standard analytical methods, molecular weights and lengths of polymers are understood to be approximate values. When such a value is expressed as "about" X or "approximately" X, the stated value of X will be understood to be accurate to ±10%.

3. Production of IL-22RA Polynucleotides or Genes

Nucleic acid molecules encoding a human IL-22RA gene can be obtained by screening a human cDNA or genomic library using polynucleotide probes based upon SEQ ID NO:1. These techniques are standard and well-established, and may be accomplished using cloning kits available by commercial suppliers. See, for example, Ausubel et al. (eds.), *Short Protocols in Molecular Biology*, 3$^{rd}$ Edition, John Wiley & Sons 1995; Wu et al., *Methods in Gene Biotechnology*, CRC Press, Inc. 1997; Aviv and Leder, *Proc. Nat'l Acad. Sci. USA* 69:1408 (1972); Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47-52.

Nucleic acid molecules that encode a human IL-22RA gene can also be obtained using the polymerase chain reaction (PCR) with oligonucleotide primers having nucleotide sequences that are based upon the nucleotide sequences of the IL-22RA gene or cDNA. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), Humana Press, Inc., 1993. Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), Humana Press, Inc. 1993. As an alternative, a IL-22RA gene can be obtained by synthesizing nucleic acid molecules using mutually priming long oligonucleotides and the nucleotide sequences described herein (see, for example, Ausubel (1995)). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)). For reviews on polynucleotide synthesis, see, for example, Glick and Pasternak, *Molecular Biotechnology, Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

4. Production of IL-22RA Gene Variants

The present invention provides a variety of nucleic acid molecules, including DNA and RNA molecules, that encode the IL-22RA polypeptides disclosed herein. Those skilled in the art will readily recognize that, in view of the degeneracy of the genetic code, considerable sequence variation is possible among these polynucleotide molecules. Moreover, the present invention also provides isolated soluble monomeric, homodimeric, heterodimeric and multimeric receptor polypeptides that comprise at least one IL-22RA receptor subunit that is substantially homologous to the receptor polypeptide of SEQ ID NO:3. Thus, the present invention contemplates IL-22RA polypeptide-encoding nucleic acid molecules comprising degenerate nucleotides of SEQ ID NO:1, and their RNA equivalents.

Table 1 sets forth the one-letter codes to denote degenerate nucleotide positions. "Resolutions" are the nucleotides denoted by a code letter. "Complement" indicates the code for the complementary nucleotide(s). For example, the code Y denotes either C or T, and its complement R denote is A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |

TABLE 2-continued

| Amino Acid | One Letter Code | Codons | Degenerate Codon |
|---|---|---|---|
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:3. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

A IL-22RA-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human IL-22RA sequences disclosed herein. In addition, a cDNA library can be used to transform or transfect host cells, and expression of the cDNA of interest can be detected with an antibody to IL-22RA polypeptide.

Those skilled in the art will recognize that the sequence disclosed in SEQ ID NO:1 represents a single allele of human IL-22RA, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the IL-22RA polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides that comprise a soluble IL-22RA receptor subunit that is substantially homologous to SEQ ID NO:1, or that encodes amino acids of SEQ ID NO:3, or allelic variants thereof and retain the ligand-binding properties of the wild-type IL-22RA receptor. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1, or to nucleic acid molecules comprising a nucleotide sequence complementary to SEQ ID NO:1, or fragments thereof.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user-defined criteria. It is well within the abilities of one skilled in the art to adapt hybridization and wash conditions for use with a particular polynucleotide hybrid.

The present invention also provides isolated IL-22RA polypeptides that have a substantially similar sequence identity to the polypeptides of SEQ ID NO:3, or their orthologs. The term "substantially similar sequence identity" is used herein to denote polypeptides having at least 70%, at least 80%, at least 90%, at least 95%, such as 96%, 97%, 98%, or greater than 95% sequence identity to the sequences shown in SEQ ID NO:3, or their orthologs. For example, variant and orthologous IL-22RA receptors can be used to generate an immune response and raise cross-reactive antibodies to human IL-22RA. Such antibodies can be humanized, and modified as described herein, and used therapeutically to treat psoriasis, psoriatic arthritis, IBD, colitis, endotoxemia as well as in other therapeutic applications described herein.

The present invention also contemplates IL-22RA variant nucleic acid molecules that can be identified using two criteria: a determination of the similarity between the encoded polypeptide with the amino acid sequence of SEQ ID NO:3, and a hybridization assay. Such IL-22RA variants include nucleic acid molecules (1) that remain hybridized with a nucleic acid molecule having the nucleotide sequence of SEQ ID NO:1 (or its complement) under stringent washing conditions, in which the wash stringency is equivalent to 0.5×–2× SSC with 0.1% SDS at 55-65° C., and (2) that encode a polypeptide having at least 70%, at least 80%, at least 90%, at least 95%, or greater than 95% such as 96%, 97%, 98%, or 99%, sequence identity to the amino acid sequence of SEQ ID NO:3. Alternatively, IL-22RA variants can be characterized as nucleic acid molecules (1) that remain hybridized with a nucleic acid molecule having the nucleotide sequence of SEQ ID NO:1 (or its complement) under highly stringent washing conditions, in which the wash stringency is equivalent to 0.1×–0.2×SSC with 0.1% SDS at 50-65° C., and (2) that encode a polypeptide having at least 70%, at least 80%, at least 90%, at least 95% or greater than 95%, such as 96%, 97%, 98%, or 99% or greater, sequence identity to the amino acid sequence of SEQ ID NO:3.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 3 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |

TABLE 3-continued

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| C | 0  | -3 | -3 | -3 | 9  |    |    |    |    |    |    |    |    |    |    |    |    |    |    |   |
| Q | -1 | 1  | 0  | 0  | -3 | 5  |    |    |    |    |    |    |    |    |    |    |    |    |    |   |
| E | -1 | 0  | 0  | 2  | -4 | 2  | 5  |    |    |    |    |    |    |    |    |    |    |    |    |   |
| G | 0  | -2 | 0  | -1 | -3 | -2 | -2 | 6  |    |    |    |    |    |    |    |    |    |    |    |   |
| H | -2 | 0  | 1  | -1 | -3 | 0  | 0  | -2 | 8  |    |    |    |    |    |    |    |    |    |    |   |
| I | -1 | -3 | -3 | -3 | -1 | -3 | -3 | -4 | -3 | 4  |    |    |    |    |    |    |    |    |    |   |
| L | -1 | -2 | -3 | -4 | -1 | -2 | -3 | -4 | -3 | 2  | 4  |    |    |    |    |    |    |    |    |   |
| K | -1 | 2  | 0  | -1 | -3 | 1  | 1  | -2 | -1 | -3 | -2 | 5  |    |    |    |    |    |    |    |   |
| M | -1 | -1 | -2 | -3 | -1 | 0  | -2 | -3 | -2 | 1  | 2  | -1 | 5  |    |    |    |    |    |    |   |
| F | -2 | -3 | -3 | -3 | -2 | -3 | -3 | -3 | -1 | 0  | 0  | -3 | 0  | 6  |    |    |    |    |    |   |
| P | -1 | -2 | -2 | -1 | -3 | -1 | -1 | -2 | -2 | -3 | -3 | -1 | -2 | -4 | 7  |    |    |    |    |   |
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative IL-22RA variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2 or SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SLAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO:3, in which an alkyl amino acid is substituted for an alkyl amino acid in a IL-22RA amino acid sequence, an aromatic amino acid is substituted for an aromatic amino acid in a IL-22RA amino acid sequence, a sulfur-containing amino acid is substituted for a sulfur-containing amino acid in a IL-22RA amino acid sequence, a hydroxy-containing amino acid is substituted for a hydroxy-containing amino acid in a IL-22RA amino acid sequence, an acidic amino acid is substituted for an acidic amino acid in a IL-22RA amino acid sequence, a basic amino acid is substituted for a basic amino acid in a IL-22RA amino acid sequence, or a dibasic monocarboxylic amino acid is substituted for a dibasic monocarboxylic amino acid in a IL-22RA amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than -1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of IL-22RA are characterized by having at least 70%, at least 80%, at least 90%, at least 95% or greater than 95% such as 96%, 97%, 98%, or 99% or greater sequence identity to the corresponding amino acid sequence (e.g., SEQ ID NO:3), wherein the variation in amino acid sequence is due to one or more conservative amino acid substitutions.

Conservative amino acid changes in a IL-22RA gene can be introduced, for example, by substituting nucleotides for the nucleotides recited in SEQ ID NO:1. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). A variant IL-22RA polypeptide can be identified by the ability to specifically bind anti-IL-22RA antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for IL-22RA amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the IL-22RA ligand binding region, amino acids that play a role in IL-22RA binding activity (such as binding of IL-22RA to ligand IL-22, or to an anti-IL-22RA antibody) can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306 (1992), Smith et al., *J. Mol. Biol.* 224:899 (1992), and Wlodaver et al., *FEBS Lett.* 309:59 (1992).

Multiple amino acid substitutions can be made and tested using known methods of mutagenesis and screening, such as those disclosed by Reidhaar-Olson and Sauer (Science 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, IL-22RA labeled with biotin or FITC can be used for expression cloning of IL-22RA ligands.

Variants of the disclosed IL-22RA nucleotide and polypeptide sequences can also be generated-through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-22RA antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of IL-22RA polypeptides and nucleic acid molecules encoding such functional fragments. Routine deletion analyses of nucleic acid molecules can be performed to obtain functional fragments of a nucleic acid molecule that encodes a IL-22RA polypeptide. As an illustration, DNA molecules having the nucleotide sequence of SEQ ID NO:1 can be digested with Bal31 nuclease to obtain a series of nested deletions. The fragments are then inserted into expression vectors in proper reading frame, and the expressed polypeptides are isolated and tested for the ability to bind anti-IL-22RA antibodies. One alternative to exonuclease digestion is to use oligonucleotide-directed mutagenesis to introduce deletions or stop codons to specify production of a desired fragment. Alternatively, particular fragments of a IL-22RA gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol.* 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

Analysis of the particular sequences disclosed herein provide a set of illustrative functional fragments presented in Table 4. The nucleotides encoding additional human IL-22RA functional varaint domains described herein, not show in Table 4, can be determined with reference to SEQ ID NO:1. Such functional fragments include for example, the following nucleotide sequences of SEQ ID NO:1: nucleotides 85-381, 206-717, and 85-717 of SEQ ID NO:1 and corresponding amino acid sequences encoded thereby as shown in SEQ ID NO:2 and SEQ ID NO:3 respectively.

TABLE 4

| IL-22RA Feature | Amino acid residues (SEQ ID NO: 2) | Nucleotides (SEQ ID NO: 1) |
|---|---|---|
| First Ig Domain | 18-116 | 85-381 |
| Second Ig Domain | 125-228 | 206-717 |
| Both Ig Domains | 18-228 | 85-717 |

The present invention also contemplates functional fragments of a IL-22RA gene that have amino acid changes, compared with an amino acid sequence disclosed herein. A variant IL-22RA gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant IL-22RA gene can hybridize to a nucleic acid molecule comprising a nucleotide sequence, such as SEQ ID NO:1.

The present invention also includes using functional fragments of IL-22RA polypeptides, antigenic epitopes, epitope-bearing portions of IL-22RA polypeptides, and nucleic acid molecules that encode such functional fragments, antigenic epitopes, epitope-bearing portions of IL-22RA polypeptides. Such fragments are used to generate polypeptides for use in generating antibodies and binding partners that bind, block, inhibit, reduce, antagonize or neutralize activity of IL-22 or both IL-20 and IL-22. A "functional" IL-22RA polypeptide or fragment thereof as defined herein is characterized by its ability to block, inhibit, reduce, antagonize or neutralize IL-20 or IL-22 inflammatory, proliferative or differentiating activity, by its ability to induce or inhibit specialized cell functions, or by its ability to bind specifically to an anti-IL-22RA antibody, cell, IL-20 or IL-22. As previously described herein, IL-22RA is characterized by a class II cytokine receptor structure and domains as described herein. Thus, the present invention further contemplates using fusion proteins encompassing: (a) polypeptide molecules comprising one or more of the domains described above; and (b) functional fragments comprising one or more of these domains. The other polypeptide portion of the fusion protein may be contributed by another class II cytokine receptor, such as IL-10R, IL-13R, IL-20RA, IL-20RB, IL-10RB (CRF2-4), IL-22RA2, or by a non-native and/or an unrelated secretory signal peptide that facilitates secretion of the fusion protein.

The present invention also provides polypeptide fragments or peptides comprising an epitope-bearing portion of a IL-22RA polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides, antigenic peptides, epitopes, and polypeptides of the present invention are useful to raise antibodies that bind with the polypeptides described herein, as well as to identify and screen anti-IL-22RA monoclonal antibodies that are neutralizing, and that may bind, block, inhibit, reduce, antagonize or neutralize the activity of IL-22 and IL-20 (individually or together). Such neutralizing monoclonal antibodies of the present invention can bind to an IL-22RA antigenic epitope. Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Enpineering* 11:153-169, 1998). The profile is based on a sliding six-residue window. Buried G, S, and T residues and exposed H, Y, and W residues were ignored. In IL-22RA these regions can be determined by one of skill in the art. Moreover, IL-22RA antigenic epitopes within SEQ ID NO:3 as predicted by a Jameson-Wolf plot, e.g., using DNASTAR Protean program (DNASTAR, Inc., Madison, Wis.) serve as preferred antigenic epitpoes, and can be determined by one of skill in the art. Such antigenic epitpoes include (1) amino acid residues 1 (Pro) to 6 (Asp) of SEQ ID NO:3; (2) amino acid residues 26 (Ser) to 32 (Pro) of SEQ ID NO:3; (3) amino acid residues 41 (Lys) to 47 (Asp) of SEQ ID NO:3; (4) amino acid residues 49 (Val) to 62 (Cys) of SEQ ID NO:3; (5) amino acid residues 41 (Lys) to 62 (Cys) of SEQ ID NO:3; (6) amino acid residues 84 (Ala) to 97 (Ser) of SEQ ID NO:3; (7) amino acid residues 103 (Thr) to 108 (Asp) of SEQ ID NO:3; (8) amino acid residues 130 (Arg) to 135 (His) of SEQ ID NO:3; (9) amino acid residues 164 (Gly) to 166 (Lys) of SEQ ID NO:3; (10) amino acid residues 175 (Tyr) to 179 (Glu) of SEQ ID NO:3; (11) amino acid residues 193 (Lys) to 196 (Ala) of SEQ ID NO:3; (12) amino acid residues 203 (Lys) to 209 (Thr) of SEQ ID NO:3. Additional epitopes include the following peptides are potentially generated from non-reduced full-length human IL-22RA cleaved with CnBr: peptide 6 (SEQ ID NO:56), peptide 7 (SEQ ID NO:57); peptide 8 (SEQ ID NO:58); peptide 9 (SEQ ID NO:59); peptide 10 (SEQ ID NO:60); and peptide 11 (SEQ ID NO:61). Cysteines are disulfide-bonded, which results in a possible link between peptides 7 (SEQ ID NO:57) and 10

(SEQ ID NO:60. Specifically, SEQ ID NO:56 corresponds to amino acid residues 1 (Pro) to 92 (Met) of SEQ ID NO:3; SEQ ID NO:57 corresponds to amino acid residues 93 (Thr) to 120 (Met) of SEQ ID NO:3, SEQ ID NO:58 corresponds to amino acid residues 121 (Ile) to 160 (Met) of SEQ ID NO:3, SEQ ID NO:59 corresponds to amino acid residues 161 (His) to 185 (Met) of SEQ ID NO:3, SEQ ID NO:60 corresponds to amino acid residues 186 (Ile) to 199 (Met) of SEQ ID NO:3 and SEQ ID NO:61 corresponds to amino acid residues 200 (Cys) to 211 (Thr) of SEQ ID NO:3. In addition, residues of SEQ ID NO:2 (and corresponding residues of SEQ ID NO:3) that are important to ligand-receptor binding comprise Tyr-60, and Phe-164, Tyr-93, Arg-112, Lys-210, and Glu-211 of SEQ ID NO:2 and (and corresponding residues of SEQ ID NO:3). Moreover, primary residues of SEQ ID NO:2 (and corresponding residues of SEQ ID NO:3) that are important to direct ligand-receptor binding comprise Tyr-60, and Phe-164 of SEQ ID NO:2 (and corresponding residues of SEQ ID NO:3), and secondary residues comprise residues Tyr-93, Arg-112, Lys-210, and Glu-211 of SEQ ID NO:2 and (and corresponding residues of SEQ ID NO:3). In preferred embodiments, antigenic epitopes to which neutralizing antibodies of the present invention bind would contain residues of SEQ ID NO:2 (and corresponding residues of SEQ ID NO:3) that are important to ligand-receptor binding, for example, with IL-22RA and IL-20 or IL-22 (individually or together).

Antigenic epitope-bearing peptides and polypeptides can contain at least four to ten amino acids, at least ten to fifteen amino acids, or about 15 to about 30 amino acids of an amino acid sequence disclosed herein. Such epitope-bearing peptides and polypeptides can be produced by fragmenting a IL-22RA polypeptide, or by chemical peptide synthesis, as described herein. Moreover, epitopes can be selected by phage display of random peptide libraries (see, for example, Lane and Stephen, *Curr. Opin. Immunol.* 5:268 (1993), and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105-116 (The Humana Press, Inc. 1992), Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.) *Current Protocols in Immunology*, pages 9.3.1-9.3.5 and pages 9.4.1-9.4.11 (John Wiley & Sons 1997).

For any IL-22RA polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise IL-22RA variants based upon the nucleotide and amino acid sequences described herein.

5. Production of IL-22RA Polypeptides

The polypeptides of the present invention, including full-length polypeptides; soluble monomeric, homodimeric, heterodimeric and multimeric receptors; full-length receptors; receptor fragments (e.g. ligand-binding fragments and antigenic epitopes), functional fragments, and fusion proteins, can be produced in recombinant host cells following conventional techniques. To express a IL-22RA gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an IL-22RA expression vector may comprise a IL-22RA gene and a secretory sequence derived from any secreted gene.

IL-22RA proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice, Cleland et al. (eds.), pages* 163-181 (John Wiley & Sons, Inc. 1996)).

Alternatively, a prokaryotic promoter, such as the bacteriophage T3 RNA polymerase promoter, can be used to control IL-22RA gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In certain embodiments, a DNA sequence encoding a IL-22RA soluble receptor polypeptide, or a fragment of IL-22RA polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase (DHFR), which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

IL-22RA polypeptides can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

IL-22RA can also be expressed in other higher eukaryotic cells, such as avian, fungal, insect, yeast, or plant cells. The baculovirus system provides an efficient means to introduce cloned IL-22RA genes into insect cells. Suitable expression vectors are based upon the *Autographa californica* multiple nuclear polyhedrosis virus (AcMNPV), and contain-well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding the IL-22RA polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed IL-22RA polypeptide, for example, a Glu-Glu epitope tag (Grussenmeyer et al., *Proc. Nat'l Acad. Sci.* 82:7952 (1985)). Using a technique known in the art, a transfer vector containing a IL-22RA gene is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270: 1543 (1995). In such transfer vector constructs, a short or long version of the basic protein promoter can be used. Moreover, transfer vectors can be constructed which replace the native IL-22RA secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native IL-22RA secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors;" in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615,974, and Bitter, U.S. Pat. No. 4,977,092) and alcohol dehydrogenase genes. See also U.S. Pat. Nos. 4,990,446, 5,063,154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilizationfgene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Miki et al., "Procedures for Introducing Foreign DNA into Plants," in *Methods in Plant Molecular Biology and Biotechnology*, Glick et al. (eds.), pages 67-88 (CRC Press, 1993).

Alternatively, IL-22RA genes can be expressed in prokaryotic host cells. Suitable promoters that can be used to express IL-22RA polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus*, *Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene, 4th Ed.* (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a IL-22RA polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:3. As an illustration, polypeptides can comprise at least six, at least nine, or at least 15 contiguous amino acid residues of of SEQ ID NO:3. Within certain embodiments of the invention, the polypeptides comprise 20, 30, 40, 50, 100, or more contiguous residues of these amino-acid sequences. Nucleic acid molecules encoding such peptides and polypeptides are useful as polymerase chain reaction primers and probes.

Moreover, IL-22RA polypeptides and fragments thereof can be expressed as monomers, homodimers, heterodimers, or multimers within higher eukaryotic cells. Such cells can be used to produce IL-22RA monomeric, homodimeric, heterodimeric and multimeric receptor polypeptides that comprise at least one IL-22RA polypeptide ("IL-22RA-comprising receptors" or "IL-22RA-comprising receptor polypeptides"), or can be used as assay cells in screening systems. Within one aspect of the present invention, a polypeptide of the present invention comprising the IL-22RA extracellular domain is produced by a cultured cell, and the cell is used to screen for ligands for the receptor, including the natural ligand, IL-22, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

To assay the IL-20 and IL-22 antagonist polyepeptides and antibodies of the present invention, mammalian cells suitable for use in expressing IL-22RA-comprising receptors or other receptors known to bind IL-20 or IL-22 (e.g., cells expressing IL-22RA/CRF2-4; and IL-20RA, IL-20RB, IL-22RA/IL-20RB, or IL-20RA/IL-20RB) and transducing a receptor-mediated signal include cells that express other receptor subunits that may form a functional complex with IL-22RA (or IL-20RA). These subunits may include those of the interferon receptor family or of other-class II or class I cytokine receptors, e.g., CRF2-4 (Genbank Accession No. Z17227), IL-10R (Genbank Accession No.s U00672 and NM_001558), IL-22RA (commonly owned U.S. Pat. No. 5,965,704), zcytor7 (IL-20RA) (commonly owned U.S. Pat. No. 5,945,511), IL-20RA/IL-20RB (WIPO Publication No. WO 01/46232), and IL-9R. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, *Cell* 41: 727-734, (1985)) which is an IL-3 dependent murine pre-B cell line. Other cell lines include BHK, COS-1 and CHO cells. Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon another cytokine that acts through the IL-22RA receptor, such as IL-22.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55-63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563-572, (1989). A preferred such reporter gene is a luciferase gene (de Wet et al., *Mol. Cell. Biol.* 7:725, (1987)). Expression of the luciferase gene is detected by luminescence using methods known in the art (e.g., Baumgartner et al., *J. Biol. Chem.* 269:29094-29101, (1994); Schenborn and Goiffin, *Promega* Notes 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

Several IL-20 responsive cell lines are known in the art or can be constructed, for example, the Baf3/DIRS1/cytoR11 cell line (WIPO Publication No. WO 02/072607). Moreover several IL-22 responsive cell lines are known (Dumontier et al., *J. Immunol.* 164:1814-1819, 2000; Dumoutier, L. et al., *Proc. Nat'l. Acad. Sci.* 97:10144-10149, 2000; Xie M H et al., *J. Biol. Chem.* 275: 31335-31339, 2000; Kotenko S V et al., *J. Biol. Chem.* 276:2725-2732, 2001), as well as those that express the IL-22 receptor subunit IL-22RA. For example, the following cells are responsive to IL-22: TK-10 (Xie M H et al., supra.) (human renal carcinoma); SW480 (ATCC No. CCL-228) (human colon adenocarcinoma); HepG2 (ATCC No. HB-8065) (human hepatoma); PC12 (ATCC No. CRL-1721) (murine neuronal cell model; rat pheochromocytoma); and MES13 (ATCC No. CRL-1927) (murine kidney mesangial cell line). In addition, some cell lines express IL-22RA (IL-22 receptor) are also candidates for responsive cell lines to IL-22: A549 (ATCC No. CCL-185) (human lung carcinoma); G-361 (ATCC No. CRL-1424) (human melanoma); and Caki-1 (ATCC No. HTB-46) (human renal carcinoma). In addition, IL-22-responsive cell lines can be constructed, for example, the Baf3/cytoR11/CRF2-4 cell line described herein (WIPO Publication No. WO 02/12345). These cells can be used in assays to assess the functionality of IL-22RA as an IL-20 or IL-22 antagonist or anti-inflammatory factor.

An additional screening approach provided by the present invention includes the use of hybrid receptor polypeptides. These hybrid polypeptides fall into two general classes. Within the first class, the, intracellular domain of IL-22RA, is joined to the ligand-binding domain of a second receptor. A second class of hybrid receptor polypeptides comprise the extracellular (ligand-binding) domain of IL-22RA (SEQ ID NO:3) with an intracellular domain of a second receptor, preferably a hematopoietic cytokine receptor, and a transmembrane domain. Hybrid IL-22RA monomers, homodimers, heterodimers and multimers of the present invention receptors of this second class are expressed in cells known to be capable of responding to signals transduced by the second receptor. Together, these two classes of hybrid receptors enable the identification of a responsive cell type for the development of an assay for detecting IL-22 or IL-20. Moreover, such cells can be used in the presence of IL-22 or IL-20 to assay the soluble receptor antagonists of the present invention in a competition-type assay. In such assay, a decrease in the proliferation or signal transduction activity of IL-22 or IL-20 in the presence of a soluble receptor of the present invention demonstrates antagonistic activity. Moreover IL-22RA-soluble receptor binding assays, an cell-based assays, can also be used to assess whether a soluble receptor binds, blocks, inhibits, reduces, antagonizes or neutralizes IL-22 or IL-20 activity.

6. Production of IL-22RA Fusion Proteins and Conjugates

One general class of IL-22RA analogs are variants having an amino acid sequence that is a mutation of the amino acid sequence disclosed herein. Another general class of IL-22RA analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype IL-22RA antibodies mimic IL-22RA, these domains can provide IL-22RA binding activity. Methods of producing anti-idiotypic catalytic antibodies are known to those of skill in the art (see, for example, Joron et al., *Ann. N Y Acad. Sci.* 672:216 (1992), Friboulet et al., *Appl. Biochem. Biotechnol.* 47:229 (1994), and Avalle et al., *Ann. N Y Acad. Sci.* 864:118 (1998)).

Another approach to identifying IL-22RA analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

IL-22RA polypeptides have both in vivo and in vitro uses. As an illustration, a soluble form of IL-22RA can be added to cell culture medium to inhibit the effects of the IL-22RA ligand produced by the cultured cells.

Fusion proteins of IL-22RA can be used to express IL-22RA in a recombinant host, and to isolate the produced IL-22RA. As described below, particular IL-22RA fusion proteins also have uses in diagnosis and therapy. One type of fusion protein comprises a peptide that guides a IL-22RA polypeptide from a recombinant host cell. To direct a IL-22RA polypeptide into the secretory pathway of a eukaryotic host cell, a secretory signal sequence (also known as a signal peptide, a leader sequence, prepro sequence or pre sequence) is provided in the IL-22RA expression vector. While the secretory signal sequence may be derived from IL-22RA, a suitable signal sequence may also be derived from another secreted protein or synthesized de novo. The secretory signal sequence is operably linked to a IL-22RA-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of IL-22RA or another protein produced by mammalian cells (e.g., tissue-type plasminogen activator signal sequence, as described, for example, in U.S. Pat. No. 5,641,655) is useful for expression of IL-22RA in recombinant mammalian hosts, a yeast signal sequence is preferred for expression in yeast cells. Examples of suitable yeast signal sequences are those derived from yeast mating phermone α-factor (encoded by the MF α1 gene), invertase (encoded by the SUC2 gene), or acid phosphatase (encoded by the PHO5 gene). See, for example, Romanos et al., "Expression of Cloned Genes in Yeast," in *DNA Cloning 2: A Practical Approach, 2$^{nd}$ Edition*, Glover and Hames (eds.), pages 123-167 (Oxford University Press 1995).

IL-22RA soluble receptor polypeptides can be prepared by expressing a truncated DNA encoding the extracellular domain, for example, a polypeptide which contains SEQ ID NO:3, or the corresponding region of a non-human receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204-1210, (1988); available from Eastman Kodak Co., New Haven, Conn.) or another polypeptide or protein for which an antibody or other specific binding agent is available, can be fused to the receptor polypeptide. Moreover, IL-22RA antigenic epitopes from the extracellular cytokine binding domains are also prepared as described above.

In an alternative approach, a receptor extracellular domain of IL-22RA or other class I or II cytokine receptor component can be expressed as a fusion with immunoglobulin heavy chain constant regions, typically an $F_c$ fragment, which contains two constant region domains and a hinge region but lacks the variable region (See, Sledziewski, Ariz. et al., U.S. Pat. Nos. 6,018,026 and 5,750,375). The soluble IL-22RA polypeptides of the present invention include such fusions. One such fusion is shown in SEQ ID NO:4. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block, inhibit or reduce signals in vitro by specifically titrating out ligand, and as antagonists in vivo by administering them parenterally to bind circulating ligand and clear it from the circulation. To purify ligand, a IL-22RA-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

To assist in isolating anti-IL-22RA and binding partners of the present invention, an assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karisson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SEIDI(™) technology (Ciphergen, Inc., Palo Alto, Calif.). Moreover, BIA-CORE technology, described above, can be used to be used in competition experiments to determine if different momnoclonal antibodies bind the same or different epitopes on the IL-22RA polypeptide, and as such, be used to aid in epitope mapping of neutralizing antibodies of the present invention that bind, block, inhibit, reduce, antagonize or neutralize IL-22 or both IL-20 and IL-22.

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

The present invention further provides a variety of other polypeptide fusions and related multimeric proteins comprising one or more polypeptide fusions. For example, a soluble IL-22RA receptor can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble IL-22RA fusions can be expressed in genetically engineered cells to produce a variety of multimeric IL-22RA receptor analogs. Auxiliary domains can be fused to soluble IL-22RA receptor to target them to specific cells, tissues, or macromolecules (e.g., collagen, or cells expressing the IL-22RA ligands, IL-22 or IL-20). A IL-22RA polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

In bacterial cells, it is often desirable to express a heterologous protein as a fusion protein to decrease toxicity, increase stability, and to enhance recovery of the expressed protein. For example, IL-22RA can be expressed as a fusion protein comprising a glutathione S-transferase polypeptide. Glutathione S-transferease fusion proteins are typically soluble, and easily purifiable from *E. coli* lysates on immobilized glutathione columns. In similar approaches, a IL-22RA fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning 2: A Practical Approach*, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a IL-22RA polypeptide and an immunoglobulin heavy chain constant region, typically an $F_c$ fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:9). In this fusion protein, an illustrative Fc moiety is a human γ4 chain, which is stable in solution and has little or no complement activating activity. Accordingly, the present invention contemplates a IL-22RA fusion protein that comprises a IL-22RA moiety and a human Fc fragment, wherein the C-terminus of the IL-22RA moiety is attached to the N-terminus of the Fc fragment via a peptide linker, such as a peptide comprising the amino acid sequence of SEQ ID NO:4. The IL-22RA moiety can be a IL-22RA molecule or a fragment thereof. For example, a fusion protein can comprise the amino acid of SEQ ID NO:3 and an Fc fragment (e.g., a human Fc fragment) (SEQ ID NO:4).

In another variation, a IL-22RA fusion protein comprises an IgG sequence, a IL-22RA moiety covalently joined to the aminoterminal end of the IgG sequence, and a signal peptide that is covalently joined to the aminoterminal of the IL-22RA moiety, wherein the IgG sequence consists of the following elements in the following order: a hinge region, a $CH_2$ domain, and a $CH_3$ domain. Accordingly, the IgG sequence lacks a $CH_1$ domain. The IL-22RA moiety displays a IL-22RA activity, as described herein, such as the ability to bind with a IL-22RA ligand. This general approach to producing fusion proteins that comprise both antibody and nonantibody portions has been described by LaRochelle et al., EP 742830 (WO 95/21258).

Fusion proteins comprising a IL-22RA moiety and an Fc moiety can be used, for example, as an in vitro assay tool. For example, the presence of a IL-22RA ligand in a biological sample can be detected using a IL-22RA-immunoglobulin fusion protein, in which the IL-22RA moiety is used to bind the ligand, and a macromolecule, such as Protein A or anti-Fc antibody, is used to bind the fusion protein to a solid support. Such systems can be used to identify agonists and antagonists that interfere with the binding of a IL-22RA ligands, e.g., IL-22 or both IL-20 and IL-22, to their receptor.

Other examples of antibody fusion proteins include polypeptides that comprise an antigen-binding domain and a IL-22RA fragment that contains a IL-22RA extracellular domain. Such molecules can be used to target particular tissues for the benefit of IL-22RA binding activity.

The present invention further provides a variety of other polypeptide fusions. For example, part or all of a domain(s) conferring a biological function can be swapped between IL-22RA of the present invention with the functionally equivalent domain(s) from another member of the cytokine receptor family. Polypeptide fusions can be expressed in recombinant host cells to produce a variety of IL-22RA fusion; analogs. A IL-22RA polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

IL-22RA binding domains can be further characterized by physical analysis of structure, as determined by such techniques as nuclear magnetic resonance, crystallography, electron diffraction or photoaffinity labeling, in conjunction with mutation of putative contact site amino acids of IL-22RA ligand agonists. See, for example, de Vos et al., *Science* 255:306 (1992), Smith et al., *J. Mol. Biol.* 224:899 (1992), and Wlodaver et al., *FEBS Lett.* 309:59 (1992).

The present invention also contemplates chemically modified IL-22RA compositions, in which a IL-22RA polypeptide is linked with a polymer. Illustrative IL-22RA polypeptides are soluble polypeptides that lack a functional transmembrane domain, such as a polypeptide consisting of amino acid residues SEQ ID NO:3. Typically, the polymer is water soluble so that the IL-22RA conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252, 714). The polymer may be branched or unbranched. Moreover, a mixture of polymers can be used to produce IL-22RA conjugates.

IL-22RA conjugates used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone)PEG, tresyl monomethoxy PEG, PEG propionaldehyde, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-22RA conjugate can also comprise a mixture of such water-soluble polymers.

One example of a IL-22RA conjugate comprises a IL-22RA moiety and a polyalkyl oxide moiety attached to the N-terminus of the IL-22RA moiety. PEG is one suitable polyalkyl oxide. As an illustration, IL-22RA can be modified with PEG, a process known as "PEGylation." PEGylation of IL-22RA can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, IL-22RA conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a IL-22RA polypeptide. An example of an activated PEG ester is PEG esterified to N-hydroxysuccinimide. As used herein, the term "acylation" includes the following types of linkages between IL-22RA and a water soluble polymer: amide, carbamate, urethane, and the like. Methods for preparing PEGylated IL-22RA by acylation will typically comprise the steps of (a) reacting a IL-22RA polypeptide with PEG (such as a reactive ester of an aldehyde derivative of PEG) under conditions whereby one or more PEG groups attach to IL-22RA, and (b) obtaining the reaction product(s). Generally, the optimal reaction conditions for acylation reactions will be determined based upon known parameters and desired results. For example, the larger the ratio of PEG:IL-22RA, the greater the percentage of polyPEGylated IL-22RA product.

The product of PEGylation by acylation is typically a polyPEGylated IL-22RA product, wherein the lysine ε-amino groups are PEGylated via an acyl linking group. An example of a connecting linkage is an amide. Typically, the resulting IL-22RA will be at least 95% mono-, di-, or tri-pegylated, although some species with higher degrees of PEGylation may be formed depending upon the reaction conditions. PEGylated species can be separated from unconjugated IL-22RA polypeptides using standard purification methods, such as dialysis, ultrafiltration, ion exchange chromatography, affinity chromatography, and the like.

PEGylation by alkylation generally involves reacting a terminal aldehyde derivative of PEG with IL-22RA in the presence of a reducing agent. PEG groups can be attached to the polypeptide via a —$CH_2$—NH group.

Moreover, anti-IL-22RA antibodies or antibody fragments of the present invention can be PEGylated using methods in the art and described herein.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of IL-22RA monopolymer conjugates.

Reductive alkylation to produce a substantially homogenous population of monopolymer IL-22RA conjugate molecule can comprise the steps of: (a) reacting a IL-22RA polypeptide with a reactive PEG under reductive alkylation conditions at a pH suitable to permit selective modification of the α-amino group at the amino terminus of the IL-22RA, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer IL-22RA conjugates, the reductive alkylation reaction conditions are those that permit the selective attachment of the water-soluble polymer moiety to the N-terminus of IL-22RA. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:IL-22RA need not be as large because more reactive groups are available. Typically, the pH will fall within the range of 3 to 9, or 3 to 6. This method can be employed for making IL-22RA-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to IL-22RA will generally be in the range of 1:1 to 100:1. Typically, the molar ratio of water-soluble polymer to IL-22RA will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)). This method can be employed for making IL-22RA-comprising homodimeric, heterodimeric or multimeric soluble receptor conjugates.

The present invention contemplates compositions comprising a peptide or polypeptide, such as a soluble receptor or antibody described herein. Such compositions can further comprise a carrier. The carrier can be a conventional organic or inorganic carrier. Examples of carriers include water, buffer solution, alcohol, propylene glycol, macrogol, sesame oil, corn oil, and the like.

7. Isolation of IL-22RA Polypeptides

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of IL-22RA purified from natural sources (e.g., human tissue sources), synthetic IL-22RA polypeptides, and recombinant IL-22RA polypeptides and fusion IL-22RA polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in IL-22RA isolation and purification can be devised by those of skill in the art. For example, anti-IL-22RA antibodies, obtained as described below, can be used to isolate large quantities of protein by immunoaffinity purification.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the ligand-binding properties of IL-22RA extracellular domain can be exploited for purification, for example, of IL-22RA-comprising soluble receptors; for example, by using affinity chromatography wherein IL-22 ligand is bound to a column and the IL-22RA-comprising receptor is bound and subsequently eluted using standard chromatography methods.

IL-22RA polypeptides or fragments thereof may also be prepared through chemical synthesis, as described above. IL-22RA polypeptides may be monomers or multimers; glycosylated or non-glycosylated; PEGylated or non-PEGylated; and may or may not include an initial methionine amino acid residue.

8. Production of Antibodies to IL-22RA Proteins

Antibodies to IL-22RA can be obtained, for example, using the product of a IL-22RA expression vector or IL-22RA isolated from a natural source as an antigen. Particularly useful anti-IL-22RA antibodies "bind specifically" with IL-22RA. Antibodies are considered to be specifically binding if the antibodies exhibit at least one of the following two properties: (1) antibodies bind to IL-22RA with a threshold level of binding activity, and (2) antibodies do not significantly cross-react with polypeptides related to IL-22RA.

With regard to the first characteristic, antibodies specifically bind if they bind to a IL-22RA polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect IL-22RA, but not presently known polypeptides using a standard Western blot analysis. Examples of known related polypeptides include known cytokine receptors.

Anti-IL-22RA antibodies can be produced using antigenic IL-22RA epitope-bearing peptides and polypeptides. Antigenic epitope-bearing peptides and polypeptides of the present invention contain a sequence of at least nine, or between 15 to about 30 amino acids contained within SEQ ID NO:3 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-22RA. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in IL-22RA were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index." Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible.

The results of this analysis indicated that the following amino acid sequences of SEQ ID NO:3 would provide suitable antigenic peptides: Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. Moreover, IL-22RA antigenic epitopes within SEQ ID NO:3 as predicted by a Jameson-Wolf plot, e.g., using DNASTAR Protean program (DNASTAR, Inc., Madison, WI) serve as preferred antigenic epitopes, and can be determined by one of skill in the art. Such antigenic epitopes include (1) amino acid residues 1 (Pro) to 6 (Asp) of SEQ ID NO:3; (2) amino acid residues 26 (Ser) to 32 (Pro) of SEQ ID NO:3; (3) amino acid residues 41 (Lys) to 47 (Asp) of SEQ ID NO:3; (4) amino acid residues 49 (Val) to 62 (Cys) of SEQ ID NO:3; (5) amino acid residues 41 (Lys) to 62 (Cys) of SEQ ID NO:3; (6) amino acid residues 84 (Ala) to 97 (Ser) of SEQ ID NO:3; (7) amino acid residues 103 (Thr) to 108 (Asp) of SEQ ID NO:3; (8) amino acid residues 130 (Arg) to 135 (His) of SEQ ID NO:3; (9) amino acid residues 164 (Gly) to 166 (Lys) of SEQ ID NO:3; (10) amino acid residues 175 (Tyr) to 179 (Glu) of SEQ ID NO:3; (11) amino acid residues 193 (Lys) to 196 (Ala) of SEQ ID NO:3; (12) amino acid residues 203 (Lys) to 209 (Thr) of SEQ ID NO:3. The present invention contemplates the use of any one of antigenic peptides 1 to 12 to generate antibodies to IL-22RA or as a tool to screen or identify neutralizing monoclonal antibodies of the present invention. The present invention also contemplates polypeptides comprising at least one of antigenic peptides 1 to 10. The present invention contemplates the use of any antigenic peptides or epitopes described herein to generate antibodies to IL-22RA, as well as to identify and screen anti-IL-22RA monoclonal antibodies that are neutralizing, and that may bind, block, inhibit, reduce, antagonize or neutralize the activity of IL-22 and IL-20 (individually or together).

Moreover, suitable antigens also include the IL-22RA polypeptides comprising a IL-22RA cytokine binding, or extracellular domain disclosed above in combination with another class I or II cytokine extracellular domain, such as those that form soluble IL-22RA heterodimeric or multimeric polypeptides, such as soluble IL-22RA/CRF2-4, IL-22RA/zcytor11, IL-22RA/zcytor7, and the like.

Polyclonal antibodies to recombinant IL-22RA protein or to IL-22RA isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995). The immunogenicity of a IL-22RA polypeptide can be increased through the use of an adjuvant, such as alum (aluminum hydroxide) or Freund's complete or incomplete adjuvant. Polypeptides useful for immunization also include fusion polypeptides, such as fusions of IL-22RA or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-IL-22RA antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-IL-22RA antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology, Vol.* 1, pages 2.5.1-2.6.7 (John Wiley & Sons 1991) ["Coligan" ], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a IL-22RA gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-IL-22RA antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-IL-22RA antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology* Vol. 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991), (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFV can be obtained by exposing lymphocytes to IL-22RA polypeptide in vitro, and selecting antibody display libraries in phage or similar vectors (for instance, through use of immobilized or labeled IL-22RA protein or peptide). Genes encoding polypeptides having potential IL-22RA polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the IL-22RA sequences disclosed herein to identify proteins which bind to IL-22RA.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-IL-22RA antibody may be derived from a "humanized" monoclonal antibody. Humanized monoclonal antibodies are produced by transferring mouse complementary determining regions from heavy and light variable chains of the mouse immunoglobulin into-a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engi-* neering Protocols (Humana Press, Inc. 1995), Kelley, "Engineering Therapeutic Antibodies," in *Protein Engineering: Principles and Practice*, Cleland et al. (eds.), pages 399-434 (John Wiley & Sons, Inc. 1996), and by Queen et al., U.S. Pat. No. 5,693,762 (1997).

Moreover, anti-IL-22RA antibodies or antibody fragments of the present invention can be PEGylated using methods in the art and described herein.

Polyclonal anti-idiotype antibodies can be prepared by immunizing animals with anti-IL-22RA antibodies or antibody fragments, using standard techniques. See, for example, Green et al., "Production of Polyclonal Antisera," in *Methods In Molecular Biology: Immunochemical Protocols*, Manson (ed.), pages 1-12 (Humana ress 1992). Also, see Coligan at pages 2.4.1-2.4.7. Alternatively, monoclonal anti-idiotype antibodies can be prepared using anti-IL-22RA antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

An anti-IL-22RA antibody can be conjugated with a detectable label to form an anti-IL-22RA immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3H$, $^{125}I$, $^{131}I$, $^{35}S$ and $^{14}C$.

Anti-IL-22RA immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhoda-mine, phycoerytherin, phycocyanin, allophycocyanin, o-phthaldehyde and fluorescamine.

Alternatively, anti-IL-22RA immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemi-luminescent labeling compounds include luminol, isoluminol, an aromatic acridinium ester, an imidazole, an acridinium salt and an oxalate ester.

Similarly, a bioluminescent compound can be used to label anti-IL-22RA immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-22RA immunoconjugates can be detectably labeled by linking an anti-IL-22RA antibody component to an enzyme. When the anti-JL-22RA-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-22RA antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Int'l J. Cancer* 46:1101 (1990), Stein et al., *Cancer Res.* 50:1330 (1990), and Coligan, supra.

Moreover, the convenience and versatility of immunochemical detection can be enhanced by using anti-IL-22RA antibodies that have been conjugated with avidin, streptavidin, and biotin (see, for example, Wilchek et al. (eds.), "Avidin-Biotin Technology," *Methods In Enzymology*, Vol. 184 (Academic Press 1990), and Bayer et al., "Immunochemical Applications of Avidin-Biotin Technology," in *Methods In Molecular Biology*, Vol. 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for IL-22RA gene expression. Such kits comprise at least one container comprising an anti-IL-22RA antibody, or antibody fragment. A kit may also comprise a second container comprising one or more reagents capable of indicating the presence of IL-22RA antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that IL-22RA antibodies or antibody fragments are used to detect IL-22RA protein. For example, written instructions may state that the enclosed antibody or antibody fragment can be used to detect IL-22RA. The written material can be applied directly to a container, or the written material can be provided in the form of a packaging insert.

9. Use of Anti-IL-22RA Antibodies to Antagonize IL-22RA Binding to IL-22 or both IL-20 and IL-22

Alternative techniques for generating or selecting antibodies useful herein include in vitro exposure of lymphocytes to soluble IL-22RA receptor polypeptides or fragments thereof, such as antigenic epitopes, and selection of antibody display libraries in phage or similar vectors (for instance, through use of immobilized or labeled soluble IL-22RA receptor polypeptides or fragments thereof, such as antigenic epitopes). Genes encoding polypeptides having potential binding domains such as soluble soluble IL-22RA receptor polypeptides or fragments thereof, such as antigenic epitopes can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides that interact with a known target that can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the soluble IL-22RA receptor polypeptides or fragments thereof, such as antigenic epitope polypeptide sequences disclosed herein to identify proteins which bind to IL-22RA-comprising receptor polypeptides. These "binding polypeptides," which interact with soluble IL-22RA-comprising receptor "polypeptides, can be used for tagging cells; for isolating homolog polypeptides by affinity purification; they can be directly or indirectly conjugated to drugs, toxins, radionuclides and the like. These binding polypeptides can also be used in analytical methods such as for screening expression libraries and neutralizing activity, e.g., for binding, blocking, inhibiting, reducing, antagonizing or neutralizing interaction between IL-22 ligand and receptor, or viral binding to a receptor. The binding polypeptides can also be used for diagnostic assays for determining circulating levels of soluble IL-22RA-comprising receptor polypeptides; for detecting or quantitating soluble or non-soluble IL-22RA-comprising receptors as marker of underlying pathology or disease. These binding polypeptides can also act as "antagonists" to block or inhibit soluble or membrane-bound IL-22RA monomeric receptor or IL-22RA homodimeric, heterodimeric or multimeric polypeptide binding (e.g. to ligand) and signal transduction in vitro and in vivo. Again, these binding polypeptides serve as anti-IL-22RA monomeric receptor or anti-IL-22RA homodimeric, heterodimeric or multimeric polypeptides and are useful for inhibiting IL-22 or both IL-20 and IL-22 activity, as well as receptor activity or protein-binding. Antibodies raised to the natural receptor complexes of the present invention, and IL-22RA-epitope-binding antibodies, and anti-IL-22RA neutralizing monoclonal antibodies may be preferred embodiments, as they may act more specifically against the IL-22RA and can inhibit IL-22 or both IL-20 and IL-22. Moreover, the antagonistic and binding activity of the antibodies of the present invention can be assayed in an IL-20 or IL-22 proliferation, signal trap, luciferase or binding assays in the presence of IL-20 or IL-22 respectively, and IL-22RA-comprising soluble receptors, and other biological or biochemical assays described herein.

Antibodies to soluble IL-22RA receptor polypeptides (e.g., antibodies to SEQ ID NO:3) or fragments thereof, such as antigenic epitopes may be used for inhibiting the inflammatory effects of IL-20, IL-22, or both IL-20 and IL-22 in vivo, for thraputic use against psoriasis, atopic dermatitis, inflammatory skin conditions, endotoxemia, arthritis, asthma, IBD, colitis, psoriatic arthritis, rheumatoid arthritis or other IL-20 and IL-22-induced inflammatory conditions; tagging cells that express IL-22RA receptors; for isolating soluble IL-22RA-comprising receptor polypeptides by affinity purification; for diagnostic assays for determining circulating levels of soluble IL-22RA-comprising receptor polypeptides; for detecting or quantitating soluble IL-22RA-comprising receptors as marker of underlying pathology or disease; in analytical methods employing FACS; for screening expression libraries; for generating anti-idiotypic antibodies that can act as IL-22 or IL-20 agonists; and as neutralizing antibodies or as antagonists to bind, block, inhibit, reduce, or antagonize IL-22RA receptor function, or to bind, block, inhibit, reduce, antagonize or neutralize IL-22 and/or IL-20 activity (either individually or together) in vitro and in vivo. Suitable direct tags or labels include radionuclides, enzymes, substrates, cofactors, biotin, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to soluble IL-22RA-comprising receptor polypeptides, or fragments thereof may be used in vitro to detect denatured or non-denatured IL-22RA-comprising receptor polypeptides or fragments thereof in assays, for example, Western Blots or other assays known in the art.

Antibodies to soluble IL-22RA receptor or soluble IL-22RA homodimeric, heterodimeric or multimeric receptor polypeptides are useful for tagging cells that express the corresponding receptors and assaying their expression levels, for affinity purification, within diagnostic assays for determining circulating levels of receptor polypeptides, analytical methods employing fluorescence-activated cell sorting. Moreover, divalent antibodies, and anti-idiotypic antibodies may be used as agonists to mimic the effect of the IL-22RA ligand, IL-22 or IL-20.

Antibodies herein can also be directly or indirectly conjugated to drugs, toxins, radionuclides and the like, and these conjugates used for in vivo diagnostic or therapeutic applications. For instance, antibodies or binding polypeptides which recognize soluble IL-22RA receptor or soluble IL-22RA homodimeric, heterodimeric or multimeric receptor polypeptides can be used to identify or treat tissues or organs that express a corresponding anti-complementary molecule (i.e., a IL-22RA-comprising soluble or membrane-bound receptor). More specifically, antibodies to soluble IL-22RA-comprising receptor polypeptides, or bioactive fragments or portions thereof, can be coupled to detectable or cytotoxic molecules and delivered to a mammal having cells, tissues or organs that express the IL-22RA-comprising receptor such as IL-22RA-expressing cancers.

Suitable detectable molecules may be directly or indirectly attached to polypeptides that bind IL-22RA-comprising receptor polypeptides, such as "binding polypeptides," (including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/ streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, IL-22RA binding polypeptide-cytokine or antibody-cytokine fusion proteins can be used for enhancing in vivo killing of target tissues (for example, spleen, pancreatic, blood, lymphoid, colon, and bone marrow cancers), if the binding polypeptide-cytokine or anti-IL-22RA receptor antibody targets the hyperproliferative cell (See, generally, Hornick et al., *Blood* 89:4437-47, 1997). The described fusion proteins enable targeting of a cytokine to a desired site of action, thereby providing an elevated local concentration of cytokine. Suitable anti-IL-22RA monomer, homodimer, heterodimer or multimer antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, IL-22RA receptor binding polypeptides or antibody fusion proteins described herein can be used for enhancing in vivo killing of target tissues by directly stimulating a IL-22RA receptor-modulated apoptotic pathway, resulting in cell death of hyperproliferative cells expressing IL-22RA-comprising receptors.

10. Therapeutic Uses of Polypeptides Having IL-22RA Activity or Antibodies to IL-22RA Amino acid sequences having soluble IL-22RA activity can be used to modulate the immune system by binding IL-22RA ligands IL-20 and IL-22 (either singly or together), and thus, preventing the binding of IL-22RA ligand with endogenous IL-22RA receptor. IL-22RA antagonists, such as anti-JL-22RA antibodies, can also be used to modulate the immune system by inhibiting the binding of IL-22RA ligand with the endogenous IL-22RA receptor. Accordingly, the present invention includes the use of proteins, polypeptides, and peptides having IL-22RA activity (such as soluble IL-22RA polypeptides, IL-22RA polypeptide fragments, IL-22RA analogs (e.g., anti-IL-22RA anti-idiotype antibodies), and IL-22RA fusion proteins) to a subject which lacks an adequate amount of this polypeptide, or which produces an excess of IL-22RA ligand. IL-22RA antagonists (e.g., anti-IL-22RA antibodies) can be also used to treat a subject which produces an excess of either IL-22RA ligand or IL-22RA. Suitable subjects include mammals, such as humans. For example, such IL-22RA polypeptides and anti-IL-22RA antibodies are useful in binding, blocking, inhibiting, reducing, antagonizing or neutralizing IL-20 and IL-22 (either singly or together), in the treatment of psoriasis, atopic dermatitis, inflammatory skin conditions, psoriatic arthritis, arthritis, endotoxemia, asthma, inflammatory bowel disease (IBD), colitis, and other inflammatory conditions disclosed herein.

Moreover, we have shown that the IL-22RA receptor binds a ligand called T-cell inducible Factor (IL-22) (SEQ ID NO:6; Dumoutier, L. et al., *Proc. Nat'l. Acad. Sci.* 97:10144-10149, 2000; mouse IL-22 sequence is shown in Dumontier et al., *J. Immunol.* 164:1814-1819, 2000). Moreover, commonly owned zcytor11 (IL-22RA) (U.S. Pat. No. 5,965,704) and CRF2-4 receptor also bind IL-22 as a heterodimer (See, WIPO publication WO 00/24758; Dumontier et al., *J. Immunol.* 164:1814-1819, 2000; Spencer, S D et al., *J. Exp. Med.* 187:571-578, 1998; Gibbs, V C and Pennica Gene 186:97-101, 1997 (CRF2-4 cDNA); Xie, M H et al., *J. Biol. Chem.* 275: 31335-31339, 2000; and Kotenko, S V et al., *J. Biol. Chem.* 276:2725-2732, 2001). Moreover, IL-10β receptor may be involved as a receptor for IL-22, and it is believed to be synonymous with CRF2-4 (Dumoutier, L. et al., *Proc. Nat'l. Acad. Sci.* 97:10144-10149, 2000; Liu Y et al, *J Immunol.* 152; 1821-1829, 1994 (IL-1OR cDNA). Moreover, we have shown that IL-22RA receptor binds a ligand called IL-20 (SEQ ID NO:8; WIPO Publication No. WO 99/27103). Within preferred embodiments, the soluble receptor form of IL-22RA, SEQ ID NO:3) is a monomer, homodimer, heterodimer, or multimer that binds to, blocks, inhibits, reduces, antagonizes or neutralizes IL-22 and IL-20 in vivo. Antibodies and binding polypeptides to such IL-22RA monomer, homodimer, heterodimer, or multimers also serve as antagonists of IL-22RA activity, and as IL-20 and IL-22 antagonists (singly or together), as described herein.

In addition, we have described herein, and have demonstrated that both polyclonal and monoclonal neutralizing anti-IL-22 antibodies bind to, block, inhibit, reduce, antagonize or neutralize IL-22 and IL-20 activity in cell based neutralization assays.

IL-22 has been shown to be induced in the presence of IL-9, and is suspected to be involved in promoting Th1-type immune responses, and inflammation. IL-9 stimulates proliferation, activation, differentiation and/or induction of immune function in a variety of ways and is implicated in asthma, lung mastocytosis, and other diseases, as well as activates STAT pathways. Antagonists of IL-22 or IL-9 function can have beneficial use against such human diseases. The present invention provides such novel antagonists of IL-22.

IL-22 has been show to be involved in up-regulate the production of acute phase reactants, such as serum amyloid A (SAA), α1-antichymotrypsin, and haptoglobin, and that IL-22 expression is increased upon injection of lipopolysaccharide (LPS) in vivo suggesting that IL-22 is involved in inflammatory response (Dumoutier, L. et al., *Proc. Nat'l. Acad. Sci.* 97:10144-10149, 2000). Production of acute phase proteins, such as SAA, is considered s short-term survival mechanism where inflammation is beneficial; however, maintenance of acute phase proteins for longer periods contributes to chronic inflammation and can be harmful to human health. For review, see Uhlar, C M and Whitehead, A S, *Eur. J. Biochem.* 265:501-523, 1999, and Baumann H. and Gauldie, J. *Immunology Today* 15:74-80, 1994. Moreover, the acute phase protein SAA is implicated in the pathogenesis of several chronic inflammatory diseases, is implicated in atherosclerosis and rheumatoid arthritis, and is the precursor to the amyloid A protein deposited in amyloidosis (Uhlar, CM and Whitehead, supra.). Thus, as IL-22 acts as a pro-inflammatory molecule and induces production of SAA, antagonists would be useful in treating inflammatory disease and other diseases associated with acute phase response proteins induced by IL-22. Such antagonists are provided by the present invention. For example, method of reducing IL-22-induced or IL-9 induced inflammation comprises administering to a mammal with inflammation an amount of a composition of soluble IL-22RA-comprising receptor sufficient to reduce inflammation. Moreover, a method of suppressing an inflammatory response in a mammal with inflammation can comprise: (1) determining a level of serum amyloid A protein; (2) administering a composition comprising a soluble IL-22RA cytokine receptor polypeptide as described herein in an acceptable pharmaceutical vehicle; (3) determining a post administration level of serum amyloid A protein; (4) comparithe level of serum amyloid A protein in step (1) to the level of serum amyloid A protein in step (3), wherein a lack of increase or a decrease in serum amyloid A protein level is indicative of suppressing an inflammatory response. Experimental evidence described herein shows that IL-22 antagonists, such as soluble receptors and antibodies, indeed reduce SAA levels in in vivo models for inflammatory diseases, showing that binding, blocking, inhibiting, reducing, antagonizing or neutralizing IL-22 has anti-inflammatory effects.

Evidence indicates that a role IL-20 and its receptors are involved in psoriasis. This multigenic skin disease is characterized by increased keratinocyte proliferation, altered keratinocyte differentiation, and infiltration of immune cells into the skin. The first line of evidence for a role of IL-20 in psoriasis is that the observed hyperkeratosis and thickened epidermis in the transgenic mice that resemble human psoriatic abnormalities. Decreased numbers of tonofilaments, thought to be related to defective keratinization, are a striking feature of human psoriasis. Intramitochondrial inclusions have been found in both chemically induced and naturally occurring hyperplastic skin conditions in mice. The cause of the inclusions and their effects on mitochondrial function, if any, are unknown. IL-20 transgenic mice exhibit many of the characteristics observed in human psoriasis.

Moreover, IL-20 receptor mRNA (both IL-20RA and IL-20RB mRNA) are markedly upregulated in human psoriatic skin compared to normal skin further suggesting a role for IL-20 in psoriasis. Both IL-20 receptor subunits are expressed in keratinocytes throughout the epidermis and are also expressed in a subset of immune and endothelial cells. We propose that increased expression of an activated IL-20 receptor may alter the interactions between endothelial cells, immune cells and keratinocytes, leading to dysregulation of keratinocyte proliferation and differentiation. In addition, mouse knockout data described herein, wherein the IL-22RA receptor is knocked out, show that IL-22RA was necessary for the IL-20-induced inflammatory effects in skin in transgenic animals. These results provided evidence that effectively blocking IL-22RA activity, for example via an IL-22RA gene knockout, or similarly via a neutralizing monoclonal antibody to IL-22RA of the present invention, would similarly reduce IL-20-induced skin effects, as well as IL-22-induced skin effects, for example in psoriasis, IBD, colitis, or other inflammatory diseases induced by IL-20, and or IL-22 including IBD, arthritis, asthma, psoriatic arthritis, colitis, inflammatory skin conditions, and atopic dermatitis.

Moreover, IL-20 stimulates signal transduction in the human keratinocyte HaCaT cell line, supporting a direct action of this novel ligand in skin. In addition, IL-1β, EGF and TNF-α, proteins known to be active in keratinocytes and to be involved with proliferative and pro-inflammatory signals in skin, enhance the response to IL-20. In both HaCaT and BHK cells expressing the IL-20 receptor, IL-20 signals through STAT3.

As indicated in the discussion above and the examples below, IL-20 is involved in the pathology of psoriasis. The present invention is in particular a method for treating psoriasis by administering agents that bind, block, inhibit, reduce, antagonize or neutralize IL-20. The antagonists to IL-20 can either be a soluble receptor that binds to IL-20, such a soluble IL-22RA, or antibodies, single chain antibodies or fragments of antibodies that bind to either IL-20 or the IL-20 receptor, e.g., anti-IL-22RA antibodies. The antagonists will thus prevent activation of the IL-20 receptor. Moreover, because IL-20 and IL-22 share IL-22RA as a common receptor, antagonists such as soluble IL-22RA, or antibodies, single chain antibodies or fragments of antibodies that bind to IL-22RA receptor can be used to concurrently bind to, block, inhibit, reduce, antagonize or neutralize IL-22 or both IL-20 and IL-22 activity.

Psoriasis is one of the most common dermatologic diseases, affecting up to 1 to 2 percent of the world's population. It is a chronic inflammatory skin disorder characterized by erythematous, sharply demarcated papules and rounded plaques, covered by silvery micaceous scale. The skin lesions of psoriasis are variably pruritic. Traumatized areas often develop lesions of psoriasis. Additionally, other external factors may exacerbate psoriasis including infections, stress, and medications, e.g. lithium, beta blockers, and anti-malarials.

The most common variety of psoriasis is called plaque type. Patients with plaque-type psoriasis will have stable, slowly growing plaques, which remain basically unchanged for long periods of time. The most common areas for plaque psoriasis to occur are the elbows knees, gluteal cleft, and the scalp. Involvement tends to be symmetrical. Inverse psoriasis affects the intertriginous regions including the axilla, groin, submammary region, and navel, and it also tends to affect the scalp, palms, and soles. The individual lesions are sharply demarcated plaques but may be moist due to their location. Plaque-type psoriasis generally develops slowly and runs an indolent course. It rarely spontaneously remits.

Eruptive psoriasis (guttate psoriasis) is most common in children and young adults. It develops acutely in individuals without psoriasis or in those with chronic plaque psoriasis. Patients present with many small erythematous, scaling papules, frequently after upper respiratory tract infection with beta-hemolytic streptococci. Patients with psoriasis may also develop pustular lesions. These may be localized to the palms and soles or may be generalized and associated with fever, malaise, diarrhea, and arthralgias.

About half of all patients with psoriasis have fingernail involvement, appearing as punctate pitting, nail thickening or subungual hyperkeratosis. About 5 to 10 percent of patients with psoriasis have associated joint complaints, and these are most often found in patients with fingernail involvement. Although some have the coincident occurrence of classic Although some have the coincident occurrence of classic rheumatoid arthritis, many have joint disease that falls into one of five type associated with psoriasis: (1) disease limited to a single or a few small joints (70 percent of cases); (2) a seronegative rheumatoid arthritis-like disease; (3) involvement of the distal interphalangeal joints; (4) severe destructive arthritis with the development of "arthritis mutilans"; and (5) disease limited to the spine.

Psoriasis can be treated by administering agents that bind to, block, inhibit, reduce, antagonize or neutralize to IL-22, IL-20, or both IL-20 and IL-22. The preferred antagonists are either a soluble receptor to IL-20 and IL-22, such as IL-22RA (SEQ ID NO:3) or antibodies, antibody fragments or single chain antibodies that bind to the IL-22RA receptor, such as the neutralizing antibodies of the present invention. Such antagonists can be administered alone or in combination with other established therapies such as lubricants, keratolytics, topical corticosteroids, topical vitamin D derivatives, anthralin, systemic antimetabolites such as methotrexate, psoralen-ultraviolet-light therapy (PUVA), etretinate, isotretinoin, cyclosporine, and the topical vitamin D3 derivative calcipotriol. Moreover, such antagonists can be administered to individual subcutaneously, intravenously, or transdermally using a cream or transdermal patch that contains the antagonist. If administered subcutaneously, the antagonist can be injected into one or more psoriatic plaques. If administered transdermally, the antagonists can be administered directly on the plaques using a cream, ointment, salve, or solution containing the antagonist.

Antagonists to IL-20 or IL-22 can be administered to a person who has asthma, bronchitis or cystic fibrosis or other inflammatory lung disease to treat the disease. The antagonists can be administered by any suitable method including intravenous, subcutaneous, bronchial lavage, and the use of inhalant containing the antagonist.

Analysis of the tissue distribution of the MRNA corresponding IL-22RA cDNA showed that mRNA level was highest in placenta and spleen, and the ligand to which IL-22RA binds (IL-22) is implicated in inducing inflammatory response including induction of the acute-phase response (Dumoutier, L. et al., *Proc. Nat'l. Acad. Sci.* 97:10144-10149, 2000). Thus, particular embodiments of the present invention are directed toward use of soluble IL-22RA and anti-IL-22RA antibodies as antagonists in inflammatory and immune diseases or conditions such as psoriasis, psoriatic arthritis, atopic dermatitis, inflammatory skin conditions, rheumatoid arthritis, inflammatory bowel disease (IBD), Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, sugery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-22 or IL-20 cytokines is desired.

Moreover, antibodies or binding polypeptides that bind IL-22RA polypeptides described herein, and IL-22RA polypeptides themselves are useful to:

1) Block, inhibit, reduce, antagonize or neutralize signaling via IL-20 or IL-22 receptors in the treatment of acute inflammation, inflammation as a result of trauma, tissue injury, surgery, sepsis or infection, and chronic inflammatory diseases such as asthma, inflammatory bowel disease (IBD), chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response. 2) Block, inhibit, reduce, antagonize or neutralize signaling via IL-20 or IL-22 receptors in the treatment of autoimmune diseases such as IDDM, multiple sclerosis (MS), systemic Lupus erythematosus (SLE), myasthenia gravis, rheumatoid arthritis, and IBD to prevent or inhibit signaling in immune cells (e.g. lymphocytes, monocytes, leukocytes) via IL-22RA (Hughes C et al., *J. Immunol* 153: 3319-3325, 1994). Alternatively antibodies, such as monoclonal antibodies (MAb) to IL-22RA-comprising receptors, can also be used as an antagonist to deplete unwanted immune cells to treat autoimmune disease. Asthma, allergy and other atopic disease may be treated with an MAb against, for example, soluble IL-22RA soluble receptors to inhibit the immune response or to deplete offending cells. Blocking, inhibiting, reducing, or antagonizing signaling via IL-22RA, using the polypeptides and antibodies of the present invention, may also benefit diseases of the pancreas, kidney, pituitary and neuronal cells. IDDM, NIDDM, pancreatitis, and pancreatic carcinoma may benefit. IL-22RA may serve as a target for MAb therapy of cancer where an antagonizing MAb inhibits cancer growth and targets immune-mediated killing. (Holliger P, and Hoogenboom, H: *Nature Biotech.* 16: 1015-1016, 1998). Mabs to soluble IL-22RA may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases. 3) Agonize, enhance, increase or initiate signaling via IL-20 or IL-22 receptors in the treatment of autoimmune diseases such as EDDM, MS, SLE, myasthenia gravis, rheumatoid arthritis, and IBD. Anti-IL-22RA neutralizing and monoclonal antibodies may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998). Similarly, agonistic Anti-soluble IL-22RA, anti-solubleIL-22RA/CRF2-4 heterodimers and multimer monoclonal antibodies may be used to signal, deplete and deviate immune cells involved in asthma, allergy and atopoic disease. Signaling via IL-22RA may also benefit diseases of the pancreas, kidney, pituitary and neuronal cells. IDDM, NIDDM, pancreatitis, and pancreatic carcinoma may benefit. IL-22RA may serve as a target for MAb therapy of pancreatic cancer where a signaling MAb inhibits cancer growth and targets immune-mediated killing (Tutt, A L et al., *J Immunol.* 161: 3175-3185, 1998). Similarly renal cell carcinoma may be treated with monoclonal antibodies to IL-22RA-comprising soluble receptors of the present invention.

Soluble IL-22RA polypeptides described herein can be used to bind, block, inhibit, reduce, antagonize or neutralize IL-22 or IL-20 activity, either singly or together, in the treatment of autoimmune disease, atopic disease, NIDDM, pancreatitis and kidney dysfunction as described above. A soluble form of IL-22RA may be used to promote an antibody response mediated by Th cells and/or to promote the production of IL-4 or other cytokines by lymphocytes or other immune cells.

The soluble IL-22RA-comprising receptors of the present invention are useful as antagonists of IL-20 or IL-22 cytokine. Such antagonistic effects can be achieved by direct neutralization or binding of IL-20 or IL-22. In addition to antagonistic uses, the soluble receptors of the present invention can bind IL-22 and act as carrier proteins for IL-20 or IL-22 cytokine, in order to transport the Ligand to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-22. Thus, the soluble receptors of the present invention can be used to specifically direct the action of IL-20 or IL-22. See, Cosman, D. *Cytokine* 5: 95-106, 1993; and Fernandez-Botran, R. *Exp. Opin. Invest. Drugs* 9:497-513, 2000.

Moreover, the soluble receptors of the present invention can be used to stabilize the IL-22 or IL-20, to increase the bioavailability, therapeutic longevity, and/or efficacy of the Ligand by stabilizing the Ligand from degradation or clearance, or by targeting the ligand to a site of action within the body. For example the naturally occurring IL-6/soluble IL-6R complex stabilizes IL-6 and can signal through the gp130 receptor. See, Cosman, D. supra., and Femandez-Botran, R. supra. Moreover, IL-22RA may be combined with a cognate ligand such as IL-22 to comprise a ligand/soluble receptor complex. Such complexes may be used to stimulate responses from cells presenting a companion receptor subunit such as, for example, pDIRS1 (IL-20RB) or CRF2-4 (IL-10RB). The cell specificity of IL-22RA/ligand complexes may differ from that seen for the ligand administered alone. Furthermore the complexes may have distinct pharmacokinetic properties such as affecting half-life, dose/response and organ or tissue specificity. IL-22RA/IL-22 or IL-22RA/IL-20 complexes thus may have agonist activity to enhance an immune response or stimulate mesangial cells or to stimulate hepatic cells. Alternatively only tissues expressing a signaling sub-unit the heterodimerizes with the complex may be affected analogous to the response to IL6/IL6R complexes (Hirota H. et al., *Proc. Nat'l. Acad. Sci.* 92:4862-4866, 1995; Hirano, T. in Thomason, A. (Ed.) "The Cytokine Handbook", 3$^{rd}$ Ed., p. 208-209). Soluble receptor/cytokine complexes for IL12 and CNTF display similar activities.

Moreover Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory proteins, such as IL-22RA, and anti-IL-22RA antibodies, could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of anti-inflammatory proteins, such as IL-22RA polypeptides of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-20 or IL-22, and as such a molecule that binds or inhibits IL-22 or IL-20 activity, such as IL-22RA polypeptides, or anti IL-22RA antibodies or binding partners, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

The administration of soluble IL-22RA2 comprising polypeptides (zcytor16), such as zcytor16-Fc4 or other IL-22RA2 soluble and fusion proteins to these CIA model mice was used to evaluate the use of IL-22RA2 as an antagonist to IL-22 used to ameliorate symptoms and alter the course of disease. Moreover, the results showing inhibition of IL-22 by IL-22RA2 provide proof of concept that other IL-22 antagonists, such as IL-22RA or antibodies thereto, can also be used to ameliorate symptoms and alter the course of disease. Since the ligand of IL-22RA2, IL-22, induces production of SAA, which is implicated in the pathogenesis of rheumatoid arthritis, and IL-22RA2 was demonstrated to be able to inhibit IL-22 and SAA activity in vitro and in vivo, the systemic or local administration of IL-22RA2 comprising polypeptides, such as zcytor16-Fc4 or other IL-22 soluble receptors (e.g., IL-22RA; SEQ ID NO:3) and anti-IL-22RA antibodies, and fusion proteins can potentially suppress the inflammatory response in RA. The injection of 10 ug zcytor16-Fc (three times a week for 4 weeks) significantly reduced the disease score (paw score, incident of inflammation or disease). Other potential therapeutics include IL-22RA polypeptides, anti-IL-22RA antibodies, or anti IL-22 antibodies or binding partners, and the like.

One group has shown that an anti-mouse IL-22 antibody may reduce symptoms in a mouse CIA-model relative to control mice, thus showing conceptually that soluble IL-22RA polypeptides and neutralizing antibodies to IL-22RA may be beneficial in treating human disease. The administration of a single mouse-IL-22-specific rat monoclonal antibody (P3/1) reduced the symptoms of arthritis in the animals when introduced prophylactically or after CIA-induced arthritis was induced in the model (WIPO Publication 02/068476; published Sep. 9, 2002). Therefore, the soluble IL-22RA polypeptides and anti-IL-22RA antibodies of the present invention, including the neutralizing anti-human IL-22RA antibodies of the present invention, can be used to neutralize IL-22 and IL-20 in the treatment of specific human diseases such as psoriasis, psoriatic arthritis, arthritis, endotoxemia, inflammatory bowel disease (IBD), colitis, and other inflammatory conditions disclosed herein.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as IL-22RA polypeptides and antibodies of the present invention, could aid in preventing and treating endotoxemia in humans and animals. IL-22RA polypeptides, anti-IL22RA antibodies, or anti IL-22 antibodies or binding partners, could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that lug injection of *E. coli* LPS into a C57B/16 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF.

The administration of soluble IL-22RA2 comprising polypeptides, such as Zcytor16-Fc4 or other IL-22RA soluble and fusion proteins to these LPS-induced model was used to to evaluate the use of IL-22RA2 to ameliorate symptoms and alter the course of LPS-induced disease. Moreover, the results showing inhibition of IL-22 by IL-22RA2 provide proof of concept that other IL-22 antagonists, such as IL-22RA or antibodies thereto, can also be used to ameliorate symptoms in the LPS-induced model and alter the course of disease. The model showed induction of IL-22 by LPS injection and the potential treatment of disease by IL-22RA2 polypeptides. Since LPS induces the production of pro-inflammatory IL-22, SAA or other pro-inflammatory factors possibly contributing to the pathology of endotoxemia, the neutralization of IL-22 activity, SAA or other pro-inflammatory factors by an antagonist IL-22RA2 poloyepeptide can be used to reduce the symptoms of endotoxemia, such as seen in endotoxic shock. Other potential therapeutics include IL-22RA polypeptides, anti-IL-22RA antibodies, or anti IL-22 antibodies or binding partners, and the like.

3 Inflammatory Bowel Disease. IBD

In the United States approximately. 500,000 people suffer from Inflammatory Bowel Disease (IBD) which can affect either colon and rectum (Ulcerative colitis) or both, small and large intestine (Crohn's Disease). The pathogenes is of these diseases is unclear, but they involve chronic inflammation of the affected tissues. IL-22RA polypeptides, anti-IL-22RA antibodies, or anti IL-22 antibodies or binding partners, could serve as a valuable therapeutic to reduce inflammation and pathological effects in IBD and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (eg. azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of soluble IL-22RA2 comprising polypeptides, such as zcytor16-Fc4 or other IL-22RA soluble and fusion proteins to these TNBS or DSS models can be used to evaluate the use of IL-22RA to ameliorate symptoms and alter the course of gastrointestinal disease. Moreover, the results showing inhibition of IL-22 by IL-22RA2 provide proof of concept that other IL-22 antagonists, such as IL-22RA or antibodies thereto, can also be used to ameliorate symptoms in the colitis/IBD models and alter the course of disease. We observed the increased expression of IL-22 in colon tissues of DSS-mice by RT-PCR, and the synergistic activity of IL-22 with IL-1 beta on intestinal cell lines. It indicates IL-22 may play a role in the inflammatory response in colitis, and the neutralization of IL-22 activity by administrating IL-22RA2 polypeptides is a potential therapeutic approach for IBD. Other potential therapeutics include IL-22RA polypeptides, anti-IL-22RA antibodies, or anti IL-22 antibodies or binding partners, and the like.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. IL-22RA polypeptides, anti-IL-22RA antibodies, or anti IL-22 and anti IL-20 antibodies or binding partners, could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound;, shortly after stopping immunosuppressive therapy.

IL-20 is a novel IL-10 homologue that was shown to cause neonatal lethality with skin abnormalities including aberrant epidermal differentiation in IL-20 transgenic mice (Blumberg H et al., *Cell* 104:9-19, 2001) IL-20 receptorfis dramatically upregulated in psoriatic skin. Since IL-22 shares aPreceptor subunit (zcytor11) with IL-20 receptor, and IL-22 transgenic mice display a similar phenotype, it is possible that IL-22 is also involved in the inflammatory skin diseases such as psoriasis. The administration of IL-22RA polypeptide or an anti-IL-22RA antibody antagonist, either subcutaneous or topically, may potential reduce the inflammation and symptom. Other potential therapeutics include IL-22RA polypeptides, soluble zcytor11/CRF2-4 receptor polypeptides, or anti IL-22 antibodies or binding partners, and the like.

Moroever, over expression of IL-22 and IL-20 was shown in human psoriatic lesions, suggesting that IL-22, like IL-20 is also involved in human psoriasis. Moreover, as described herein, over expression of IL-20 or IL-22 in transgenic mice showed epidermal thickening and immune cell involvement indicative of a psoriatic phenotype; and in addition injection of IL-22 into normal mice showed epidermal thickening and immune cell involvement indicative of a psoriatic phenotype which was ablated by the soluble receptor antagonist IL-22RA2 (zcytor16; WIPO Publication No. WO 01/40467). Such in vivo data further suggests that the pro-inflammatory IL-22 is involved in psoriasis. As such, antagonists to IL-22 and IL-20 activity, such as IL-22RA soluble receptors and antibodies thereto including the anti-human-IL-22RA monoclonal and neutralizing antibodies of the present invention, are useful in therapeutic treatment of inflammatory diseases, particularly as antagonists to both IL-22 and IL-20 singly or together in the treatment of psoriasis. Moreover, antagonists to IL-22 activity, such as IL-22RA soluble receptors and antibodies thereto including the anti-human-IL-22RA monoclonal and neutralizing antibodies of the present invention, are useful in therapeutic treatment of other inflammatory diseases for example as agents that bind to, block, inhibit, reduce, antagonize or neutralize IL-22 and IL-20 in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

Moreover, anti-IL-22RA antibodies and IL-22RA soluble receptorsof the Represent invention can be used in the prevention and therapy against weight loss associated with a number of inflammatory diseases described herein, as well as for cancer (e.g., chemotherapy and cachexia), and infectious diseases. For example, severe weight loss is a key marker associated with models for septicemia, MS, RA, and tumor models. In addition, weight loss is a key parameter for many human diseases including cancer, infectious disease and inflammatory disease. Weight loss was shown in mice injected with IL-22Adenovirus described herein. Anti-IL-22 antibodies and IL-22 antagonists such as the soluble IL-22RA receptors and antibodies thereto of the present invention, as well as zcytor16 (IL-22RA2) receptors, can be tested for their ability to prevent and treat weight loss in mice injected with IL-22 adenovires described herein. Methods of determining a prophylactic or therapeutic regimen for such IL-22 antagonists is known in the art and can be determined using the methods described herein.

IL-22RA soluble receptor polypeptides and antibodies thereto may also be used within diagnostic systems for the detection of circulating levels of IL-22 or IL-20 ligand, and in the detection of IL-22 associated with acute phase inflammatory response. Within a related embodiment, antibodies or other agents that specifically bind to IL-22RA soluble receptors of the present invention can be used to detect circulating receptor polypeptides; conversely, IL-22RA soluble receptors themselves can be used to detect circulating or locally-acting IL-22 or IL-20 polypeptides. Elevated or depressed levels of ligand or receptor polypeptides may be indicative of pathological conditions, including inflammation or cancer. IL-22 is known to induce associated acute phase inflammatory response. Moreover, detection of acute phase proteins or molecules such as IL-20 or IL-22 can be indicative of a chronic inflammatory condition in certain disease states (e.g., psoriasis, rheumatoid arthritis, colitis, IBD). Detection of such conditions serves to aid in disease diagnosis as well as help a physician in choosing proper therapy.

In utero administration of neutralizing anti-IL-22 or IL-20 antibodies can be used to show efficacy in vivo in disease models by reducing or eliminating the skin phenotype found IL-22 transgenic pups which over express IL-22, or IL-20 transgenic pups which over express IL-20. There are precedents in the art for in utero treatment with neutralizing monoclonal antibodies (mAbs). In one case, the development of the B-1 subset of B cells was dramatically affected bytreating pregnant female mice with a mAb specific for the B cell-specific molecule, CD19 (e.g., Krop I. Et al., *Eur. J. Immunol.* 26(1):238-42, 1996). Krop et al. injected timed pregnant mice intraperitoneally with 500 ug of rat anti-mouse CD19 mAb (or a rat isotype-matched control Ab) in PBS beginning on day 9 of gestation, with subsequent injections every other day until birth. Pups were also injected once with 500 ug of these antibodies at 10 days of age. In another case, Tanaka et al., found that in utero treatment with monoclonal antibody to IL-2 receptor beta-chain completely abrogates development of Thy-1+ dendritic epidermal cells. The two distinct subunits of the IL-2 receptor, i.e. the alpha-chain (IL-2R alpha) and the beta-chain (IL-2R beta), are expressed in an almost mutually exclusive fashion throughout fetal thymus ontogeny. Blocking IL-2R beta, a signal transducing component of IL-2R, by administering a neutralizing mAb to IL-2R beta, resulted in the complete and selective disappearance of Thy-1+ skin dendritic epidermal cells. Development of any other T cell subsets was uncompromised. This indicated that IL-2 plays a crucial role in the development of fetal V gamma 5+ cells and their descendants (see, Tanaka, T. et al., *Int Immunol.* 4(4): 487-9, 1992). In addition, Schattemann G C et al., showed that PDGF-A is required for normal murine cardiovascular development using an in utero system. Several lines of evidence suggest that platelet-derived growth factor A chain (PDGF-A) is required for normal embryonic cardiovascular development. Introduction of anti-PDGF-A neutralizing antibodies into mouse deciduas in utero resulted in the selective disruption of PDGF-A ligand-receptor interactions in vivo for a period of 18-24 hr and allowed assessment of whether PDGF-A is required for cardiovascular development and when it is required (see, Schattemann GC et al., *Dev. Biol.* 176(1):133-42, 1996). These results, as well as others described in the art, provide evidence that neutralizing mAbs can elicit strong effects in utero. Similarly, data showing the efficacy of neutralizing IL-20 or IL-22 with monoclonal antibodies in vivo in disease models to reduce or eliminate the skin phenotype found in IL-20 and IL-22 transgenic pups which over express IL-20 and IL-22 respectively can be shown. These transgenic mice are born with a "shiny" skin appearance, due at least in part to a thickening of the epidermis as described herein. The IL-20 TG pups expressing fairly low levels of the transgenic cytokine can recover and do survive to breed, but the IL-22 TG mice die shortly after birth, generally before 5 days of age.

For example, neutralizing antibodies to IL-20 include antibodies, such as neutralizing monoclonal antibodies that can bind IL-20 antigenic epitopes and neutralize IL-20 activity. Accordingly, antigenic epitope-bearing peptides and polypeptides of IL-20 are useful to raise antibodies that bind with the IL-20 polypeptides described herein, as well as to identify and screen anti-IL-20 monoclonal antibodies that are neutralizing, and that may bind, block, inhibit, reduce, antagonize or neutralize the activity of IL-20. Such neutralizing monoclonal antibodies of the present invention can bind to an IL-20 antigenic epitope. Such epitopes within SEQ ID NO:8 as predicted by a Jameson-Wolf plot, e.g., using DNASTAR Protean program (DNASTAR, Inc., Madison, Wiss.) serve as preferred antigenic epitopes, and can be determined by one of skill in the art. Such antigenic epitopes include: amino acid residues 42 (Ile) to 102 (Asp) of SEQ ID NO:8; amino acid residues 42 (Ile) to 60 (Ile) of SEQ ID NO:8; amino acid residues 42 (Ile) to 69 (Glu) of SEQ ID NO:8; amino acid residues 42 (Ile) to 81 (Cys) of SEQ ID NO:8; amino acid residues 42 (Ile) to 96 (Lys) of SEQ ID NO:8; amino acid residues 42 (Ile) to 102 (Asp) of SEQ ID NO:8; amino acid residues 60 (Ile) to 69 (Glu) of SEQ ID NO:8; amino acid residues 60 (Ile) to 81 (Cys) of SEQ ID NO:8; amino acid residues 60 (Ile) to 96 (Lys) of SEQ ID NO:8; amino acid residues 60 (Ile) to 102 (Asp) of SEQ ID NO:8; amino acid residues 69 (Glu) to 81 (Cys) of SEQ ID NO:8; amino acid residues 69 (Glu) to 96 (Lys) of SEQ ID NO:8; amino acid residues 69 (Glu) to 102 (Asp) of SEQ ID NO:8; amino acid residues 81 (Cys) to 96 (Lys) of SEQ ID NO:8; amino acid residues 81 (Cys) to 102 (Asp) of SEQ ID NO:8; and amino acid residues 96 (Lys) to 102 (Asp) of SEQ ID NO:8.

In addition to other disease models described herein, the activity of anti-IL-22RA antibodies on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in ther art may be used to evaluate IL-20 and IL-22 antagonists, such as human psoriatic skin grafts implanted into AGR129 mouse model, and challenged with an appropriate antagonist (e.g., see, Boyman, O. et al., *J. Exp. Med.* Online publication #20031482, 2004, incorporated hereing by reference). Anti-IL-22RA antibodies that bind, block, inhibit, reduce, antagonize or neutralize the activity of IL-22 or both IL-20 and IL-22 are preferred antagonists, however, anti-IL-20 and anti-IL-22 antibodies (alone or in combination), soluble IL-22RA, as well as other IL-20 and IL-22 antagonists can be used in this model. Similarly, tissues or cells derived from human colitis, IBD, arthritis, or other inflammatory lestions can be used in the SCID model to assess the anti-inflammatory properties of the IL-20 and IL-22 antagonists described herein.

Therapies designed to abolish, retard, or reduce inflammation using anti-IL-22RA antibodies or its derivatives, agonists, conjugates or variants can be tested by administration of anti-IL-22RA antibodies or soluble IL-22RA compounds to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol. Immunol.* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored overtime using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model. For example, therapeutic strategies appropriate for testing in such a model include direct treatment using anti-IL-22RA antibodies, other IL-20 and IL-22 antagonists (singly or together), or related conjugates or antagonists based on the disrupting interaction of anti-IL-22RA antibodies with its ligands IL-20 and IL-22, or for cell-based therapies utilizing anti-IL-22RA antibodies or its derivatives, agonists, conjugates or variants.

Moreover, Psoriasis is a chronic inflammatory skin disease that is associated with hyperplastic epidermal keratinocytes and infiltrating mononuclear cells, including CD4+ memory T cells, neutrophils and macrophages (Christophers, *Int. Arch. Allergy Immunol.,* 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and CD4$^+$ T cells are thought to play an important role in antigen presentation and recognition that mediate the immune response leading to the pathology. We have recently developed a model of psoriasis based on the CD4+CD45RB transfer model (Davenport et al., *Internat. Immunopharmacol.,* 2:653-672). Anti-IL20, anti-IL22 or antibodies to IL20R and/or IL22R, such as anti-IL-22RA antibodies of the present invention, or soluble IL-22RA, are administered to the mice. Inhibition of disease scores (skin lesions, inflammatory cytokines) indicates the effectiveness of IL-20 and IL-22 antagonists in psoriasis, e.g., anti-IL-22RA antibodies or IL-22RA soluble receptors, or other antagonists such as antibodies against IL20 and/or IL-22 or their receptors.

Atopic Dermatitis.

Both IL-20 and IL-22 are upregulated in human atopic dermatitis (AD) patient samples. AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of thee skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The soluble IL-22RA polypeptides and anti-IL-22RA antibodies of the present invention, including the neutralizing anti-human IL-22RA antibodies of the present invention, can be used to neutralize IL-22 and IL-20 in the treatment of specific human diseases such as atoptic dermatitis, inflammatory skin conditions, and other inflammatory conditions disclosed herein.

For pharmaceutical use, the soluble IL-22RA or anti-IL-22RA antibodies of the present invention are formulated for parenteral, particularly intravenous or subcutaneous, delivery according to conventional methods. Intravenous administration will be by bolus injection, controlled release, e.g, using mini-pumps or other appropriate technology, or by infusion over a typical period of one to several hours. In general, pharmaceutical formulations will include a hematopoietic protein in combination with a pharmaceutically acceptable vehicle, such as saline, buffered saline, 5% dextrose in water or the like. Formulations may further include one or more excipients, preservatives, solubilizers, buffering agents, albumin to provent protein loss on vial surfaces, etc. When utilizing such a combination therapy, the cytokines may be combined in a single formulation or may be administered in separate formulations. Methods of formulation are well known in the art and are disclosed, for example, in *Remington's Pharmaceutical Sciences,* Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of soluble IL-22RA or anti-IL-22RA antibodies of the present invention is an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm³, preferably 50,000/mm³, is reached. The soluble IL-22RA or anti-IL-22RA antibodies of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered soluble IL-22RA (or IL-22RA analog or fusion protein) or anti-IL-22RA antibodies will vary depending upon such factors as the patient's age, weight, height, sex, general medical condition and previous medical history. Typically, it is desirable to provide the recipient with a dosage of soluble IL-22RA or anti-IL-22RA antibodies which is in the range of from about 1 pg/kg to 10 mg/kg (amount of agent/body weight of patient), although a lower or higher dosage also may be administered as circumstances dictate.

Administration of soluble IL-22RA or anti-IL-22RA antibodies to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Illum, *Adv. Drug Deliv. Rev.* 35:199 (1999)). Dry or liquid particles comprising IL-22RA can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of truscutaneous administration (Mitragotri et al., *Science* 269:850 (1995)). Transdermal delivery using electroporation provides another means to administer a molecule having IL-22RA binding activity (Potts et al., *Pharm. Biotechnol.* 10:213 (1997)).

A pharmaceutical composition comprising a soluble IL-22RA or anti-IL-22RA antibody can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, soluble IL-22RA or anti-IL-22RA antibody molecules and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising IL-22RA (or IL-22RA analog or fusion protein) or neutralizing anti-IL-22RA antibody can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 μm to greater than 10 μm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 μm) are typically taken up by cells of the reticuloendothelial system, located principally in the liver and spleen, whereas liposomes larger than 3.0 μm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having binding IL-22RA activity such as IL-22RA monomeric, homodimeric, heterodimeric or multimeric soluble receptors, and IL-22RA antagonists, for example anti-IL-22RA antibodies or binding polypeptides, or neutralizing anti-IL-22RA antibodies, which a polypeptide is linked with a polymer, as discussed above.

Other dosage forms can be devised by those skilled in the art, as shown, for example, by Ansel and Popovich, *Pharmaceutical Dosage Forms and Drug Delivery Systems*, $5^{th}$ Edition (Lea & Febiger 1990), Gennaro (ed.), *Remington's Pharmaceutical Sciences*, $19^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises a polypeptide with a IL-22RA extracellular domain, e.g., IL-22RA monomeric, homodimeric, heterodimeric or multimeric soluble receptors, or a IL-22RA antagonist (e.g., an antibody or antibody fragment that binds a IL-22RA polypeptide, or neutralizing anti-IL-22RA antibody). Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the IL-22RA composition is contraindicated in patients with known hypersensitivity to IL-22RA.

A pharmaceutical composition comprising Anti-IL-22RA antibodies or binding partners (or Anti-IL-22RA antibody fragments, antibody fusions, humanized antibodies and the like), or IL-22RA soluble receptor, can be furnished in liquid form, in an aerosol, or in solid form. Liquid forms, are illustrated by injectable solutions, aerosols, droplets, topological solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps,"

in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):S61 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a resultv; liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macroph ages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., Japanese Patent 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formnulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drup, Carrier Syst.* 14:287 (1997); Murahashi et al., *Biol. Pharm. Bull.* 20:259 (1997)). Similarly, Wu et al., *Hepatolopy* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Anti-IL-22RA neutralizing antibodies and binding partners with IL-22 OR IL-20 binding activity, or IL-22RA soluble receptor, can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome. Technology,* 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly (ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified Anti-IL-22RA antibody or binding partner, for example anti-Anti-IL-22RA antibodies or IL-22RA soluble receptor, linked with a polymer, as discussed above.

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

The present invention contemplates compositions of anti-IL-22 antibodies, and methods and therapeutic uses comprising an antibody, peptide or polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

11. Production of Transgenic Mice

Over expression of both IL-20 and IL-22 was shown in human psoriatic lesions, suggesting that both IL-20 and IL-22 are involved in human psoriasis. Moreover, as described herein, over expression of IL-20 and IL-22 in transgenic mice showed epidermal thickening and immune cell involvement indicative of a psoriatic phenotype; and in addition injection of IL-22 into normal mice showed epidermal thickening and immune cell involvement indicative of a psoriatic phenotype which was ablated by the soluble receptor antagonist zcytor16 (IL-22RA2). Such in vivo data further suggests that the pro-inflammatory IL-22 is involved in psoriasis. As such, antagonists to IL-22 activity, such as the anti-human-IL-22RA neutralizing and momoclonal antibodies of the present invention, as well as soluble IL-22RA receptors, are useful in therapeutic treatment of inflammatory diseases, particularly as antagonists to IL-22 and IL-20 in the treatment of psoriasis. Moreover, aagents that bind to, block, inhibit, reduce, antagonize or neutralize IL-22 or both IL-20 and IL-22 activity, such as the anti-human-IL-22RA neutralizing and monoclonal antibodies of the present invention, as well as soluble IL-22RA receptors, are useful in therapeutic treatment of other inflammatory diseases for example as antagonists to IL-22 or both IL-20 and IL-22 in the treatment of atopic dermatitis, IBD, colitis, Endotoxemia, arthritis, rheumatoid arthritis, and psoriatic arthritis adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease, and the like.

Within one aspect, the preseht invention provides a method of producing an antibody to a polypeptide comprising: inoculating an animal with a polypeptide selected from the group consisting of: (a) a polypeptide consisting of the amino acid sequence of SEQ ID NO:3 from amino acid number 1 (Pro), to amino acid number 6 (Asp); (b) a polypeptide consisting of the amino acid sequence of SEQ ID NO:3 from amino acid number 26 (Ser), to amino acid number 32 (Pro); (c) a polypeptide consisting of the amino acid sequence of SEQ ID NO:3 from amino acid number 41 (Lys), to amino acid number 47 (Asp); (d) a polypeptide consisting of the amino acid sequence of SEQ ID NO:2 from amino acid number 49 (Val), to amino acid number 62 (Cys); (e) a polypeptide consisting of the amino acid sequence of SEQ ID NO:3 from amino acid number 41 (Lys) to amino acid number 62 (Cys); (f) a polypeptide consisting of the amino acid sequence of SEQ ID NO:3 from amino acid number 84 (Ala) to amino acid number 97 (Ser); (g) a polypeptide consisting of the amino acid sequence of SEQ ID NO:3 from amino acid number 103 (Thr) to amino acid number 108 (Asp); (h) a polypeptide consisting of the amino acid sequence of SEQ ID NO:3 from amino acid number 130 (Arg) to amino acid number 135 (His); (i) a polypeptide consisting of the amino acid sequence of SEQ ID NO:3 from amino acid number 164 (Gly) to amino acid number 166 (Lys); (j) a polypeptide consisting of the amino acid sequence of SEQ ID NO:3 from amino acid number 175 (Tyr), to amino acid number 179 (Glu); (k) a polypeptide consisting of the amino acid sequence of SEQ ID NO:3 from amino acid number 193 (Lys) to amino acid number 196 (Ala); (l) a polypeptide consisting of the amino acid sequence of SEQ ID NO:3 from amino acid number 203 (Lys) to amino acid number 209 (Thr); and (m) a polypeptide consisting of the amino acid sequence of SEQ ID NO:3; and (n) a polypeptide consisting of the amino acid sequence of SEQ ID NO:4; and wherein the polypeptide elicits an immune response in the animal to produce the antibody; and isolating the antibody from the animal; and wherein the antibody specifically binds to an IL-22RA polypeptide (SEQ ID NO:2 or SEQ ID NO:3); and reduces the activity of either IL-20 (SEQ ID NO:8) or IL-22 (SEQ ID NO:6). In one embodiment the method is as described above, wherein the antibody produced by the method reduces the pro-inflammatory activity of either IL-20 (SEQ ID NO:8) or IL-22 (SEQ ID NO:6). In another embodiment the method is as described above, wherein the antibody produced by the method neutralizes the interaction of either IL-20 (SEQ ID NO:8) or IL-22 (SEQ ID NO:6) with IL-22RA (SEQ ID NO:2). In another embodiment the method is as described above, wherein the neutralization by the antibody is measured by showing neutralization of either IL-20 (SEQ ID NO:8) or IL-22 (SEQ ID NO:6) in an in vitro a cell-based neutralization assay. In another embodiment the method is as described. above, wherein the antibody produced by the method reduces the pro-inflammatory activity of both IL-20 (SEQ ID NO:8) and IL-22 (SEQ ID NO:6). In another embodiment the method is as described above, wherein the antibody produced by the method neutralizes the interaction of both IL-20 (SEQ ID NO:8) and IL-22 (SEQ ID NO:6) with IL-22RA (SEQ ID NO:2). In another embodiment the method is as described above, wherein the neutralization by the antibody is measured by showing neutralization of both IL-20 (SEQ ID NO:8) and IL-22 (SEQ ID NO:6) in an in vitro a cell-based neutralization assay.

Within another aspect, the present invention provides an antibody produced by the method as disclosed herein, which binds to a polypeptide of SEQ ID NO:2 or SEQ ID NO:3. In one embodiment the antibody is as described above, wherein the antibody is (a) a polyclonal antibody, (b) a murine monoclonal antibody, (c) a humanized antibody derived from (b), (d) an antibody fragment, or (e) a human monoclonal antibody. In another embodiment the antibody is as described above, wherein the antibody further comprises a radionuclide, enzyme, substrate, cofactor, fluorescent marker, chemiluminescent marker, peptide tag, magnetic particle, or toxin. In another embodiment the antibody is as described above, wherein the antibody further comprises PEGylation. In another embodiment the antibody is as described above, wherein the antibody is (a) a polyclonal antibody, (b) a murine monoclonal antibody, (c) a humanized antibody derived from (b), (d) an antibody fragment, or (e) a human monoclonal antibody. In another embodiment the antibody is as described above, wherein the antibody further comprises a radionuclide, enzyme, substrate, cofactor, fluorescent marker, chemiluminescent marker, peptide tag, magnetic particle, drug, or toxin. In another embodiment the antibody is as described above, wherein the antibody further comprises PEGylation.

Within another aspect, the present invention provides a antibody or antibody fragment that binds to a polypeptide comprising a sequence of amino acid residues as shown in SEQ ID NO:3; and reduces the pro-inflammatory activity of either IL-20 (SEQ ID NO:8) or IL-22 (SEQ ID NO:6). In one embodiment the antibody or antibody fragment is as described above, wherein the antibody or antibody fragment reduces the pro-inflammatory activity of both IL-20 (SEQ ID NO:8) and IL-22 (SEQ ID NO:6). In another embodiment the antibody or antibody fragment is as described above, wherein the or antibody fragment is.(a) a polyclonal antibody, (b) a murine monoclonal antibody, (c) a humanized antibody derived from (b), (d) an antibody fragment, or (e) a human monoclonal antibody. In another embodiment the antibody or antibody fragment is as described above, wherein the antibody further comprises a radionuclide, enzyme, substrate, cofactor, fluorescent marker, chemiluminescent marker, peptide tag, magnetic particle, drug, or toxin. In another embodiment the antibody or antibody fragment is as described above, wherein the antibody further comprises PEGylation. In another embodiment the antibody or antibody fragment is as described above, wherein the or antibody fragment is (a) a polyclonal antibody, (b) a murine monoclonal antibody, (c) a humanized antibody derived from (b), (d) an antibody fragment, or (e) a human monoclonal antibody. In another embodiment the antibody or antibody fragment is as described above, wherein the antibody further comprises a radionuclide, enzyme, substrate, cofactor, fluorescent marker, chemiluminescent marker, peptide tag, magnetic particle, drug, or toxin. In another embodiment the antibody or antibody fragment is as described above, wherein the antibody further comprises PEGylation.

Within another aspect, the present invention provides a method for reducing or inhibiting either IL-22-induced or IL-20-induced proliferation or differentiation of hematopoietic cells and hematopoietic cell progenitors comprising culturing bone marrow or peripheral blood cells with a composition comprising an amount of an antibody as disclosed herein sufficient to reduce proliferation or differentiation of the hematopoietic cells in the bone marrow or peripheral blood cells as compared to bone marrow or peripheral blood cells cultured in the absence of the antibody. In one embodiment the method is as described above, wherein the hematopoietic cells and hematopoietic progenitor cells are lymphoid cells. In another embodiment the method is as described above, wherein the lymphoid cells are macrophages or T cells.

Within another aspect, the present invention provides a method of reducing IL-22-induced or IL-20-induced inflammation comprising administering to a mammal with inflammation an amount of a composition of an antibody as disclosed herein sufficient to reduce inflammation.

Within another aspect, the present invention provides a method for reducing or inhibiting IL-22-induced and IL-20-induced proliferation or differentiation of hematopoietic cells and hematopoietic cell progenitors comprising culturing bone marrow or peripheral blood cells with a composition comprising an amount of an antibody as disclosed herein sufficient to reduce proliferation or differentiation of the hematopoietic cells in the bone marrow or peripheral blood cells as compared to bone marrow or peripheral blood cells cultured in the absence of the antibody. In one embodiment the method is as described above, wherein the hematopoietic cells and hematopoietic progenitor cells are lymphoid cells. In another embodiment the method is as described above, wherein the lymphoid cells are macrophages or T cells.

Within another aspect, the present invention provides a method of reducing IL-22-induced and IL-20-induced inflammation comprising administering to a mammal with inflammation an amount of a composition of an antibody as disclosed herein sufficient to reduce inflammation.

Within another aspect, the present invention provides a method for reducing or inhibiting IL-22-induced and IL-20-induced proliferation or differentiation of hematopoietic cells and hematopoietic cell progenitors comprising culturing bone marrow or peripheral blood cells with a composition comprising an amount of an antibody or antibody fragment as disclosed herein sufficient to reduce proliferation or differentiation of the hematopoietic cells in the bone marrow or peripheral blood cells as compared to bone marrow or peripheral blood cells cultured in the absence of the antibody or antibody fragment. In another embodiment the method is as described above, wherein the hematopoietic cells and hematopoietic progenitor cells are lymphoid cells. In another embodiment the method is as described above, wherein the lymphoid cells are macrophages or T cells.

Within another aspect, the present invention provides a method of reducing IL-22-induced and IL-20-induced inflammation comprising administering to a mammal with inflammation an amount of a composition of an antibody or antibody fragment as disclosed herein sufficient to reduce inflammation.

Within another aspect, the present invention provides a method for reducing or inhibiting IL-22-induced and IL-20-induced proliferation or differentiation of hematopoietic cells and hematopoietic cell progenitors comprising culturing bone marrow or peripheral blood cells with a composition comprising an amount of an antibody or antibody fragment as disclosed herein sufficient to reduce proliferation or differentiation of the hematopoietic cells in the bone marrow or peripheral blood cells as compared to bone marrow or peripheral blood cells cultured in the absence of the antibody. In another embodiment the method is as described above, wherein the hematopoietic cells and hematopoietic progenitor cells are lymphoid cells. In another embodiment the method is as described above, wherein the lymphoid cells are macrophages or T cells.

Within another aspect, the present invention provides a method of reducing IL-22-induced and IL-20-induced inflammation comprising administering to a mammal with inflammation an amount of a composition of an antibody or antibody fragment as disclosed herein sufficient to reduce inflammation.

Within another aspect, the present invention provides a method of suppressing an inflammatory response in a mammal with inflammation comprising: (1) determining a level of serum amyloid A protein; (2) administering a composition comprising an antibody according to an antibody or antibody fragment described herein in an acceptable pharmaceutical vehicle; (3) determining a post administration level of serum amyloid A protein; (4) comparing the level of serum amyloid A protein in step (1) to the level of serum amyloid A protein in step (3), wherein a lack of increase or a decrease in serum amyloid A protein level is indicative of suppressing an inflammatory response.

Within another aspect, the present invention provides a method of treating a mammal afflicted with an inflammatory disease in which IL-22 or IL-20 plays a role, comprising: administering an antagonist of IL-22 or IL-20 to the mammal such that the inflammation is reduced, wherein the antagonist comprises (i) an antibody, antibody fragment, or binding polypeptide that specifically binds a polypeptide or polypeptide fragment of IL-22RA (SEQ ID NO:3) or (ii) a polypeptide or polypeptide fragment of IL-22RA (SEQ ID NO:3); and wherein the inflammatory activity of either IL-22 (SEQ ID NO:6) or IL-20 (SEQ ID NO:8) is reduced. In one embodiment the method is as described above, wherein the disease is a chronic inflammatory disease. In another embodiment the method is as described above, wherein the disease is a chronic inflammatory disease comprising inflammatory bowel disease, ulcerative colitis, Crohn's disease, arthritis, atopic dermatitis, or psoriasis. In another embodiment the method is as described above, wherein the disease is an acute inflammatory disease. In another embodiment the method is as described above, wherein the disease is an acute inflammatory disease comprising endotoxemia, septicemia, toxic shock syndrome or infectious disease. In another embodiment the method is as described above, wherein the antibody, antibody fragment, or binding polypeptide further comprises a radionuclide, enzyme, substrate, cofactor, fluorescent marker, chemiluminescent marker, peptide tag, magnetic particle, drug, or toxin.

Within another aspect, the present invention provides a method of treating a mammal afflicted with an inflammatory disease in which IL-22 and IL-20 plays a role, comprising: administering an antagonist of both IL-22 and IL-20 to the mammal such that the inflammation is reduced, wherein the antagonist comprises (i) an antibody, antibody fragment, or binding polypeptide that specifically binds a polypeptide or polypeptide fragment of IL-22RA (SEQ ID NO:3) or (ii) a polypeptide or polypeptide fragment of IL-22RA (SEQ ID NO:3); and wherein the inflammatory activity of both IL-22 (SEQ ID NO:6) and L-20 (SEQ ID NO:8) is reduced. In one embodiment the method is as described above, wherein the disease is a chronic inflammatory disease. In another embodiment the method is as described above, wherein the disease is a chronic inflammatory disease comprising inflammatory bowel disease, ulcerative colitis, Crohn's disease, arthritis, atopic dermatitis, or psoriasis. In another embodiment the method is as described above, wherein the disease is an acute inflammatory disease. In another embodiment the method is as described above, wherein the disease is an acute inflammatory disease comprising endotoxemia, septicemia, toxic shock syndrome or infectious disease. In another embodiment the method is as described above, wherein the antibody, antibody fragment, or binding polypeptide further comprises a radionuclide, enzyme, substrate, cofactor, fluorescent marker, chemiluminescent marker, peptide tag, magnetic particle, drug, or toxin.

Within another aspect, the present invention provides an antibody comprising a monoclonal antibody that specifically binds to an antigenic epitope of human IL-22RA (SEQ ID NO:3) selected from the group consisting of: (a) an epitope consisting of the amino acid sequence of SEQ ID NO:3 from amino acid number 1 (Pro), to amino acid number 6 (Asp); (b) an epitope consisting of the amino acid sequence of SEQ ID NO:3 from amino acid number 26 (Ser), to amino acid number 32 (Pro); (c) an epitope consisting of the amino acid sequence of SEQ ID NO:3 from amino acid number 41 (Lys), to amino acid number 47 (Asp); (d) an epitope consisting of the amino acid sequence of SEQ ID NO:2 from amino acid number 49 (Val), to amino acid number 62 (Cys); (e) an epitope consisting of the amino acid sequence of SEQ ID NO:3 from amino acid number 41 (Lys) to amino acid number 62 (Cys); (f) an epitope consisting of the amino acid sequence of SEQ ID NO:3 from amino acid number 84 (Ala) to amino acid number 97 (Ser); (g) an epitope consisting of the amino acid sequence of SEQ ID NO:3 from amino acid number 103 (Thr) to amino acid number 108 (Asp); (h) an epitope consisting of the amino acid sequence of SEQ ID NO:3 from amino acid number 130 (Arg) to amino acid number 135 (His); (i) an epitope consisting of the amino acid sequence of SEQ ID NO:3 from amino acid number 164 (Gly) to amino acid number 166 (Lys); (j) an epitope consisting of the amino acid sequence of SEQ ID NO:3 from amino acid number 175 (Tyr), to amino acid number 179 (Glu); (k) an epitope consisting of the amino acid sequence of SEQ ID NO:3 from amino acid number 193 (Lys) to amino acid number 196 (Ala); (1) an epitope consisting of the amino acid sequence of SEQ ID NO:3 from amino acid number 203 (Lys) to amino acid number 209 (Thr); and (m) an epitope consisting of the amino acid sequence of SEQ ID NO:3; and (n) an epitope consisting of the amino acid sequence of SEQ ID NO:4; and wherein the antibody reduces or neutralizes the activity of either human IL-22 (SEQ ID NO:6) or IL-20 (SEQ ID NO:8). In one embodiment the antibody is as described above, wherein the antibody reduces or neutralizes the activity of both human IL-22 (SEQ ID NO:6) and IL-20 (SEQ ID NO:8). In another embodiment the antibody is as described above, wherein the antibody is selected from the group consisting of: (a) a murine monoclonal antibody, (b) a humanized antibody derived from (a), (c) an antibody fragment, and (d) a human monoclonal antibody. In another embodiment the antibody is as described above, wherein the antibody further comprises PEGylation. In another embodiment the antibody is as described above, wherein the antibody is selected from the group consisting of: (a) a murine monoclonal antibody, (b) a humanized antibody derived from (a), (c) an antibody fragment, and (d) a human monoclonal antibody. In another embodiment the antibody is as described above, wherein the antibody further comprises PEGylation.

Within another aspect, the present invention provides a method of treating a pathological condition in a subject associated with IL-22RA activity comprising administering an effective amount of the antibody as disclosed herein, thereby treating said pathological condition. In one embodiment the method is as described above, wherein said pathological condition is a chronic inflammatory condition. In another embodiment the method is as described above, wherein said chronic inflammatory condition comprising inflammatory bowel disease, ulcerative colitis, Crohn's disease, arthritis, atopic dermatitis, or psoriasis. In another embodiment the method is as described above, wherein said pathological condition is an acute inflammatory condition. In another embodiment the method is as described above, wherein said acute inflammatory condition comprises endotoxemia, septicemia, toxic shock syndrome, or infectious disease.

Within another aspect, the present invention provides a method of treating a mammal afflicted with an inflammatory disease in which IL-22RA plays a role, comprising: administering an antagonist of IL-22RA to the mammal such that the inflammation is reduced, wherein the antagonist comprises an antibody, antibody fragment, or binding polypeptide that specifically binds a polypeptide or polypeptide fragment of IL-22RA (SEQ ID NO:3); and wherein the inflammatory activity is reduced. In one embodiment the method is as described above, wherein the disease is a chronic inflammatory disease. In another embodiment the method is as described above, wherein the disease is a chronic inflammatory disease comprising inflammatory bowel disease, ulcerative colitis, Crohn's disease, arthritis, atopic dermatitis, or psoriasis. In another embodiment the method is as described above, wherein the disease is an acute inflammatory disease. In another embodiment the method is as described above, wherein the disease is an acute inflammatory disease comprising endotoxemia, septicemia, toxic shock syndrome or infectious disease. In another embodiment the method is as described above, wherein the antibody, antibody fragment, or binding polypeptide further comprises a radionuclide, enzyme, substrate, cofactor, fluorescent marker, chemiluminescent marker, peptide tag, magnetic particle, drug, or toxin. In another embodiment the method is as described above, wherein the antibody, antibody fragment, or binding polypeptide further comprises, wherein the antibody further comprises PEGylation.

Within another aspect, the present invention provides a method of reducing inflammation comprising administering to a mammal with inflammation an amount of a composition of an antibody as disclosed herein sufficient to reduce inflammation.

The invention is further illustrated by the following non-limiting examples.

EXAMPLE 1

Purification of IL-22RA2-Fc4 Polypeptide from Transfected BHK 570 Cells

Unless otherwise noted, all operations were carried out at 4° C. The following procedure was used for purifying IL-22RA2 polypeptide (mature soluble receptor polyeptpide from residues 23 to 231 of SEQ ID NO:13; polynucleotides as shown in SEQ ID NO:12) containing C-terminal fusion to human Fc4 (SEQ ID NO: 14), designated IL-22RA2-Fc4. About 16,500 ml of conditioned media from BHK 570 cells transfected with IL-22RA2-Fc4 was filtered through a 0.2 um sterilizing filter and then supplemented with a solution of protease inhibitors, to final concentrations of, 0.001 mM leupeptin (Boerhinger-Mannheim, Indianapolis, Ind.), 0.001 mM pepstatin (Boerhinger-Mannheim) and 0.4 mM Pefabloc (Boerhinger-Mannheim). A Poros protein A50 column (20 ml bed volume, Applied Biosystems) was packed and washed with 400 ml PBS (Gibco/BRL) The supplemented conditioned media was passed over the column with a flow rate of 15 ml/minute, followed by washing with 800 ml PBS (BRUGibco). IL-22RA2-Fc4 was eluted from the column with 0.1 M Glycine pH 3.0 and 5 ml fractions were collected directly into 0.5 ml 2M Tris pH 7.8, to adjust the final pH to 7.4 in the fractions.

Column performance was characterized through western blotting of reducing SDS-PAGE gels of the starting media and column pass through. Western blotting used anti-human IgG HRP (Amersham) antibody, which showed an immunoreactive protein at 60,000 Da in the starting media, with nothing in the pass through, suggesting complete capture. The protein A50 eluted fractions were characterized by reducing SDS PAGE gel. This gel showed an intensely Coomassie stained band at 60,000 Da in fractions 3 to 11. Fractions 3 to 11 were pooled.

Protein A 50 elution pool was concentrated from 44 ml to 4 ml using a 30,000 Da Ultrafree Biomax centrifugal concentrator (15 ml volume, Millipore). A Sephacryl S-300 gel filtration column (175 ml bed volume; Pharmacia) was washed with 350 ml PBS (BRL/Gibco). The concentrated pool was injected over the column with a flow rate of 1.5 ml/min, followed by washing with 225 ml PBS (BRL/Gibco). Eluted peaks were collected into 2 ml fractions.

Eluted fractions were characterized by reducing and non-reducing silver stained (Geno Technology) SDS PAGE gels. Reducing silver stained SDS PAGE gels showed an intensely stained band at 60,000 Da in fractions 14-31, while non-reducing silver stained SDS PAGE gels showed an intensely stained band at 160,000 Da in fractions 14-31. Fractions 1-13 showed many bands of various sizes. Fractions 14-31 were pooled, concentrated to 22 ml using 30,000 Da Ultrafree Biomax centrifugal concentrator (15 ml volume, Milipore). This concentrate was filtered through a 0.2 µm Acrodisc sterilizing filter (Pall Corporation).

The protein concentration of the concentrated pooled fractions was performed by BCA analysis (Pierce, Rockford, Ill.) and the material was aliquoted, and stored at −80° C. according to our standard procedures. The concentration of the pooled fractions was 1.50 mg/ml.

EXAMPLE 2

Construction of BaF3 Cells Expressing the CRF2-4 Receptor (BaF3/CRF2-4 Cells) and BaF3 Cells Expressing the CRF2-4 Receptor with the IL-22RA Receptor (BaF3/CRF2-4/IL-22RA Cells)

BaF3 cells expressing the full-length CRF2-4 receptor were constructed, using 30 µg of a CFR2-4 expression vector, described below. The BaF3 cells expressing the CFR2-4 expression vector, described below. The BaF3 cells expressing the CFR2-4 receptor were designated as BaF3/CFR2-4. These cells were used as a control, and were further transfected with full-length IL-22RA receptor (U.S. Pat. No. 5,965,704) and used to construct a screen for IL-22 activity as described below.

A. Construction of BaF3 Cells Expressing the CRF2-4 Receptor

The full-length cDNA sequence of CRF2-4 (Genbank Accession No. Z17227) was isolated from a Daudi cell line cDNA library, and then cloned into an expression vector pZP7P.

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, CRF2-4/pZP7P was prepared and purified using a Qiagen Maxi Prep kit (Qiagen) as per manufacturer's instructions. For electroporation, BaF3 cells were washed once in serum-free RPMI media and then resuspended in serum-free RPMI media at a cell density of $10^7$ cells/ml. One ml of resuspended BaF3 cells was mixed with 30 µg of the CRF2-4/pZP7P plasmid DNA and transferred to separate disposable electroporation chambers (GIBCO BRL). Following a 15-minute incubation at room temperature the cells were given two serial shocks (800 1Fad/300 V.; 1180 1Fad/300 V.) delivered by an electroporation apparatus (CELL-PORATOR™; GIBCO BRL). After a 5-minute recovery time, the electroporated cells were transferred to 50 ml of complete media and placed in an incubator for 15-24 hours (37° C., 5% $CO_2$). The cells were then spun down and resuspended in 50 ml of complete media containing 2 µg/ml puromycin in a T-162 flask to isolate the puromycin-resistant pool. Pools of the transfected BaF3 cells, hereinafter called BaF3/CRF2-4 cells, were assayed for signaling capability as described below. Moreover these cells were further transfected with IL-22RA receptor as described below.

B. Construction of BaF3 Cells Expressing CRF2-4 and IL-22RA Receptors

BaF3/CRF2-4 cells expressing the full-length IL-22RA receptor were constructed as per above, using 30 µg of a IL-22RA expression vector. Following recovery, transfectants were selected using 200 µg/ml zeocin and 2 µg/ml puromycin. The BaF3/CRF2-4 cells expressing the IL-22RA receptor were designated as BaF3/CRF2-4/IL-22RA cells. These cells were used to screen for IL-22 activity as well as IL-22RA2 antagonist activity described herein.

EXAMPLE 3

Screening for IL-22 Antagonist Activity Using BaF3/CRF2-4/IL-22RA Cells Using an Alamar Blue Proliferation Assay A. Screening for IL-22 Activity Using BaF3/CRF2-4/IL-22RA Cells Using an Alamar Blue Proliferation Assay Purified IL-22-CEE (Example 4) was used to test for the presence of proliferation activity as described below. Purified IL-22RA2-Fc4 (Example 1) was used to antagonize the proliferative response of the IL-22 in this assay as described below.

BaF3/CRF2-4/IL-22RA cells were spun down and washed in the complete media, (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)), but without mIL-3 (hereinafter referred to as "mIL-3 free media"). The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/CRF2-4/IL-22RA cells was assessed using IL-22-CEE protein diluted with mIL-3 free media to 50, 10, 2, 1, 0.5, 0.25, 0.13, 0.06 ng/ml concentrations. 100 µl of the diluted protein was added to the BaF3/CRF2-4/IL-22RA cells. The total assay volume is 200 µl. The assay plates were incubated at 37° C., 5% $CO_2$ for 3 days at which time Alamar Blue (Accumed, Chicago, Ill.) was added at 20 µl/well. Plates were again incubated at 37° C., 5% $CO_2$ for 24 hours. Alamar Blue gives a fluourometric readout based on number of live cells, and is thus a direct measurement of cell proliferation in comparison to a negative control. Plates were again incubated at 37° C., 5% $CO_2$ for 24 hours. Plates were read on the Fmax™ plate reader (Molecular Devices Sunnyvale, Calif.) using the SoftMax™ Pro program, at wavelengths 544 (Excitation) and 590 (Emmission). Results confirmed the dose-dependent proliferative response of the BaF3/CRF2-4/IL-22RA cells to IL-22-CEE. The response, as measured, was approximately 15-fold over background at the high end of 50 ng/ml down to a 2-fold induction at the low end of 0.06 ng/ml. The BaF3 wild type cells, and BaF3/CRF2-4 cells did not proliferate in response to IL-22-CEE, showing that IL-22 is specific for the CRF2-4/IL-22RA heterodimeric receptor. In order to determine if IL-22RA2 is capable of antagonizing IL-22 activity, the assay described above was repeated using purified soluble IL-22RA2/Fc4. When IL-22 was combined with IL-22RA2 at 10µg/ml, the response to IL-22 at all concentrations was brought down to background. That the presence of soluble IL-22RA2 ablated the proliferative effects of IL-22 demonstrates that it is a potent antagonist of the IL-22 ligand. This assay can be used to test other antagonists of IL-22 activity described herein, such as anti-IL-22RA antibodies.

EXAMPLE 4

Purification of IL-22-CEE from BHK 570 Cells

Unless otherwise noted, all operations were carried out at 4° C. The following procedure was used for purifying IL-22 polypeptide containing C-terminal GluGlu (EE) tag (SEQ ID NO:15; or SEQ ID NO:16). Conditioned media from BHK cells expressing IL-22-CEE was concentrated with an Amicon S10Y3 spiral cartridge on a ProFlux A30. A Protease inhibitor solution was added to the concentrated conditioned media to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated conditioned media were determined via SDS-PAGE and Western blot analysis with the anti-EE HRP conjugated antibody.

About 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated conditioned media was thawed, 0.2 micron sterile filtered, pH adjusted to 7.4, then loaded on the column overnight with about 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml/minute. The EE peptide used has the sequence EYMPME (SEQ ID NO:15). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate IL-22-CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris (Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate IL-22-CEE polypeptide from free EE peptide and any contaminating co-purifying proteins, the pooled concentrated fractions were subjected to size exclusion chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified IL-22-CEE polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the IL-22-CEE polypeptide was one major band. The protein concentration of the purified material was performed by BCA analysis (Pierce, Rockford, Ill.) and the protein was aliquoted, and stored at −80° C. according to standard procedures.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

EXAMPLE 5

In vivo Affects of IL-22 Polypeptide

Mice (female, C57BL/6N, 8 weeks old; Charles River Labs, Kingston, N.Y.) were divided into three groups. An adenovirus expressing an IL-22 polypeptide (SEQ ID NO:6) was previously made using standard methods. On day 0, parental or IL-22 adenovirus was administered to the first (n=8) and second (n=8) groups, respectively, via the tail vein, with each mouse receiving a dose of ~1×10$^{11}$ particles in ~0.1 ml volume. The third group (n=8) received no treatment. On days 12, mice were weighed and blood was drawn from the mice. Samples were analyzed for complete blood count (CBC) and serum chemistry. Statistically significant elevations in neutrophil and platelet counts were detected in the blood samples from the IL-22 adenovirus administered group relative to the parental adenovirus treated group. Also, lymphocyte and red blood cell counts were significantly reduced from the IL-22 adenovirus administered group relative to the parental adenovirus treated group. In addition, the IL-22 adenovirus treated mice decreased in body weight, while parental adenovirus treated mice gained weight. Also the serum IL-22 level was increased and the glucose level decreased at day 3. In summary, IL-22 adeno-mice displayed acute phase resonse that can also be initiated by other pro-inflammatory cytokines such as TNF-alpha, IL-1beta, and gp130 cytokines. The acute phase response is the set of immediate inflammatory responses initiated by pattern recognition molecules. The acute phase proteins provide enhanced protection against microorganisms and modify inflammatory responses by effects on cell trafficking and mediator release. For example, SAA has potent leukocyte activating fuction including induction of chemotaxis, enhancemnent of leukocyte adhesion to endothelial cells, and increased phagocytosis. Understanding the factors that initiate and alter the magnitude and duration of the acute phase response respresents an important step in the development of new therapies for infectious and inflammatory diseases.

The results suggested that IL-22 affects hematopoiesis, i.e., blood cell formation in vivo. As such, IL-22 could have biological activities effecting different blood stem cells, thus resulting increase or decrease of certain differentiated blood cells in a specific lineage. For instance, IL-22 appears to reduce lymphocytes, which is likely due to inhibition of the committed progenitor cells that give rise to lymphoid cells. IL-22 also decreases red blood cells, supporting the notion that IL-22 could play a role in anemia, infection, inflammation, and/or immune diseases by influencing blood cells involved in these process. Antagnists against IL-22, such as antibodies or its soluble receptor IL-22RA2, could be used as therapeutic reagents in these diseases.

Moreover, these experiments using IL-22 adenovirus in mice suggest that IL-22 over-expression increases the level of neutrophils and platelets in vivo. It is conceivable that there are other factors (such as cytokines and modifier genes) involved in the responses to IL-22 in the whole animal system. Nevertheless, these data strongly support the involvement of IL-22 in hematopoiesis. Thus, IL-22 and its receptors are suitable reagents/targets for the diagnosis and treatment in variety of disorders, such as inflammation, immune disorders, infection, anemia, hematopoietic and other cancers, and the like.

EXAMPLE 6

IL-22-Expressing Transgenic Mice

A. Generation of Transgenic Mice Expressing Mouse IL-22

DNA fragments from a transgenic vector containing 5' and 3' flanking sequences of the lymphoid specific EμLCK promoter, mouse IL-22 (SEQ ID NO:10; polypeptide shown in SEQ ID NO:11), the rat insulin II intron, IL-22 cDNA and the human growth hormone poly A sequence were prepared using standard methods, and used for microinjection into fertilized B6C3f1 (Taconic, Germantown, N.Y.) murine oocytes, using a standard microinjection protocol. See, Hogan, B. et al., *Manipulating the Mouse Embryo. A Laboratory Manual*, Cold Spring Harbor Laboratory Press, 1994.

Twenty-five mice transgenic for mouse IL-22 with the lymphoid-specific EμLCK promoter were identified among 154 pups. Eleven of the transgenic pups died within hours of birth, 9 transgenic pups with a shiny appearance were necropsied the day of birth, and 2 grew to adulthood. Expression levels were low in one adult animal. Tissues from the necropsied pups were prepared and histologically examined as described below.

The shiny appearance of the neonate pups appeared to be associated with a stiffening of the skin, as if they were drying out, resulting in a reduction of proper nursing. Their movements became stiffened in general.

B. Genotypic and Expression Analysis from Transgenic Mice

From the mouse IL-22 transgenic line driven by the EµLck promoter, described above, newborn pups were observed for abnormalities on day one (day of birth) and sacrificed for tissue collection. All pups were given a unique ear tag number, and those designated as having a shiny skin phenotype at the time of sacrifice were noted. Of the twelve pups, six were observed to have the shiny skin phenotype, with two designated as "severe" phenotypes. Severe phenotypes were defined as small pups with little mobility whose skin was especially shiny and very dry. Skin was collected from the left lateral side of each pup, and frozen in Tissue-Tek embedding medium.

Genotyping confirmed that shiny skin was a good indicator of transgenic status, although no expression data was collected. Frozen skin blocks were sectioned to 7 microns on a cryostat and stained to look for the presence of CD3, CD4, CD8, mouse macrophages, B-cells, CD80, and MHC class II. The staining protocol involved binding of commercially available antibodies to the tissue, detection with a peroxidase labeled secondary antibody, and DAB chromogen reaction to visualize staining.

Transgenic animals were found to be higher in MHC class II and CD80, which stain for antigen-presenting cells and dendritic cells respectively. The macrophage marker also detected more cells in the severe and non-severe transgenics than in the wild type animals, although the distribution of these cells was very localized in the high dermis. Animals classified as severe phenotypes had the most robust staining with all three of these markers, showing a dramatic increase in cell intensity and number when compared to the wild type. This variability may be due to a difference in expression level of IL-22 in these transgenic founder pups. The MHC class II positive cells were located in the lower dermis arranged in loose open clusters, while the CD80 positive cells were predominantly below the dermis either in or just above the muscle/fat layer. These two cell populations do not appear to overlap. All other markers were of equivalent staining in all animals. Toluidine blue staining for mast cells revealed slight to no difference between wild type and transgenic animals.

C. Microscopic Evaluation of Tissues from Transgenic Mice: IL-22 TG with EuLck Promoter has a Neonatal Lethal-histology On the day of birth, pups from litters containing IL-22 transgenics were humanely euthanized and the whole body immersion fixed in 10% buffered formalin. Six transgenic and two non-transgenic pups were submitted for further workup. Four of the six transgenics were noted to have shiny skin at the time of euthanasia. The fixed tissues were trimmed into 5 sections (longitudinal section of the head and cross sections of the upper and lower thorax and upper and lower abdomen). The tissues were embedded in paraffin, routinely processed, sectioned at 5 um (Jung 2065 Supercut microtome, Leica Microsystems, Wetzlar, Germany) and stained with H&E. The stained tissues were evaluated under a light microscope (Nikon Eclipse E600, Nikon Inc., Melville, N.Y.) by a board (ACVP) certified veterinary pathologist.

On microscopic examination, the epidermis of two of the transgenic pups was observed to be thicker than the epidermis of the other six mice including the controls. No other abnormalities were noted in the skin and other tissues of any of the mice. Representative areas of skin from corresponding regions of the thorax and abdomen were imaged with the 40× objective lens and with a CoolSnap digital camera (Roper Scientific, Inc., San Diego, Calif.) that was attached to the microscope. The thickness of the epidermis was then determined using histomorphometry software (Scion Image for Windows (NIH Image), Scion Corp., Frederick, Md., v. B4.0.2). The results shown in Table 5 were as follows:

TABLE 5

| Genotype/phenotype | Average thoracic skin thickness (µm) | Average abdominal skin thickness (µm) |
|---|---|---|
| Non-transgenic/normal | 5.2 | 5.4 |
| Transgenic/non-shiny | 5.0 | 6.7 |
| Transgenic/shiny | 8.2 | 7.4 |
| Transgenic/all | 7.1 | 7.1 |

There were insufficient numbers of mice to determine statistical significance; however, the transgenics, especially those with shiny skin, tended to have a thicker epidermis than the non-shiny transgenics and non-transgenic controls. The shiny transgenics may have a higher expression level of IL-22 than the non-shiny transgenics.; however, expression levels were not determined for these mice. These suggested a role for IL-22 in psoriasis, psoriatic arthritis, or other inflammatory skin conditions or other inflammatory diseases.

EXAMPLE 7

In vivo Affects of IL-22 Polypeptide

A. Mice Infected with IL-22 Adenovirus Show Induction of SAA

Mice (female, C57BL/6N, 8 weeks old; Charles River Labs, Kingston, N.Y.) were divided into three groups. An adenovirus expressing an IL-22 polypeptide (SEQ ID NO:6) was previously made using standard methods. On day 0, parental or IL-22 adenovirus was administered to the first (n=8) and second (n=8) groups, respectively, via the tail vein, with each mouse receiving a dose of ~1×10$^{11}$ particles in ~0.1 ml volume. The third group (n=8) received no treatment. On day 12, mice were weighed and blood was drawn from the mice. On day 20 of the study, mice were sacrificed, body weight was recorded, and blood and tissues were collected for analysis.

All blood samples were analyzed for complete blood count (CBC) and serum chemistry. At both day 12 and 20, statistically significant elevations in neutrophil and platelet counts were detected in the blood samples from the IL-22 adenovirus administered group relative to the parental adenovirus treated group. Also, lymphocyte counts were significantly reduced from the IL-22 adenovirus administered group relative to the parental adenovirus treated group at day 12, but at day 20 the opposite effect was observed. In addition, the IL-22 adenovirus treated mice decreased in body weight, while parental adenovirus treated mice gained weight. Glucose was significantly reduced at both time points in the serum samples from the IL-22 adenovirus administered group relative to the parental adenovirus treated group. Serum albumin was also significantly reduced at both time points. Blood urea nitrogen levels were significantly reduced at day 20. Serum globulin levels were significantly increased the IL-22 adenovirus administered group relative to the parental adenovirus treated group at both time points. Microscopically, one observed histomorphological change attributed to IL-22 was tubular regeneration in the kidney. While not uncommon in mice, there was an increased incidence and severity in this group of animals. Nephropathy is characterized as multifocal areas of basophilia of cortical tubular epithelial cells.

An additional experiment, identical in design to the one described above, was carried out in order to verify results and collect additional samples. In this study, body weight was recorded every three days, blood was collected from the mice 3 days following adenovirus injection, and mice were sacrificed for blood and tissue collection on day 10 (n=4 per group) and day 20 (n=4 per group). Elevated neutrophil and platelet counts were again detected in blood samples from the IL-22 adenovirus administered group relative to the parental adenovirus treated group. This effect was evident for neutrophils by day 3, but platelet count was not significantly different until day 10. Also, lymphocyte counts were significantly reduced from the IL-22 adenovirus administered group relative to the parental adenovirus treated group at 3 and 10, but they were not elevated on day 20 as in the previous study. Again, mice given IL-22 adenovirus lost weight over the course of the study, while control virus treated and untreated mice gained weight. Serum chemistry parameters were consistent with the previous study. Histological findings of tubular regeneration in the kidney associated with IL-22 adenovirus treatment were also confirmed in this study. This was consistent with the additional finding of moderate proteinurea in mice given IL-22 adenovirus (day 20).

The results suggested that IL-22 affects hematopoiesis, i.e., blood cell formation in vivo. As such, IL-22 could have biological activities effecting different blood stem cells, thus resulting in an increase or decrease of certain differentiated blood cells in a specific lineage. For instance, IL-22 appears to reduce lymphocytes, which is likely due to inhibition of the committed progenitor cells that give rise to lymphoid cells, supporting the notion that IL-22 could play a role in anemia, infection, inflammation, and/or immune diseases by influencing blood cells involved in these processes. Antagonists against IL-22, such as antibodies or its soluble receptor IL-22RA2, could be used as therapeutic reagents in these diseases.

Moreover, these experiments using IL-22 adenovirus in mice suggest that IL-22 over-expression increases the level of neutrophils and platelets in vivo. It is. conceivable that there are other factors (such as cytokines and modifier genes) involved in the responses to IL-22 in the whole animal system. Nevertheless, these data strongly support the involvement of IL-22 in hematopoiesis. Thus, IL-22, anti-IL-22 antibodies, IL-22RA soluble receptors (e.g., SEQ ID NO:3), and anti-IL-22RA antibodies are suitable reagents/targets for the diagnosis and treatment in variety of disorders, such as inflammation, immune disorders, infection, anemia, hematopoietic and other cancers, and the like.

Association of IL-22 expression with weight loss, appearance of acute phase protein SAA, and metabolic perturbations evidenced by decreased serum glucose, albumin and urea nitrogen suggest that IL-22 is a cytokine which acts early in certain inflammatory responses. Mice given IL-22 adenovirus may represent a state of chronic inflammation, such as that observed in IBD, ulcerative colitis, arthritis, psoriasis, psoriatic arthritis, asthma, and the like. Certain detrimental inflammatory processes might be inhibited by use of an antagonist to IL-22, such as anti-IL-22 antibodies, and its receptors, such as IL-22RA soluble receptors (e.g., SEQ ID NO:3), and anti-IL-22RA antibodies and the like.

B. IL-22 is a Pro-inflammatory Cytokine: Serum Level of SAA in Adeno-IL-22 Mice:

An ELISA was performed to determine the level of SAA in IL-22-Adeno mice, using a Mouse SAA Immunoassay Kit and protocol (Biosource International, California, USA). Diluted standards and unknowns were plated along with HRP-anti-mouse SAA into assay plates pre-coated with anti-mouse SAA antibody. Plates were incubated for one hour at 37 degrees C. and then washed according to kit instructions. Plates were developed for 15 minutes at room temperature using TMB and stopped with 2M $H_2SO_4$, The absorbance at 450 nm was read using a Spectromax 190 (Molecular Devices, California, USA). The resulting data was analyzed using Softmax Pro (Molecular Devices, California, USA) and Excel (Microsoft Corp., Washington, USA).

Mice infected with IL-22-Adenovirus had highly elevated levels of mSAA, over 10-fold, relative to the Parental-Adenovirus control.

C. Flow Cytometry Analysis of IL-22-adenovirus Infected Mice

To analyze the effects of IL-22 expression in vivo by adenovirus, we isolated peripheral blood, spleen, and, bone marrow from IL-22-adenovirus infected C57BL/6N mice, at day 10 and day 20 after infection. Approximately 100 µl of blood was collected in heparinized tubes, then depleted of red blood cells by hypotonic lysis (cells were lysed in 4.5 ml $dH_2O$ for ~5 seconds before adding 1.5 ml 3.6% NaCl). Spleens were crushed between two frosted glass slides, and the cells released were passed over a Nytex membrane (cell strainer) and pelleted. Bone marrow was obtained by crushing one femur in a mortar and pestle and passing the cells over a cell strainer (Falcon). Cells were resuspended in FACS wash buffer (WB=HBSS/1% BSA/10 mM hepes), counted in trypan blue, and $1\times10^6$ viable cells of each type were aliquoted into 5 ml polystyrene tubes. Cells were washed and pelleted, then incubated for 20 min on ice with cocktails of fluorescently-labeled (FITC, PE, and CyChrome) monoclonal antibodies (PharMingen, San Diego, Calif.) recognizing various cell surface markers used to identify particular immune cell subsets. These markers include the following (listed in the groups of 3 we tested). For blood staining: CD3, Gr1, and B220; for spleen staining: CD62L, CD44, and CD3; CD21, CD23, and B220; IgD, IgM, and B220; CD11b, Gr1, and CD8; for bone marrow staining: CD11b, Gr1, CD3; IgD, IgM, and B220. Cells were washed with 1.5 ml WB and pelleted, then resuspended in 0.4 ml of WB and analyzed on a FACScan using CellQuest software (Becton Dickinson, Mountain View, Calif.).

We found that the fraction of neutrophils in the blood of IL-22-adeno-treated mice was elevated 4-13 fold at Day 10 and 2-3-fold at Day 20. At Day 10, this difference resulted in a concomitant decrease in the fraction of lymphocytes and monocytes in the blood. In the bone marrow, we found that the total number of B cells decreased ~1.5-fold while the percentage of mature recirculating B cells increased and the total number of immature B cells dropped slightly at Day 10. At Day 20, many of these differences were not apparent, though we did find a slight increase in the fraction of mature recirculating B cells. In the spleen, the total number of B cells decreased slightly (1.5-2-fold) on both days tested, while on Day 20, the fraction of marginal zone B cells (CD21+CD23-B220+) increased by 2-fold and the number of follicular B cells (CD21+CD23+B220+) dropped 2-fold. Marginal zone B cells are considered to be the first line of defense against pathogens, as they are more sensitive to B cell mitogens (e.g. LPS) than the more common follicular B cells, and when they encounter their cognate antigen they differentiate very quickly into antibody-secreting cells. It is possible that IL-22 either enhances the conversion of follicular to marginal zone B cells, or that it selectively depletes the less mature follicular cells. The changes in B cell numbers found in the bone marrow may reflect an enhanced differentiation of pre/pro and/or immature B cells, or an increased influx of recirculating B cells from the blood/spleen, and perhaps a coincident increase in export of immature B cells to the periphery. The actual number of mature BM B cells does not increase, so IL-22 may not enhance their proliferation. Alternatively, IL-22 may block, reduce or inhibit differentiation of immature B cells and thereby increase the relative representation of mature B cells.

D. IL-22RA2-Fc4 Neutralizes IL-22 Activity in vivo: SAA ELISA Showing SAA Expression Induced by IL-22 is Inhibited by IL-22RA2-Fc4 Injection:

To assess whether IL-22RA2 could inhibit the SAA induction by IL-22 mice (female, C3H/HEJ, 8 weeks old; Jackson Labs, Bar Harbor, Me.) were divided into five groups of three animals each and treated by IP injection of proteins as shown in Table 6 below:

TABLE 6

| Group # | IL-22 | IL-22RA2 |
|---|---|---|
| Group 1: | — | — |
| Group 2: | — | 100 µg |
| Group 3: | 3 µg | — |
| Group 4: | 3 µg | 20 µg |
| Group 5: | 3 µg | 100 µg |

The IL-22RA2 injections preceded the IL-22 injection by 15 minutes. Both protein injections were given by the intraperitoneal route. A blood sample was taken from each mouse prior to treatment, then at 2 and 6 hours after treatment. Serum was prepared from each of the samples for measurement of SAA and IL-22.

An ELISA was performed as described previously to determine the level of SAA in mice treated with IL-22 and a soluble receptor for IL-22, IL-22RA2-Fc4 described herein. Mice treated with 3 µg IL-22 in conjunction with IL-22RA2-Fc4 at concentrations between 20-100 ug showed a reduction in the level of SAA induced by IL-22 alone to background levels, demonstrating that IL-22RA2 inhibited the SAA induction activity of IL-22 in vivo.

EXAMPLE 8

Expression of IL-22 in Inflammatory Bowel Disease Mouse Model

Inflammatory Bowel disease (IBD) is a multifactorial disease, divided into two types, ulcerative colitis (UC) and Crohn's Disease (CD). The etiology of these diseases is currently not known and clinical manifestations differ. UC is restricted to the colon, and symptoms include bloody diarrhea, weight loss and abdominal pain. Macroscopic features of UC include punctuated ulcers and a shortened colon. In contrast, Crohn's Disease can also affect other parts of the bowel. Symptoms include diarrhea (which is less often bloody than seen in UC), a low-grade fever and pain. Macroscopic features include fibrotic and stenotic bowel with strictures, deep ulcers, fissures and fistulas.

Several animal models are available that mimic these human diseases. Three commonly used models of colitis for new drug screening are the 2,4,6-trinitrobenzene sulphonic acid (TNBS) induced rat model, the mouse T-cell transfer model, and the dextran sodium sulfate, or DSS-induced mouse model. The DSS model was derived from a model by Dr. S. Murthy, using a disease activity index scoring system (S. N. S. Murthy, *Treatment of Dextran Sulfate Sodium-Induced Murine Colitis by Intracolonic Cyclosporin*, Digestive Diseases and Sciences, Vol. 38, No. 9 (September 1993), pp. 1722-1734).

In the present study; an acute colitis resulted when mice were fed DSS in their drinking water for 6 days. The animals exhibited weight loss and bloody diarrhea, mimicking the condition of UC patients. The mechanism of the DSS injury is not well characterized, but it is thought that it induces a nonspecific inflammatory immune response and mimics environmental effects on the bowel. It is possible that $H_2S$ is produced, which could be toxic to cells. In addition, changes in luminal bacterial flora occur. Activated monocytes, macrophages and mast cells have been demonstrated in the colon. Mediators for all three animal models include inflammatory prostaglandins, leukotriene metabolites and cytokines.

A. Method

Colitis was induced by DSS ingestion in Swiss Webster female mice from Charles River Laboratories. The mice were 10 and 11 weeks old at the start of the study. Mice were given 4% DSS in the drinking water for a period of 6 days (treated mice), or were given only normal drinking water (control mice). A Disease Activity Index clinical score (DAI) was used, which comprises a combination of measurements including stool quality, occult blood and weight loss. DAI was obtained daily for each mouse beginning one day after DSS treatment. After 6 days, DSS was removed from the drinking water of the treated mice. All mice were monitored by DAI clinical score until sacrifice at either 2, 7 or 10 days from the start of the study. On each of days 2 and 7, four DSS-treated mice and one control mouse were sacrificed. On day 10, four DSS-treated mice and two control mice were sacrificed. For all animals after sacrifice, the colon length was measured. Colon sections were fixed in 10% neutral buffered formalin for histologic analysis or frozen for mRNA extraction.

B. Histologic Scoring and Disease Activity Index (DAI) Scoring

Histologic index scores were obtained following the method in reference 1. Generally, the colon sections were scored blinded by a pathologist for crypt scores, hyperplastic epithelium, crypt distortion and inflammation.

Daily, each mouse was graded as to a clinical score based on weight loss, stool consistence and intestinal bleeding. Higher scores were assigned for increasing amounts of weight loss, diarrhea and bleeding. The daily score for each mouse was the mean grade obtained from the three results/observations.

C. Results

The colon lengths for DSS-treated mice were somewhat shorter on days 7 and 10 than non-treated controls, but the results may not have been significant (not checked by a statistical application). The clinical DAI scores reflected a rise in disease symptoms in the DSS-treated mice similar to that seen in past studies using this model. Occult blood was greatest on approximately days 4 and 5, while loose stools were more prevalent on days 6 and 7. Histopathology results show that disease scores were different from the controls on all sacrifice days, especially days 7 (peak) and 10. The histopathology screening scores were: controls=0.5, day 2 DSS-treated mice=8.8, day 7 DSS-treated mice=21, day 10 DSS-treated mice=18. Clinical and histopathology scores show that the DSS-treated mice had significant colon disease relative to the non-treated controls. The frozen tissue samples were used later for mRNA determinations as described below.

D. Tissue Expression of IL-22 RNA in Murine IBD Colon Samples Using RT-PCR:

To determine the relative expression of mouse IL-22 RNA (SEQ ID NO:10; SEQ ID NO:11) in an inflammatory bowel disease model, the distal colons of DSS-treated mice were collected and snap frozen in liquid nitrogen. In this experiment mice were treated with DSS and samples were taken on days 2, 7 and 10 post-treatment. Samples from normal untreated mice were collected as well. RNA was then isolated from the samples using the standard RNeasy Midiprep™ Kit (Qiagen, Valencia, Calif.) as per manufacturer's instructions.

The RT-PCR reactions used the 'Superscript One-Step RT-PCR System with Platinum Taq.' (Life Technologies, Gaithersburg, Md.) Each 25 µl reaction consisted of the following: 12.5 µl of 2× Reaction Buffer, 0.5 ul (20 pmol/µl) ZC39,289 (SEQ ID NO:17), 0.5 µl (20 pmol/ul) ZC39,290 (SEQ ID NO:18), 0.4 µl RT/Taq polymerase mix, 10 ul RNase-free water, 1.0 µl total RNA (100 ng/µl). The amplification was carried out as follows: one cycle at 50° for 30 minutes followed by 35 cycles of 94°, 30 seconds; 58°, 30 seconds; 72°, 60 seconds; then ended with a final extension at 72° for 7 minutes. 8 to 10 µl of the PCR reaction product was subjected to standard agarose gel electrophoresis using a 2% agarose gel. The correct predicted cDNA fragment size was observed as follows: There was a faint band in both day 2 samples. Two of three day 7 samples generated a strong band while the third day 7 sample generated a very strong band. The three day 10 samples generated a strong band. Finally, the two 'normal' control samples did not generate any band. These results suggest that there may be an upregulation of IL-22 in certain types of inflammatory responses in the colon, including those associated with IBD, UC, and CD. The data is summarized in Table 7 below where Relative Expression was scored as follows: 0=No band, 1=faint band, 2=strong band, 3=very strong band.

TABLE 7

| Tissue | Relative Expression (0-3) |
|---|---|
| Normal Colon | 0 |
| Normal Colon | 0 |
| Day 2 Post Treatment | 1 |
| Day 2 Post Treatment | 1 |
| Day 7 Post Treatment | 3 |
| Day 7 Post Treatment | 2 |
| Day 7 Post Treatment | 2 |
| Day 10 Post Treatment | 2 |
| Day 10 Post Treatment | 2 |
| Day 10 Post Treatment | 2 |

EXAMPLE 9

IL-22RA2 Decreases IL-6 and SAA Levels in Mouse Collagen Induced Arthritis (CIA) Model A. Mouse Collagen Induced Arthritis (CIA) Model Ten week old male DBA/1J mice (Jackson Labs) were divided into 3 groups of 13 mice/group. On day-21, animals were given a subcutaneous injection of 50-100 µl of 1 mg/ml chick Type II collagen formulated in Complete Freund's Adjuvant (prepared by Chondrex, Redmond, Wash.), and three weeks later on Day 0 they were given a 100 µl (25 µg) injection of LPS from $E. coli$ 0111:B4, prepared as 250 µg/ml from a lyophilized aliquot (Sigma, St. Louis, Mo.). IL-22RA2 was administered as an intraperitoneal injection 3 times a week for 4 weeks, from Day 0 to Day 25. The first two groups received either 100 or 10 µg of IL-22RA2 per animal per dose, and the third group received the vehicle control, PBS (Life Technologies, Rockville, Md.). Animals began to show symptoms of arthritis following the LPS injection, with most animals developing inflammation within 2-3 weeks. The extent of disease was evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

Monitoring Disease:

Animals can begin to show signs of paw inflammation soon after the second collagen injection, and some animals may even begin to have signs of toe inflammation prior to the second collagen injection. Most animals develop arthritis within 2-3 weeks of the boost injection, but some may require a longer period of time. Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals were observed daily to assess the status of the disease in their paws, which was done by assigning a qualitative clinical score to each of the paws. Every day, each animal has its 4 paws scored according to its state of clinical disease. To determine the clinical score, the paw can be thought of as having 3 zones, the toes, the paw itself (manus or pes), and the wrist or ankle joint. The extent and severity of the inflammation relative to these zones was noted including observation all the toes for any joint swelling, torn nails, or redness, notation of any evidence of edema or redness in any of the paws, and notation any loss of fine anatomic demarcation of tendons or bones, and evaluation the wrist or ankle for any edema or redness, and notation if the inflammation extends proximally up the leg. A paw a score of 1, 2, or 3 was based first on the overall impression of severity, and second on how many zones were involved. The scale used for clinical scoring is shown below.

Clinical Score:
0=Normal
0.5=One or more toes involved, but only the toes are inflamed
1=mild inflammation involving the paw (1 zone), and may include a toe or toes
2=moderate inflammation in the paw & may include some of the toes and/or the wrist/ankle (2 zones)
3=severe inflammation in the paw, wrist/ankle, and some or all of the toes (3 zones)

Established disease is defined as a qualitative score of paw inflammation ranking 2 or more, that persists overnight (two days in a row). Once established disease is present, the date is recorded and designated as that animal's first day with "established disease".

Blood was collected throughout the experiment to monitor serum levels of anti-collagen antibodies. Animals were euthanized on Day 21, and blood was collected for serum and for CBC's. From each animal, one affected paw was collected in 10% NBF for histology and one was frozen in liquid nitrogen and stored at −80° C. for mRNA analysis. Also, ½ spleen, ½ thymus, ½ mesenteric lymph node, one liver lobe and the left kidney were collected in RNAlater for RNA analysis, and .½ spleen, ½ thymus, ½ mesenteric lymph node, the remaining liver, and the right kidney were collected in 10% NBF for histology. Serum was collected and frozenat −80° C. for immunoglobulin and cytokine assays.

No statistically significant differences were found between the groups when the paw scores and measurements data were analyzed, although there was a suggestion that one treatment group receiving IL-22RA2 may have had a delay in the onset and progression of paw inflammation. There were no significant differences between the groups for change& in body weight, CBC parameters, or anti-collagen antibody levels. These early results indicate that IL-22RA2 does not adversely effect body weight, red or white blood cells, or antibody production, but may be able to reduce inflammation. Further investigations into dosing, mechanism of action, and efficacy are under way (e.g., Example 10).

B. Anti-collagen ELISA Data in Mouse CIA Model

Serum samples were collected on days 0, 7, 14, 21 and 28 relative to date of LPS challenge (day 0) from the murine model of collagen induced arthritis (Example 9A above). The serum samples were screened by ELISA for anti-collagen antibody titers. There were no statistically significant effects of IL-22RA2 treatment in 100 µg or 10 µg treatment groups on levels of anti-collagen antibodies compared with PBS controls. Below is a description of anti-collagen ELISA methods and materials.

Reagents used for anti-collagen ELISAs were Maxisorp 96-well microtiter plates (NUNC, Rochester, N.Y.), chick type-II collagen (Chondrex, Redmond, Wash.), Super Block (Pierce, Rockford, Ill.), horseradish peroxidase (HRP)-conjugated goat anti-mouse IgG+A+M (H+L) (Zymed, South San Francisco, Calif.) and o-phenylenediamine dihydrochloride substrate (Pierce, Rockford, Ill.). Buffers used in all assays were ELISA B diluent buffer (PBS+0.1% BSA+0.05% Tween (Sigma, St. Louis, Mo.)), ELISA C wash buffer (PBS+0.05% Tween) and NovoD developing buffer (0.063M sodium citrate, 0.037M citric acid), $H_2O_2$ (Sigma) and 1N $H_2SO_4$ (VWR, Tukwilla, Wash.).

Approximately 100 µL of peripheral blood was collected by retro-orbital bleed into serum separator tubes (Becton Dickinson). Serum was collected by centrifugation (2-3 min, 16,000×g, 4-6° C.) and stored at −20° C. until analyzed. To determine anti-collagen Ig antibody levels, NUNC plates were coated with 10 µg/mL chick type-II collagen (Chondrex, Redmond Wash.) and incubated overnight at 4° C. Plates were washed with ELISA C, blocked (5 minutes, room temperature) with Super Block (Pierce, Rockford, Ill.), and washed with ELISA C. Diluted serum samples (diluted in ELISA B 5-fold from 1:5000 to 1:625,000) were added to ELISA plates in triplicate and the plates were incubated overnight at 4° C. After incubation, the plates were washed with ELISA C, and peroxidase-labeled goat anti-mouse Ig Fc (Zymed, 1:2000 in ELISA B) was added. The plates were incubated (room temperature, 90 minutes), rinsed again using ELISA C, and HRP activity was developed using o-phenylenediamine dihydrochloride substrate (10 mL NovoD+1 tablet OPD+10 µL $H_2O_2$, Pierce). The reaction was stopped with 1N $H_2SO_4$. Relative optical density measurements of serum samples at 1:25,000 dilution were taken at 490 nm using a Spectra MAX 190, and data were analyzed using SoftMax Pro software (Molecular Devices Corporation, Palo Alto, Calif.).

C. IL-6 and SAA Analysis in Mouse CIA Model

Day 0 serum samples were harvested from CIA mice (Example 9A above) 4 hr post administration of 25 µg LPS intraperitoneally. Samples were screened for IL-6 and serum amyloid A (SAA) concentrations by commercial ELISA kits purchased for Biosource International (Camarillo, Calif.) as per manufacturer's instructions.

The IL-6 levels were 9651+/−1563 pg/ml, 10,865+/−1478 pg/ml and 15,006+/−2,099 pg/ml in the mice groups subjected to 100 µg IL-22RA2, 10 µg IL-22RA2 and PBS control, respectively. The IL-6 concentration in the group of CIA mice exposed to the 100 µg dose of IL-22RA2 was significantly lower compared to PBS control mice with p=0351. Statistical significance was calculated using Fisher's PLSD with a significance level of 5% (ABACUS Concepts, INC, Berkeley, Calif.).

In addition, SAA concentrations were 381+/−40 µg/ml, 348+/−37 µg/ml and 490+/−50 µg/ml in the mice groups subjected to 100 µg IL-22RA2, 10 µg IL-22RA2 and PBS control groups, respectively. The SAA concentration in the group of CIA mice exposed to the 10 µg dose of IL-22RA2 was significantly lower compared with PBS control mice with p=0.0257. Statistical significance was calculated using Fisher's PLSD with a significance level of 5% (ABACUS Concepts, INC, Berkeley, Calif.).

EXAMPLE 10

Anti-IL-22RA mAbs or Anti-IL-22 mAbs Inhibit Disease Severity in a Mouse CIA Model The collagen-induced arthritis (CIA) model is a mouse model for rheumatoid arthritis that reflects to large extent the disease seen in humans. (Moore, *Methods Mol. Biol.* 225: 175-179, 2003: Waksman, *Scand. J. Immunol.*, 56:12-34, 2002). Mice are immunized with 2 doses of collagen emulsified in CFA at the base of the tail. This results in swelling of the paws that increases over a period of time and can be both visually scored and measured using calipers. Furthermore, serum anti-collagen antibodies correlates well with severity of disease. Based on data showing IL-20 and IL-22 induce inflammation, anti-IL-22RA and anti-IL-22 mAbs are administered to groups of collagen-immunized mice, and effects on disease scores are evaluated. A decrease in paw scores and paw thickness after administration of anti-IL-22RA mAbs or anti-IL-22 mAbs_suggests IL-20 and IL-22 promote ongoing immune response in a model for autoimmunity and blocking, inhibiting, reducing, antagonizing or neutralizing their function may inhibit autoimmune disorders. Inhibition of serum TNFa and anti-collagen antibodies also suggests that blocking IL-22RA may be beneficial in autoimmune disease.

Thus, to determine if anti-IL-22RA mAbs or anti-IL-22 mAbs have an effect on autoimmunity, they are tested in a mouse model for rheumatoid arthritis—collagen-induced arthritis (CIA). Specifically, DBA1J mice are given collagen injections to induce rheumatoid-like arthritis. The inoculation on Day 0 is a subcutaneous injection of a homogenate consisting of Complete Freund's Adjuvant (CFA) and Type II collagen (50-100 µl, prepared as 2 mg/ml of collagen). The injection is given near the base of the tail. On Day 21, a second inoculation is administered, the only difference being that the homogenate is prepared using Incomplete Freund's Adjuvant (IFA), instead of the CFA. Paw scores and thickness are measured daily. Groups of mice receive PBS, 20-200 ug control isotype matched monoclonal antibody or 20-200 ug anti-IL-22RA mAb or anti-IL-22 mAb i.p 2× or 3×/week for 1-4 weeks starting at second collagen injection. Mice are monitored daily till day 30. Mice are sacrificed on day 30, serum taken for anti-collagen antibody analysis and serum cytokine analysis (TNF☐).

Inhibition of paw scores, paw thickness, serum TNFa and serum anti-collagen antibodies by administration of anti-IL-22RA or anti-IL-22 mAbs suggests that blocking IL-22RA can bind, block, inhibit, reduce, antagonize or neutralize IL-22, and inhibit an ongoing immune response in a model for autoimmunity and may inhibit autoimmune disorders.

EXAMPLE 11

Expression of IL-22 Receptor, IL-22RA, in the DSS Mouse Model

Quantitative RT-PCR was performed to measure expression levels of mouse IL-22RA in the colons of mice with DSS-induced IBD (Example 8). RNA was isolated from normal mouse colon and from the distal colons of DSS-treated mice from treatment days 2, 7 and 10. RT-PCR was performed using Applied Biosystems 7700 TaqMan instrument and protocols. Briefly, "Primer Express" software was used to designed primers against the mouse IL-22RA sequence (ZC39776 (SEQ ID NO:19) and ZC39777 (SEQ ID NO:20)) and a FAM/TAMRA labeled TaqMan probe (ZC38752 (SEQ ID NO:21)) according to Applied Biosystems guidelines. 25 ng of RNA was added to each reaction, along with PE/Applied Biosystems TaqMan EZ RT-PCR Core Reagents and the above mentioned primers and probe. RT-PCR reactions were run in duplicate under the following conditions: 50° C. for 2 minutes, 60° C. for 30 minutes, 95° C. for 5 minutes, 40 cycles of 94° C. for 20 seconds and 60° C. for 1 minute. Expression values were compared to a standard curve of known numbers of molecules of a synthetic mouse IL-22RA RNA transcript, and expression is reported as absolute number of molecules of mouse IL-22RA per reaction. Preliminary data suggests that mouse IL-22RA expression may be slightly down-regulated in the distal colons of day 7 and day 10 mice with DSS-induced IBD when compared to expression levels in normal mouse colon.

EXAMPLE 12

IL-22 and Proinflammatory Iindicators in Mild Endotoxemia Model: LPS-induced Endotoxemia Mouse Model A. LPS-induced Endotoxemia Mouse Model: Assessment Proinflammatory Cytokines and Body Temperature in the LPS-induced Endotoxemia Mouse Model An in vivo experiment was designed to examine the effect of IL-22RA2 (IL-22RA2) in a mouse LPS model of mild endotoxemia. To initially assess the model, we measured proinflammatory cytokines and body temperature to collect reference data for the model.

Briefly, six month Balb/c (CRL) female mice were injected with 25 μg LPS (Sigma) in sterile PBS intraperitoneally (IP). Serum samples were collected at 0, 1, 4, 8, 16, 24, 48 and 72 hr from groups of 8 mice for each time point. Serum samples were assayed for inflammatory cytokine levels. IL-1b, IL-6, TNFa, IL-10 and serum amyloid A protein (SAA) levels were measured using commercial ELISA kits purchased from Biosource International (Camarillo, Calif.).

TNFa levels peaked to 4000 pg/ml and IL-10 levels were 341 pg/ml at 1 hr post LPS injection. At 4 hr post LPS injection, IL-6, IL-1b and IL-10 were 6,100 pg/ml, 299 pg/ml and 229 pg/ml, respectively. The SAA levels in serum were 0.405 mg/ml by 4 hr post LPS injection. SAA concentrations in serum continued to increase to 3.9 mg/ml by 24 hr post LPS, however SAA levels greater than 1 to 2 mg/ml in serum are difficult to measure accurately or reproducibly with the existing ELISA kit due to interactions between SAA and other serum components. These results indicated that proinflammatory cytokines, in addition to IL-22 (Example 11B), were indeed produced in this model. Thus the following criteria were established as biological markers for the LPS model of mild endotoxemia: TNFa serum levels 1 hr post LPS, IL-6 serum levels 4 hr post LPS and SAA serum levels 4 and 8 hr post LPS.

Body temperatures in a separate group of animals were monitored by surgically implanted telemetry devices over the course of the 72 hr experiment. Body temperatures in mice dropped maximally by 2° C. from 37.07° C. to 34.98° C. 30 minutes after LPS injection.

Injection of 100 ug IL-22RA2-Fc fusion protein 30 minutes prior to the LPS injection significantly reduced about 50% of the SAA induction at 4 hr and 8 hr time point, while 10 ug IL-22RA2-Fc did not have significant effect. There is no significant change to the TNF-alpha and IL-6 level. IL-22RA2-Fc injection reduced neutrophil count in circulation at 1 hr time point. It showed the administration of IL-22RA2-Fc can neutralize IL-22 activity in terms of SAA induction.

B. Detection of IL-22 Activity in Mouse Serum from LPS-induced Endotoxemia Mouse Model Using BaF3/CRF2-4/IL-22RA Cells in an Alamar Blue Proliferation Assay BaF3/CRF2-4/IL-22RA cells, described herein, were spun down and washed in PBS 2 times to ensure the removal of the mIL-3, and then spun a third time and re-suspended in the complete media (RPMI 1640, 10% FBS, 1% GlutaMAX, 1% Sodium Pyruvate), but without mIL-3 (hereinafter referred to as "mIL-3 free media"). Cells were then counted in a hemocytometer. Cells were plated in a 96-well format at 5000 cells per well in a volume of 100 μl per well using the mIL-3 free media.

Serum from the LPS-induced endotoxemia mice from the experiment described in Example 11A above, was diluted to 2% in mIL-3 free media on the top row of the plate and then diluted serially 1:2 down the remaining 7 rows on the 96-well plate, leaving a volume of 100 μl in each well. This was then added to the 100 μl of cells, for final serum concentrations of 1%, 0.5%, 0.25%, 0.125%, 0.063%, 0.031%, 0.016%, and 0.018% in a total assay volume of 200 μl. The assay plates were incubated at 37° C., 5% $CO_2$ for 4 days at which time Alamar Blue (Accumed, Chicago, Ill.) was added at 20 μl/well. Plates were again incubated at 37° C., 5% $CO_2$ for 16 hours. Alamar Blue gives a fluourometric readout based on number of live cells, and is thus a direct measurement of cell proliferation in comparison to a negative control. Plates were read on the Wallac Victor 2 1420 Multilabel Counter (Wallac, Turku, Finland) at wavelengths 530 (Excitation) and 590 (Emmssion).

Results showed no significant proliferation above background levels in the 0 hour, 1 hour, 8 hour, and 16 hour time points. Serum samples from the 4 hour time point showed 4-fold to greater than 10-fold increases in proliferation above background, indicating the presence of IL-22 in those samples.

C. LPS-induced Endotoxemia Mouse Model: Experiment to Assess Effects of IL-22RA2

The ability of IL-22RA2 treatment to effect proinflammatory indicators induced with a single 25 μg LPS dose IP in mice was tested. All samples were analyzed for SAA, IL-22 and circulating neutrophil counts. Subsets from each group were analyzed for particular cytokine levels (1 hour samples were screened for TNF alpha, 4 hour samples were analyzed for IL-6). Animals were sacrificed at indicated time points in Table 8 below and whole blood and serum were collected and aliquoted for analysis.

72 C57BL6N female mice (CRL) were given a single IP dose of IL-22RA2 as described in Table 8, below. Control mice were C57BL/6N (CRL).

30 minutes later, they received another IP injection of 25 µg LPS (Sigma) in 100 µl, to initiate an endotoxemia cascade. Mice in each group were sacrificed at corresponding time points as indicated in Table 8, 50 µl whole blood were collected to measure total numbers of circulating neutrophils and the rest were spun for serum and aliquoted for various assays described herein.

TABLE 8

| Group | No | Treatment | LPS | Sacrifice | Samples |
|---|---|---|---|---|---|
| A | 8 | 100 µg IL-22RA2 IP | 25 µg IP 30 min post tx | 1 hour | Serum aliquots Blood for CBC |
| B | 8 | 10 µg IL-22RA2 IP | 25 µg IP 30 min post tx | 1 hour | Serum aliquots Blood for CBC |
| C | 8 | 200 µl PBS IP | 25 µg IP 30 min post tx | 1 hour | Serum aliquots Blood for CBC |
| D | 8 | 100 µg IL-22RA2 IP | 25 µg IP 30 min post tx | 4 hours | Serum aliquots Blood for CBC |
| E | 8 | 10 µg IL-22RA2 IP | 25 µg IP 30 min post tx | 4 hours | Serum aliquots Blood for CBC |
| F | 8 | 200 µl PBS IP | 25 µg IP 30 min post tx | 4 hours | Serum aliquots Blood for CBC |
| G | 8 | 100 µg IL-22RA2 IP | 25 µg IP 30 min post tx | 8 hours | Serum aliquots Blood for CBC |
| H | 8 | 10 µg IL-22RA2 IP | 25 µg IP 30 min post tx | 8 hours | Serum aliquots Blood for CBC |
| J | 8 | 200 µl PBS IP | 25 µg IP 30 min post tx | 8 hours | Serum aliquots Blood for CBC |
| K | 5 | controls | none | Pre LPS | Serum aliquots Blood for CBC |

D. IL-22RA2-Fc4 Neutralizes SAA Induction in vivo: SAA ELISA Showing SAA Expression Induced by LPS in LPS-induced Endotoxemia Mouse Model is Inhibited by IL-22RA2-Fc4 Injection:

To assess whether IL-22RA2 could inhibit the SAA induction in the LPS-induced endotoxemia mouse model, mice were injected with IL-22RA2, 30 minutes prior to LPS injection, as shown in Table 8 in Example 11C above.

An ELISA to determine SAA levels in the 4 hour and 8 hour samples was performed using the Mouse SAA Immunoassay Kit (BioSource International, California) following the manufacturer's directions. At the 4 hour time point, mice treated with 100 µg or 10 µg of IL-22RA2 showed a dose-dependant, statistically significant reduction in SAA levels relative to the PBS injected mice. At the 8 hour time point, mice treated with 100 µg, continued to show a statistically significant reduction in SAA levels relative to the PBS injected mice. This indicates that the presence of IL-22RA2 is able to inhibit the induction of SAA by LPS in vivo.

EXAMPLE 13

In vivo Effects of IL-22 Polypeptide on Skin

A. IL-22-induced Acanthosis

Mice (female, C3H/HEJ, 8 weeks old; Jackson Labs, Bar Harbor, Me.) were divided into three groups of six animals and one group of 4. Human BHK-produced IL-22 was administered by constant infusion via mini-osmotic pumps, resulting in local and steady state serum concentrations proportional to the concentration of the IL-22 contained in the pump. Alzet mini-osmotic pumps (model 2002; Alza corporation Palo Alto, Calif.) were loaded under sterile conditions with IL-22 protein (A601F, 0.22 mL) diluted in phosphate buffered saline (pH 7.0) to a concentration within the pump of 2 mg/mL for group 1 mice, 0.2 mg/mL for group 2 mice, 0.02 mg/mL for group 3 mice, or 0 mg/mL (diluent only) for group 4 mice. Pumps were implanted subcutaneously in mice through a 1 cm incision in the dorsal skin, and the skin was closed with sterile wound closures. These pumps are designed to deliver their contents at a rate of 0.5 µl per hour over a period of 14 days. Using this nominal rate of infusion, dose levels were calculated to be 24 µg/day, 2.4 µg/day, 0.24 µg/day and 0 µg/day for groups 1-4, respectively.

At the end of the 14-day period, the mice were euthanized and an approximately 1 cm square sample of skin surrounding the pump area was collected from each mouse. The skin was fixed in 10% neutral buffered formalin. Formalin fixed samples of skin were embedded in paraffin, routinely processed, sectioned at 5 um and stained with hematoxylin and eosin. The tissues were microscopically examined in blinded fashion by an ACVP board certified veterinary pathologist. Histological changes were noted, and the severity of acanthosis (i.e. epidermal thickening) scored in a subjective manner using the following scoring system: 0-normal, 1-minimal acanthosis, 2-mild acanthosis, 3-moderate acanthosis and 4-severe acanthosis. In addition, the skin of selected groups was imaged with a CoolSnap digital camera (Roper Scientific, Inc., San Diego, Calif.) and epidermal thickness measured using histomorphometry software (Scion Image for Windows, v. 4.02, Scion Corp., Frederick, Md.).

Administration of IL-22 at 2.4, and 24 µg/day resulted in epidermal thickening as shown by the average acanthosis score (see s) consistently greater than observed in control group skin. Moreover, IL-22 treated animals also had mononuclear cell infiltrates in the epidermis. These infiltrates were not observed in the vehicle treated controls.

Acanthosis scores of epidermal thickness and measurements of skin thickness (in generic units of pixels) by groups are shown in Table 9 below, as follows:

TABLE 9

| Group # | n = | Pump | Average Acanthosis | Measured Thickness |
|---|---|---|---|---|
| 1 | 6 | 24 µg IL-22/day | 3.0 | ND |
| 2 | 6 | 2.4 µg IL-22/day | 2.4 | 67.5 |
| 3 | 6 | 0.24 µg IL-22/day | 2.2 | ND |
| 4 | 4 | PBS infusion | 1.8 | 45.6 |

B. Effect of IL-22RA2 on IL-22-induced Acanthosis

Mice (female, C3H HEJ, 8 weeks old; Jackson Labs, Bar Harbor, Me.) were divided into eight groups of eight animals each. IL-22 was administered by constant infusion via mini-osmotic pumps, as described in Example 12A. Alzet mini-osmotic pumps (model 2001; Alza corporation Palo Alto, Calif.) were loaded under sterile conditions with IL-22 protein (A#601F, 0.22 mL) diluted in phosphate buffered saline (pH 7.0) to a concentration within the pump of 0.22 mg/mL for group 1-2 mice, 0.45 mg/mL for group 3-4 mice, 0.9 mg/mL for group 5-6 mice, or 0 mg/mL (diluent only) for group 7-8 mice. These pumps are designed to deliver their contents at a rate of 0.5 µl per hour over a period of 14 days.

Using this nominal rate of infusion, dose levels were calculated to be 10 μg/day in groups 1-2, 5 μg/day on groups 3-4, 2.5 μg/day in groups 5-6 and 0 μg/day for groups 7-8. For each pair of groups at a given dose level of IL-22, one of the groups was injected three times (days 1, 3, and 5) with 0.1 mg of human IL-22RA2 Fc protein (described herein) by the interperitoneal route. The other group was injected in the same fashion with vehicle (PBS).

On day 8 of the study, mice were euthanized and an approximately 1 cm square sample of skin surrounding the pump area was collected from each mouse. The skin was fixed in 10% neutral buffered formalin. Formalin fixed samples of skin were embedded in paraffin, routinely processed, sectioned at 5 um and stained with hematoxylin and eosin. The tissues were microscopically examined in blinded fashion by an ACVP board certified veterinary pathologist. This study was scored in a different manner than the previous example. The number of layers in the epidermis, from stratum basalis to stratum granulosum, was determined. Based on the results, the sections were scored as follows: 0-normal (2-3 layers), 1-mild thickening (3-4 layers), 2-moderate thickening (4-6 layers) and 3-severe thickening (>6 layers).

Administration of IL-22 at 2.5, 5, 10 μg/day resulted in epidermal thickening (see Table 10). Moreover, IL-22 treated animals also had mononuclear cell infiltrates in the epidermis. These infiltrates were not observed in the vehicle treated controls. Concurrent administration of 100 μg IL-22RA2 (3 injections) decreased the amount of epidermal thickening in mice treated with 5 μg IL-22/day.

Acanthosis scores of epidermal thickness by groups are shown in Table 10, below, as follows:

TABLE 10

| Group # | n = | Pump | Injection | Average Acanthosis |
|---|---|---|---|---|
| 1 | 8 | 2.5 μg IL-22/day | 100 μL vehicle (3 injections) | 1.1 |
| 2 | 8 | 2.5 μg IL-22/day | 100 μg IL-22RA2 (3 injections) | 0.8 |
| 3 | 8 | 5 μg IL-22/day | 100 μLvehicle (3 injections) | 2.0 |
| 4 | 8 | 5 μg IL-22/day | 100 μg IL-22RA2 (3 injections) | 0.6 |
| 5 | 8 | 10 μg IL-22/day | 100 μL vehicle (3 injections) | 2.0 |
| 6 | 8 | 10 μg IL-22/day | 100 μg IL-22RA2 (3 injections) | 1.9 |
| 7 | 8 | Vehicle | 100 μL vehicle (3 injections) | 0.0 |
| 8 | 8 | Vehicle | 100 μg IL-22RA2 (3 injections) | 0.0 |

Epidermal thickening and immune infiltrates were also observed in human psoriatic skins. The skin phenotype observed in IL-22 subcutaneous injection further indicated the potential role of IL-22 in the pathogenesis of psoriasis. The fact that IL-22RA2-Fc can neutralize the IL-22 induced skin phenotype suggests the potential use of other IL-22 antagonists such as and anti-IL-22 neutralizing antibody or soluble receptor for the treatment of psoriasis and other IL-22 induced inflammatory diseases.

C. Effect of IL-22RA Soluble Receptors, and Anti-IL-22RA Antibodies on IL-22-induced or IL-20-induced Acanthosis The activity of IL-22RA soluble receptors, or an antibody to IL-22RA, to inhibit the in vivo activity of IL-22 or IL-20 is evaluated in a similar manner, using the histological endpoint of acanthosis caused by subcutaneous infusion of IL-22 or IL-20 protein. In an example of this model C3H/HEJ mice are implanted with subcutaneous mini-osmotic pumps as described in examples 12(A) and 12(B) above. During the period of exposure to IL-22 or IL-20, the mice are treated by injection with the purified monoclonal antibody to IL-22 or similarly injected with vehicle as control. At the end of the IL-22 infusion period, skin would be sampled from the pump area for histological analysis. Similar to the IL-22RA2 soluble receptor IL-22 antagonist, IL-22 or IL-20 antagonist IL-22RA soluble receptors, or anti-IL-22RA antibodies of the present invention are expected to show reduction in epidermal thickening and immune cell infiltrates caused by IL-22 or IL-20, and hence be useful as IL-22 or IL-20 antagonists as a therapeutic for psoriasis and other IL-22 or IL-20 induced inflammatory disease.

EXAMPLE 14

IL-22 is Upregulated in Human Psoriatic Skin Samples

RNA Samples:

Normal skin samples as well as skin from psoriasis patients were obtained. The latter included involved skin from stable plaque-type psoriasis and from adjacent uninvolved skin. RNA was isolated from human skin samples using conventional methods. The integrity and quality of RNA samples was tested on the Agilent 2100 Bioanalyzer (Agilent Technologies, Waldbronn Germany). Primers and Probes for Quantitative RT-PCR- Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-22 expression were designed using the primer design software Primer Express™ (PE Applied Biosystems, Foster City, Calif.). Primers for human IL-22 were designed spanning an intron-exon junction to eliminate amplification of genomic DNA. The forward primer, ZC42459 (SEQ ID NO:22) and the reverse primer, ZC42458 (SEQ ID NO:23) were used in a PCR reaction (below) at a 800 nM concentration to synthesize a 72 bp product. The corresponding IL-22 probe, ZC42460 (SEQ ID NO:24) was synthesized and labeled in house at ZymoGenetics. The IL-22 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

C. Real-time Quantitative RT-PCR-

Relative levels of IL-22 mRNA were determined by analyzing total RNA samples using the TaqMan EZ RT-PCR Core Reagents Kit (PE Applied Biosystems). Runoff IL-22 transcript was made to generate a standard curve used for quantitation. The curve consisted of 10-fold serial dilutions ranging from about 1e8 to 1e3 total copies of whole message for IL-22 with each standard curve point analyzed in triplicate. The total RNA samples from skin were also analyzed in triplicate for human IL-22 transcript levels and for levels of hGUS as an endogenous control. In a total volume of 25 μl, each RNA sample was subjected to TaqMan EZ RT-PCR reaction (PE Applied Biosystems) containing: approximately 25 ng of total RNA in DEPC treated water (Dnase/Rnase free); appropriate primers (approximately 800 nM ZC 42459 (SEQ ID NO:22) and ZC 42458 (SEQ ID NO:23); appropriate probe (approximately 100 nM ZC 42460 (SEQ ID NO:24); 1× TaqMan EZ Buffer; 3 mM Manganese acetate; 300 μM each d-CTP, d-ATP, and d-GTP and 600 μM of d-UTP; rTth DNA Polymerase (0.1 U/μl); and AmpErase UNG (0.01 U/μl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-22 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize the IL-22 levels. Data are shown in Table 11 below.

TABLE 11

| Skin Sample | IL-22 |
|---|---|
| Normal | 0 |
| Uninvolved | 0 |
| Involved | 1149 |

IL-22 mRNA was undetectable in skin samples from normal patients or from uninvolved areas. In contrast, there was dramatic upregulation for IL-22 message in involved skin from psoriasis patients. These data support a strong disease association for IL-22 to human psoriasis.

Over expression of IL-22 was shown in human psoriatic lesions, suggesting that IL-22 is involved in human psoriasis. Moreover, as described herein, over expression of IL-22 in transgenic mice showed epidermal thickening and immune cell involvement indicative of a psoriatic phenotype, and in addition injection of IL-22 into normal mice showed epidermal thickening and immune cell involvement indicative of a psoriatic phenotype which was ablated by the soluble receptor antagonist IL-22RA2. Such in vivo data further suggests that the pro-inflammatory IL-22 is involved in psoriasis. As such, antagonists to IL-22 activity, such as the anti-human-IL-22 monoclonal antibodies of the present invention, as well as soluble receptors and antibodies thereto, are useful in therapeutic treatment of inflammatory diseases, particularly as antagonists to IL-22 in the treatment of psoriasis. Moreover, antagonists to IL-22 activity, such as the anti-human-IL-22 monoclonal antibodies of the present invention, as well as soluble receptors and antibodies thereto, are useful in therapeutic treatment of other inflammatory diseases for example as antagonists to IL-22 in the treatment of atopic dermatitis, IBD, colitis, Endotoxemia, arthritis, rheumatoid arthritis, and psoriatic arthritis, adult respiratory disease (ARD), septic shock, multiple organ failure, inflammatory lung injury such as asthma or bronchitis, bacterial pneumonia, psoriasis, eczema, atopic and contact dermatitis, and inflammatory bowel disease such as ulcerative colitis and Crohn's disease.

EXAMPLE 15

IL-22 is Upregulated in Human Atopic Dermatitis Skin Samples

Normal skin samples (n=4) as well as skin from atopic dermatitis patients (n=4) were obtained. RNA was isolated from human skin samples using conventional methods. The integrity and quality of RNA samples was tested on the Agilent 2100 Bioanalyzer (Agilent Technologies, Waldbronn Germany). Primers and Probes for Quantitative RT-PCR- Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-22 expression were designed using the primer design software Primer Express™ (PE Applied Biosystems, Foster City, Calif.). Primers for human IL-22 were designed spanning an intron-exon junction to eliminate amplification of genomic DNA. The forward primer, ZC42459 (SEQ ID NO:22) and the reverse primer, ZC42458 (SEQ ID NO:23) were used in a PCR reaction (below) at a 800 nM concentration to synthesize a 72 bp product. The corresponding IL-22 probe, ZC42460 (SEQ ID NO:24) was synthesized and labeled in house at ZymoGenetics. The IL-22 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

C. Real-time Quantitative RT-PCR-

Relative levels of IL-22 mRNA were determined by analyzing total RNA samples using the TaqMan EZ RT-PCR Core Reagents Kit (PE Applied Biosystems). Runoff IL-22 transcript was made to generate a standard curve used for quantitation. The curve consisted of 10-fold serial dilutions ranging from about 1e8 to 1e3 total copies of whole message for IL-22 with each standard curve point analyzed in triplicate. The total RNA samples from skin were also analyzed in triplicate for human IL-22 transcript levels and for levels of hGUS as an endogenous control. In a total volume of 25 μl, each RNA sample was subjected to TaqMan EZ RT-PCR reaction (PE Applied Biosystems) containing: approximately 25 ng of total RNA in DEPC treated water (Dnase/Rnase free); appropriate primers (approximately 800 nM ZC 42459 (SEQ ID NO:22) and ZC 42458 (SEQ ID NO:23); appropriate probe (approximately 100 nM ZC 42460 (SEQ ID NO:24); 1× TaqMan EZ Buffer; 3 mM Manganese acetate; 300 μM each d-CTP, d-ATP, and d-GTP and 600 μM of d-UTP; rTth DNA Polymerase (0.1 U/μl); and AmpErase UNG (0.01 U/μl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-22 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize the IL-22 levels.

IL-22 mRNA was undetectable in skin samples from normal patients. In contrast, there was dramatic upregulation for IL-22 message in 3 out of 4 skin samples from atopic dermatitis patients (about 400-2300 copies). These data support a strong disease association for IL-22 to human atopic dermatitis.

Over expression of IL-22 was shown in human atopic dermatitis skins, suggesting that IL-22 is involved in human atopic dermatitis. Moreover, as described herein, over expression of IL-22 in transgenic mice showed epidermal thickening and immune cell involvement indicative of an atopic dermatitis phenotype, and in addition injection of L-22 into normal mice showed epidermal thickening and immune cell involvement indicative of a atopic dermatitis phenotype which was ablated by the soluble receptor antagonist IL-22RA2. Such in vivo data further suggests that the pro-inflammatory IL-22 is involved in atopic dermatitis. As such, antagonists to IL-22 activity, such as the anti-human-IL-22 monoclonal antibodies of the present invention, as well as soluble receptors and antibodies thereto, are useful in therapeutic treatment of inflammatory diseases, particularly as antagonists to IL-22 in the treatment of atopic dermatitis. Moreover, antagonists to IL-22 activity, such as the anti-human-IL-22 monoclonal antibodies of the present invention, as well as soluble receptors and antibodies thereto, are useful in therapeutic treatment of other inflammatory diseases for example as antagonists to IL-22 in the treatment of atopic dermatitis, IBD, colitis, Endotoxemia, arthritis, rheumatoid arthritis, and psoriatic arthritis, adult respiratory disease (ARD), septic shock, multiple organ failure, inflammatory lung injury such as asthma or bronchitis, bacterial pneumonia, atopic dermatitis, eczema, atopic and contact dermatitis, and inflammatory bowel disease such as ulcerative colitis and Crohn's disease.

EXAMPLE 16

Human IL-22 Polyclonal Antibodies

Anti IL-22 Polyclonal antibodies were prepared by immunizing 2 female New Zealand white rabbits with the purified mature recombinant human IL-22 polypeptide (amino acid residues 22 (Ala) to 167 (Ile) of SEQ ID NO:6), produced from BHK cells (IL-22-BHK). The rabbits were each given an initial intraperitoneal (ip) injection of 200 μg of purified protein in Complete Freund's Adjuvant followed by booster IP injections of 100 μg peptide in Incomplete Freund's Adjuvant every three weeks. Seven to ten days after the administration of the second booster injection (3 total injections), the animals were bled and the serum was collected. The animals were then boosted and bled every three weeks.

The human IL-22-specific polyclonal antibodies were affinity purified from the immune rabbit serum using a CNBr-SEPHAROSE 4B protein column (Pharmacia LKB) that was prepared using 10 mg of the specific antigen purified recombinant protein human IL-22-BHK per gram of CNBr-SEPHAROSE, followed by 20× dialysis in PBS overnight. Human IL-22-specific antibodies were characterized by ELISA using 500 ng/ml of the purified recombinant protein human IL-22-BHK as antibody target. The lower limit of detection (LLD) of the rabbit anti-human IL-22 affinity purified antibody is 280 pg/ml on its specific purified recombinant antigen human IL-22-BHK.

The human IL-22-specific polyclonal antibodies were characterized further for their ability to block the cell-proliferative activity ("neutralization assay") of purified recombinant human IL-22-BHK on BaF3/CRF2-4/IL-22RA cells (Example 2 and Example 3). A 50× molar excess of the human IL-22-specific polyclonal antibodies was sufficient to inhibit cell proliferation.

EXAMPLE 17

Anti-human IL-22 Monoclonal Antibodies

Monoclonal antibodies were prepared by immunizing 4 female Sprague-Dawley Rats (Charles River Laboratories, Wilmington, Mass.), with the purified mature recombinant human IL-22 polypeptide (amino acid residues 22 (Ala) to 167 (Ile) of SEQ ID NO:6), produced from BHK cells (IL-22-BHK). The rats were each given an initial intraperitoneal (IP) injection of 100 μg of the purified human recombinant IL-22 protein in Complete Freund's Adjuvant (Pierce, Rockford, Ill.) followed by booster IP injections of 50 μg of the purified recombinant protein in Incomplete Freund's Adjuvant every two weeks. Seven to ten days after the administration of the third booster injection, the animals were bled and the serum was collected.

The human IL-22-specific rat sera samples were characterized by ELISA using 500 ng/ml biotinylated human IL-22-BHK and 500 ng/ml biotinylated mouse IL-22, biotinylated muIL-22-E.coli (R+D Systems, Minneapolis, Minn.) antibody targets. Three rat serum samples had titer to the specific antibody target biotinylated human IL-22-BHK at a dilution of 1:1E5 and to the specific antibody target biotinylated muIL-22-E.coli at a dilution of 1:1E4.

Splenocytes and lymphatic node cells were harvested from 2 high-titer rats and fused to SP2/0 (mouse) myeloma cells using PEG 1500 in two separate fusion procedures (4:1 fusion ratio, splenocytes to myeloma cells, "Antibodies A Laboratory Manual, E. Harlow and D. Lane, Cold Spring Harbor Press). Following 10 days growth post-fusion, specific antibody-producing hybridoma pools were identified by ELISA using the biotinylated recombinant protein human IL-22-BHK and the biotinylated recombinant protein muIL-22-E.coli as separate antibody targets. Hybridoma pools positive in both ELISA protocols were analyzed further for their ability to block or reduce the cell-proliferative activity ("neutralization assay") of purified recombinant muIL-22-E.coli on BaF3/CRF2-4/IL-22RA cells (Example 2 and Example 3).

Hybridoma pools yielding positive results by ELISA only or ELISA and the "neutralization assay" were cloned at least two times by limiting dilution.

Monoclonal antibodies purified from tissue culture media were characterized for their utility in an ELISA for the quantitative determination of recombinant and native human IL-22 in mouse and human serum samples. The two antibodies selected resulted in a quantitative assay with a lower limit of detection of approximately 1 ng/ml recombinant huIL-22-E.coli in 100% human serum. Monoclonal antibodies purified from tissue culture media were characterized for their ability to block or reduce the cell-proliferative activity ("neutralization assay") of purified recombinant huIL-22-*E.coli* or muIL-22-*E.coli* on BaF3/CRF2-4/IL-22RA cells (Example 2 and Example 3). Six "neutralizing" monoclonal antibodies were identified in this manner. Hybridomas expressing the neutralizing monoclonal antibodies to human IL-22 described above were deposited with the American Type Tissue Culture Collection (ATCC; Manassas Va.) patent depository as original deposits under the Budapest Treaty and were given the following ATCC Accession No.s: clone 266.16.1.4.4.1 (ATCC Patent Deposit Designation PTA-5035); clone 266.5.1.2.2.3 (ATCC Patent Deposit Designation PTA-5033); clone 267.17.1.1.4.1 (ATCC Patent Deposit Designation PTA-5038); clone 267.4.1.1.4.1 (ATCC Patent Deposit Designation PTA-5037); clone 266.12.6.1.3.2.1 (ATCC Patent Deposit Designation PTA-5034); clone 266.19.1.10.5.2 (ATCC Patent Deposit Designation PTA-5036); and clone 267.9.1.1.4.1 (ATCC Patent Deposit Designation PTA-5353).

EXAMPLE 18

Anti-IL-22RA Monoclonal Antibodies

Monoclonal antibodies were prepared by immunizing 4 Lewis Rats (Rockland Immunochemicals, Gilbertsville, Pa.), with the cleaved and purified recombinant fusion protein, muIL-22RA-Fc (SEQ ID NO:4). The rats were each given an initial intraperitoneal (IP) injection of 100 μg of the purified recombinant fusion protein in Complete Freund's Adjuvant (Pierce, Rockford, Ill.) followed by booster IP injections of 50 μg of the purified recombinant protein in Incomplete Freund's Adjuvant every two weeks for four weeks. Following the first four weeks of immunizations, booster IP injections of 50 ug of the cleaved purified recombinant protein coupled to the carrier protein keyhole limpet hemocyanin (KLH, Pierce, Rockford, Ill.) in Incomplete Freund's were administered eyery two weeks for four weeks. Seven to ten days after the administration of the fourth booster injection, the animals were bled and the serum was collected.

The muIL-22RA-specific rat serum samples were characterized by ELISA using 500 ng/ml of the purified recombinant fusion protein muIL-22RA-Fc as the specific antibody target and an unrelated fusion protein as a non-specific antibody target.

Splenocytes were harvested from one high-titer rat and fused to SP2/0 (mouse) myeloma cells in an optimized PEG-mediated fusion protocol (Rockland Immunochemicals). Following 12 days growth post-fusion, specific antibody-producing hybridoma pools were identified by ELISA using 500 ng/ml each of the purified recombinant fusion protein muIL-22RA-Fc-Bv as the specific antibody target and an unrelated fusion protein as a non-specific antibody target. Hybridoma pools positive to the specific antibody target only were analyzed further for their ability to block or reduce the cell-proliferative activity ("neutralization assay") of purified recombinant muIL-22-*E.coli* on BaF3/CRF2-4/IL-22RA cells (Example 2 and Example 3) and an ability to bind via FACS analysis to BaF3/CRF2-4/IL-22RA cells (Example 2 and Example 3) as antibody target.

Hybridoma pools yielding a specific positive result in the ELISA assay and positive results in either the FACS or "neutralization assay" were cloned at least two times by limiting dilution.

Monoclonal antibodies in tissue culture media were characterized for their ability to block or reduce proliferation of BaF3/CRF2-4/IL-22RA cells (Example 2 and Example 3), grown in the presence of the purified recombinant proteins muIL-22-*E.coli* or huIL-22-BHK. Fourteen "neutralizing" monoclonal antibodies have been identified and nine monoclonal antibodies have been cloned.

Hybridomas expressing the neutralizing monoclonal antibodies to mouse IL-22RA described above were deposited with the American Type Tissue Culture Collection (ATCC; Manassas Va.) patent depository as original deposits under the Budapest Treaty and were given the following ATCC Accession No.s: clone R2.1.1G11.1 (ATCC Patent Deposit Deposit Designation PTA-6035); clone R2.1.5F4.1 (ATCC Patent Deposit Designation PTA-6024); clone R2.1.5H8.1 (ATCC Patent Deposit Designation PTA-6025); clone R2.1.12G7.1 (ATCC Patent Deposit Designation PTA-6036); clone R2.1.13C8.1 (ATCC Patent Deposit Designation PTA-5037); clone R2.1.15E2.1 (ATCC Patent Deposit Designation PAT-6038); clone R2.1.16C11.1 (ATCC Patent Deposit Designation PTA-6039); clone R2.1.18C8.1 (ATCC Patent Deposit Deposit Designation PTA-6040); and clone R2.1.21G8.2(ATCC Patent Deposit Deposit Designation PTA-6111).

Hybridomas expressing the neutralizing monoclonal antibodies to human IL-22RA will be deposited with the American Type Tissue Culture Collection (ATCC; Manassas Va.) patent depository as original deposits under the Budapest Treaty and have been given the following ATCC Accession No.s: 280.46.3.4 (ATCC Patent Deposit Designation PTA-6284); clone 281.73.49.1.1 (ATCC Patent Deposit Designation PTA-6285); clone 283.4.1.2 (ATCC Patent Deposit Designation PTA-6287); clone 283.52.5.4 (ATCC Patent Deposit Designation PTA-6311); and clone 283.108.2.3 (ATCC Patent Deposit Designation PTA-6286).

EXAMPLE 19

Binding Affinity of Two Rat-anti-Ms-IL-22RA MAb

Goat-anti-Rat IgG-Fc gamma specific Antibody (Jackson) was immobilized onto a CM5 Biacore chip. The assay was optimized to bind each mAb onto the anti-Rat capture surface and then a concentration series of IL-22RA was injected across the mAb to see association (Ka) and dissociation (Kd). After preliminary testing, non-specific binding was observed between the fusion protein and the capture surface on the chip. A vial of IL-22RA that had the Fc4 tag cleaved by thrombin was acquired and subsequently tested to show no background effects. After each run, the surface was regenerated back to the anti-Rat Antibody with 2 injections of 20 mM HCl. Data was generated for each MAb and evaluation software (BIAevaluation software version 3.2, Pharmacia BIAcore, Uppsala, Sweden) was used to assess the kinetics of the anti-IL-22RA antibody binding to the IL-22RA protein, as shown in Table 12 below:

TABLE 12

| Clone R2.1.5F4.1** | | Clone R2.1.15E2.1** | |
|---|---|---|---|
| ka (M−1s−1) | 1.49E+06 | ka (M−1s−1) | 1.76E+06 |
| kd (s−1) | 1.70E−04 | kd (s−1) | 2.55E−04 |
| KA (M−1) | 8.76E+09 | KA (M−1) | 6.66E+09 |
| KD (M) | 1.14E−10 | KD (M) | 1.504E−10 |
| Chi2 | 2.08 | Chi2 | 1.5 |

**Equilibrium association (Ka) and dissociation (Kd) rate constants for each anti IL-22RA MAB are shown and values fall in machine limits. Chi2 refers to the sum of the square of the residuals between the binding curvesand the evaluation fitting curves. The closer the 0, the more confidence in the data.

As shown by Table 12, both anti-IL-22RA MAb's bind strongly to the IL-22RA protein, as evinced by the binding in pico-molar concentration to the IL-22RA (thrombin-cleaved Fc4 tag). This data is shown with good confidence based on the low Chi$^2$ values and shows mAb Clone R2.1.5F4.1 to have a slightly stronger affinity for the IL-22RA receptor.

EXAMPLE 20

Immunohistochemical Analysis of IL-22 Protein Expression in vivo in Tissue Samples A. Summary Immunohistochemical (IHC) analysis of IL-22 protein expression and localization was achieved using anti-human IL-22 (anti-hIL-22) monoclonal antibody (Mab 266.19.1.10.5.2) in the following tissue samples: a Human multi-Normal Grid and Tumor Grid; Human pancreatitis, lung and renal disease samples; Human psoriasis skin samples; INS IL-22 TG (expressed from the rat insulin promoter) and WT mouse pancreas; muIL-22-EuLCK TG and WT mouse skin sample; and DSS (WT and IL-22 KO) mouse colon sample. Moreover the staining pattern of anti-hIL-22 monoclonal antibody MAB 266.19.1.10.5.2 (Example 17) vs. polyclonal antibody (rabbit anti-hIL-22) (Example 16) was compared.

The rat anti-Human IL-22 monoclonal antibodies MAb 266.16.1.4.4.1, and MAb 266.19.1.10.5.2 (Example 17) were tested were shown to stain the majority of BHK/human IL-22 (>50%) but also some BHK/mouse IL-22 cells (1-5%), and were used to investigate the tissue distribution and expression of L-22 in both human patient and animal model samples and used to compare the staining pattern with polyclonal rabbit antibody to confirm the results.

B. Materials and Methods

Formalin-fixed and paraffin-embedded cells and tissues from human sources and mouse animal models were sectioned at 5 μm. The cells included BHK cells expressing either human or mouse IL-22 and wild type as positive control and negative control, respectively. The human tissues included a Multi-tissue control slide (NormalGrid™; Biomeda, Foster City, Calif.) with 50 sections of various normal human tissues (e.g., brain, pituitary gland, adrenal gland, breast, kidney, heart, stomach, small intestine, large intestine, fetal liver, liver, skin, pancreas, lung, tonsil, ovary, testis, prostate, uterus, placenta, thyroid and spleen); a Multi-tissue control slide (TumorGrid™; Biomeda, Foster City, Calif.) with 50 sections of various human tumors (e.g., lung adeno Ca., liver adeno Ca., kidney adeno Ca., colon adeno Ca., breast adeno Ca., thyroid adeno Ca., stomach adeno Ca., prostate adeno Ca., pancreas adeno Ca., ovary adeno Ca., lymphoma, melanoma, sarcoma ewings, sarcoma epithelioid, sarcoma MFH, sarcoma Rhabdo, carcinoid, undiff. Ca., mesothelioma, teretoma and seminoma); lung carcinoma from CHTN (Cooperation Human Tissue Network, Cleveland, Ohio); normal pancreas, pancreas with chronic pancreatitis, lung with chronic perivascular inflammation, kidneys with either multifocal glomerulosclerosis, mesangioproliferative glomerulonephritis, or sclerotic glomeruli interstitial fibrosis from NDRI (National Disease Research Interchange, Philadelphia, Pa.); and psoriatic skin samples from human. The mouse tissues included colons from inflammatory bowel disease animal model (DSS model disclosed herein, Swiss Webster female mice) and from IL-20 WT and KO colitis animal model (DSS mice, wild type and IL-20 (IL-20) knock out female mice) treated with either vehicle or 4% DSS in drinking water for 7 days; and skin samples from transgenic (TG) animal models including mIL-22-EuLCK TG and mIL-22-INS control and TG animals. One section per block/slide was stained with hematoxylin and eosin (H&E) for histologic examination and the subsequent section were immunohistochemically stained for IL-22 protein expression and localization.

For immunohistochemistry, the cell and tissue sections were placed on ChemMate™ Capillary Gap Plus microscope slides (BioTek, Winooski, Vt.), dried at 60° C. oven for 60 minutes and dewaxed using standard conditions of 3×5 minutes in xylene, 4 minutes in 100% EtOH, 3 minutes in 100% EtOH, and 2 minutes in 95% EtOH. The tissue sections were then subjected to a 20-minute enzyme-induced epitope retrieval process at 37° C. with pepsin (NeoMarkers Fremont Calif.) followed by an avidin/biotin-blocking step done according to the manufacturers instructions (Zymed, South San Francisco, Calif.). TechMate 500™ Automated Immunostainer and Immunoperoxidase (IP) immunohistochemical protocol with avidin-biotin-complex detection system (Ventana Biotek Systems, Tucson, Ariz.) were employed for the staining. The TechMate 500™ Automated Immunostainer employed the principle of capillary action and the IP protocol utilized a type of immunostaining referred to as a "sandwich" technique. The sections were preblocked with 5% normal goat serum (Vector, Burlingame Calif.) in PBS for 10 minutes followed by 1× buffer1 wash (Signet, Dedham Mass.) and then incubated with a primary antibody against IL-22 (MAB 266.19.1.10.5.2) (Example 17), PAS purified at 2.04 mg/ml) diluted at 1:800 for 30 minutes at room temperature followed by 5× buffer1 wash. The primary antibody was diluted in TechMate 500™ antibody dilution buffer (Ventana). Biotinylated goat anti-rat IgG (Vector) diluted at 1:200 plus 5% normal goat serum and 2.5% nonfat dry milk in PBS was used as the secondary-linking antibodies for 25 minutes at room temperature followed by 1× buffer1 wash and 1× Buffer2&3 wash (Signet). The tissues sections were then subjected to a 3×7 minutes 3% hydrogen peroxide (HP) blocking (Ventana) followed by 3× buffer2&3 wash. Immunoperoxidase labeling was performed with a peroxides DAB kit (Ventana), incubating with avidin-biotin-complex (ABC) for 30 minutes followed by 5× buffer2&3 wash and diaminobenzidine (DAB) for 4×4 minutes followed by 2× buffer2&3 wash and 1× water wash (Signet, Cat. No. 2340). Tissues were then counter stained with methyl green (Dako, Cat. No. S1962) for 10 minutes followed by 2× buffer2&3 wash and 3× water wash. Control included non-immune primary sera using rat primary antibody isotype control (Zymed) to replace the primary antibody.

Immunostaining was observed using an Olympus BH-2 microscope and images were captured by CoolSNAP HQ digital camera (Roper Scientific, Tucson, Ariz.).

C. Results

Positive and negative control cell lines: MAB 266.19.1.10.5.2, an anti-hIL-22 monoclonal antibody, demonstrated positive staining on both human IL-22 expressing BHK cells (+++) and murine IL-22 expressing BHK cells (+), and no staining on the wild type BHK cells (−). All the positive and negative BHK cell lines stained with rat isotype negative control to replace the primary antibody showed no staining (−) which indicated that the antibody is specific to IL-22 ligand. The antibody had cross immunoreactivity to both human and mouse IL-22.

Human tissues: Human multi-Normal Grid and Tumor Grid; pancreas, lung and renal disease samples; and human psoriasis skin samples were examined. These human tissues included 1). Brain, pituitary gland, adrenal gland, breast, kidney, heart, stomach, small intestine, large intestine, fetal liver, liver, skin, pancreas, lung, tonsil, ovary, uterus, testis, placenta, thyroid and spleen on the Multi-tissue control slides (NormalGrid™)/normal human tissues; 2). Lung adeno Ca., liver adeno Ca., kidney adeno Ca., thyroid adeno Ca., stomach adeno Ca., prostate adeno Ca., pancreas adeno Ca., ovary adeno Ca., lymphoma, melanoma, sarcoma ewings, sarcoma epithelioid, sarcoma MFH, sarcoma Rhabdo, carcinoid, undiff. Ca., mesothelioma, teratoma, and seminoma, on the Multi-tissue control slides (TumorGrid™)/human abnormal tissues/tumor; 3). Normal pancreas, pancreas with chronic pancreatitis, lung with chronic perivascular inflammation, lung Ca., kidney with multifocal glomerulosclerosis, kidney with mesangioproliferative glomerulonephritis, kidney with sclerotic glomeruli interstitial fibrosis from CHTN and/or NDRI; 4).

Mouse tissues: INS IL-22 TG and WT mouse pancreas were examined. Scattered cells throughout the islets in the INS IL-22 TG pancreas demonstrated strong positive staining (+++) with Mab MAB 266.19.1.10.5.2 and WT pancreas showed no staining (−).

Comparison of polyclonal and monoclonal antibodies. The anti-IL-22 polyclonal antibody (Example 16) was shown to be sensitive, whereas monoclonal antibody MAB 266.19.1.10.5.2 was specific. The polyclonal antibody showed positive staining on human IL-22 expressing BHK cells (+++), on murine IL-22 expressing BHK cells (+), in various human and mouse tissue samples (+), and in the islets of INS mIL-22 TG mice (+++). A greater percentage of the islets of the transgenics (vs. wild-type) contained positive staining. The staining in the transgenic islets was generally distributed throughout the islet (+++) while staining in the wild-type islets was generally limited to the periphery of the islet (+). However, this antibody also showed non-specific staining on the WT BHK negative control cells (+). MAB 266.19.1.10.5.2 showed positive staining on human L-22 expressing BHK cells (+++), on murine IL-22 expressing BHK cells (+), and in the islets of INC mIL-22 TG mice (+++) The staining in the transgenic islets was generally distributed throughout the islet (+++) while the wild-type islets demonstrated negative staining (−).

EXAMPLE 21

IL-20 is Upregulated in Human Psoriatic Skin Samples

A. RNA Samples:

Normal skin samples as well as skin from psoriasis patients were obtained. The latter included involved skin from psoriasis and from adjacent uninvolved skin. RNA was isolated from human skin samples using conventional methods. The integrity and quality of RNA samples was tested on the Agilent 2100 Bioanalyzer (Agilent Technologies, Waldbronn Germany).

B. Primers and Probes for Quantitative RT-PCR-

Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-20 expression were designed using the primer design software Primer Express™ (PE Applied Biosystems, Foster City, Calif.). The forward primer, ZC40541 (SEQ ID NO:25) and the reverse primer, ZC 40542 (SEQ ID NO:26) were used in a PCR reaction (below) at a 800 nM concentration to synthesize a 71 bp product. The corresponding IL-20 TaqMan® probe, ZC 40544 (SEQ ID NO:27) was synthesized and labeled by PE Applied Biosystems. The IL-20 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

C. Real-time Quantitative RT-PCR

Relative levels of IL-20 mRNA were determined by analyzing total RNA samples using the TaqMan EZ RT-PCR Core Reagents Kit (PE Applied Biosystems). Runoff JL-20 transcript was made to generate a standard curve used for quantitation. The curve consisted of 10-fold serial dilutions ranging from about 1e8 to 1e3 total copies of whole message for IL-20 with each standard curve point analyzed in triplicate. The total RNA samples from skin were also analyzed in triplicate for human IL-20 transcript levels and for levels of hGUS as an endogenous control. In a total volume of 25 µl, each RNA sample was subjected to TaqMan EZ RT-PCR reaction (PE Applied Biosystems) containing: approximately 25 ng of total RNA in DEPC treated water (Dnase/Rnase free); appropriate primers (approximately 800 nM ZC40541 (SEQ ID NO:25) and ZC40542 (SEQ ID NO:26); appropriate probe (approximately 100 nM ZC40544 (SEQ ID NO:27); 1× TaqMan EZ Buffer; 3 mM Manganese acetate; 300 µM each d-CTP, d-ATP, and d-GTP and 600 µM of d-UTP; rTth DNA Polymerase (0.1 U/µl); and AmpErase UNG (0.01 U/µl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-20 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize IL-20 levels. Data are shown in Table 13 below.

TABLE 13

| Skin Sample | IL-20 |
|---|---|
| Normal | 2903 |
| Uninvolved | 7233 |
| Involved | 27,695 |

Although IL-20 mRNA was detectable in skin samples from normal patients or from uninvolved areas, there was upregulation for IL-20 message in involved skin from psoriasis patients. The receptor subunits for L-20, including IL-20RA, IL-22RA (IL-22RA), and IL-20RB were expressed in human normal and diseased skin. These data support a strong disease association for IL-20 to human psoriasis.

Overexpression of IL-20 was shown in human psoriatic lesions, suggesting that IL-20 is involved in human psoriasis. Moreover, as described herein, over expression of IL-20 in transgenic mice showed epidermal thickening and immune cell involvement indicative of a psoriatic phenotype. Such in vivo data further suggests that IL-20 is involved in psoriasis. As such, antagonists to IL-20 activity, such as the anti-human-IL-22RA monoclonal antibodies of the present invention, as well as soluble receptors and antibodies thereto, and anti-IL-20 neutralizing and monoclonal antibodies, are useful therapeutically as antagonists to IL-20 in the treatment of inflammatory diseases, such as psoriasis, as well as other indications as disclosed herein.

EXAMPLE 22

IL-20 is Upregulated in Human Atopic Dermatitis Skin Samples

C. RNA Samples:

Normal skin samples as well as skin from atopic dermatitis patients were obtained. RNA was isolated from human skin samples using conventional methods. The integrity and quality of RNA samples was tested on the Agilent 2100 Bioanalyzer (Agilent Technologies, Waldbronn Germany).

D. Primers and Probes for Quantitative RT-PCR-

Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., *Genome Research* 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by the 5' to 3' nucleolytic activity of the rTth DNA Polymerase which releases the reporter dye from the probe resulting in an increase in fluorescent emission.

The primers and probes used for real-time quantitative RT-PCR analyses of IL-20 expression were designed using the primer design software Primer Express™ (PE Applied Biosystems, Foster City, Calif.). The forward primer, ZC40541 (SEQ ID NO:25) and the reverse primer, ZC 40542 (SEQ ID NO:26) were used in a PCR reaction (below) at a 800 nM concentration to synthesize a 71 bp product. The corresponding IL-20 TaqMan® probe, ZC 40544 (SEQ ID NO:27) was synthesized and labeled by PE Applied Biosystems. The IL-20 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA) (PE Applied Biosystems).

C. Real-time Quantitative RT-PCR

Relative levels of IL-20 mRNA were determined by analyzing total RNA samples using the TaqMan EZ RT-PCR Core Reagents Kit (PE Applied Biosystems). Runoff IL-20 transcript was made to generate a standard curve used for quantitation. The curve consisted of 10-fold serial dilutions ranging from about 1e8 to 1e3 total copies of whole message for IL-20 with each standard curve point analyzed in triplicate. The total RNA samples from skin were also analyzed in triplicate for human IL-20 transcript levels and for levels of hGUS as an endogenous control. In a total volume of 25 µl, each RNA sample was subjected to TaqMan EZ RT-PCR reaction (PE Applied Biosystems) containing: approximately 25 ng of total RNA in DEPC treated water (Dnase/Rnase free); appropriate primers (approximately 800 nM ZC40541 (SEQ ID NO:25) and ZC40542 (SEQ ID NO:26); appropriate probe (approximately 100 nM ZC40544 (SEQ ID NO:27); 1× TaqMan EZ Buffer; 3 mM Manganese acetate; 300 µM each d-CTP, d-ATP, and d-GTP and 600 µM of d-UTP; rTth DNA Polymerase (0.1 U/µl); and AmpErase UNG (0.01 U/µl). PCR thermal cycling conditions were as follows: an initial UNG treatment step of one cycle at 50° C. for 2 minutes; followed by a reverse transcription (RT) step of one cycle at 60° C. for 30 minutes; followed by a deactivation of UNG step of one cycle at 95° C. for 5 minutes; followed by 40 cycles of amplification at 94° C. for 20 seconds and 60° C. for 1 minute.

Relative IL-20 RNA levels were determined by using the Standard Curve Method as described by the manufacturer, PE Biosystems (User Bulletin #2: ABI Prism 7700 Sequence Detection System, Relative Quantitation of Gene Expression, Dec. 11, 1997). The hGUS measurements were used to normalize IL-20 levels.

IL-20 mRNA was detectable at a low level (about 800 copies) in skin samples. In contrast, there was upregulation for IL-20 message in skins from atopic dermatitis patients (about 8600 copies). The receptor subunits for IL-20, including IL-20RA), IL-22RA, and IL-20RB are expressed in human normal and diseased skin. These data support a strong disease association for IL-20 to human atopic dermatitis. Overexpression of IL-20 was shown in human atopic dermatitis skins, suggesting that IL-20 is involved in human atopic dermatitis. Moreover, as described herein, over expression of IL-20 in transgenic mice showed epidermal thickening and immune cell involvement indicative of an atopic dermatitis phenotype. Such in vivo data further suggests that IL-20 is involved in atopic dermatitis. As such, antagonists to IL-20 activity, such as the anti-human-IL-22RA monoclonal antibodies of the present invention, as well as soluble receptors and antibodies thereto, and anti-IL-20 neutralizing and monoclonal antibodies, are useful therapeutically as antagonists to IL-20 in the treatment of inflammatory diseases, such as atopic dermatitis, as well as other indications as disclosed herein.

EXAMPLE 23

Up-regulation of IL-8 by IL-20

Normal Human Epidermal neonatal keratinocytes (NHEK) (from Clonetics) at passage 2 were plated and grown to confluency in 12 well tissue culture plates. KGM (Keratinocyte growth media) was purchased from Clonetics. When cells reached confluency, they were washed with KGM media minus growth factors=KBM (keratinocyte basal media). Cells were serum starved in KBM for 72 hours prior to the addition of test compounds. Thrombin at 1 I.U./mL and trypsin at 25 nM were used as positive controls. One mL of media/well was added. KBM only was used as the negative control.

IL-20 was made up in KBM media and added at varying concentrations, from 2.5 µg/ml down to 618 ng/mL in a first experiment and from 2.5 µg/mL down to 3 ng/mL in a second experiment.

Cells were incubated at 37° C., 5% $CO_2$ for 48 hours. Supernatants were removed and frozen at −80° C. for several days prior to assaying for IL-8 and GM-CSF levels. Human IL-8 Immunoassay kit # D8050 (RandD Systems, Inc.) and human GM-CSF Immunoassay kit # HSGMO (RandD Systems, Inc.) were used to determine cytokine production following manufacturer's instructions.

The results indicated that the expression of IL-8 and GM-CSF were induced by IL-20.

EXAMPLE 24

Up-regulation of Inflammatory Cytokines by IL-20

The human keratinocyte cell line, HaCaT was grown at 37° C. to several days post-confluence in T-75 tissue culture flasks. At this point, normal growth media (DMEM+10% FBS) was removed and replaced with serum-free media. Cells were then incubated for two days at 37° C. DMEM was then removed and four flasks of cells per treatment were treated with one of each of the following conditions for four hours at 37° C.: recombinant human (rh) IL-1 alpha at 5 ng/mL, rh IL-1 alpha at 20 ng/mL, rh IL-1 alpha at 5 ng/mL+ IL-20 at 1 µg/mL, IL-20 at 1 µg/mL, or rh IL-10 at 10 ng/mL.

Following cytokine treatment, media was removed and cells were lysed using a guanidium thiocyanate solution. Total RNA was isolated from the cell lysate by an overnight spin on a cesium chloride gradient. The following day, the RNA pellet was resuspended in a TE/SDS solution and ethanol precipitated. RNA was then quantitated using a spectrophotometer, followed by a DNase treatment as per Section V.B. of Clontech's Atlas™ cDNA Expression Arrays User Manual (version PT3140-1/PR9x390, published Nov. 5, 1999). Quality of RNA samples was verified by purity calculations based on spec readings, and by visualization on agarose gel. Genomic contamination of the RNA samples was ruled out by PCR analysis of the beta-actin gene.

Clontech's protocols for polyA+ enrichment, probe synthesis and hybridization to Atlas™ arrays were followed (see above, plus Atlas™ Pure Total RNA Labeling System User Manual, PT3231-1/PR96157, published Jun. 22, 1999). Briefly, polyA+RNA was isolated from 50 mg of total RNA using streptavidin coated magnetic beads (by Clontech, Paolo Alto, Calif.) and a magnetic particle separator. PolyA+ RNA was then labeled with $^{alpha 32}$P-dATP via RT-PCR. Clontech CDS primers specific to the 268 genes on the Atlas™ human cytokine/receptor array (Cat. #7744-1) were used in the reaction. Labeled probe was isolated using column chromatography and counted in scintillation fluid.

Atlas™ arrays were pre-hybridized with Clontech ExpressHyb plus 100 mg/mL heat denatured salmon sperm DNA for at least thirty minutes at 68° C. with continuous agitation. Membranes were then hybridized with $1.9 \times 10^6$ CPM/mL (a total of $1.14 \times 10^7$ CPM) overnight at 68° C. with continuous agitation. The following day, membranes were washed for thirty minutesx4 in 2xSSC, 1% SDS at 68° C., plus for thirty minutesx1 in 0.1x SSC, 0.5% SDS at 68° C., followed by one final room temperature wash for five minutes in 2x SSC. Array membranes were then placed in Kodak plastic pouches sealed and exposed to a phosphor imager screen overnight at room temperature. The next day, phosphor screens were scanned on a phosphor imager and analyzed using Clontech's AtlasImage™ 1.0 software.

Genes Up-regulated by IL-20:
1. Tumor necrosis factor (TNF) was up-regulated 1.9-2.4 fold by IL-20.
2. Placental growth factors 1 & 2 (PLGF) were up-regulated 1.9-2.0 fold by IL-20.
3. Coagulating factor II receptor was up-regulated 2.0-2.5 fold by IL-20.
4. Calcitonin receptor was up-regulated 2.2-2.3 fold by IL-20.
5. TNF-inducible hyaluronate-binding protein TSG-6 was up-regulated 2.1-2.2 fold by IL-20.
6. Vascular endothelial growth factor (VEGF) receptor-1 precursor, tyrosine-protein kinase receptor (FLT-1) (SFLT) was up-regulated 2.1-2.7 fold by IL-20.
7. MRP-8 (calcium binding protein in macrophages MIF-related) was up-regulated 2.9-4.1 fold by IL-20.
8. MRP-14 (calcium binding protein in macrophages MIF-related) was up-regulated 3.0-3.8 fold by IL-20.
9. Relaxin H2 was up-regulated 3.14 fold by IL-20.
10. Transforming growth factor beta (TGFβ) receptor m 300 kDa was up-regulated 2.4-3.6 fold by IL-20.

Genes Showing Synergy with IL-20 +IL-1 Treatment:
1. Bone morphogenic protein 2a was up-regulated 1.8 fold with IL-20 treatment alone, 2.5 fold with IL-1 treatment alone, and 8.2 fold with both IL-20 and IL-1 treatment together.
2. MRP-8 was up-regulated 2.9 fold with IL-20 treatment alone, 10.7 fold with IL-1 treatment alone and 18.0 fold with both IL-20 and IL-1 treatment together.
3. Erythroid differentiation protein (EDF) was up-regulated 1.9 fold with IL-20 treatment alone, 9.7 fold with IL-1 treatment alone and 19.0 fold with both IL-20 and IL-1 treatment together.
4. MRP-14 (calcium binding protein in macrophages, MIF related) was up-regulated 3.0 fold with IL-20 treatment alone, 12.2 fold with IL-1 treatment alone and 20.3 fold with both IL-20 and IL-1 treatment together.
5. Heparin-binding EGF-like growth factor was up-regulated 2.0 fold with IL-20 treatment alone, 14 fold with IL-1 treatment alone and 25.0 fold with both IL-20 and IL-1 treatment together.
6. Beta-thromboglobulin-like protein was up-regulated 1.5 fold with IL-20 treatment alone, 15 fold with IL-1 treatment alone and 27 fold with both IL-20 and IL-1 treatment together.
7. Brain-derived neurotrophic factor (BDNF) was up-regulated 1.7 fold with IL-20 treatment alone, 25 fold with IL-1 treatment alone and 48 fold with both IL-20 and IL-1 treatment together.
8. Monocyte chemotactic and activating factor MCAF was up-regulated 1.3 fold with IL-20 treatment alone, 32 fold with IL-1 treatment alone and 56 fold with both IL-20 and IL-1 treatment together.

EXAMPLE 25

IL-20 Transgenic Phenotype

Both human and mouse IL-20 were overexpressed in transgenic mice using a variety of promoters. The liver-specific mouse albumin promoter, directing expression of human IL-20, was used initially in an attempt to achieve circulating levels of protein. Subsequent studies were conducted using the keratin 14 (K14) promoter, which primarily targets expression to the epidermis and other stratified squamous epithelia; the mouse metallothionein-1 promoter, which gives a broad expression pattern; and the EµLCK promoter, which drives expression in cells of the lymphoid lineage. Similar results were obtained in all four cases, possibly because these promoters all give rise to circulating levels of IL-20.

In all cases, transgenic pups expressing the IL-20 transgene were smaller than non-transgenic littermates, had a shiny appearance with tight, wrinkled skin and died within the first few days after birth. Pups had milk in their stomachs indicating that they were able to suckle. These mice had swollen extremities, tail, nostril and mouth regions and had difficulty moving. In addition, the mice were frail, lacked visible adipose tissue and had delayed ear and toe development. Low expression levels in liver (less than 100 mRNA molecules/cell) were sufficient for both the neonatal lethality and skin abnormalities. Transgenic mice without a visible phenotype either did not express the transgene, did not express it at detectable levels, or were mosaic.

Histologic analysis of the skin of the IL-20 transgenic mice showed a thickened epidermis, hyperkeratosis and a compact stratum corneum compared to non-transgenic littermates Serocellular crusts (scabs) were observed occasionally. Electron microscopic (EM) analysis of skin from transgenic mice showed intramitochondrial lipid inclusions, mottled keratohyaline granules, and relatively few tonofilaments similar to that observed in human psoriatic skin and in mouse skin disease models. In addition, many of the transgenic mice had apoptotic thymic lymphocytes. No other abnormalities were detected by histopathological analysis. These histological and EM results support and extend the observed gross skin alterations.

EXAMPLE 26

Construction of Expression Vector for Expression of Soluble Human IL-22RA-muFc

A human IL-22RA soluble receptor-muFc fusion (denoted as IL-22RA-C(mG2a) containing the extracellular domain of IL-22RA fused to the murine gamma 2a heavy chain Fc region (mG2a), was prepared. An expression plasmid containing IL-22RA-C(mG2a) was constructed via homologous recombination using two separate DNA fragments and the expression vector pZMP40. Fragments of polynucleotide sequence of IL-22RA (SEQ ID NO:1), and mG2a SEQ ID NO:39 were generated by PCR amplification using the following primers: (a) IL-22RA primers ZC45,593 (SEQ ID NO:28), and ZC45,592 (SEQ ID NO:29); and (b) mG2a primers ZC45,591 (SEQ ID NO:30), and ZC45,594 (SEQ ID NO:31).

The first fragment contained the IL-22RA extracellular domain coding region, which was made using an IL-22RA polynucleotide (e.g., SEQ ID NO:1) as the template. The first fragment included a 5' overlap with a partial pZMP40 vector sequence, the IL-22RA segment, and a 3' overlap containing a linker sequence and partial mG2a sequence. PCR conditions: 1 cycle, 94° C., 5 minutes; 35 cycles, 94° C., 1 minute, followed by 55° C., 2 minutes, followed by 72° C., 3 minutes; 1 cycle, 72° C., 10 minutes.

The second fragment included a 5' overlap with a linker sequence and partial IL-22RA sequence, the mG2a segment, and a 3' overlap containing a partial pZMP40 vector sequence. The murine gamma 2a heavy chain Fc region (mG2a) (SEQ ID NO:39) was generated from a clone of murine Ig gamma 2a heavy chain cDNA. The mG2a contains the hinge, $C_H2$, and $C_H3$ domains of the murine immunoglobulin gamma 2a heavy chain constant region. PCR conditions: 1 cycle, 94° C., 5 minutes; 35 cycles, 94° C., 1 minute, followed by 55° C., 2 minutes, followed by 72° C., 3 minnutes; 1 cycle, 72° C., 10 minutes.

The PCR reaction mixtures were run on a 1% agarose gel and a band corresponding to the sizes of the inserts were gel-extracted using a QIAquick™ Gel Extraction Kit (Qiagen).

The plasmid pZMP40, which was cut with BglII, was used in a three-way recombination with both of the PCR insert fragments. Plasmid pZMP40 is a mammalian expression vector containing an expression cassette having the MPSV promoter, and multiple restriction sites for insertion of coding sequences; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae. Plasmid pZMP40 was constructed from pZMP21 (deposited at the American Type Culture Collection, 10801 University Boulevard, Manassas, Va. 20110-2209, and designated No. PTA-5266) by addition of several restriction enzyme sites to the polylinker.

One hundred microliters of competent yeast (S. cerevisiae) cells were independently combined with 10 µl of the insert DNA and 100 ng of cut pZMP40 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 µF. Six hundred µl of 1.2 M sorbitol was added to the cuvette, and the yeast was plated in a 100-µl and 300 µl aliquot onto two URA-D plates and incubated at 30° C. After about 72 hours, the Ura$^+$ yeast transformants from a single plate were resuspended in 1 ml H$_2$O and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 µl acid-washed glass beads and 300 µl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 µl ethanol (EtOH) and 30 µl 3M sodium acetate, followed by centrifugation for 30 minutes at maximum speed. The tube was decanted and the pellet was washed with 1 mL of 70% ethanol. The tube was decanted and the DNA pellet was resuspended in 30 µl TE.

Transformation of electrocompetent E. coli host cells (DH12S) was done using 5 µl of the yeast DNA prep and 50 µl of cells. The cells were electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was added and then the cells were plated in a 50 µl and 200 µl aliquot on two LB AMP plates (LB broth (Lennox), 1.8% Bacto™ Agar (Difco), 100 mg/L Ampicillin).

The inserts of three clones for the construct was subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions.

EXAMPLE 27

Expression and Purification of Human Soluble IL-22RA-muFc Polypeptide

Three sets of 200 µg of the IL-22RA-C(mG2a) construct (Example 22) were each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 µl of PF-CHO media in a sterile environment, and allowed to incubate at 60° C. for 30 minutes. 5E6 APFDXB11 cells were spun down in each of three tubes and were resuspended using the DNA-media solution. The DNA/cell mixtures were placed in a 0.4 cm gap cuvette and electroporated using the following parameters: 950 µF, high capacitance, and 300 V. The contents of the cuvettes were then removed, pooled, and diluted to 25 mLs with PF-CHO media and placed in a 125 mL shake flask. The flask was placed in an incubator on a shaker at 37° C., 6% $CO_2$, and shaking at 120 RPM.

The cell line was subjected to nutrient selection followed by step amplification to 100 nM methotrexate (MTX), then to 500 nM MTX, and finally to 1 µM MTX. Step amplification was followed by a CD8 cell sort. The CD8 cell sort was accomplished by taking a stable 1 µM MTX amplified pool and staining approximately 5E6 cells with a monoclonal FITC anti-CD8 antibody (BD PharMingen, cat# 30324X) using manufacturers recommended concentration. The stained cells were processed and sorted on a FACS Vantage (BD) flow cytometer. The top 5% of cells were collected and outgrown. Expression was confirmed by western blot, and the cell line was scaled-up and protein purification using standard methods followed.

EXAMPLE 28

Neutralization of huIL-22RA by Sera from Mice Immunized with huL22RA-mG2a

A. Cell-based Neutralization Assay to Test for Inhibition of IL-20 and/or IL-22.

The factor-dependent pre-B cell line BaF3 co-transfected with IL-22RA and IL-20RB (pDIRS1) (BAF/IL-22RA/IL-20RB cells; Example 38) was used to assess neutralization potential of anti-IL-22RA antibodies by antagonizing IL-20 on the IL-22RA/IL-20RB receptor. Similarly, BaF3 co-transfected with IL-22RA and IL-10RB (CRF2-4) (BAF/IL-22RA/CRF2-4 cells; Example 2) was used to assess neutralization potential of anti-IL-22RA antibodies by antagonizing IL-22 on the IL-22RA/IL10RB receptor. Proliferation in the presence of IL-20 or IL22 on its respective receptor-expressing cell line, and inhibition of such proliferation in the presence of the antagonist antibodies, was assessed using an Alamar blue assay as described in Example 3. Inhibition of proliferation on these cells is indicative of neutralizing activity in this assay.

B. Anti-IL-22RA Serum Neutralizes Both IL-20 and IL-22 in Cell-based Neutralization Assay.

Using the assay described in Example 28A, serum from IL-22RA knockout mice immunized with huIL-22RA-muG2a (Example 30(A)(1)) was added as a serial dilution at 1%, 0.5%, 0.25%, 0.13%, 0.06%, 0.03%, 0.02%, and 0%. The assay plates were incubated at 37□C, 5% $CO_2$ for 4 days at which time Alamar Blue (Accumed, Chicago, Ill.) was added at 20□l/well. Plates were again incubated at 37□C, 5% $CO_2$ for 16 hours. Alamar Blue gives a fluorometric readout based on number of live cells, and is thus a direct measurement of cell proliferation in comparison to a negative control. Plates were read on the Wallac Victor 2 1420 Multilabel Counter (Wallac, Turku, Finland) at wavelengths 530 (Excitation) and 590 (Emission). Results showed that serum from all seven immunized animals could neutralize signaling of both huIL-22 and huIL20 through huIL-22RA. For example, at the 1% concentration, serum from five animals (16517, 16518, 16519, 16520, and 16527) completely neutralized proliferation induced by huIL-22, with the inhibition of proliferation decreasing in a dose dependent fashion at the lower concentrations. Moreover, at the 1% concentration, serum from the other two animals (16471 and 16701) inhibited about 90% of the proliferation induced by huIL-22, with the inhibition of proliferation decreasing in a dose dependent fashion at the lower concentrations. Similarly, at the 1% and 0.5% concentrations, serum from five animals (16517, 16518, 16519, 16520, and 16527) completely neutralized proliferation induced by huIL-20, with the inhibition of proliferation decreasing in a dose dependent fashion at the lower concentrations. Moreover, at the 1% concentration, serum from animal 16701 completely neutralized proliferation induced by huIL-20, with the inhibition of proliferation decreasing in a dose dependent fashion at the lower concentrations. At the 1% concentration, serum from animal 16471 neutralized about 95% of the proliferation induced by huIL-20, with the inhibition of proliferation, decreasing in a dose dependent fashion at the lower concentrations. Thus, sera from all seven animals were able to neutralize the proliferation induced by either IL-20 or IL-22 through the huIL-22RA receptor. These results further demonstrated that antibodies to IL-22RA could indeed antagonize the activity of the pro-inflammatory ligands, IL-20 and IL-22 at low concentrations.

These results provided additional evidence that effectively blocking IL-22RA activity by binding, blocking, inhibiting, reducing, antagonizing or neutralizing IL-20 or IL-22 activity (individually or together), for example via a neutralizing monoclonal antibody to IL-22RA of the present invention, could be advantageous in reducing the effects of IL-20 and IL-22 (alone or together) in vivo and may be reduce IL-20 and/or IL-22-induced inflammation, such as that seen in IL-20-induced skin effects, as well as IL-22-induced skin effects, for example in psoriasis, IBD, colitis, or other inflammatory diseases induced by IL-20, and or IL-22 including IBD, arthritis, asthma, psoriatic arthritis, colitis, inflammatory skin conditions, and atopic dermatitis.

EXAMPLE 29

Generation of P815/hIL-22RA Cells and Immunization of Mice

A. P815/hIL-22RA Cell Generation and Injection into Mice for Generation of Anti-hIL-22RA Antibodies:

WT P815 Cells (ATCC No. TIB-64) were transfected with a plasmid vector containing the hIL-22RA cDNA sequence (e.g., SEQ ID NO:1) and a selectable puromycin-resistance marker, using Fugene Reagent according to the manufacturer's protocol (Roche, Indianapolis, Ind.). Cells were placed under Puromycin selection 48 hours following transfection. Puromycin-resistant transfectants were cloned by limiting dilution, and screened for their level of hIL-22RA cell surface expression by flow cytometry, using biotinylated human IL-22 (huIL-22-biotin). Briefly, cells were incubated with 5 ug/ml huIL-22-biotin for 30 minutes on ice and then washed. Binding of huIL-22-biotin to the cells was then detected using PE-labeled streptavidin at 1:500. Cells were analyzed on a Facscan flow cytometer using Cellquest software. (Becton Dickinson, San Jose, Calif.).

The selected P815/IL-22RA cell clone was grown up and then harvested for injection. Cells were collected, washed three times in PBS, counted, resuspended at $1 \times 10^8$ cells per milliliter, and irradiated with 10,000 rads. The cell suspension was then transferred to a 1 ml syringe, and injected by the intra-peritoneal route into DBA/2 Mice. Mice were boosted in an identical manner 3 weeks later and sera were screened for binding to hIL-22RA transfectant cell line. Briefly, sera were diluted 1:100 in Facs buffer (HBSS, 2% BSA, 0.02% NaN$_3$), and then incubated with Fc-blocked 293 human kidney cells over-expressing hIL-22RA. Binding of anti-IL-22RA antibodies to the cells was then detected using fluorescein-conjugated Goat-anti-Mouse IgG diluted to 1:200. (Southern Biotech, Birmingham, Ala.) Cells were analyzed as described previously. Mice were boosted again a total of 3 more times and sera were screened as described. Two mice were selected for hybridoma fusion, using standard methods in the art for generation of monoclonal antibodies (Example 25), based on the level of their serum binding to the hIL-22RA transfectants.

The above method is also used for generation of P815 cells expressing heterodimeric IL-22RA receptors, such as IL-22RA/CRF2-4 (P815/IL-22RA/CRF2-4 cells), IL-22RA/pDIRS1 (P815/IL-22RA/pDIRS1 cells), or IL-22RA/CRF2-4/pDIRS1 (P815/IL-22RA/CRF2-4/pDIRS1 cells), for example to immunize mice for the generation of monoclonal antibodies against IL-22RA and IL-22RA-comprising heterodimeric receptors.

EXAMPLE 30

Generation of Murine Anti-human IL-22RA (IL-22RA) mAbs

A. Immunization for Generation of Anti-IL-22RA Antibodies:

(1) Using Soluble IL-22RA-muFc

Six to twelve week old IL-22RA knockout mice (Example 26) were immunized by intraperitoneal injection with 25-50 ug of soluble human IL-22RA-muFc protein (Example 23) mixed 1:1 (v:v) with Ribi adjuvant (Sigma) on a biweekly schedule. Seven to ten days following the third immunization, blood samples were taken via retroorbital bleed, the serum harvested and evaluated for its ability to inhibit the binding of IL-22 or both IL-20 and IL-22 to IL-22RA in neutralization assays (e.g., described herein) and to stain IL-22RA transfected versus untransfected 293 cells in a FACS staining assay. Mice continued to be immunized and blood samples taken and evaluated as described above until neutralization titers reached a plateau. At that time, mice with the highest neutralization titers were injected intravascularly with 25-50 ug of soluble IL-22RA-Fc protein in PBS. Three days later, the spleen and lymph nodes from these mice were harvested and used for hybridoma generation, for example using mouse myeloma (P3-X63-Ag8.653.3.12.11) cells or other appropriate cell lines in the art, using standard methods known in the art (e.g., see Kearney, J. F. et al., *J Immunol.* 123:1548-50, 1979; and Lane, R. D. *J Immunol Methods* 81:223-8, 1985).

(2) Using P815 Transfectants that Express the IL-22RA Receptor.

Six to ten week old female DBA/2 mice are immunized by intraperitoneal injection of 1×10$^5$ live, transfected P815 cells, for example P815/IL-22RA cells, P815/IL-22RA/CRF2-4, P815/IL-22RA/pDIRS1 or P815/IL-22RA/CRF2-4/pDIRS1 cells (Example 24) (e.g., 0.5 ml at a cell density of 2×10$^5$ cells/ml). Prior to injection, the cells are maintained in the exponential growth phase. For injection the cells are harvested, washed three times with PBS and then resuspended in PBS to a density of 2×10$^5$ cells/ml. In this model, the mice develop an ascites tumor within 2-3 weeks and progress to death by 4-6 weeks unless an immune response to the transfected target antigen has been mounted. At three weeks mice with no apparent abdominal swelling (indicative of ascites) are re-immunized as above at 2-3 week intervals. Seven to ten days following the second immunization, blood samples are taken via retroorbital bleed, the serum harvested and evaluated for its ability to inhibit the binding of IL-22 or both IL-20 and IL-22 to IL-22RA in neutralization assays (e.g., described herein) and to stain IL-22RA transfected versus untransfected 293 cells in a FACS staining assay. Mice continue to be immunized and blood samples taken and evaluated as described above until neutralization titers reach a plateau. At that time, the mice with the highest neutralization titers are injected intraperitonealy with 1×10$^5$ live, transfected P815 cells. Four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., supra.; and Lane, R. D. supra.).

An alternative to the above immunization scheme with live, transfected P815 cells involves intraperitoneal injection of 1-5×10$^6$ irradiated, transfected cells every 2-3 weeks. In this approach, no animals develop and die of ascites. Instead, animals are monitored for a neutralizing immune response to IL-22RA in their serum as outlined above, starting with a bleed after the second immunization. Once neutralization titers have reached a maximal level, the mice with highest titers are given a pre-fusion, intraperitoneal injection of 5×10$^6$ irradiated cells and four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., supra.; and Lane, R. D. supra.).

B. Screening the Hybridoma Fusions for Antibodies that Bind IL-22RA and Inhibit the Binding of IL-22 to IL-22RA:

Two different primary screens were performed on the hybridoma supernatants at 8-10 days post-fusion. For the first assay, antibodies in supernatants were tested for their ability to bind to plate bound soluble human IL-22RA-muFc protein by ELISA using HRP-conjugated goat anti-mouse kappa and anti-lambda light chain second step reagents to identify bound mouse antibodies. To demonstrated specificity for the IL-22RA portion of the IL-22RA-muFc protein, positive supernatants in the initial assay were evaluated on an irrelevant protein fused to the same murine Fc region (mG2a). Antibody in those supernatants that bound to IL-22RA-muFc and not the irrelevant muFc containing fusion protein were deemed to be specific for IL-22RA. For the second assay, antibodies in all hybridoma supernatants were evaluated by ELISA for their ability to inhibit the binding of biotinylated human IL-22 to plate bound IL-22RA-muFc.

All supernatants containing antibodies that bound specifically to IL-22RA, whether they inhibited the binding of IL-22 to IL-22RA or not in the ELISA assay, were subsequently tested for their ability to inhibit the binding (and concomitant pro-proliferative effect) of IL-20 or IL-22 to IL-22RA/IL-20RB and IL-22RA/CRF2-4 transfected Baf3 cells, respectively. All supernatants that were neutralization positive in either the IL-22 inhibition assay or both the IL-20 and IL-22 inhibition assays were subsequently evaluated for their ability to stain IL-22RA transfected versus untransfected Baf3 cells by FACS analysis. This analysis was designed to confirm that inhibition of IL-22 binding to IL-22RA/CRF2-4, or IL-20 binding to IL-22RA/IL-20RB, was indeed due to an antibody that specifically binds the IL-22RA receptor. Additionally, since the FACS analysis was performed with an anti-IgG second step reagent, specific FACS positive results indicate that the neutralizing antibody was likely to be of the IgG class. By these means, a master well was identified that bound IL-22RA in the plate bound ELISA, inhibited the binding of IL-22 to IL-22RA in the ELISA based inhibition assay, blocked the interaction of IL-20 and IL-22 with IL-22RA/IL-20RB and IL-22RA/CRF2-4 transfected Baf3 cells (Example 28), respectively, and was strongly positive for the staining of both IL-22RA/IL-20RB and IL-22RA/CRF2-4 transfected Baf3 cells with an anti-mouse IgG second step reagent.

D. Cloning Anti-IL-22RA Specific Antibody Producing Hybridomas:

A hybridoma producing an anti-IL-22RA mAb that cross-neutralized the binding of IL-20 and IL-22 to appropriately transfected BaF3 cells was cloned by a standard low-density dilution (less than 1 cell per well) approach. Approximately 5-7 days after plating, the clones were screened by ELISA on plate bound human IL-22RA-muFc followed by a retest of positive wells by ELISA on irrelevant muFc containing fusion protein as described above. Selected clones, whose supernatants bound to IL-22RA-muFc and not the irrelevant muFc containing fusion protein, were further confirmed for specific antibody activity by repeating both neutralization assays as well as the FACS analysis. All selected IL-22RA antibody positive clones were cloned a minimum of two times to help insure clonality and to assess stability of antibody production. Further rounds of cloning were performed and screened as described until, preferably, at least 95% of the resulting clones were positive for neutralizing anti-IL-22RA antibody production.

E. Biochemical Characterization of the Molecule Recognized by Anti-IL-22RA mAbs:

Biochemical confirmation that the target molecule, IL-22RA, recognized by the putative anti-IL-22RA mAbs is indeed IL-22RA are performed by standard immunoprecipitation followed by SDS-PAGE analysis or western blotting procedures, both employing soluble membrane preparations from IL-22RA transfected versus untransfected Baf3 cells. Moreover, soluble membrane preparations of non-transfected cell lines that express IL-22RA are used show that the mAbs recognize the native receptor chain as well as the transfected one. Alternatively, the mAbs are tested for their ability to specifically immunoprecipitate or western blot the soluble IL-22RA-muFc protein.

EXAMPLE 31

Neutralization of huL22RA by Sera from Mice Injected with P815 Cells Transfected with huL22RA Using the cell based neutralization assay described in Example 28, Serum from mice injected with live huIL-22RA transfected P815 cells (Example 30.A.2) was added as a serial dilution at 1%, 0.5%, 0.25%, 0.13%, 0.06%, 0.03%, 0.02%, and 0%. The assay plates were incubated at 37☐C, 5% $CO_2$ for 4 days at which time Alamar Blue (Accumed, Chicago, Ill.) was added at 20☐l/well. Plates were again incubated at 37☐C, 5% $CO_2$ for 16 hours. Results showed that serum from four of the animals could neutralize signalling of both huIL-22 and huIL20 through huIL-22RA.

At the 1% concentration, serum from six animals (7125, 7127, 7128, 7118, 7124 and 7117) neutralized between 50% and 80% of the proliferation induced by huIL-22, with the inhibition of proliferation decreasing in a dose dependent fashion at the lower concentrations. Moreover, at the 1% concentration, serum from four animals (7125, 7127, 7118, and 7117) neutralized between 40% and 70% of the proliferation induced by huIL20, with the inhibition of proliferation decreasing in a dose dependent fashion at the lower concentrations. These results further demonstrated that antibodies to IL-22RA could indeed antagonize the activity of the pro-inflammatory ligands, IL-20 and IL-22 at low concentrations.

These results provided additional evidence that effectively blocking IL-22RA activity by binding, blocking, inhibiting, reducing, antagonizing or neutralizing IL-20 or IL-22 activity (individually or together), for example via a neutralizing monoclonal antibody to IL-22RA of the present invention, could be advantageous in reducing the effects of IL-20 and IL-22 (alone or together) in vivo and may be reduce IL-20 and/or IL-22-induced inflammation, such as that seen in IL-20-induced skin effects, as well as IL-22-induced skin effects, for example in psoriasis, IBD, colitis, or other inflammatory diseases induced by IL-20, and or IL-22 including IBD, arthritis, asthma, psoriatic arthritis, colitis, inflammatory skin conditions, and atopic dermatitis.

EXAMPLE 32

Phenotype of IL-22RA Knockout Mice

A. Generation of Mice Carrying Genetic Modifications

1. Generation of Transgenic Mice Expressing Murine IL-20 with a Neonate Shine a). Construct for Expressing Murine IL-20 from the K14 Promoter.

In order to investigate biological function of IL-20 in vivo, a transgenic construct was made, in which murine IL-20 was driven by human K14 promoter (also see, Example 21). Oligonucleotides were designed to generate a PCR fragment containing a consensus Kozak sequence and the murine IL-20 coding region. These oligonucleotides were designed with an FseI site at the 5' end and an AscI site at the 3' end to facilitate cloning into pRSK14, a standard transgenic vector, containing a human keratinocyte and epithelial cell-specific promoter.

PCR reactions were carried out with about 200 ng murine IL-20 template (SEQ ID NO:33) and oligonucleotides designed to amplify the full-length of the IL-20 (SEQ ID NO:34). PCR reaction conditions were determined using methods known in the art. PCR products were separated by agarose gel electrophoresis and purified using a QiaQuick™ (Qiagen) gel extraction kit. The isolated, correct sized DNA fragment was digested with FseI and AscI (Boerhinger-Mannheim), ethanol precipitated and ligated into pRSK14, previously digested with FseI and AscI. The pRSK14 plasmid, designed for expressing a gene of interest in keratinocyte and epithelial in transgenic mice, contains an expression cassette flanked by about 3 Kb human keratin specific K14 promoter.

About one microliter of ligation reaction was electroporated into DH10B ElectroMax™ competent cells (GIBCO BRL, Gaithersburg, Md.) according to manufacturer's direction and plated onto LB plates containing 100 µg/ml ampicillin, and incubated overnight. Colonies were picked and grown in LB media containing 100 µg/ml ampicillin. Miniprep DNA was prepared from the picked clones and screened for the murine IL-20 insert by restriction digestion FseI and AscI combined, and subsequent agarose gel electrophoresis.

The TG construct with correct cDNA inserts were confirmed by sequencing analysis. Maxipreps of the correct pRSK14-murine IL-20 were performed.

b) Generation and Characterization of K14 IL-20 Transgenic Mice.

A NotI fragment of about 4 Kb in length was isolated from the transgenic (TG) vector containing 5' and 3' flanking sequences of the keratin specific K14 promoter, mouse IL-20 (SEQ ID NO:33; polypeptide shown in SEQ ID NO:34), the Gormon intron, IL-20 cDNA and the human growth hormone polyA signal sequences. It was used for microinjection into fertilized B6C3f1 (Taconic, Germantown, N.Y.) murine oocytes. Microinjection and production of transgenic mice were produced as described in Hogan, B. et al. *Manipulating the Mouse Embryo*, $2^{nd}$ ed., Cold Spring Harbor Laboratory Press, NY, 1994.

A TaqMan™ RT-PCR reactiori was used to quantitate expression of TG RNA by using PCR primers specific to the human growth hormone polyA signal portion of the transgene.

All TG constructs expressing IL-20 exhibit a high rate of paranatal mortality, and the TG pups that were born typically exhibits a "shiny" phenotype. The shiny appearance of the neonate pups appeared to be associated with a stiffening of the skin, as if they were drying out, resulting in a reduction of proper nursing. Their movements become stiffened in general. HistoPathologically the shiny pups have a thickened epidermis and the keratin layer was compacted. Most of these shiny founder pups died within the first 5 days, and the surviving and weaned pups were in general not expressing the transgene (per transcript analysis), or they were chimeric (per low transmittion of the transgene to the offspring).

One line expressing murine IL-20, driven by the K14 promotor, was established. The expression level in the skin and the thymus was low, and all the neonates were born with a shiny phenotype. In general this line had 20% TG offspring, indicating 50-60% of the transgenic pups die in utero. (In a Hemizygous mating 50% of the offspring should be TG.)

2. Generation of Mice with Ablated IL-22RA Expression; IL-22RA Knockout Mice a). Generation of Knockout (KO) Construct for Murine IL-22RA.

To further study biological function of IL-22RA in vivo, a mouse Knockout (KO) strain was created to ablate IL-22RA expression. First, Mouse IL-22RA cDNA probes were used to screen a mouse 129/SvJ genomic BAC library. Clones containing IL-22RA genomic locus were identified and characterized. Murine IL-22RA polynucleotide is shown in SEQ ID NO:41 and polypeptide in SEQ ID NO:42.

To create a knockout construct for ablation of IL-22RA, a Knockout vector was made by using ET cloning technique (Zhang et al. 1998. A new logic for DNA engineering using recombination in *E. coli*. Nat. Genet. Vol. 20:123-8). Briefly, the KO vector contains a 1.8 kb 5' arm (short arm), an IRES-LacZ/MClneo Selectable marker, and a 10 Kb 3' arm (long arm) of IL-22RA gene. In the KO vector, exons 2, 3 and 4 as well as Introns 2 and 3 of IL-22RA genomic sequence were replace by the IRES-LacZ/MC1neo Selectable marker so that a deletion of about 4.4 Kb was generated by homologous recombination in ES cells.

After linearization of the KO vector by restriction enzyme PmeI, it was electroporated into 129/SvJ ES cells. Selection of homologous recombination events, as well as identification of recombinant ES clones were performed as described in Robertson, E. J. et al. *Teratocarcinomas and Embryonic Stem Cells: A Practical Approach*, $2^{nd}$ ed., IRL Press Limited, Oxford, 1987.

b). Creation and Analysis of Mice with Ablated IL-22RA Expression.

Positive ES clones, in which deletion of Exons 2-4 and Introns 2-3 of IL-22RA genomic locus occurs, were expanded. They were injected into balstocysts of C57B1/6j mice. After brief re-expansion of the injected blastocysts, they were introduced into pseudo-pregnant foster mothers to generate chimeras. Blastocyst injection, chimera breeding and subsequent germline transmission of mutated IL-22-RA were performed as described in Robertson, E. J. et al. *Teratocarcinomas and Embryonic Stem Cells: A Practical Approach*, $2^{nd}$ ed., IRL Press Limited, Oxford, 1987.

The KO mutant mice were identified by PCR genotyping strategy. Three PCR primers, ZC22901 (SEQ ID NO:35), ZC45039 ((SEQ ID NO:36), ZC38573 (SEQ ID NO:37) were used in a multiplex PCR reaction to detect wild-type allele and mutant allele. The wild-type (WT) allele yields a DNA fragment of 229 bp in length, while the mutant allele generates a DNA fragment of 371 bp in length.

The pairing of Hemizygote mice produce a normal ratio of Homozygote (HOM), Heterozygote (Het), and wild type (WT) offspring, as well as a normal sex ratio. Inspecting the mice through a PhysioScreen (Collecting body weight, tissue weight, complete blood count (CBC), clinical chemistry, gross observation, and HistoPathology) revealed no apparent differences between HOM, Het, and WT animals.

B. IL-22RA was Necessary for IL-22 Induced SAA: SAA ELISA Showing SAA Expression Induced by IL-22 was Absent in IL-22RA Knockout Mice:

To assess whether IL-22RA was necessary for SAA induction in mice injected with IL-22, IL-22RA KO mice were injected with 5 ug IL-22 and bled 6 hr later.

An Elisa to determine SAA levels in the serum samples was performed using the Mouse SAA Immunoassay Kit (BioSource International, California) following the manufacturer's directions, with the serum diluted 1:1000. Four out of five WT mice showed elevated SAA levels in response to IL-22 injection, while four out of five HOM IL-22RA KO mice showed basal levels of SAA. Both Het IL-22RA KO mice tested have elevated SAA levels, but lower than the SAA levels in the elevated WT mice. This indicates that IL-22RA was necessary for the induction of SAA by IL-22.

These results provided evidence that effectively blocking IL-22RA activity, for example via an IL-22RA gene knockout or similarly via a neutralizing monoclonal antibody to IL-22RA of the present invention, would similarly reduce IL-22-induced inflammation, for example in psoriasis, IBD, colitis, endotoxemia, or other inflammatory diseases induced by IL-22.

C. IL-22RA was Necessary for IL-22 Induced Epithelial Thickening: Administration of IL-22 Pure Protein via Osmotic Mini-pump Implanted Sub-cutaneous Does not Cause Thickening of the Epidermis in IL-22R KO Mice.

To assess whether IL-22RA was necessary for the IL-22 induced epithelial thickening, IL-22 was administered subcutaneously to IL-22RA HOM and WT KO mice via osmotic mini-pumps The pumps delivered IL-22 at a rate of 18.4 μL per day for 7 days. Four HOM and 6 WT IL-22RA KO mice received IL-22 protein, while 3 HOM and 1 WT received PBS.

Serum samples from IL-22 treated mice were tested in BaF3 proliferation assay to confirm the presence of IL-22. BaF3 cells transfected with IL-22RA and CRF2-4 require the presence of either IL-22 or murine IL3 to proliferate. These cells were spun down and washed in the complete media, without mIL-3 (RPMI medium (JRH Bioscience Inc., Lenexa, Kans.) supplemented with 10% heat-inactivated fetal calf serum, 2 mM L-glutaMax-1™ (Gibco BRL), 1 mM Sodium Pyruvate (Gibco BRL), and PSN antibiotics (GIBCO BRL)) (hereinafter referred to as "mIL-3 free media"). The cells were spun and washed 3 times to ensure the removal of mIL-3. Cells were then counted in a hemacytometer and plated in a 96-well format at 5000 cells per well in a final volume of 200 ul per well using the mIL-3 free media. Mouse serum was present in the wells at 1%, 0.5%, 0.25% or 0.125%. The assay plates were incubated at 37□C, 5% $CO_2$ for 3 days at which time Alamar Blue (Accumed, Chicago, Ill.) was added at 20 μl/well. Plates were again incubated at 37□C, 5% $CO_2$ for 24 hours. Alamar Blue gives a fluorometric readout based on number of live cells, and was thus a direct measurement of cell proliferation in comparison to a negative control. Plates were again incubated at 37° C., 5% $CO_2$ for 24 hours. Plates were read on the Wallac Victor 2 1420 Multilabel Counter (Wallac, Turku, Finland) at wavelengths 530 (Excitation) and 590 (Emission). Results showed none of the PBS injected animals had IL-22 activity, while 1 of 1 Het animals, 2 of 4 HOM animals, and 3 of 6 WT animals had detectable IL-22 activity. Proliferation induced by this serum was blocked by the presence of 1 ug/ml IL-22BP, proving that it was IL-22 specific.

Skin samples from IL-22 treated and untreated IL-22RA HOM and Het knockout (KO) and WT control mice were immersion fixed in 10% buffered formalin. The tissues were trimmed and embedded in paraffin, routinely processed, sectioned at 5 μm (Jung 2065 Supercut microtome, Leica Microsystems, Wetzlar, Germany) and stained with H&E. The stained tissues were evaluated under a light microscope (Nikon Eclipse E600, Nikon Inc., Melville, N.Y.) by an ACVP board certified veterinary pathologist.

Each skin sample was evaluated on a 0 (none) to 4 (severe) scale for severity of inflammation in the tissue bordering the pump implantation site in the hypodermis, on a 0 (none) to 3 (diffuse) scale for extent of epidermal thickening (acanthosis), and the number of epithelial layers were counted in the thickest part of the epidermis. No difference was found between the HOM mice and the WT mice that had been given PBS. The results from these two groups were pooled into one PBS group. The mean and standard deviation was determined for each treatment group and was shown in Table 14 below.

TABLE 14

| Treatment | PBS control | HOM KO: IL-22 | WT: IL-22 |
|---|---|---|---|
| Number of mice | 4 | 4 | 6 |
| Epithelial thickness | 3.5 ± 1.0 | 3.2 ± 0.5 | 5.9 ± 2.3 |
| Extent of acanthosis | 0.5 ± 1.0 | 0.2 ± 0.5 | 1.9 ± 1.3 |
| Inflammation | 1.5 ± 1.0 | 1.2 ± 1.0 | 2.0 ± 1.0 |

Results showed a trend toward increased epithelial thickness and acanthosis in WT mice treated with IL-22 and less epithelial thickness and acanthosis in IL-22RA HOM mice when exposed to IL-22.

These results provide evidence that effectively blocking IL-22RA activity, for example via an IL-22RA gene knockout or similarly via a neutralizing monoclonal antibody to IL-22RA of the present invention, would similarly reduce IL-22-induced skin effects, for example in psoriasis, IBD, colitis, or other inflammatory diseases induced by IL-22.

D. IL-22RA was Necessary for IL-20 Induced Shine of Neonate Pups Skin: Crossbreeding of Transgenic Mice Expressing Murine IL-20 with IL-22RA KO Mice Produce Transgenic Pups that do not Shine To assess whether IL-22RA was necessary for the IL-20 induced shine of neonate TG pups, the K14 muIL-20 transgene was crossed into the IL-22RA KO line, and the neonates were observed for the shiny phenotype.

Sixty-nine pups have been born with a Mendelian genotype ratio. All the TG on a Het KO background were shiny, while none of the non-TG, nor the TG on the HOM KO background were shiny.

An alamar blue proliferation assay using BaF3 cells expressing IL-20RA and IL-20RB was performed to assess the presence of IL-20 in the mouse serum. These cells will proliferate in response to either IL-20 or murine IL3. Procedure was the same as the one described in Section C, above. Results of the assay showed that all the TG mice had comparable IL-20 activity, and at the same level as IL-20 TG on the C57BL/6N background. The absence of any shiny neonate phenotype indicate that skinny neonate phenotype was dependent on the presence of IL-22RA. The proliferation assay showed that all the TG mice had comparable IL-20 activity, and at the same level as IL-20 TG on the C57BL/6N background. The absence of any shiny neonate phenotype indicate that skinny neonate phenotype was dependent on the presence of IL-22RA.

On day three post partum, pups from litters containing K14 muIL-20 TG on the IL-22RA KO background were humanely euthanized and the whole body immersion fixed in 10% buffered formalin. The fixed tissues were trimmed into cross-sections of the thorax and abdomen, embedded in paraffin, routinely processed, sectioned at 5 um (Jung 2065 Supercut microtome, Leica Microsystems, Wetzlar, Germany) and stained with H&E. The stained tissues were evaluated under a light microscope (Nikon Eclipse E600, Nikon Inc., Melville, N.Y.) in blinded fashion by an ACVP board certified veterinary pathologist. Tissue abnormalities were noted and the number of epithelial layers in the epidermis of the dorsal anterior thorax counted.

Tissues from three IL-20 TG on HOM IL-22RA KO background (IL-20 TG/IL-22RA KO HOM) and three non-TG on IL-22RRA HOM KO background (non-TG/IL-22RA KO HOM) mice were microscopically examined and found to contain no abnormalities. Tissues from two IL-20 TG on Het IL-22RA KO background (IL-20 TG/IL-22RA KO Het) mice were also examined. The numbers of epithelial layers in the epidermis was similar in all animals. However, the epidermis of the two IL-20 TG/IL-22RA KO Het mice was hypereosinophilic as compared to the other animals and exhibited loss of granularity in the stratum granulosum. No other abnormalities were noted in the skin or other tissues of any of the mice.

These results provide evidence that effectively blocking IL-22RA activity, for example via an IL-22RA gene knockout or similarly via a neutralizing monoclonal antibody to IL-22RA of the present invention, would similarly reduce IL-20-induced skin effects, as well as IL-22-induced skin effects, for example in psoriasis, IBD, colitis, or other inflammatory diseases induced by IL-20, and or IL-22 including IBD, arthritis, asthma, psoriatic arthritis, colitis, inflammatory skin conditions, and atopic dermatitis.

EXAMPLE 33

Histomorphometric Image Analysis of IL-22RA Knockout Mice

A line of k14 IL-20 m transgenic (TG) mice has been established, and the TG neonates exhibit a shiny phenotype. The transgene is expressed by the k14 promoter, which directs expression to the keratin producing cells in the skin. A line of IL-22RA knock out (KO) mice has also been established, and no significant changes have been observed in the un-challenged mice. The two lines were crossed together and neonates were collected having the following four different genotypes: (1) TG/-HOM: expressing the k14 IL-20 m transgene on a background not expressing IL-22RA; (2) TG/-Het: expressing the k14 IL-20 m transgene on a background expressing some IL-22RA from one copy of the IL-22RA gene; (3) WT/HOM: not expressing the k14 IL-20 m transgene on a background not expressing IL-22RA; and (4) WT/Het: not expressing the k14 IL-20 m transgene on a background expressing some IL-22RA from one copy of the IL-22RA gene. Thirty-four neonate pups of these various genotypes were euthanized at day 3, approximately 48 hours post partum (Table 15):

TABLE 15

| | TG/—HOM* (Group 1) | TG/—Het* (Group 2) | WT/HOM* (Group 3) | WT/Het* (Group 4) |
|---|---|---|---|---|
| Total | n = 10 | n = 10 | n = 9 | n = 5 |

TG = transgenic;
WT = wild type;
HOM = homozygous;
Het = heterozygous; and
n = number of pups.

Each pup was transversely cut into three sections (cranial thorax, caudal thorax and abdomen) through the body and the head was discarded. The tissue specimens, 4.0-5.0 mm in thickness, were fixed in 10% neutral buffered formalin, processed into paraffin blocks and stained with hematoxylin and eosin (H&E) for routine histological examination and histomorphometric image analysis. Epidermis from the dorsal area of spinal cord in each tissue sample was chosen for histomorphometric image analysis using an Olympus BH-2 microscope, a video camera (Dage-MTI, Michigan City, Ind.) and BioQuant True Color windows 98 software (R&M Biometrics, Inc. Nashville, Tenn. 37209) with the following set up: Parameter: mag. 10×, Z off set 0; Array: length ($\Box$m); Measure: manual and additive mode. The thickness ($\Box$m) of epidermis and stratum comeum or cornified layer from each skin sample were individually measured 10 times, with about 0.1 mm interval between each measurement, in each 10× microscopic field and the mean value, SD and SEM were obtained by Excel calculation. All of the sections were randomized and measured in a blinded fashion. After the measurement, the sections were unblinded, and the results matched to treatment groups. Final results by treatment group were classified as follows: 1. Average epidermal thickness ($\Box$m) in cranial thorax, caudal thorax and abdomen, and then sub-classified as (a) Average epidermal thickness in cranial thorax; (b) Average epidermal thickness in caudal thorax; and (c) Average epidermal thickness in abdomen. 2. Average thickness of stratum comeum ($\Box$m) in cranial thorax, caudal thorax and abdomen, and sub-classified as (a) Average thickness of stratum comeum in cranial thorax; (b) Average thickness of stratum comeum in caudal thorax; and (c) Average thickness of stratum comeum in abdomen. 3. Average thickness of epidermis plus stratum corneum in cranial thorax, caudal thorax and abdomen. The resulting data was analyzed using GraphPad InStat software (GraphPad Software, Inc., San Diego, Calif. 92121). One-way analysis of variance (ANOVA) was applied to examine the statistical significance of differences in mean values from group1 to group 4. Tukey-Kramer Multiple Comparisons Test was used for the determination of statistical differences in mean values between two groups ($*P<0.05$; $P<0.01$; $*P<0.001$; $****P<0.0001$). Observations of $P<0.05$ were considered significant.

(1) Histomorphometric Results (a) Average Epidermal Thickness (μm) in Cranial Thorax, Caudal Thorax and Abdomen Epidermal thickness increased significantly in IL-20 transgenic pups lacking one copy of the IL-22RA gene (TG/-Het) versus the IL-20 transgenic pups with no expression of IL-22RA (TG/-HOM, P=0.001*) and versus the control littermates (WT/HOM, P=0.001* and WT/Het, P=0.001***), respectively (Table 16). The TG/-Het pups showed increased thickness of non-keratinized epidermis possibly due to keratinocyte hypertrophy. This increase might involve all three nonkeratinized layers (basal, prickle, and granular) but most often affected the prickle cell layer. The epidermis of the TG/-Het pup increased about 25% in thickness and the prickle became prominent. Whereas the epidermis of TG/-HOM pups were slightly thicker than the controls (WT/HOM and WT/Het) and statistics indicated no significant difference between the groups (P>0.05). The epidermal thickness in cranial thorax, caudal thorax and abdomen were also compared. The normally thin epidermis of the abdomen is thicker than caudal thorax and the caudal thorax is thicker than the cranial thorax (Table 16).

TABLE 16

| | TG/—HOM (N = 28) | TG/—Het (N = 30) | WT/HOM (N = 27) | WT/Het (N = 15) |
|---|---|---|---|---|
| Mean | 32.58 ± 1.25 | 41.05 ± 2.04 | 31.31 ± 1.08 | 30.83 ± 1.43 |

Results represent mean values ± SEM.
N = number of sections measured.

The squamous epithelium of the skin in the cranial thorax from the TG/-Het pups showed increase in thickness accompanied by hypertrophy of the epidermal cells (keratinocytes); however there was no statistical difference compared with other groups, the TG/-HOM, WT/HOM and WT/Het (P=0.1565, Table 17). This seems to result from either histological artifact, e.g., section-to-section variability, the nature architecture of the epidermis, or there was not much effect in the thin skin in the cranial thorax. Note: the histology procedure or tissue section of the cranial thorax might disqualify for histomorphometric analysis to obtain statistical significance.

TABLE 17

| | TG/—HOM (N = 10) | TG/—Het (N = 10) | WT/HOM (N = 9) | WT/Het (N = 5) |
|---|---|---|---|---|
| Mean | 29.18 ± 2.24 | 33.20 ± 2.24 | 27.28 ± 0.62 | 29.38 ± 1.77 |

Results represent mean values ± SEM.
N = number of sections measured

The IL-20 (TG/-) with one copy of the IL-22RA gene (Het) showed increased mean value of the epidermal thickness compared to the TG/-HOM (P<0.05*), WT/HOM (P<0.001***), and WT/Het (P<0.01*), respectively (Table 18). Statistics indicated extremely significant among the groups (P<0.0001****). The TG/-Het epidermis increased about 29% than that of WT/Het. The phenotype of IL-20 (TG/-) pups with absence of IL-22RA (HOM) in part resembled to that of the pups lacking one copy of the IL-22RA gene (Het) associated with thicker epidermis than that of the control littermates (WT/HOM and WT/Het), however, it demonstrated no statistical difference compared to the controls (P>0.05). The TG/-HOM epidermis increased about 14% than that of WT/HOM. Unlike the IL-20 TG/-pups, the IL-22RAm receptor-deficient pups (WT/HOM and WT/Het) demonstrated relatively thinner epidermal thickness. Noticeably, the histomorphometric result of epidermal thickness in caudal thorax was a consistent finding correlated to the average epidermal thickness in the cranial thorax, caudal thorax and abdomen (Table 15), which indicated that the histological procedure and tissue section of the caudal thorax carried out the best quality for histomorphometric image analysis.

TABLE 18

|      | TG/—HOM (N = 10) | TG/—Het (N = 10) | WT/HOM (N = 9) | WT/Het (N = 5) |
|------|------------------|------------------|----------------|----------------|
| Mean | 35.91 ± 1.37     | 43.79 ± 2.35     | 30.83 ± 1.86   | 30.94 ± 2.83   |

Results represent mean values ± SEM.
N = number of sections measured.

The results of average epidermal thickness in abdomen (Table 19) were similar to that in the caudal thorax (Table 18) except that the TG/-HOM showed no differences compared to the control littermates (WT/HOM and WT/Het, P>0.05). There were some variations in the tissue sections and also two sections were missing, i.e. without epidermis covering the dorsal area in the TG/-HOM group.

TABLE 19

|      | TG/—HOM (N = 8) | TG/—Het (N = 10) | WT/HOM (N = 9) | WT/Het (N = 5) |
|------|-----------------|------------------|----------------|----------------|
| Mean | 32.35 ± 1.44    | 46.33 ± 3.10     | 35.81 ± 1.90   | 32.16 ± 2.97   |

Results represent mean values ± SEM.
N = number of sections measured.

(b) Average Thickness (µm) of Stratum Corneum in Cranial Thorax, Caudal Thorax and Abdomen Despite the increased epidermal thickness in the IL-20 transgenic pups (TG/-) on a background either not expressing IL-22RA (HOM) or expressing one copy of the gene (Het), predominate reduction of stratum corneum or cornified layer thickness was observed in the TG/-HOM and TG/-Het skins compared to the control littermates (WT/HOM and WT/Het) and statistics indicated extremely significant among the groups (P<0.0001**, Table 20). The TG/-Het pups showed about 36%, 50% and 49% decreased amounts of keratin on the surface of the epidermis versus the TG/-HOM (P<0.01), WT/HOM (P<0.001*) and WT/Het (P<0.001*), respectively. The TG/-HOM pups showed about 22% significant reduction in the stratum corneum thickness compared with its control (WT/HOM, P<0.05*) and only 17% reduction versus the WT/Het that revealed no statistical significance (P>0.05). The thickness of stratum corneum in the control pups, WT/HOM and WT/Het were about the same. Apparently, the stratum corneum in the caudal thorax is thicker than that in the abdomen and the abdomen is thicker than that in the cranial thorax.

TABLE 20

|      | TG/—HOM (N = 8) | TG/—Het (N = 10) | WT/HOM (N = 9) | WT/Het (N = 5) |
|------|-----------------|------------------|----------------|----------------|
| Mean | 33.26 ± 2.69    | 21.41 ± 1.27     | 42.54 ± 2.01   | 40.31 ± 3.82   |

Results represent mean values ± SEM.
N = number of sections measured.

The average thickness of stratum corneum in the cranial thorax (Table 21) resembled to that in the cranial thorax, caudal thorax and abdomen (Table 20), however significant reduction of stratum corneun was only found in the TG/-Het vs. TG/-HOM (P<0.05*) and vs. WT/HOM (P<0.01**), respectively. The standard deviation and standard error of the mean were high which might be due to poor section, missing skin samples, nature architecture of the epidermis, or there was not much effect in the cranial thorax. Note: the histology procedure or tissue section of the cranial thorax might disqualify for histomorphometric analysis in order to obtain quality result.

TABLE 21

|      | TG/—HOM (N = 28) | TG/—Het (N = 30) | WT/HOM (N = 26) | WT/Het (N = 14) |
|------|------------------|------------------|-----------------|-----------------|
| Mean | 34.96 ± 3.53     | 18.14 ± 3.99     | 40.47 ± 4.38    | 32.96 ± 8.11    |

Results represent mean values ± SEM.
N = number of sections measured

The result of average thickness of stratum corneum in the caudal thorax (Table 22) was similar to that in the cranial thorax, caudal thorax and abdomen but with three exceptions: (1) TG/-HOM vs. TG/-Het and TG/-HOM vs. WT/HOM showed no statistical differences (P>0.05); (2) TG/-HOM vs. WT/Het showed significant difference (P<0.01**); (3) The stratum corneum in the WT/Het remarkably thickened which might be the consequence of tissue processing artifact, e.g., the keratin swelled or expanded when placed it in hypotonic solution or left in the water bath too long.

TABLE 22

|      | TG/—HOM (N = 10) | TG/—Het (N = 10) | WT/HOM (N = 8) | WT/Het (N = 4) |
|------|------------------|------------------|----------------|----------------|
| Mean | 35.64 ± 3.4      | 24.22 ± 1.54     | 44.35 ± 3.51   | 53.77 ± 7.21   |

Results represent mean values ± SEM.
N = number of sections measured.

Only the TG/-HOM vs. WT/HOM and TG/-Het vs. WT/HOM showed statistical significant difference, P<0.05* and P<0.001***, respectively (Table 23). The TG/-pups displayed a reduction in the thickness of stratum corneum in the abdomen compared to its control littermates (WT/HOM and WT/Het).

TABLE 23

|      | TG/—HOM (N = 8) | TG/—Het (N = 10) | WT/HOM (N = 9) | WT/Het (N = 4) |
|------|-----------------|------------------|----------------|----------------|
| Mean | 28.84 ± 4.36    | 21.86 ± 1.30     | 42.45 ± 3.15   | 33.25 ± 3.96   |

Results represent mean values ± SEM.
N = number of sections measured (c) Average Thickness (µm) of Epidermis Plus Stratum Corneum in Cranial Thorax, Caudal Thorax and Abdomen TG/-Het pups displayed a significant increase in the epidermal thickness and a significant decrease in the thickness of stratum corneum compared with the control littermates (WT/HOM and WT/Het) and the TG/-HOM pups produced a similar result but with a minimal effect (Table 24).

TABLE 24

|  | TG/—HOM (N = 10) | TG/—Het (N = 10) | WT/HOM (N = 9) | WT/Het (N = 4) |
|---|---|---|---|---|
| Stratum corneum | 32.58 | 41.05 | 31.31 | 30.83 |
| Epidermis | 33.26 | 21.41 | 42.54 | 40.31 |

Results represent mean values.
N = number of pups (d) Signaling of IL-20 Through Both IL-20RA and IL-22RA The epidermis is a stratified, continually renewing epithelium dependent on a balance among cell proliferation, differentiation, and death for homeostasis. In normal epidermis, a mitotically active basal layer gives rise to terminally differentiating keratinocytes that migrate outward and are ultimately sloughed from the skin surface as enucleated squames, the keratin or cornified layer located in the stratum corneum. Although many proteins are known to function in maintaining epidermal homeostasis, the molecular coordination of these events is poorly understood. IL-20 is a novel receptor-interacting protein and it signals through either IL20RA or IL-22RA receptors (IL-22RA) expressed in a layer of skin associated with the proliferation of keratinocytes. IL-20 transgenic neonates display abnormal thickened and shiny skin phenotype. IL-22RAm (HOM) deficiency in mice showed no response to IL-22 treatment, whereas wild type mice with the IL-22RA gene and treated with IL-22 demonstrated significant increase in the epidermal thickness (P<0.001***, see the results in IL-22RAm KO/IL-22 histomorphometric image analysis, PID 59.2). To investigate whether the absence of IL-22RA has an effect on the shiny phenotype observed in the K14 IL-20m TG neonates, transgenic mice ectopically expressing IL-20 were mated with IL-22RA homozygous (HOM) or IL-22RA heterozygous (Het) deficient. A quantitative image analysis of epidermal thickness was previously performed on fewer pups in the caudal thorax from this study (i.e. 19 pups, 1 section per pup, for a total of 19 sections) but no statistical significance was obtained due to the limited number of animals studied and the variation within the groups. The aim of the present study was to histomorphometrically quantitate more skin samples in cranial thorax, caudal thorax and abdomen from each pup from the same study (i.e. 34 pups, 3 section per pup, for a total of 102 sections) to explore the biology of IL-20 and obtain reliable quantitative results. For effective image analysis, we made sure that the orientation of the skin in the paraffin block was consistent and the skin samples were measured from the same respective locations in all individual and groups of pups. Two kinds of measurements were performed: (1) The thickness of epidermis was measured 10 times per 10× microscopic field in each skin sample, each at the dorsal side of spinal cord, to investigate the role of IL-20 in mediating keratinocyte proliferation and differentiation; (2) The thickness of cornified layer or the stratum corneum was measured in the same manner to correlate the results with the shiny skin appearance in the IL-20 TG neonates.

Histomorphometric image analysis of the epidermal thickness revealed that the TG/–Het neonates, expressing the k14 IL-20m transgene on a background expressing some IL-22RA from one copy of the IL-22RA gene displayed thickened epidermis and the TG/–HOM neonates, expressing the k14 IL-20m transgene on a background not expressing IL-22RA had no significant change. The epidermal thickness increased significantly in IL-20 transgenic pups lacking one copy of the IL-22RA gene (TG/–Het) versus the IL-20 transgenic pups lacking both copy of the IL-22RA genes (TG/–HOM, P=0.001*) and versus the control littermates (WT/HOM, P=0.001* and WT/Het, P=0.001***). The TG/–Het pups showed increased thickness of the non-keratinized epidermis mainly due to hypertrophy of the keratinocytes in the prickle layer. The epidermis of the TG/–Het pup increased about 25% in thickness, whereas the epidermis of TG/–HOM pups were only slightly thicker, increased about 4-5%, than the controls (WT/HOM and WT/Het) and statistics indicated no significant difference between the TG/–HOM and its control WT/HOM (P>0.05).

Histomorphometric results of the stratum corneum showed that despite the epidermal thickening in the TG/–Het neonates, predominate reduction of keratin or cornified layer thickness was observed in TG/–HOM and TG/–Het skins compared to the control littermates (WT/HOM and WT/Het) and statistics indicated extremely significant among the groups (P<0.0001**). The TG/–Het pups showed about 36%, 50% and 49% decreased amounts of keratin on the surface of the epidermis versus the TG/–HOM (P<0.01), WT/HOM (P<0.001*) and WT/Het (P<0.001*), respectively. The TG/–HOM pups showed about 22% significant reduction in the stratum corneum thickness compared to its control (WT/HOM, P<0.05*) and only 17% reduction versus the WT/Het (P>0.05). The thickness of stratum corneum in the control pups, WT/HOM and WT/Het were about the same. The reduction in average thickness of stratum corneum in the TG/–HOM and TG/–Het neonates seemed to correlate the gross finding at sac, in which at gross level the IL-20 (TG)/IL-22RA (Het) neonates appear to have reduced shine (e.g., with less keratin), called a sheen, while the IL-20 (TG)/IL-22RA (HOM) neonates do not shine (e.g., with more keratin). Histologically, the keratin in the stratum corneum in the TG/–pups appeared to be more compact than that in the WT pups. Together, the thickened epidermis associated with hypertrophic keratinocytes and the thin layer of stratum corneum in the IL-20 transgenic neonates might explain why they displayed shiny skin phenotype.

Increased hypertrophy and disturbed terminal differentiation of keratinocytes were observed in the IL-20 transgenic neonates with a targeted knock out of one copy of the IL-22RA gene (Het). The skin exhibited hypertrophy in keratinocytes but fails fully differentiate, lacking keratin or the stratum corneum. The IL-20 transgenic neonates with disruption of two copy of the IL-22RA genes (HOM) displayed a phenotype that resembled the TG/–Het skin but showed less or minimal effect (FIG. 12-15). It seems that the absence of IL-22RA (HOM) has a partial effect on the shiny phenotype observed in the K14 IL-20m TG neonates and the absence of IL-22RA (Het) has minimal or no effect on the shiny phenotype. In other words, the signaling of IL-20, a novel receptor-interacting protein which signals through either IL-20RA or IL-22RA receptor (IL-22RA) is probably not obstructed by deficient expression of one copy of the IL-22RA gene (Het) but is partially obstructed by deficient expression of two copies of the IL-22RA gene (HOM).

These results provide evidence that effectively blocking IL-22RA activity, for example via an IL-22RA gene knockout or similarly via a neutralizing monoclonal antibody to IL-22RA of the present invention, would similarly reduce IL-20-induced skin effects, as well as IL-22-induced skin effects, for example in psoriasis, IBD, colitis, or other inflammatory diseases induced by IL-20, and or IL-22.

EXAMPLE 34

Effect of IL-22 on IL-22RA Knock Out Mice

Thirty-six mice including 23 IL-22RA KO (HOM) and 13 controls (WT) were treated with either IL-22 or PBS administered subcutaneously by implanted a minipump with tube or a minipump alone (Table 25):

TABLE 25

|  | HOM/PBS (Group1) | HOM/IL-22 (Group 2) | WT/PBS (Group 3) | WT/IL-22 (Group 4) |
|---|---|---|---|---|
| Male | n = 3 | n = 10 | n = 3 | n = 8 |
| Female | n = 0 | n = 10 | n = 0 | n = 2 |
| Total | n = 3 | n = 20 | n = 3 | n = 10 |

Skin sample, 1.5-2.5 cm in length and 4.0-5.0 mm in thickness, from the pumping site of each animal was obtained for routine histological examination and histomorphometric image analysis. All tissue specimens were fixed in 10% neutral buffered formalin and processed into paraffin blocks. Six segmental sections, 5 um in thickness and 10 um interval between adjacent sections with epithelium covering the entire surface, from each skin sample per animal were stained with hematoxylin and eosin (H&E). Histomorphometric image analysis of the skin samples was performed using an Olympus BH-2 microscope, a video camera (Dage-MTI, Michigan City, Ind.) and BioQuant True Color windows 98 software (R&M Biometrics, Inc. Nashville, Tenn. 37209) with the was following set up: Parameter: mag. 10×, Z off set 0; Array: length (um); Measure: manual and additive mode. The thickness (um) of epidermis was measured 5 times in each 10× microscopic field from a total of 4 fields captured from the center 0.4 cm of each skin section (e.g., one 10× microscopic field=0.1 cm and four 10× microscopic fields=0.4 cm). Total of 6 sections from each animal were measured and the mean value, SD and SEM were obtained by Excel calculation. All of the sections were randomized and measured in a blinded fashion. After the measurement, the sections were unblended, and the results matched to treatment groups. Final results by treatment group were classified as follows: 1.Epidermal thickness from HOM and WT male and female mice. 2. Epidermal thickness from HOM and WT male mice. The resulting data was analyzed using GraphPad InStat software (GraphPad Software, Inc., San Diego, Calif. 92121). One-way analysis of variance (ANOVA) was applied to examine the statistical significance of differences in mean values from group1 to group 4. Tukey-Kramer Multiple Comparisons Test and Unpaired-T test were applied to analyze the significance in mean values between two groups. Observations of P<0.05 were considered significant.

III. Histomorphometric Results(1) Epidermal Thickness (μm) from HOM and WT Male and Female Mice Epidermal thickness increased significantly in the WT mouse skins treated with IL-22 (WT/IL-22) versus the WT/PBS controls (P=0.0001). IL-22RAm KO mouse skin treated with IL-22 (HOM/IL-22) showed increased mean value of the epidermal thickness compared with the HOM/PBS controls, however statistics indicated no significant difference between the two groups (P>0.05). Predominate reduction of epidermal thickness was observed in the IL-22RA KO mice compared with the WT mice (e.g., HOM/IL-22 vs. WT/IL-22: P<0.001) (Table 26).

TABLE 26

|  | HOM/PBS (N = 3) | HOM/IL-22 (N = 19) | WT/PBS (N = 3) | WT/IL-22 (N = 10) |
|---|---|---|---|---|
| Mean | 14.15 ± 0.19 | 19.01 ± 1.03 | 23.34 ± 5.49 | 43.08 ± 1.85 |

Results represent mean values ± SEM.
N = animal number.

(2) Epidermal Thickness (um) from HOM and WT Male Mice

Epidermal thickness increased about 2-fold in the WT male mouse skins treated with IL-22 (WT/IL-22) when compared with WT/PBS male controls (P=0.0001), however, IL-22RAm KO male mouse epidermis treated with IL-22 (HOM/IL-22) only showed slightly increase compared with the HOM/PBS male controls (P>0.05). Noticeably, IL-22RAm KO mice exhibited marked reduction of epidermal thickness when compared with its control, the WT male mice (e.g., HOM/PBS VS WT/PBS: P<0.05; HOM/IL-22 VS WT/IL-22: P<0.001) (Table 27).

TABLE 27

|  | HOM/PBS (N = 3) | HOM/IL-22 (N = 9) | WT/PBS (N = 3) | WT/IL-22 (N = 8) |
|---|---|---|---|---|
| Mean | 14.15 ± 0.19 | 15.86 ± 0.75 | 23.34 ± 5.49 | 41.41 ± 1.71 |

Results represent mean values ± SEM.

(3) Epidermal Thickness (um) from HOM and WT Mice, Male vs. Female

Epidermis of the female mice was found thicker than that of the male mice (e.g., HOM/IL-22/male VS HOM/IL-22/female: P<0.01; WT/IL-22/male VS WT/IL-22/female: P<0.05) (Table 28).

TABLE 28

|  | HOM/IL-22 (Male, N = 9) | HOM/IL-22 (Female, N = 10) | WT/IL-22 (Male, N = 8) | WT/IL-22 (Female, N = 2) |
|---|---|---|---|---|
| Mean | 15.86 ± 0.75 | 21.85 ± 1.3 | 41.41 ± 1.71 | 49.75 ± 4.82 |

Results represent mean values ± SEM.

(4) Epidermal Thickness (μm) from HOM Mice, IL-22 Pump vs. IL-22 Pump with Tube

Epidermis from IL-22RAm KO (HOM) mice with IL-22 pump & tube were found significantly thicker than that of the IL-22RAm KO (HOM) mice with pump only (P<0.0001, by unpaired-T test) (Table 29).

TABLE 29

|  | HOM w/IL-22 pump (M = 8 &F = 2, N = 10) | HOM w/IL-22 pump with tube (M = 2 &F = 8, N = 10) |
|---|---|---|
| Mean | 15.85 + 0.65 | 23.30 + 1.36 |

Results represent mean values ± SEM.
M: male;
F: female;
N: total number of mice.

IV. Discussion:

Taken together, the aim of this study is to characterize the epidermal effects in the IL-22 treated skins from both IL-22RAm KO and WT mice and relates these findings to clinical indications. A quantitative image analysis was performed to determine the thickness of the epidermis in H&E stained skin sections. The skin samples from each animal were histomorphometrically measured 120 times (i.e. 20 times/each section ×6 segmental sections from each mouse=120 measurements) and the average epidermal thickness was obtained by Excel calculation. Histomorphometric study demonstrated that IL-22 resulted in significant increase in the epidermal thickness especially in the WT mice with presence of the IL-22RA receptor ($P<0.0001$ by ANOVA, considered extremely significant) and showed less or minimal effects on the IL-22RAm KO (HOM) mice with absence of the IL-22RA receptor ($P>0.05$). The epidermal thickness in the IL-22 treated WT mice was increased about 43% than that treated with PBS (e.g., WT/PBS, $P<0.001$), whereas the IL-22 treated IL-22RAm KO (HOM) mice only showed 26% increase in epidermal thickness compared with the control (HOM/PBS, $P>0.05$). IL-22RAm KO mice exhibited thinner epidermis when compared with the WT mice ($P<0.001$). Overall, the biologic effects of IL-22 on mouse skin suggest that this factor might be involved in the regulation of epidermal growth and proliferation.

EXAMPLE 35

Pharmacokinetics of an Anti-human IL-20 Monoclonal Antibody (Clone #262.7.1.3.2.4)

The test monoclonal antibody, anti-human IL-20 mAb, (clone #262.7.1.3.2.4) was provided in 3×3 mL aliquots at a concentration of 1.08 mg/mL (determined by UV Absorbance at 280 nM) and was stored at −80° C. until use. The vehicle was 1×PBS (50 mM NaPO4, 109 mM NaCl), pH 7.3. The mAb was thawed at room temperature before use and aliquots 1 and 2 were used as provided for the 100 µg IV and SC dosing groups, respectively. Half of aliquot 3 was diluted 1:2 in 1×PBS for the 50 µg SC dose group and the second half of aliquot 3 was diluted 1:10 in 1×PBS for the 10 µg SC dose group. Female SCID mice (n=96), were received from Charles River Labs. Animals were checked for health on arrival and group-housed (3 animals per cage). The mice were 12 weeks old with an average body weight of 22 g at the beginning of the study.

A. Dosing Protocol

Female SCID mice (n=24/dose group) were randomly placed into four dosing groups (see Table 30). Group 1 was administered the anti-huIL-20 mAb via IV injection of approximately 93 µL in a tail vein and Groups 2, 3, and 4 were administered the mAb via SC injection of approximately 93 µL in the scruff of the neck.

B. Sample Collection

Prior to blood collection, mice were fully anesthetized with halothane or isoflurane. Blood samples were collected via cardiac stick for all timepoints except the 168 hr timepoint (collected via eye bleed and the same animals were bled again at the 504 hr timepoint via cardiac stick). Blood was collected into serum separator tubes and allowed to clot for 15 minutes. Samples were subsequently centrifuged for 3 minutes at 14,000 rpm. Following centrifugation, aliquots of 125-150 uL were dispensed into labeled eppendorf tubes and immediately stored at −80° C. until analysis (Table 30).

TABLE 30

| Group # | Dose (ROA) | Animals | PK Timepoints |
|---|---|---|---|
| 1 | 100 µg (IV) | 3 mice/timepoint* | 0.25, 1, 4, 8, 24, 72, 168, 336 and 504 hr |
| 2 | 100 µg (SC) | 3 mice/timepoint* | 0.25, 1, 4, 8, 24, 72, 168, 336 and 504 hr |
| 3 | 50 µg (SC) | 3 mice/timepoint* | 0.25, 1, 4, 8, 24, 72, 168, 336 and 504 hr |
| 4 | 10 µg (SC) | 3 mice/timepoint* | 0.25, 1, 4, 8, 24, 72, 168, 336 and 504 hr |

*The same animals were used for the 168 and 504 hr timepoints.

C. Quantification of Serum Anti-huIL-20 mAb Concentrations by ELISA

An Enzyme Linked Immunosorbant Assay (ELISA) was developed and qualified to analyze mouse serum samples from animals dosed with anti-IL-20 mAb 267.7.1.3.2.4 during pharmacokinetic studies. This assay was designed to take advantage of a commercially available secondary antibody and colorimetric detection using TMB. The dilutions used for the standard curve were modified to improve the definition of the linear portion of the standard curve. A standard curve in the range of 100 ng/mL to 0.231 ng/mL with 2-fold dilutions allowed for quantitation of the mouse serum samples. QC samples were diluted to 1:100, 1:1000 and 1:10000 in 10% SCID mouse serum and back calculated from the standard curve.

D. Pharmacokinetic Analysis

Serum concentration versus time data were downloaded into WinNonlin Professional 4.0 software (Pharsight, Inc.; Cary, N.C.) for pharmacokinetic analysis. Noncompartmental analysis was used to determine pharmacokinetic parameters based on the mean data at each time point.

E. Results

Mean serum anti-human IL-20 mAb concentrations following administration of 100 µg IV and 100, 50, and 10 µg SC are shown in Table 31:

TABLE 31

| Time (hr) | 100 µg IV Conc (µg/mL) | 10 µg SC Conc (µg/mL) | 50 µg SC Conc (µg/mL) | 100 µg SC Conc (µg/mL) |
|---|---|---|---|---|
| 0.25 | 196 (12) | LTR | 0.101 (0.065) | 0.481 (0.485) |
| 1 | 154 (18) | 0.356 (0.146) | 1.61 (0.52) | 3.48 (1.72) |
| 4 | 118 (20) | 2.42 (0.53) | 10.4 (3.4) | 19.7 (4.7) |
| 8 | 112 (20) | 3.41 (0.30) | 18.9 (3.6) | 40.2 (6.4) |
| 24 | 103 (13) | 4.95 (0.05) | 26.3 (0.7) | 50.1 (6.2) |
| 72 | 101 (16) | 4.27 (0.79) | 21.0 (3.4) | 43.4 (2.7) |
| 168 | 45.6 (15.4) | 2.92 (0.53) | 19.6 (2.7) | 37.6 (3.4) |
| 336 | 36.4 (16.6) | 3.60 (0.31) | 23.5 (3.5) | 34.4 (5.8) |
| 504 | 28.8 (3.8) | 2.74 (0.39) | 20.5 (3.6) | 25.7 (2.1) |

LTR: less than reportable

Following IV administration, the mAb concentration versus time profile demonstrated a biexponential decline. Following SC administration, the mAb appeared to have a slow absorption phase, with absorption rate-limited elimination. The serum pharmacokinetic parameters based on the mean data at each time point are shown in Table 32:

TABLE 32

| Parameter | Units | 100 µg IV | 10 µg SC | 50 µg SC | 100 µg SC |
|---|---|---|---|---|---|
| $C_0$(IV); $C_{max}$ (SC) | µg/mL | 212 | 4.95 | 26.3 | 50.1 |
| $T_{max}$ | hr | N/A | 24 | 24 | 24 |
| $t_{1/2,\lambda z}$ | hr | 509 | ND | ND | 612 |
| $AUC_{(0-t)}$ | hr · µg/mL | 27059 | 1730 | 10845 | 18110 |
| $AUC_{(0-inf)}$ | hr · µg/mL | 48269 | ND | ND | 41561 |
| AUC (% extrapolated) | % | 43.9 | ND | ND | 56.4 |
| $V_{ss}$ (IV); $V_z$/F (SC) | mL | 1.34 | ND | ND | 2.12 |
| Cl (IV); Cl/F (SC) | mL/hr | 0.002 | ND | ND | 0.002 |
| F (bioavailability) | % | N/A | ND | ND | 86.1 |

ND: not determinable due to lack of data in the terminal elimination phase of the concentration versus time profile Following IV administration, the mAb demonstrated a very low clearance (Cl=0.002 mL/hr) and long elimination half-life ($t_{1/2,\lambda z} \approx 21$ days). The mAb demonstrated a steady-state volume of distribution ($V_{ss}$=1.3 mL) that is less than the blood volume in a mouse ($\approx 1.7$ mL), suggesting that the mAb did not distribute substantially out of the vascular compartment. The back-calculated maximum concentration ($C_0$) was higher than expected based on the injected dose and the blood volume in the mouse. This, along with the small $V_{ss}$, suggests that the mAb may be confined, to a large extent, in the serum fraction of the blood.

Following SC administration, $C_{max}$ values increased linearly with dose. At the 100 µg SC dose, the mAb had a $t_{1/2,\lambda z}$ of approximately 25 days with clearance and an apparent volume of distribution similar to that following IV dosing.

Bioavailability was 86%. At the lower two SC doses, most pharmacokinetic parameters 20 could not be estimated due to the lack of a measurable terminal elimination phase, even though samples were taken out to 504 hours. The absorption of the mAb following SC dosing appears to reach a steady-state with elimination throughout the duration of the study.

EXAMPLE 36

IL-20 and IL-22 Antagonists in CD4+CD45RB$^{hi}$ (CD25−) Colitis and Psoriasis Model A. Summary Transfer of CD4+CD45RB$^{hi}$ or CD4+CD25− T cells into syngeneic SCID mice results in colitis in the mice. Co-transfer of regulatory T cells (CD4+CD25+ or CD4+CD45RB$^{lo}$) inhibits this colitis. After transfer of CD4+CD25− T cells into mice, if mice are additionally injected with staphylococcal enterotoxin B (SEB), mice not only develop colitis, but also psoriasis. Antibodies against IL-22RA, IL-20, IL-22, IL20R and/or IL-22R, or soluble IL-22RA receptors are administered from days 0-21 after cell transfer and symptoms for colitis and psoriasis are monitored. Inhibition of psoriatic score or colitis (histology) indicates that IL-21 can inhibit these autoimmune diseases.

B. Study Design

Spleens and inguinal lymph nodes are isolated from B10.D2 mice. Single cell suspensions are formed and counted. Using the Miltenyi Bead system, CD25+ cells are sorted out by positive selection. Cells are stained with CD25-PE (BD Pharmingen) at 1:100 dilution and incubated for 15 minutes. Excess antibody is washed out and the cells are incubated with 10 ul anti-PE beads/$10^6$ cells for 20 minutes. The cells are washed with PBS and passed over an LS column (Miltenyi Biotech). Cells that pass through the column (CD25−) are retained for further analysis. A CD4 enrichment cocktail (Stem Cell technologies) is added (1:100) to these CD25− cells and incubated for 15 minutes. Cells are washed with PBS. A 1:10 dilution of anti-biotin tetramer is added to the cells for 15 minutes followed by a magnetic colloid (60 ul/$10^6$ cells) for 15 minutes (all from Stem Cell Technologies). Cells are passed through a negative selection column (0.5", Stem cell Technologies). Cells that pass through are the CD4+CD25− cells. Purity is analyzed using flow cytometry. 0.4×$10^6$ cells are injected i.v into nayve CB-17 SCID mice in a total volume of 200 □l. Mice are injected i.p with 10 □g SEB the following day (d1). Symptoms for psoriasis and colitis are followed from 2-5 weeks. Mice are scored for psoriasis disease under the following criteria. 0—no lesions, 1—mild lesions on the neck, 2—severe lesions on the neck and back (trunk) 3—very severe lesions on the neck, back and the belly of mice. Ear thickening is also measured as a measure of disease severity. Groups of mice are injected i.p. with PBS, 100 □g control antibody or 10-100 □g antibodies against IL-22RA, IL-20, IL-22, IL-20R or IL-22R, or soluble IL-22RA from days 1-30 under different dosing regimen (3×/week or 2×/week).

C. Results and Conclusion

Inhibiton of psoriatic and colitis symptoms in antibody treated mice indicates that inhibition of IL-20 and/or IL-22 function can inhibit autoimmune symptoms in this model for psoriasis and colitis.

EXAMPLE 37

IL-20, and IL-22 Antagonists in SCID-hu Transplant Psoriasis Model

Human psoriasis skin grafted on SCID mouse can maintain its clinical, light microscopic, and immunohistochemical psoriatic features for several weeks. This model provides a system for evaluating therapies intended to restore lesional tissue to a normal phenotype. Once the human skin is successfully grafted, antibodies against IL-22RA, IL-20, IL-22, IL-20R and/or IL-22R, or soluble IL-20 or IL-22 receptors can be administered for several weeks, and the epidermal thickness can be analyzed to evaluate the effect of these antagonists on psoriasis.

B. Study Design

Full-thickness 6-mm punch biopsies consisting of the entire epidermis and several mm of dermis are obtained healthy adult volunteers and psoriatic lesional skins. Four to six biopsies are obtained from each donor. One punch biopsy from each donor is transplanted onto the dorsal surface of recipient SCID mouse (CB-17, Taconic). The animals are maintained in a pathogen-free environment. The treatment is initiated after a successful grafting (2-3 weeks post-transplantation) as following: one biopsy for negative control (PBS or isotype mAb), one biopsy for positive control (Cyclosporin A), and 2-3 biopsies for treatment with anti-human IL-22RA, anti-human IL-20, anti-human IL-22 mAb or soluble receptors for IL-20 or IL-22 (intraperitoneal injection, three times a week for 2-4 weeks on a M-W-F schedule).

C. Quantitative Analysis:

Clinical observations and assessments will be made regularly throughout the experiments, and will be recorded. The severity of the psoriatic lesions is assessed for scaliness, induration, and erythema in a blinded fashion. The parameters can be scored using the three-point scale: 0=complete lack of cutaneous involvement; 1=slight involvement; 2=moderate involvement; 3=severe involvement. At the end of the dosing period each animal is euthanized and tissues are collected for histology and IHC. (1) Part of the tissue is fixed in 10% formalin and stained with hematoxylin and eosin. Epidermal area is measured as a function of changes in epidermal thickness per unit length using NIH Image software. Multiple areas from each transplant are quantified to provide a high n value and mean epidermal area. (2) number of inflammatory mononuclear cells per high-power field (0.103×0.135 mm) in the upper dermis; (3) the grade of parakeratosis is rated on an arbitrary scale from 0 to 3, where 0 is no parakeratosis, 1 is parakeratosis in less than one third of the section, 2 was parakeratosis in more than one third but less than two thirds of the section, a d 3 is parakeratosis in more than two thirds of the section. (4) The remaining of the tissue will be stained for Ki67 (marker of proliferating keratinocytes), to evaluate the number of Ki67 cycling keratinocytes-per-millimeter length of the section. The reduced severity of psoriasis as measured by epidermal thickness, indicates the neutralization of IL-20 and IL-22 function can be effective in this psoriasis model. To quantify the reduced severity of psoriasis, we measure epidermal thickness, the number of inflammatory cells in the upper dermis, the numbers of Ki67 cycling keratinocytes, and the grades of parakeratosis. The significantly reduced all four parameters for the treated groups compared to the control mice, indicate the potential therapeutic use of IL-20, IL-22 antagonists.

EXAMPLE 38

Screening for IL-20 Antagonist Activity Using BaF3/IL-22RA/IL-20RB Cells Using an Alamar Blue Proliferation Assay The factor-dependent pre-B cell line BaF3 was co-transfected with IL-22RA and IL-20RB (see, method in Example 3) and treated with IL-20 at various concentrations. Proliferation was assessed using an alamar blue assay as described in Example 3. IL-20 stimulated proliferation in a dose-dependent manner at concentrations expected for a cytokine, demonstrating that IL-20 binds and activates the heterodimeric IL-22RA/IL-20RB receptor at concentrations expected for a cytokine. The negative controls containing untransfected BaF3 did not proliferate.

In order to determine if anti-IL-22RA antibodies are capable of antagonizing IL-20 activity, the assay described above is performed using anti-IL-22RA antibodies as an antagonist to IL-20 activity. When IL-20 is combined with such antagonist, the response to IL-20 is brought down to background levels. That the presence of an antagonist that ablates or reduces the proliferative effects of IL-20 demonstrates that it is an antagonist of the IL-20 ligand. This assay can be used to test other antagonists of IL-20 activity described herein, such as antagonist polypeptides comprising a soluble IL-22RA receptor.

EXAMPLE 39

Neutralization of IL-20 and IL-22 Activity by Anti-huL22RA Monoclonal Antibody

Using the cell-based neutralization assay described in Example 28, a purified mouse anti-huIL-22RA monoclonal antibody (Example 30(D)) was added as a serial dilution, for example, at 10 ug/ml, 5 ug/ml, 2.5 ug/ml, 1.25 ug/ml, 625 ng/ml, 313 ng/ml, 156 ng/ml and 78 ng/ml. The assay plates were incubated at 37□C, 5% $CO_2$ for 4 days at which time Alamar Blue (Accumed, Chicago, Ill.) was added at 20□l/well. Plates were again incubated at 37□C, 5% $CO_2$ for 16 hours. Results showed that the purified anti-huIL-22RA monoclonal antibody could neutralize signalling of both huIL-22 and huIL-20 through huIL-22RA. At the 10 ug/ml concentration, the antibody completely neutralized proliferation induced by huIL-22 or huIL-20, with the inhibition of proliferation decreasing in a dose dependent fashion at the lower concentrations. An isotype-matched negative control mouse mAb, tested at the concentrations described above, provided no inhibition of proliferation of either cytokine. These results further demonstrate that monoclonal antibodies to IL-22RA could indeed antagonize the activity of the pro-inflammatory ligands, IL-20 and IL-22 at low concentrations.

These results provided additional evidence that effectively blocking IL-22RA activity, for example via a neutralizing monoclonal antibody to IL-22RA of the present invention, could be advantageous in blocking, inhibiting, reducing, antagonizing or neutralizing the effects of IL-20 and IL-22 (alone or together) in vivo and maybe reduce IL-20 and/or IL-22-induced inflammation, such as that seen in IL-20-induced skin effects, as well as IL-22-induced skin effects, for example in psoriasis, IBD, colitis, or other inflammatory diseases induced by IL-20, and or IL-22 including IBD, arthritis, asthma, psoriatic arthritis, colitis, inflammatory skin conditions, and atopic dermatitis.

EXAMPLE 40

Treatment of Pregnant IL-20 and IL-22 Transgenic Mice with Neutralizing Anti-IL-22RA Monoclonal Antibody To test the rat anti-mouse IL-22RA monoclonal antibody (mAb) for neutralizing activity in vivo, pregnant IL-20 transgenic (Tg) and IL-22 Tg mice are injected intraperitoneally with an anti-mouse IL-22RA mAb. The newborn pups are then assessed for the presence or absence of the "shiny" skin phenotype that normally characterizes these strains of mice.

Specifically, male IL-20 Tg (which are generated using the keratin-14) or IL-22 Tg (using the insulin promoter) mice are bred to C57BL/6N females in estrus and the bred females are identified by the presence of a vaginal plug the following day. Each pregnant female is set aside in a separate cage and monitored daily. Treatment groups include at least 4 pregnant females each, to allow for a statistically significant analysis of both Tg and nonTg pups. Based on prior experience with these Tg mice, a litter usually ranges between approximately 6 to 8 pups per litter, of which between 2 to 3 are Tg+.

Seven to nine days after the mice are bred (embryonic age 7-9; e7-9), the females are injected intraperitoneally with 250-500 ug of the rat anti-mouse IL-22RA mAb (rat IgG2a isotype) in a volume of 200-250 ul of PBS. Short needles are used at a shallow injection angle to avoid directly injecting the uterus. The pregnant females are injected in this manner 3 days a week (Monday, Wednesday, and Friday) for 2 weeks (until birth) in order to successfully access the developing embryos. Control groups (of not less than 4 pregnant female mice each) include the following: isotype control rat IgG2a mAb, anti-human/mouse IL-22 mAb (rat IgGI isotype), and an isotype control rat IgG1 mAb. As a control for neutralization of murine IL-20, pregnant females are injected with either a soluble IL-20R-Fc4 fusion protein that can bind and neutralize both human and murine IL-20 or an Fc4 control protein.

From days 1 to 2 after birth, the pups are closely monitored for the appearance of the shiny skin phenotype. On day 2, the pups are euthanized and a portion of the tail is collected for DNA isolation to determine the genotype (Tg or nonTg) of each pup. Skin samples are collected for histological analysis in order to assess whether the pups exhibit the thickened epidermal cell layers that usually characterize these Tg mice. Trunk blood is also collected from the pups (and an eyebleed from the dams one day after birth) to quantitate, via ELISA, the levels of anti-IL-22RA mAb in the serum of each mouse. Because these mAbs are potent inhibitors of IL-20 and/or IL-22 in vivo, the Tg pups have normal skin (i.e. no epidermal thickening or "shiny" appearance).

EXAMPLE 41

IL-20 and IL-22 Antagonists in Organ Culture Psoriasis Model

Human psoriatic plaque skin can be maintained in organ culture, and the abnormal histological features of lesional skin are maintained in the absence of exogenous growth factors. Antibodies against IL-22RA, IL-20, IL-22, IL20R and/or IL-22R, or soluble IL-20 or IL-22 receptors can be administered, and the histological features of psoriatic lesional skin can be ameliorated.

B. Study Design

Full-thickness 2-mm punch biopsies consisting of the entire epidermis and several mm of dermis are obtained from either healthy adult volunteers or from psoriatic lesional skin. Immediately upon biopsy, the tissue is immersed in culture medium consisting of Keratinocyte Basal Medium (KBM) (Clonetics Inc, Walkersville, Md.). The culture medium is supplemented with CaCl2 to bring the final Ca2+ concentration to 1.4 mM (Varani et al, 1993, 1994). The biopsies are then incubated in wells of a 96-well dish containing 200 ul of Ca2+ supplemented KBM with or without additional treatments of antibodies against human IL-20, IL-22, IL-22RA, or soluble receptors of IL-20 or IL-22. Cultures are incubated at 37° C. in an atmosphere of 95% air and 5% $CO_2$ for 8 days.

C. Quantitative Analysis:

At the end of incubation period, tissue is fixed in 10% buffered formalin and examined histologically after staining with hematoxylin and eosin. The appearance of psoriatic tissue exposed to the antibodies or soluble receptors could be more closely resembled that of normal tissues, including the following observation: the initially disorganized, irregular-shaped basal epithelial cells developed a more columnar appearance with restored polarity; epidermal rete ridges regressed, with fewer areas of epithelial cell expansion into the dermal space; and there was less overall degeneration of the upper epidermal layers. The organ culture model provides a rapid and sensitive means for determining if a particular compound has potential as an anti-hyperproliferative agent. The abnormal histological feature may be ameliorated in the presence of an IL-20, IL-22 antagonist, suggesting the effectiveness of such agent in the treatment of psoriasis.

EXAMPLE 42

Mapping of mIL22RA (zCytoR11m) Regions Binding to Neutralizing mAbs R2.1.5F4.1 and R2.1.15E2.1

A. Epitopes on Murine IL-22RA wherein Neutralizing Monoclonal Antibodies Bind.

The experiments described below were aimed at identifying a region or regions in the amino acid sequence of murine IL-22RA soluble receptor protein (SEQ ID NO:62) that were important for receptor activity, or for antagonist or neutralizing antibody binding. The murine IL-22RA-Fc protein, which was previously cleaved with thrombin to remove the Fc, was then cleaved C-terminally to the methionine residues in the sequence by incubation with cyanogen bromide (CNBr). The CNBr-generated peptides were fractionated, and fractions were tested for binding activity as detected by ELISA and reactivity by Western analysis using monoclonal antibodies with neutralizing properties, clones R2.1.5F4.1 and R2.1.15E2.1.

Upon cleavage with CNBr, the following peptides were potentially generated from non-reduced full-length mIL-22RA (Table 33). Under non-reducing conditions, cysteines are disulfide-bonded, which may result in an internal linkage in peptide 1 and a link between peptides 3 and 5. The residues in bold font are potentially involved in ligand binding that correspond with human IL-22RA residues potentially involved in ligand binding in SEQ ID NO:2 or SEQ ID NO:3, as described in Example 42B. Specifically, SEQ ID NO:48 corresponds to amino acid residues 16 (His) to 83 (Met) of SEQ ID NO:42; SEQ ID NO:49 corresponds to amino acid residues 84 (Glu) to 109 (Met) of SEQ ID NO:42, SEQ ID NO:50 corresponds to amino acid residues 110 (Thr) to 137 (Met) of SEQ ID NO:42, SEQ ID NO:51 corresponds to amino acid residues 138 (Leu) to 177 (Met) of SEQ ID NO:42, and SEQ ID NO:52 which corresponds to amino acid residues 163 (His) to 208 (Pro) of SEQ ID NO:42 or 163 (His) to 212 (Arg) of SEQ ID NO:62.

TABLE 33

| Peptide Number | From | To | Sequence |
|---|---|---|---|
| CNBr Peptide 1 | 1 | 68 | HTTVDTSGLLQHVKFQSSNFENILTWDGGP ASTSDTVYSVEYKKYGERKWLAKAGCQRI TQKFCNLTM (SEQ ID NO: 48) |
| | | | non-reduced: cysteines in peptide 1 are linked |
| CNBr Peptide 2 | 69 | 94 | ETRNHTEFYYAKVTAVSAGGPPVTKM (SEQ ID NO: 49) |
| CNBr Peptide 3 | 95 | 122 | TDRFSSLQHTTIKPPDVTCIPKVRSIQM (SEQ ID NO: 50) |
| | | | non-reduced: peptides 3-5 are linked |
| CNBr Peptide 4 | 123 | 162 | LVHPTLTPVLSEDGHQLTLEEIFHDLFYRLE LHVNHTYQM (SEQ ID NO: 51) |
| CNBr Peptide 5 | 163 | 212 | HLEGKQREYEFLGLTPDTEFLGSITILTPILS KESAPYVCRVKTLPLVPR (SEQ ID NO: 52) |

1. CNBr Cleavage and Isolation of Peptide Fractions

50 μg of mIL22RA was lyophilized and reconstituted in 180 μL of formic acid (70%). 1 μL of 5M CNBr dissolved in acetonitrile was added. The sample was mixed and left to react for 18 hours at room temperature in the dark. 150 μL of the reaction mixture were fractionated by reversed-phase HPLC fitted with an analytical Zorbax SB300-C8 column. Peaks were separated using a gradient starting at 25% acetonitrile (0.085% TFA) and 75% water (0.1% TFA) and finishing at 95% acetonitrile (0.085% TFA) and 5% water (0.1% TFA). UV analysis showed three main and two minor peaks, which were collected. Each fraction was divided in half; one portion was submitted to ELISA, the other portion was lyophilized and reconstituted in 150 μL of phosphate-buffered saline solution (PBS). UV analysis of the PBS fractions confirmed the recovery of all peaks collected from the analytical column. The PBS fractions were submitted for Western analysis.

2. ELISA

HPLC fractions containing peptide sequences from IL-22RA cleaved with CNBr were diluted to an estimated equal concentration using HPLC buffer (90% acetonitrile, 10% H₂O, 0.09% trifluoroacetic acid). Samples were loaded to ninety-six-well microtiter plates in 4 wells each at 100 □L/well and allowed to dry down overnight at room temperature in a fume hood. The plates were washed with ELISA C buffer (PBS, 0.05% Tween-20), and then blocked with ELISA B buffer (PBS, 0.1% BSA, 0.05% Tween-20) for 2 hours at 37° C. Two monoclonal antibodies (mAb) to IL22RA (Clone R2.1.5F4.1, and Clone R2.1.15E2.1) were diluted to 2 □g/mL in ELISA B. Each mAb was added to each peptide sequence sample at 100 □L/well and plates were incubated for 60 minutes at 37° C. The plates were washed to remove unbound antibody, and a secondary antibody (goat anti-rat IgG conjugated to horseradish peroxidase (Jackson)) was diluted to 1 □g/mL in ELISA B buffer and added to all wells at 100 □L/well. Plates were incubated for 1 hour at 37° C. The wells were washed with ELISA C buffer, and then incubated with TMB 1 Component HRP Microwell Substrate (BioFx) for 5 minutes. The reaction was stopped by the addition of 450 nm Stop Reagent for TMB Microwell (BioFx) and the plates read at absorbance 450 nm in a Dynatech ELISA plate reader (Molecular Devices).

Results indicate mAb R2.1.5F4.1 reacted with HPLC fraction #4 of the mIL22RA CNBr reaction, which also produced a band in the Western blotting experiments.

3. Western

HPLC fractions containing peptide sequences from IL22RA cleaved with CNBr were lyophilized over night at room temp, and reconstituted in PBS. Samples were then mixed with non-reducing sample buffer (Invitrogen) and boiled for 10 min. Samples were loaded and electrophoresed by SDS-PAGE on 4-12% Bis-Tris gels (Invitrogen) using 1×MES-SDS Running Buffer (Invitrogen) and transferred to nitrocellulose (0.2 □m; Bio-Rad) in 20% Methanol transfer buffer, all at room temperature. Filters were allowed to dry over night at room temperature. The filters were blocked with 10% non-fat dry milk in buffer A (50 mM Tris, pH 7.4, 5 mM EDTA, 0.05% Igepal CA-630, 150 mM NaCl, 0.25% gelatin) for 30 minutes at room temperature. A monoclonal antibody (mAb) to IL22RA (Clone R2.1.5F4.1) was diluted to 2 □g/mL in buffer A containing 2.5% non-fat dry milk. Blots were incubated in this primary antibody for 1 hour at room temperature. Following incubation, blots were washed three times in buffer A and incubated 1 hour at room temperature with a 1:5000 dilution of secondary antibody (Goat anti-Rat IgG-horseradish peroxidase; Jackson, Inc) in buffer A with 2.5% non-fat dry milk. The blots were then washed, developed with a chemiluminescent substrate (Lumi-Light Western Blotting Substrate; Roche), and exposed using a luminescent imager (Mannheim Boehringer Lumi-Imager).

Using a 30 minute exposure, the non-reducing gel showed very strong bands for fractions #4 and #5, along with a faint band for fraction #3. Fraction #4 also tested positive in the ELISA.

N-Terminal Sequencing of Active Fraction #4

Of the five CNBr peptide fractions collected from the analytical reversed-phase column, fraction #4 showed activity in the ELISA and was also positive by Western blotting. To identify the peptides present in the active fraction #4, the sample was submitted to Edman degradation using well-known methods. Three N-termini were identified from the active fraction that were consistent with peptides 2 (SEQ ID NO:49), 3 (SEQ ID NO:50), and 5 (SEQ ID NO:52). These results indicated that the antibodies bound to peptides 2 (SEQ ID NO:49), 3 (SEQ ID NO:50), and 5 (SEQ ID NO:52).

TABLE 34

| Edman Degradation | N-Terminal Sequence | Peptide Identification |
|---|---|---|
| First Sequence Obtained from Fraction #4 | HLEGK QREYE FLGLT PDTEF | CNBr Peptide 5 (SEQ ID NO: 52) |
| CNBr-generated mIL22RA Sequence | HLEGK QREYE FLGLT PDTEF LGSIT ILTPI LSKES APYVC R VKTL PLVPR (SEQ ID NO: 53) | |
| Second Sequence Obtained from Fraction #4 | ETRNH TEFYY AKVTA VSAGG | CNBr Peptide 2 (SEQ ID NO: 49) |
| CNBr-generated mIL22RA Sequence | ETRNH TEFYY AKVTA VSAGG PPVTK M (SEQ ID NO: 54) | |
| Third Sequence Obtained from Fraction #4 | TDRFS XLQHT XIXPX DXXXI | CNBr Peptide 3 (SEQ ID NO: 50) |
| CNBr-generated mIL22RA Sequence | TDRFS SLQHT TIKPP DVTCIPKVRS IQM (SEQ ID NO: 55) | |

Discussion

Five fractions were isolated from a mixture of CNBr-cleaved mIL22RA peptides. Of these, only fraction #4 was active in an ELISA and positive by Western. Edman degradation identified three N-termini consistent with CNBr peptides 2 (SEQ ID NO:49), 3 (SEQ ID NO:50), and 5 (SEQ ID NO:52) in fraction #4. Within these regions, six residues are potentially involved in ligand binding. These residues are Y93, R112, K210, and E211 of SEQ ID NO:42, which also correspond to residues Y78, R97, K195, and E196 of SEQ ID NO:62. Residues Y60 and F164 of SEQ ID NO:42 are also involved in ligand binding.

B. Epitopes on Human IL-22RA wherein Neutralizing Monoclonal Antibodies Bind.

The experiments described below are aimed at identifying a region or regions in the extracellular domain for amino acid sequence of human IL-22RA protein (SEQ ID NO:2) that are important for receptor activity, or for antagonist or neutralizing antibody binding. A human soluble receptor IL-22RA protein (e.g., comprising SEQ ID NO:3, such as, IL-22RA-Fc cleaved with thrombin to remove the Fc) is then cleaved C-terminally to the methionine residues in the sequence by incubation with cyanogen bromide (CNBr), or other agent known in the art that cleaves the human protein into defined fragments. The CNBr-generated peptides are fractionated, and the resulting fractions are tested for binding activity as detected by ELISA and reactivity by Western analysis using monoclonal antibodies with neutralizing properties.

Four cysteines are predicted to be disulfide-bonded with a linkage pattern of Cys71-Cys79 and Cys204-Cys217 of SEQ ID NO:2. Upon cleavage with CNBr, the following peptides are potentially generated from non-reduced full-length human IL-22RA: peptide 6 (SEQ ID NO:56), peptide 7 (SEQ ID NO:57); peptide 8 (SEQ ID) NO:58); peptide 9 (SEQ ID NO:59); peptide 10 (SEQ ID NO:60); and peptide 11 (SEQ ID NO:61) (Table 35). Cysteines are disulfide-bonded, which results in a possible link between peptides 7 (SEQ ID NO:57) and 10 (SEQ ID NO:60. Specifically, SEQ ID NO:56 corresponds to amino acid residues 1 (Pro) to 92 (Met) of SEQ ID NO:3; SEQ ID NO:57 corresponds to amino acid residues 93 (Thr) to 120 (Met) of SEQ ID NO:3, SEQ ID NO:58 corresponds to amino acid residues 121 (Ile) to 160 (Met) of SEQ ID NO:3, SEQ ID NO:59 corresponds to amino acid residues 161 (His) to 185 (Met) of SEQ ID NO:3, SEQ ID NO:60 corresponds to amino acid residues 186 (Ile) to 199 (Met) of SEQ ID NO:3 and SEQ ID NO:61 corresponds to amino acid residues 200 (Cys) to 211 (Thr) of SEQ ID NO:3.

TABLE 35

| Peptide Number | From | To | Sequence |
|---|---|---|---|
| CNBr Peptide 6 | 1 | 92 | Pro Glu Asp Pro Ser Asp Leu Leu Gln His Val Lys Phe Gln Ser Ser Asn Phe Glu Asn Ile Leu Thr Trp Asp Ser Gly Pro Glu Gly Thr Pro Asp Thr Val Tyr Ser Ile Glu Tyr Lys Thr Tyr Gly Glu Arg Asp Trp Val Ala Lys Lys Gly Cys Gln Arg Ile Thr Arg Lys Ser Cys Asn Leu Thr Val Glu Thr Gly Asn Leu Thr Glu Leu Tyr Tyr Ala Arg Val Thr Ala Val Ser Ala Gly Gly Arg Ser Ala Thr Lys Met (SEQ ID NO: 56) |
| CNBr Peptide 7 | 93 | 120 | Thr Asp Arg Phe Ser Ser Leu Gln His Thr Thr Leu Lys Pro Pro Asp Val Thr Cys Ile Ser Lys Val Arg Ser Ile Gln Met (SEQ ID NO: 57) |
| CNBr Peptide 8 | 121 | 160 | Ile Val His Pro Thr Pro Thr Pro Ile Arg Ala Gly Asp Gly His Arg Leu Thr Leu Glu Asp Ile Phe His Asp Leu Phe Tyr His Leu Glu Leu Gln Val Asn Arg Thr Tyr Gln Met (SEQ ID NO: 58) |
| CNBr Peptide 9 | 161 | 185 | His Leu Gly Gly Lys Gln Arg Glu Tyr Glu Phe Phe Gly Leu Thr Pro Asp Thr Glu Phe Leu Gly Thr Ile Met (SEQ ID NO: 59) |
| CNBr Peptide 10 | 186 | 199 | Ile Cys Val Pro Thr Trp Ala Lys Glu Ser Ala Pro Tyr Met (SEQ ID NO: 60) |
| CNBr Peptide 11 | 200 | 211 | Cys Arg Val Lys Thr Leu Pro Asp Arg Thr Trp Thr (SEQ ID NO: 61) |

4. CNBr Cleavage and Isolation of Peptide Fractions, Western and ELISA, and N-terminal Sequencing About 50 μg of human IL22RA is lyophilized and is reconstituted, fractionated, collected and analysed using Western analysis, and ELISA as described in EXAMPLE 42A, to identify fractions containing anti-IL-22RA monoclonal antibodies, and those that bind IL-22RA as shown by ELISA and Western analysis. The CNBr peptide fractions that are collected from the analytical reversed-phase column, are then tested for activity in the ELISA and are confirmed as positive by Western blotting. For positive fractions, peptides are identified via Edman degradation using well-known methods.

Discussion

The mouse CNBr peptide #5 (SEQ ID NO:52) corresponds to human CNBr peptides #9, and #10 (SEQ ID NO:59 and SED ID NO:60); mouse CNBr peptide #2 (SEQ ID NO:49) corresponds to human CNBr #6 (SEQ ID NO:56); and mouse CNBr peptide #3 (SEQ ID NO:50) corresponds to human CNBr #7 (SEQ ID NO:57). Of the fractions that are isolated from a mixture the CNBr-cleaved human IL-22RA peptides, six residues within the possible regions are potentially involved in ligand binding: Residues of SEQ ID NO:2 (and corresponding residues of SEQ ID NO:3) that are important to ligand-receptor binding comprise Tyr-60, and Phe-164, Tyr-93, Arg-112, Lys-210, and Glu-211 of SEQ ID NO:2 and (and corresponding residues of SEQ ID NO:3). Moreover, primary residues of SEQ ID NO:2 (and corresponding residues of SEQ ID NO:3) that are important to direct ligand-receptor binding comprise Tyr-60, and Phe-164 of SEQ ID NO:2 (and corresponding residues of SEQ ID NO:3), and secondary residues comprise residues Tyr-93, Arg-112, Lys-210, and Glu-211 of SEQ ID NO:2 and (and corresponding residues of SEQ ID NO:3).

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated antibody or antigen-binding fragment thereof that can compete with a monoclonal antibody expressed by a hybridoma from the group of:
   (a) the hybridoma clone 280.46.3.4 (ATCC Patent Deposit Designation PTA-6284);
   (b) the hybridoma clone 281.73.49.1.1 (ATCC Patent Deposit Designation PTA-6285);
   (c) the hybridoma clone 283.4.1.2 (ATCC Patent Deposit Designation PTA-6287);
   (d) the hybridoma clone 283.52.5.4 (ATCC Patent Deposit Designation PTA-6311); and
   (e) the hybridoma clone 283.108.2.3 (ATCC Patent Deposit Designation PTA-6286)
   for binding to the polypeptides of SEQ ID NO:2 or SEQ ID NO:3.

2. The antibody or antigen-binding fragment according to claim 1, wherein the antibody or antigen-binding fragment binds to SEQ ID NO:2 or SEQ ID NO:3.

3. The antibody or antigen-binding fragment according to claim 1, wherein the antibody or antigen-binding fragment reduces or neutralizes the pro-inflammatory activity of SEQ ID NO:2 or SEQ ID NO:3.

4. The antibody or antigen-binding fragment according to claim 1, wherein the antibody or antigen-binding fragment is pegylated.

5. The antibody or antigen-binding fragment according to claim 1, wherein the antibody or antigen-binding fragment further comprises a radionuclide, enzyme, substrate, cofactor, fluorescent marker, chemiluminescent marker, peptide tag, magnetic particle, drug, or toxin.

6. A pharmaceutical composition comprising the antibody or antigen-binding fragment according to claim 1.

7. The antibody or antigen-binding fragment thereof according to claim 1, wherein the antibody or antibody-binding fragment thereof is expressed by a hybridoma from the group of:
   (a) the hybridoma clone 280.46.3.4 (ATCC Patent Deposit Designation PTA-6284);
   (b) the hybridoma clone 281.73.49.1.1 (ATCC Patent Deposit Designation PTA-6285);
   (c) the hybridoma clone 283.4.1.2 (ATCC Patent Deposit Designation PTA-6287);
   (d) the hybridoma clone 283.52.5.4 (ATCC Patent Deposit Designation PTA-6311); and
   (e) the hybridoma clone 283.108.2.3 (ATCC Patent Deposit Designation PTA-6286).

8. The antibody or antigen-binding fragment according to claim 7, wherein the antibody or antigen-binding fragment binds to SEQ ID NO:2 or SEQ ID NO:3.

9. The antibody or antigen-binding fragment according to claim 7, wherein the antibody or ntigen-binding fragment reduces or neutralizes the pro-inflammatory activity of SEQ ID NO:2 or SEQ ID NO:3.

10. The antibody or antigen-binding fragment according to claim 7, wherein the antibody or antigen-binding fragment is pegylated.

11. The antibody or antigen-binding fragment according to claim 7, wherein the antibody or antigen-binding fragment further comprises a radionuclide, enzyme, substrate, cofactor, fluorescent marker, chemiluminescent marker, peptide tag, magnetic particle, drug, or toxin.

12. A pharmaceutical composition comprising the antibody or antigen-binding fragment according to claim 7.

13. An immunoconjugate comprising a monoclonal antibody expressed by a hybridoma from the group of:
   (a) the hybridoma clone 280.46.3.4 (ATCC Patent Deposit Designation PTA-6284);
   (b) the hybridoma clone 281.73.49.1.1 (ATCC Patent Deposit Designation PTA-6285);
   (c) the hybridoma clone 283.4.1.2 (ATCC Patent Deposit Designation PTA-6287);
   (d) the hybridoma clone 283.52.5.4 (ATCC Patent Deposit Designation PTA-6311); and
   (e) the hybridoma clone 283.108.2.3 (ATCC Patent Deposit Designation PTA-6286).

14. The immunoconjugate according to claim 13, wherein the monoclonal antibody binds to SEQ ID NO:2 or SEQ ID NO: 3.

15. The immunoconjugate according to claim 13, wherein the monoclonal antibody reduces or neutralizes the pro-inflammatory activity of SEQ ID NO:2 or SEQ ID NO:3.

16. The immunoconjugate according to claim 13, wherein the monoclonal antibody is pegylated.

17. The immunoconjugate according to claim 13, wherein the monoclonal antibody further comprises a radionuclide, enzyme, substrate, cofactor, fluorescent marker, chemiluminescent marker, peptide tag, magnetic particle, drug, or toxin.

18. A pharmaceutical composition comprising the immunoconjugate according to claim 13.

19. A hybridoma from the group of:
   (a) the hybridoma clone 280.46.3.4 (ATCC Patent Deposit Designation PTA-6284);
   (b) the hybridoma clone 281.73.49.1.1 (ATCC Patent Deposit Designation PTA-6285);
   (c) the hybridoma clone 283.4.1.2 (ATCC Patent Deposit Designation A-6287);
   (d) the hybridoma clone 283.52.5.4 (ATCC Patent Deposit Designation PTA-6311); and
   (e) the hybridoma clone 283.108.2.3 (ATCC Patent Deposit Designation PTA-6286).

* * * * *

SEQUENCE LISTING

<160> NUMBER OF SEQ ID NOS: 62

<210> SEQ ID NO 1
<211> LENGTH: 2831
<212> TYPE: DNA
<213> ORGANISM: Homo sapiens
<220> FEATURE:
<221> NAME/KEY: CDS
<222> LOCATION: (34)...(1755)

<400> SEQUENCE: 1

```
tagaggccaa gggagggctc tgtgccagcc ccg atg agg acg ctg ctg acc atc        54
                                    Met Arg Thr Leu Leu Thr Ile
                                    1               5 ttg act gtg gga tcc ctg gct gct cac gcc cct gag gac ccc tcg gat       102
Leu Thr Val Gly Ser Leu Ala Ala His Ala Pro Glu Asp Pro Ser Asp
        10                  15                  20 ctg ctc cag cac gtg aaa ttc cag tcc agc aac ttt gaa aac atc ctg       150
Leu Leu Gln His Val Lys Phe Gln Ser Ser Asn Phe Glu Asn Ile Leu
    25                  30                  35 acg tgg gac agc ggg cca gag ggc acc cca gac acg gtc tac agc atc       198
Thr Trp Asp Ser Gly Pro Glu Gly Thr Pro Asp Thr Val Tyr Ser Ile
```

-continued

```
             40                  45                  50                  55
gag tat aag acg tac gga gag agg gac tgg gtg gca aag aag ggc tgt        246
Glu Tyr Lys Thr Tyr Gly Glu Arg Asp Trp Val Ala Lys Lys Gly Cys
                     60                  65                  70 cag cgg atc acc cgg aag tcc tgc aac ctg acg gtg gag acg ggc aac        294
Gln Arg Ile Thr Arg Lys Ser Cys Asn Leu Thr Val Glu Thr Gly Asn
             75                  80                  85 ctc acg gag ctc tac tat gcc agg gtc acc gct gtc agt gcg gga ggc        342
Leu Thr Glu Leu Tyr Tyr Ala Arg Val Thr Ala Val Ser Ala Gly Gly
         90                  95                 100 cgg tca gcc acc aag atg act gac agg ttc agc tct ctg cag cac act        390
Arg Ser Ala Thr Lys Met Thr Asp Arg Phe Ser Ser Leu Gln His Thr
    105                 110                 115 acc ctc aag cca cct gat gtg acc tgt atc tcc aaa gtg aga tcg att        438
Thr Leu Lys Pro Pro Asp Val Thr Cys Ile Ser Lys Val Arg Ser Ile
120                 125                 130                 135 cag atg att gtt cat cct acc ccc acg cca atc cgt gca ggc gat ggc        486
Gln Met Ile Val His Pro Thr Pro Thr Pro Ile Arg Ala Gly Asp Gly
                140                 145                 150 cac cgg cta acc ctg gaa gac atc ttc cat gac ctg ttc tac cac tta        534
His Arg Leu Thr Leu Glu Asp Ile Phe His Asp Leu Phe Tyr His Leu
            155                 160                 165 gag ctc cag gtc aac cgc acc tac caa atg cac ctt gga ggg aag cag        582
Glu Leu Gln Val Asn Arg Thr Tyr Gln Met His Leu Gly Gly Lys Gln
        170                 175                 180 aga gaa tat gag ttc ttc ggc ctg acc cct gac aca gag ttc ctt ggc        630
Arg Glu Tyr Glu Phe Phe Gly Leu Thr Pro Asp Thr Glu Phe Leu Gly
    185                 190                 195 acc atc atg att tgc gtt ccc acc tgg gcc aag gag agt gcc ccc tac        678
Thr Ile Met Ile Cys Val Pro Thr Trp Ala Lys Glu Ser Ala Pro Tyr
200                 205                 210                 215 atg tgc cga gtg aag aca ctg cca gac cgg aca tgg acc tac tcc ttc        726
Met Cys Arg Val Lys Thr Leu Pro Asp Arg Thr Trp Thr Tyr Ser Phe
                220                 225                 230 tcc gga gcc ttc ctg ttc tcc atg ggc ttc ctc gtc gca gta ctc tgc        774
Ser Gly Ala Phe Leu Phe Ser Met Gly Phe Leu Val Ala Val Leu Cys
            235                 240                 245 tac ctg agc tac aga tat gtc acc aag ccg cct gca cct ccc aac tcc        822
Tyr Leu Ser Tyr Arg Tyr Val Thr Lys Pro Pro Ala Pro Pro Asn Ser
        250                 255                 260 ctg aac gtc cag cga gtc ctg act ttc cag ccg ctg cgc ttc atc cag        870
Leu Asn Val Gln Arg Val Leu Thr Phe Gln Pro Leu Arg Phe Ile Gln
    265                 270                 275 gag cac gtc ctg atc cct gtc ttt gac ctc agc ggc ccc agc agt ctg        918
Glu His Val Leu Ile Pro Val Phe Asp Leu Ser Gly Pro Ser Ser Leu
280                 285                 290                 295 gcc cag cct gtc cag tac tcc cag atc agg gtg tct gga ccc agg gag        966
Ala Gln Pro Val Gln Tyr Ser Gln Ile Arg Val Ser Gly Pro Arg Glu
                300                 305                 310 ccc gca gga gct cca cag cgg cat agc ctg tcc gag atc acc tac tta       1014
Pro Ala Gly Ala Pro Gln Arg His Ser Leu Ser Glu Ile Thr Tyr Leu
            315                 320                 325 ggg cag cca gac atc tcc atc ctc cag ccc tcc aac gtg cca cct ccc       1062
Gly Gln Pro Asp Ile Ser Ile Leu Gln Pro Ser Asn Val Pro Pro Pro
        330                 335                 340 cag atc ctc tcc cca ctg tcc tat gcc cca aac gct gcc cct gag gtc       1110
Gln Ile Leu Ser Pro Leu Ser Tyr Ala Pro Asn Ala Ala Pro Glu Val
    345                 350                 355 ggg ccc cca tcc tat gca cct cag gtg acc ccc gaa gct caa ttc cca       1158
```

```
Gly Pro Pro Ser Tyr Ala Pro Gln Val Thr Pro Glu Ala Gln Phe Pro
360                 365                 370                 375 ttc tac gcc cca cag gcc atc tct aag gtc cag cct tcc tcc tat gcc     1206
Phe Tyr Ala Pro Gln Ala Ile Ser Lys Val Gln Pro Ser Ser Tyr Ala
                380                 385                 390 cct caa gcc act ccg gac agc tgg cct ccc tcc tat ggg gta tgc atg     1254
Pro Gln Ala Thr Pro Asp Ser Trp Pro Pro Ser Tyr Gly Val Cys Met
            395                 400                 405 gaa ggt tct ggc aaa gac tcc ccc act ggg aca ctt tct agt cct aaa     1302
Glu Gly Ser Gly Lys Asp Ser Pro Thr Gly Thr Leu Ser Ser Pro Lys
        410                 415                 420 cac ctt agg cct aaa ggt cag ctt cag aaa gag cca cca gct gga agc     1350
His Leu Arg Pro Lys Gly Gln Leu Gln Lys Glu Pro Pro Ala Gly Ser
    425                 430                 435 tgc atg tta ggt ggc ctt tct ctg cag gag gtg acc tcc ttg gct atg     1398
Cys Met Leu Gly Gly Leu Ser Leu Gln Glu Val Thr Ser Leu Ala Met
440                 445                 450                 455 gag gaa tcc caa gaa gca aaa tca ttg cac cag ccc ctg ggg att tgc     1446
Glu Glu Ser Gln Glu Ala Lys Ser Leu His Gln Pro Leu Gly Ile Cys
                460                 465                 470 aca gac aga aca tct gac cca aat gtg cta cac agt ggg gag gaa ggg     1494
Thr Asp Arg Thr Ser Asp Pro Asn Val Leu His Ser Gly Glu Glu Gly
            475                 480                 485 aca cca cag tac cta aag ggc cag ctc ccc ctc ctc tcc tca gtc cag     1542
Thr Pro Gln Tyr Leu Lys Gly Gln Leu Pro Leu Leu Ser Ser Val Gln
        490                 495                 500 atc gag ggc cac ccc atg tcc ctc cct ttg caa cct cct tcc ggt cca     1590
Ile Glu Gly His Pro Met Ser Leu Pro Leu Gln Pro Pro Ser Gly Pro
    505                 510                 515 tgt tcc ccc tcg gac caa ggt cca agt ccc tgg ggc ctg ctg gag tcc     1638
Cys Ser Pro Ser Asp Gln Gly Pro Ser Pro Trp Gly Leu Leu Glu Ser
520                 525                 530                 535 ctt gtg tgt ccc aag gat gaa gcc aag agc cca gcc cct gag acc tca     1686
Leu Val Cys Pro Lys Asp Glu Ala Lys Ser Pro Ala Pro Glu Thr Ser
                540                 545                 550 gac ctg gag cag ccc aca gaa ctg gat tct ctt ttc aga ggc ctg gcc     1734
Asp Leu Glu Gln Pro Thr Glu Leu Asp Ser Leu Phe Arg Gly Leu Ala
            555                 560                 565 ctg act gtg cag tgg gag tcc tgaggggaat gggaaggct tggtgcttcc          1785
Leu Thr Val Gln Trp Glu Ser
        570 tccctgtccc tacccagtgt cacatccttg gctgtcaatc ccatgcctgc ccatgccaca   1845 cactctgcga tctggcctca gacgggtgcc cttgagagaa gcagagggag tggcatgcag   1905 ggccctgcc atgggtgcgc tcctcaccgg aacaaagcag catgataagg actgcagcgg    1965 gggagctctg gggagcagct tgtgtagaca gcgcgtgct cgctgagccc tgcaaggcag    2025 aaatgacagt gcaaggagga aatgcaggga aactcccgag gtccagagcc ccacctccta   2085 acaccatgga ttcaaagtgc tcagggaatt tgcctctcct tgccccattc ctggccagtt   2145 tcacaatcta gctcgacaga gcatgaggcc cctgcctctt ctgtcattgt tcaaaggtgg   2205 gaagagagcc tggaaaagaa ccaggcctgg aaaagaacca gaaggaggct gggcagaacc   2265 agaacaacct gcacttctgc caaggccagg gccagcagga cggcaggact ctagggaggg   2325 gtgtggcctg cagctcattc ccagccaggg caactgcctg acgttgcacg atttcagctt   2385 cattcctctg atagaacaaa gcgaaatgca ggtccaccag ggagggagac acacaagcct   2445 tttctgcagg caggagtttc agaccctatc ctgagaatgg ggtttgaaag gaaggtgagg   2505
```

-continued

```
gctgtggccc ctggacgggt acaataacac actgtactga tgtcacaact ttgcaagctc    2565
tgccttgggt tcagcccatc tgggctcaaa ttccagcctc accactcaca agctgtgtga    2625
cttcaaacaa atgaaatcag tgcccagaac ctcggtttcc tcatctgtaa tgtggggatc    2685
ataacaccta cctcatggag ttgtggtgaa gatgaaatga agtcatgtct ttaaagtgct    2745
taatagtgcc tggtacatgg gcagtgccca ataaacggta gctatttaaa aaaaaaaaa    2805 aaaaaaaaaa atagcggccg cctcga                                        2831
```

```
<210> SEQ ID NO 2
<211> LENGTH: 574
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
| Met | Arg | Thr | Leu | Leu | Thr | Ile | Leu | Thr | Val | Gly | Ser | Leu | Ala | Ala | His |
| 1 | | | | 5 | | | | | 10 | | | | | 15 | |

Ala Pro Glu Asp Pro Ser Asp Leu Leu Gln His Val Lys Phe Gln Ser
          20                  25                  30

Ser Asn Phe Glu Asn Ile Leu Thr Trp Asp Ser Gly Pro Glu Gly Thr
    35                  40                  45

Pro Asp Thr Val Tyr Ser Ile Glu Tyr Lys Thr Tyr Gly Glu Arg Asp
50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

```
Leu Ser Glu Ile Thr Tyr Leu Gly Gln Pro Asp Ile Ser Ile Leu Gln
                325                 330                 335

Pro Ser Asn Val Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
            355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
            435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
        515                 520                 525

Pro Trp Gly Leu Leu Glu Ser Leu Val Cys Pro Lys Asp Glu Ala Lys
        530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570

<210> SEQ ID NO 3
<211> LENGTH: 211
<212> TYPE: PRT
<213> ORGANISM: Homo sapiens

<400> SEQUENCE: 3

Pro Glu Asp Pro Ser Asp Leu Leu Gln His Val Lys Phe Gln Ser Ser
1               5                   10                  15

Asn Phe Glu Asn Ile Leu Thr Trp Asp Ser Gly Pro Glu Gly Thr Pro
            20                  25                  30

Asp Thr Val Tyr Ser Ile Glu Tyr Lys Thr Tyr Gly Glu Arg Asp Trp
        35                  40                  45

Val Ala Lys Lys Gly Cys Gln Arg Ile Thr Arg Lys Ser Cys Asn Leu
    50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met Thr Asp Arg Phe
                85                  90                  95

Ser Ser Leu Gln His Thr Thr Leu Lys Pro Pro Asp Val Thr Cys Ile
            100                 105                 110

Ser Lys Val Arg Ser Ile Gln Met Ile Val His Pro Thr Pro Thr Pro
```

-continued

```
                115                 120                 125
Ile Arg Ala Gly Asp Gly His Arg Leu Thr Leu Glu Asp Ile Phe His
    130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175

Asp Thr Glu Phe Leu Gly Thr Ile Met Ile Cys Val Pro Thr Trp Ala
            180                 185                 190

Lys Glu Ser Ala Pro Tyr Met Cys Arg Val Lys Thr Leu Pro Asp Arg
            195                 200                 205

Thr Trp Thr
    210

<210> SEQ ID NO 4
<211> LENGTH: 541
<212> TYPE: PRT
<213> ORGANISM: Artificial Sequence
<220> FEATURE:
<223> OTHER INFORMATION: A Soluble IL-22RA-Fc Fusion Polypeptide

<400> SEQUENCE: 4

Pro Glu Asp Pro Ser Asp Leu Leu Gln His Val Lys Phe Gln Ser Ser
1               5                   10                  15

Asn Phe Glu Asn Ile Leu Thr Trp Asp Ser Gly Pro Glu Gly Thr Pro
                20                  25                  30

Asp Thr Val Tyr Ser Ile Glu Tyr Lys Thr Tyr Gly Glu Arg Asp Trp
            35                  40                  45

Val Ala Lys Lys Gly Cys Gln Arg Ile Thr Arg Lys Ser Cys Asn Leu
    50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met Thr Asp Arg Phe
                85                  90                  95

Ser Ser Leu Gln His Thr Thr Leu Lys Pro Pro Asp Val Thr Cys Ile
            100                 105                 110

Ser Lys Val Arg Ser Ile Gln Met Ile Val His Pro Thr Pro Thr Pro
        115                 120                 125

Ile Arg Ala Gly Asp Gly His Arg Leu Thr Leu Glu Asp Ile Phe His
    130                 135                 140

Asp Leu Phe Tyr His Leu Glu Leu Gln Val Asn Arg Thr Tyr Gln Met
145                 150                 155                 160

His Leu Gly Gly Lys Gln Arg Glu Tyr Glu Phe Phe Gly Leu Thr Pro
                165                 170                 175

Asp Thr Glu Phe Leu Gly Thr Ile Met Ile Cys Val Pro Thr Trp Ala
            180                 185                 190

Lys Glu Ser Ala Pro Tyr Met Cys Arg Val Lys Thr Leu Pro Asp Arg
        195                 200                 205

Thr Trp Thr Ala Ser Thr Lys Gly Pro Ser Val Phe Pro Leu Ala Pro
    210                 215                 220

Ser Ser Lys Ser Thr Ser Gly Gly Thr Ala Ala Leu Gly Cys Leu Val
225                 230                 235                 240

Lys Asp Tyr Phe Pro Glu Pro Val Thr Val Ser Trp Asn Ser Gly Ala
                245                 250                 255

Leu Thr Ser Gly Val His Thr Phe Pro Ala Val Leu Gln Ser Ser Gly
```

```
                260                 265                 270
Leu Tyr Ser Leu Ser Ser Val Val Thr Val Pro Ser Ser Leu Gly
            275                 280                 285

Thr Gln Thr Tyr Ile Cys Asn Val Asn His Lys Pro Ser Asn Thr Lys
    290                 295                 300

Val Asp Lys Lys Val Glu Pro Lys Ser Cys Asp Lys Thr His Thr Cys
305                 310                 315                 320

Pro Pro Cys Pro Ala Pro Glu Leu Leu Gly Gly Pro Ser Val Phe Leu
                325                 330                 335

Phe Pro Pro Lys Pro Lys Asp Thr Leu Met Ile Ser Arg Thr Pro Glu
            340                 345                 350

Val Thr Cys Val Val Val Asp Val Ser His Glu Asp Pro Glu Val Lys
        355                 360                 365

Phe Asn Trp Tyr Val Asp Gly Val Glu Val His Asn Ala Lys Thr Lys
    370                 375                 380

Pro Arg Glu Glu Gln Tyr Asn Ser Thr Tyr Arg Val Val Ser Val Leu
385                 390                 395                 400

Thr Val Leu His Gln Asp Trp Leu Asn Gly Lys Glu Tyr Lys Cys Lys
                405                 410                 415

Val Ser Asn Lys Ala Leu Pro Ala Pro Ile Glu Lys Thr Ile Ser Lys
            420                 425                 430

Ala Lys Gly Gln Pro Arg Glu Pro Gln Val Tyr Thr Leu Pro Pro Ser
        435                 440                 445

Arg Asp Glu Leu Thr Lys Asn Gln Val Ser Leu Thr Cys Leu Val Lys
    450                 455                 460

Gly Phe Tyr Pro Ser Asp Ile Ala Val Glu Trp Glu Ser Asn Gly Gln
465                 470                 475                 480

Pro Glu Asn Asn Tyr Lys Thr Thr Pro Pro Val Leu Asp Ser Asp Gly
                485                 490                 495

Ser Phe Phe Leu Tyr Ser Lys Leu Thr Val Asp Lys Ser Arg Trp Gln
            500                 505                 510

Gln Gly Asn Val Phe Ser Cys Ser Val Met His Glu Ala Leu His Asn
        515                 520                 525

His Tyr Thr Gln Lys Ser Leu Ser Leu Ser Pro Gly Lys
    530                 535                 540

<210> SEQ ID NO 5
<211> LENGTH: 1116
<212> TYPE: DNA
<213> ORGANISM: Homo sapiens
<220> FEATURE:
<221> NAME/KEY: CDS
<222> LOCATION: (21)...(557)

<400> SEQUENCE: 5
tcgagttaga attgtctgca atg gcc gcc ctg cag aaa tct gtg agc tct ttc         53
                     Met Ala Ala Leu Gln Lys Ser Val Ser Ser Phe
                       1               5                  10 ctt atg ggg acc ctg gcc acc agc tgc ctc ctt ctc ttg gcc ctc ttg        101
Leu Met Gly Thr Leu Ala Thr Ser Cys Leu Leu Leu Leu Ala Leu Leu
            15                  20                  25 gta cag gga gga gca gct gcg ccc atc agc tcc cac tgc agg ctt gac        149
Val Gln Gly Gly Ala Ala Ala Pro Ile Ser Ser His Cys Arg Leu Asp
        30                  35                  40 aag tcc aac ttc cag cag ccc tat atc acc aac cgc acc ttc atg ctg        197
Lys Ser Asn Phe Gln Gln Pro Tyr Ile Thr Asn Arg Thr Phe Met Leu
    45                  50                  55
```

```
gct aag gag gct agc ttg gct gat aac aac aca gac gtt cgt ctc att    245
Ala Lys Glu Ala Ser Leu Ala Asp Asn Asn Thr Asp Val Arg Leu Ile
 60              65                  70                  75 ggg gag aaa ctg ttc cac gga gtc agt atg agt gag cgc tgc tat ctg    293
Gly Glu Lys Leu Phe His Gly Val Ser Met Ser Glu Arg Cys Tyr Leu
                 80                  85                  90 atg aag cag gtg ctg aac ttc acc ctt gaa gaa gtg ctg ttc cct caa    341
Met Lys Gln Val Leu Asn Phe Thr Leu Glu Glu Val Leu Phe Pro Gln
                     95                 100                 105 tct gat agg ttc cag cct tat atg cag gag gtg gtg ccc ttc ctg gcc    389
Ser Asp Arg Phe Gln Pro Tyr Met Gln Glu Val Val Pro Phe Leu Ala
        110                 115                 120 agg ctc agc aac agg cta agc aca tgt cat att gaa ggt gat gac ctg    437
Arg Leu Ser Asn Arg Leu Ser Thr Cys His Ile Glu Gly Asp Asp Leu
            125                 130                 135 cat atc cag agg aat gtg caa aag ctg aag gac aca gtg aaa aag ctt    485
His Ile Gln Arg Asn Val Gln Lys Leu Lys Asp Thr Val Lys Lys Leu
140                 145                 150                 155 gga gag agt gga gag atc aaa gca att gga gaa ctg gat ttg ctg ttt    533
Gly Glu Ser Gly Glu Ile Lys Ala Ile Gly Glu Leu Asp Leu Leu Phe
                    160                 165                 170 atg tct ctg aga aat gcc tgc att tgaccagagc aaagctgaaa atgaataac    587
Met Ser Leu Arg Asn Ala Cys Ile
                175 taaccccctt tccctgctag aaataacaat tagatgcccc aaagcgattt tttttaacca  647 aaaggaagat gggaagccaa actccatcat gatgggtgga ttccaaatga acccctgcgt  707 tagttacaaa ggaaaccaat gccacttttg tttataagac cagaaggtag actttctaag  767 catagatatt tattgataac atttcattgt aactggtgtt ctatacacag aaaacaattt  827 attttttaaa taattgtctt tttccataaa aaagattact ttccattcct ttaggggaaa  887 aaacccctaa atagcttcat gtttccataa tcagtacttt atatttataa atgtatttat  947 tattattata agactgcatt ttatttatat cattttatta atatggattt atttatagaa 1007 acatcattcg atattgctac ttgagtgtaa ggctaatatt gatatttatg acaataatta 1067 tagagctata acatgtttat ttgaccctcaa taaacacttg gatatccta             1116
```

```
<210> SEQ ID NO 6
<211> LENGTH: 179
<212> TYPE: PRT
<213> ORGANISM: Homo sapiens

<400> SEQUENCE: 6
```

```
Met Ala Ala Leu Gln Lys Ser Val Ser Ser Phe Leu Met Gly Thr Leu
 1               5                  10                  15

Ala Thr Ser Cys Leu Leu Leu Ala Leu Leu Val Gln Gly Gly Ala
                 20                  25                  30

Ala Ala Pro Ile Ser Ser His Cys Arg Leu Asp Lys Ser Asn Phe Gln
                 35                  40                  45

Gln Pro Tyr Ile Thr Asn Arg Thr Phe Met Leu Ala Lys Glu Ala Ser
     50                  55                  60

Leu Ala Asp Asn Asn Thr Asp Val Arg Leu Ile Gly Glu Lys Leu Phe
 65                  70                  75                  80

His Gly Val Ser Met Ser Glu Arg Cys Tyr Leu Met Lys Gln Val Leu
                 85                  90                  95

Asn Phe Thr Leu Glu Glu Val Leu Phe Pro Gln Ser Asp Arg Phe Gln
                100                 105                 110
```

```
Pro Tyr Met Gln Glu Val Val Pro Phe Leu Ala Arg Leu Ser Asn Arg
            115                 120                 125
Leu Ser Thr Cys His Ile Glu Gly Asp Asp Leu His Ile Gln Arg Asn
    130                 135                 140
Val Gln Lys Leu Lys Asp Thr Val Lys Lys Leu Gly Glu Ser Gly Glu
145                 150                 155                 160
Ile Lys Ala Ile Gly Glu Leu Asp Leu Leu Phe Met Ser Leu Arg Asn
                165                 170                 175
Ala Cys Ile

<210> SEQ ID NO 7
<211> LENGTH: 926
<212> TYPE: DNA
<213> ORGANISM: Homo sapiens
<220> FEATURE:
<221> NAME/KEY: CDS
<222> LOCATION: (45)...(575)
<220> FEATURE:
<221> NAME/KEY: variation
<222> LOCATION: (188)...(188)
<223> OTHER INFORMATION: Nucleotide may be C or G at position 188

<400> SEQUENCE: 7
ctttgaattc ctagctcctg tggtctccag atttcaggcc taag atg aaa gcc tct    56
                                              Met Lys Ala Ser
                                                1 agt ctt gcc ttc agc ctt ctc tct gct gcg ttt tat ctc cta tgg act   104
Ser Leu Ala Phe Ser Leu Leu Ser Ala Ala Phe Tyr Leu Leu Trp Thr
  5                  10                  15                  20 cct tcc act gga ctg aag aca ctc aat ttg gga agc tgt gtg atc gcc   152
Pro Ser Thr Gly Leu Lys Thr Leu Asn Leu Gly Ser Cys Val Ile Ala
                 25                  30                  35 aca aac ctt cag gaa ata cga aat gga ttt tct gas ata cgg ggc agt   200
Thr Asn Leu Gln Glu Ile Arg Asn Gly Phe Ser Xaa Ile Arg Gly Ser
         40                  45                  50 gtg caa gcc aaa gat gga aac att gac atc aga atc tta agg agg act   248
Val Gln Ala Lys Asp Gly Asn Ile Asp Ile Arg Ile Leu Arg Arg Thr
     55                  60                  65 gag tct ttg caa gac aca aag cct gcg aat cga tgc tgc ctc ctg cgc   296
Glu Ser Leu Gln Asp Thr Lys Pro Ala Asn Arg Cys Cys Leu Leu Arg
 70                  75                  80 cat ttg cta aga ctc tat ctg gac agg gta ttt aaa aac tac cag acc   344
His Leu Leu Arg Leu Tyr Leu Asp Arg Val Phe Lys Asn Tyr Gln Thr
 85                  90                  95                 100 cct gac cat tat act ctc cgg aag atc agc agc ctc gcc aat tcc ttt   392
Pro Asp His Tyr Thr Leu Arg Lys Ile Ser Ser Leu Ala Asn Ser Phe
                105                 110                 115 ctt acc atc aag aag gac ctc cgg ctc tgt cat gcc cac atg aca tgc   440
Leu Thr Ile Lys Lys Asp Leu Arg Leu Cys His Ala His Met Thr Cys
            120                 125                 130 cat tgt ggg gag gaa gca atg aag aaa tac agc cag att ctg agt cac   488
His Cys Gly Glu Glu Ala Met Lys Lys Tyr Ser Gln Ile Leu Ser His
        135                 140                 145 ttt gaa aag ctg gaa cct cag gca gca gtt gtg aag gct ttg ggg gaa   536
Phe Glu Lys Leu Glu Pro Gln Ala Ala Val Val Lys Ala Leu Gly Glu
150                 155                 160 cta gac att ctt ctg caa tgg atg gag gag aca gaa tag gaggaaagtg   585
Leu Asp Ile Leu Leu Gln Trp Met Glu Glu Thr Glu  *
165                 170                 175 atgctgctgc taagaatatt cgaggtcaag agctccagtc ttcaatacct gcagaggagg   645
```

-continued

```
catgacccca aaccaccatc tctttactgt actagtcttg tgctggtcac agtgtatctt    705
atttatgcat tacttgcttc cttgcatgat tgtctttatg catccccaat cttaattgag    765
accatacttg tataagattt ttgtaatatc tttctgctat tggatatatt tattagttaa    825
tatatttatt tattttttgc tattaatgta tttaattttt tacttgggca tgaaacttta    885
aaaaaaattc acaagattat atttataacc tgactagagc a                       926
```

```
<210> SEQ ID NO 8
<211> LENGTH: 176
<212> TYPE: PRT
<213> ORGANISM: Homo sapiens
<220> FEATURE:
<221> NAME/KEY: VARIANT
<222> LOCATION: (48)...(48)
<223> OTHER INFORMATION: Amino acid at position 48 can be a D (Asp) or E
      (Glu)
<220> FEATURE:
<221> NAME/KEY: VARIANT
<222> LOCATION: 48
<223> OTHER INFORMATION: Xaa = Any Amino Acid

<400> SEQUENCE: 8
```

Met Lys Ala Ser Ser Leu Ala Phe Ser Leu Leu Ser Ala Ala Phe Tyr
1               5                   10                  15

Leu Leu Trp Thr Pro Ser Thr Gly Leu Lys Thr Leu Asn Leu Gly Ser
            20                  25                  30

Cys Val Ile Ala Thr Asn Leu Gln Glu Ile Arg Asn Gly Phe Ser Xaa
        35                  40                  45

Ile Arg Gly Ser Val Gln Ala Lys Asp Gly Asn Ile Asp Ile Arg Ile
    50                  55                  60

Leu Arg Arg Thr Glu Ser Leu Gln Asp Thr Lys Pro Ala Asn Arg Cys
65                  70                  75                  80

Cys Leu Leu Arg His Leu Leu Arg Leu Tyr Leu Asp Arg Val Phe Lys
                85                  90                  95

Asn Tyr Gln Thr Pro Asp His Tyr Thr Leu Arg Lys Ile Ser Ser Leu
            100                 105                 110

Ala Asn Ser Phe Leu Thr Ile Lys Lys Asp Leu Arg Leu Cys His Ala
        115                 120                 125

His Met Thr Cys His Cys Gly Glu Glu Ala Met Lys Lys Tyr Ser Gln
    130                 135                 140

Ile Leu Ser His Phe Glu Lys Leu Glu Pro Gln Ala Ala Val Val Lys
145                 150                 155                 160

Ala Leu Gly Glu Leu Asp Ile Leu Leu Gln Trp Met Glu Glu Thr Glu
                165                 170                 175

```
<210> SEQ ID NO 9
<211> LENGTH: 16
<212> TYPE: PRT
<213> ORGANISM: Artificial Sequence
<220> FEATURE:
<223> OTHER INFORMATION: Peptide Linker

<400> SEQUENCE: 9
```

Gly Gly Ser Gly Gly Ser Gly Gly Gly Ser Gly Gly Gly Gly Ser
1               5                   10                  15

```
<210> SEQ ID NO 10
<211> LENGTH: 1050
<212> TYPE: DNA
<213> ORGANISM: Mus musculus
```

```
<220> FEATURE:
<221> NAME/KEY: CDS
<222> LOCATION: (5)...(589)

<400> SEQUENCE: 10 aaca ggc tct cct ctc act tat caa ctt ttg aca ctt gtg cga tcg gtg        49
     Gly Ser Pro Leu Thr Tyr Gln Leu Leu Thr Leu Val Arg Ser Val
     1               5                  10                  15 atg gct gtc ctg cag aaa tct atg agt ttt tcc ctt atg ggg act ttg        97
Met Ala Val Leu Gln Lys Ser Met Ser Phe Ser Leu Met Gly Thr Leu
                20                  25                  30 gcc gcc agc tgc ctg ctt ctc att gcc ctg tgg gcc cag gag gca aat       145
Ala Ala Ser Cys Leu Leu Leu Ile Ala Leu Trp Ala Gln Glu Ala Asn
            35                  40                  45 gcg ctg ccc atc aac acc cgg tgc aag ctt gag gtg tcc aac ttc cag       193
Ala Leu Pro Ile Asn Thr Arg Cys Lys Leu Glu Val Ser Asn Phe Gln
        50                  55                  60 cag ccg tac atc gtc aac cgc acc ttt atg ctg gcc aag gag gcc agc       241
Gln Pro Tyr Ile Val Asn Arg Thr Phe Met Leu Ala Lys Glu Ala Ser
    65                  70                  75 ctt gca gat aac aac aca gac gtc cgg ctc atc ggg gag aaa ctg ttc       289
Leu Ala Asp Asn Asn Thr Asp Val Arg Leu Ile Gly Glu Lys Leu Phe
80                  85                  90                  95 cga gga gtc agt gct aag gat cag tgc tac ctg atg aag cag gtg ctc       337
Arg Gly Val Ser Ala Lys Asp Gln Cys Tyr Leu Met Lys Gln Val Leu
                100                 105                 110 aac ttc acc ctg gaa gac att ctc ctc ccc cag tca gac agg ttc cgg       385
Asn Phe Thr Leu Glu Asp Ile Leu Leu Pro Gln Ser Asp Arg Phe Arg
            115                 120                 125 ccc tac atg cag gag gtg gtg cct ttc ctg acc aaa ctc agc aat cag       433
Pro Tyr Met Gln Glu Val Val Pro Phe Leu Thr Lys Leu Ser Asn Gln
        130                 135                 140 ctc agc tcc tgt cac atc agt ggt gac gac cag aac atc cag aag aat       481
Leu Ser Ser Cys His Ile Ser Gly Asp Asp Gln Asn Ile Gln Lys Asn
    145                 150                 155 gtc aga agg ctg aag gag aca gtg aaa aag ctt gga gag agc gga gag       529
Val Arg Arg Leu Lys Glu Thr Val Lys Lys Leu Gly Glu Ser Gly Glu
160                 165                 170                 175 atc aaa gcg atc ggg gaa ctg gac ctg ctg ttt atg tct ctg aga aat       577
Ile Lys Ala Ile Gly Glu Leu Asp Leu Leu Phe Met Ser Leu Arg Asn
                180                 185                 190 gct tgc gtc tga gcgagaagaa gctagaaaac gaagaactgc tccttcctgc           629
Ala Cys Val * cttctaaaaa gaacaataag atccctgaat ggactttttt actaaaggaa agtgagaagc     689
taacgtccac catcattaga agatttcaca tgaaacctgg ctcagttgaa agagaaaata     749
gtgtcaagtt gtccatgaga ccagaggtag acttgataac cacaaagatt cattgacaat     809
attttattgt cattgataat gcaacagaaa agtatgtac tttaaaaaat tgtttgaaag      869
gaggttacct ctcattcctc tagaagaaaa gcctatgtaa cttcatttcc ataaccaata     929
ctttatatat gtaagtttat ttattataag tatacatttt atttatgtca gtttattaat     989
atggatttat ttatagaaaa attatctgat gttgatattt gagtataaag caaataatat    1049
t                                                                    1050

<210> SEQ ID NO 11
<211> LENGTH: 194
<212> TYPE: PRT
<213> ORGANISM: Mus musculus
```

```
<400> SEQUENCE: 11

Gly Ser Pro Leu Thr Tyr Gln Leu Leu Thr Leu Val Arg Ser Val Met
  1               5                  10                  15

Ala Val Leu Gln Lys Ser Met Ser Phe Ser Leu Met Gly Thr Leu Ala
             20                  25                  30

Ala Ser Cys Leu Leu Leu Ile Ala Leu Trp Ala Gln Glu Ala Asn Ala
             35                  40                  45

Leu Pro Ile Asn Thr Arg Cys Lys Leu Glu Val Ser Asn Phe Gln Gln
         50                  55                  60

Pro Tyr Ile Val Asn Arg Thr Phe Met Leu Ala Lys Glu Ala Ser Leu
 65                  70                  75                  80

Ala Asp Asn Asn Thr Asp Val Arg Leu Ile Gly Glu Lys Leu Phe Arg
                 85                  90                  95

Gly Val Ser Ala Lys Asp Gln Cys Tyr Leu Met Lys Gln Val Leu Asn
            100                 105                 110

Phe Thr Leu Glu Asp Ile Leu Leu Pro Gln Ser Asp Arg Phe Arg Pro
            115                 120                 125

Tyr Met Gln Glu Val Val Pro Phe Leu Thr Lys Leu Ser Asn Gln Leu
        130                 135                 140

Ser Ser Cys His Ile Ser Gly Asp Asp Gln Asn Ile Gln Lys Asn Val
145                 150                 155                 160

Arg Arg Leu Lys Glu Thr Val Lys Lys Leu Gly Glu Ser Gly Glu Ile
                165                 170                 175

Lys Ala Ile Gly Glu Leu Asp Leu Leu Phe Met Ser Leu Arg Asn Ala
            180                 185                 190

Cys Val

<210> SEQ ID NO 12
<211> LENGTH: 2149
<212> TYPE: DNA
<213> ORGANISM: Homo sapiens
<220> FEATURE:
<221> NAME/KEY: CDS
<222> LOCATION: (1)...(693)

<400> SEQUENCE: 12 atg atg cct aaa cat tgc ttt cta ggc ttc ctc atc agt ttc ttc ctt    48
Met Met Pro Lys His Cys Phe Leu Gly Phe Leu Ile Ser Phe Phe Leu
  1               5                  10                  15 act ggt gta gca gga act cag tca acg cat gag tct ctg aag cct cag    96
Thr Gly Val Ala Gly Thr Gln Ser Thr His Glu Ser Leu Lys Pro Gln
             20                  25                  30 agg gta caa ttt cag tcc cga aat ttt cac aac att ttg caa tgg cag   144
Arg Val Gln Phe Gln Ser Arg Asn Phe His Asn Ile Leu Gln Trp Gln
         35                  40                  45 cct ggg agg gca ctt act ggc aac agc agt gtc tat ttt gtg cag tac   192
Pro Gly Arg Ala Leu Thr Gly Asn Ser Ser Val Tyr Phe Val Gln Tyr
     50                  55                  60 aaa ata tat gga cag aga caa tgg aaa aat aaa gaa gac tgt tgg ggt   240
Lys Ile Tyr Gly Gln Arg Gln Trp Lys Asn Lys Glu Asp Cys Trp Gly
 65                  70                  75                  80 act caa gaa ctc tct tgt gac ctt acc agt gaa acc tca gac ata cag   288
Thr Gln Glu Leu Ser Cys Asp Leu Thr Ser Glu Thr Ser Asp Ile Gln
                 85                  90                  95 gaa cct tat tac ggg agg gtg agg gcg gcc tcg gct ggg agc tac tca   336
Glu Pro Tyr Tyr Gly Arg Val Arg Ala Ala Ser Ala Gly Ser Tyr Ser
            100                 105                 110
```

```
gaa tgg agc atg acg ccg cgg ttc act ccc tgg tgg gaa aca aaa ata       384
Glu Trp Ser Met Thr Pro Arg Phe Thr Pro Trp Trp Glu Thr Lys Ile
        115                 120                 125 gat cct cca gtc atg aat ata acc caa gtc aat ggc tct ttg ttg gta       432
Asp Pro Pro Val Met Asn Ile Thr Gln Val Asn Gly Ser Leu Leu Val
130                 135                 140 att ctc cat gct cca aat tta cca tat aga tac caa aag gaa aaa aat       480
Ile Leu His Ala Pro Asn Leu Pro Tyr Arg Tyr Gln Lys Glu Lys Asn
145                 150                 155                 160 gta tct ata gaa gat tac tat gaa cta cta tac cga gtt ttt ata att       528
Val Ser Ile Glu Asp Tyr Tyr Glu Leu Leu Tyr Arg Val Phe Ile Ile
            165                 170                 175 aac aat tca cta gaa aag gag caa aag gtt tat gaa ggg gct cac aga       576
Asn Asn Ser Leu Glu Lys Glu Gln Lys Val Tyr Glu Gly Ala His Arg
        180                 185                 190 gcg gtt gaa att gaa gct cta aca cca cac tcc agc tac tgt gta gtg       624
Ala Val Glu Ile Glu Ala Leu Thr Pro His Ser Ser Tyr Cys Val Val
195                 200                 205 gct gaa ata tat cag ccc atg tta gac aga aga agt cag aga agt gaa       672
Ala Glu Ile Tyr Gln Pro Met Leu Asp Arg Arg Ser Gln Arg Ser Glu
210                 215                 220 gag aga tgt gtg gaa att cca tgacttgtgg aatttggcat tcagcaatgt          723
Glu Arg Cys Val Glu Ile Pro
225                 230 ggaaattcta aagctccctg agaacaggat gactcgtgtt tgaaggatct tatttaaaat      783
tgttttgta ttttcttaaa gcaatattca ctgttacacc ttggggactt ctttgtttat      843
ccattctttt atcctttata tttcatttta aactatattt gaacgacatt cccccgaaa      903
aattgaaatg taaagatgag gcagagaata aagtgttcta tgaaattcag aactttattt     963
ctgaatgtaa catccctaat aacaaccttc attcttctaa tacagcaaaa taaaaattta    1023
acaaccaagg aatagtattt aagaaaatgt tgaaataatt ttttttaaaat agcattacag   1083
actgaggcgg tcctgaagca atggttttc actctcttat tgagccaatt aaattgacat    1143
tgctttgaca atttaaaact tctataaagg tgaatatttt tcatacattt ctattttata   1203
tgaatatact ttttatatat ttattattat taaaatatttc tacttaatga atcaaaattt  1263
tgttttaaag tctactttat gtaaataaga acaggtttg gggaaaaaaaa tcttatgatt   1323
tctggattga tatctgaatt aaaactatca acaacaagga agtctactct gtacaattgt   1383
ccctcattta aaagatatat taagcttttc ttttctgttt gttttgttt tgtttagttt    1443
ttaatcctgt cttagaagaa cttatcttta ttctcaaaat taaatgtaat ttttttagtg   1503
acaaagaaga aaggaaacct cattactcaa tccttctggc caagagtgtc ttgcttgtgg   1563
cgccttcctc atctctatat aggaggatcc catgaatgat ggtttattgg gaactgctgg   1623
ggtcgacccc atacagagaa ctcagcttga agctggaagc acacagtggg tagcaggaga   1683
aggaccggtg ttggtaggtg cctacagaga ctatagagct agacaaagcc ctccaaactg   1743
gcccctcctg ctcactgcct ctcctgagta gaaatctggt gacctaaggc tcagtgcggt   1803
caacagaaag ctgccttctt cacttgaggc taagtcttca tatatgttta aggttgtctt   1863
tctagtgagg agatacatat cagagaacat ttgtacaatt ccccatgaaa attgctccaa   1923
agttgataac aatatagtcg gtgcttctag ttatatgcaa gtactcagtg ataaatggat   1983
taaaaaatat tcagaaatgt attgggggt ggaggagaat aagaggcaga gcaagagcta    2043
gagaattggt ttccttgctt ccctgtatgc tcagaaaaca ttgatttgag catagacgca   2103
gagactgaaa aaaaaaaaat gctcgagcgg ccgccatatc cttggt                   2149
```

<210> SEQ ID NO 13
<211> LENGTH: 231
<212> TYPE: PRT
<213> ORGANISM: Homo sapiens

<400> SEQUENCE: 13

Met Met Pro Lys His Cys Phe Leu Gly Phe Leu Ile Ser Phe Phe Leu
1               5                   10                  15

Thr Gly Val Ala Gly Thr Gln Ser Thr His Glu Ser Leu Lys Pro Gln
            20                  25                  30

Arg Val Gln Phe Gln Ser Arg Asn Phe His Asn Ile Leu Gln Trp Gln
        35                  40                  45

Pro Gly Arg Ala Leu Thr Gly Asn Ser Ser Val Tyr Phe Val Gln Tyr
    50                  55                  60

Lys Ile Tyr Gly Gln Arg Gln Trp Lys Asn Lys Glu Asp Cys Trp Gly
65                  70                  75                  80

Thr Gln Glu Leu Ser Cys Asp Leu Thr Ser Glu Thr Ser Asp Ile Gln
                85                  90                  95

Glu Pro Tyr Tyr Gly Arg Val Arg Ala Ala Ser Ala Gly Ser Tyr Ser
            100                 105                 110

Glu Trp Ser Met Thr Pro Arg Phe Thr Pro Trp Trp Glu Thr Lys Ile
        115                 120                 125

Asp Pro Pro Val Met Asn Ile Thr Gln Val Asn Gly Ser Leu Leu Val
    130                 135                 140

Ile Leu His Ala Pro Asn Leu Pro Tyr Arg Tyr Gln Lys Glu Lys Asn
145                 150                 155                 160

Val Ser Ile Glu Asp Tyr Tyr Glu Leu Leu Tyr Arg Val Phe Ile Ile
                165                 170                 175

Asn Asn Ser Leu Glu Lys Glu Gln Lys Val Tyr Glu Gly Ala His Arg
            180                 185                 190

Ala Val Glu Ile Glu Ala Leu Thr Pro His Ser Ser Tyr Cys Val Val
        195                 200                 205

Ala Glu Ile Tyr Gln Pro Met Leu Asp Arg Arg Ser Gln Arg Ser Glu
    210                 215                 220

Glu Arg Cys Val Glu Ile Pro
225                 230

<210> SEQ ID NO 14
<211> LENGTH: 699
<212> TYPE: DNA
<213> ORGANISM: Artificial Sequence
<220> FEATURE:
<223> OTHER INFORMATION: C-Terminal Fc4 tag

<400> SEQUENCE: 14
gagcccagat cttcagacaa aactcacaca tgcccaccgt gcccagcacc tgaagccgag      60
ggggcaccgt cagtcttcct cttccccca aaacccaagg acaccctcat gatctcccgg     120 accctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc catcctccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480

-continued

```
gacatcgccg tggagtggga gagcaatggg cagccggaga acaactacaa gaccacgcct    540
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaataa                            699
```

<210> SEQ ID NO 15
<211> LENGTH: 6
<212> TYPE: PRT
<213> ORGANISM: Artificial Sequence
<220> FEATURE:
<223> OTHER INFORMATION: Glu-Glu (CEE) Peptide Tag (Synthetic Linker)

<400> SEQUENCE: 15

Glu Tyr Met Pro Met Glu
 1               5

<210> SEQ ID NO 16
<211> LENGTH: 10
<212> TYPE: PRT
<213> ORGANISM: Artificial Sequence
<220> FEATURE:
<223> OTHER INFORMATION: Glu-Glu (CEE) Peptide Tag with spacer
      (Synthetic Linker)

<400> SEQUENCE: 16

Gly Ser Gly Gly Glu Tyr Met Pro Met Glu
 1               5                  10

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer ZC39289

<400> SEQUENCE: 17

```
tccgaggagt caatgctaag                                                 20
```

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide Primer ZC39290

<400> SEQUENCE: 18

```
tccaagcttt ttcactgtct                                                 20
```

<210> SEQ ID NO 19
<211> LENGTH: 16
<212> TYPE: DNA
<213> ORGANISM: Artificial Sequence
<220> FEATURE:
<223> OTHER INFORMATION: Oligonucleotide Primer ZC39776

<400> SEQUENCE: 19

```
gggcccgcta gcacct                                                     16
```

<210> SEQ ID NO 20
<211> LENGTH: 16
<212> TYPE: DNA
<213> ORGANISM: Artificial Sequence
<220> FEATURE:
<223> OTHER INFORMATION: Oligonucleotide Primer ZC39777

<400> SEQUENCE: 20
gggtgatccg ctggca                                                                   16

<210> SEQ ID NO 21
<211> LENGTH: 36
<212> TYPE: DNA
<213> ORGANISM: Artificial Sequence
<220> FEATURE:
<223> OTHER INFORMATION: IL-20 FAM/TAMRA labeled TaqMan probe ZC38752

<400> SEQUENCE: 21
ccagccactt tctctctccg tatttcttat attcca                                             36

<210> SEQ ID NO 22
<211> LENGTH: 16
<212> TYPE: DNA
<213> ORGANISM: Artificial Sequence
<220> FEATURE:
<223> OTHER INFORMATION: forward primer, ZC42459

<400> SEQUENCE: 22
tggccaggct cagcaa                                                                   16

<210> SEQ ID NO 23
<211> LENGTH: 21
<212> TYPE: DNA
<213> ORGANISM: Artificial Sequence
<220> FEATURE:
<223> OTHER INFORMATION: reverse primer, ZC42458

<400> SEQUENCE: 23
gcacattcct ctggatatgc a                                                             21

<210> SEQ ID NO 24
<211> LENGTH: 31
<212> TYPE: DNA
<213> ORGANISM: Artificial Sequence
<220> FEATURE:
<223> OTHER INFORMATION: IL-22 TaqMan probe, ZC42460

<400> SEQUENCE: 24
aggctaagca catgtcatat tgaaggtgat g                                                  31

<210> SEQ ID NO 25
<211> LENGTH: 21
<212> TYPE: DNA
<213> ORGANISM: Artificial Sequence
<220> FEATURE:
<223> OTHER INFORMATION: forward primer, ZC40541

<400> SEQUENCE: 25
tcgccaattc ctttcttacc a                                                             21

<210> SEQ ID NO 26
<211> LENGTH: 20
<212> TYPE: DNA
<213> ORGANISM: Artificial Sequence
<220> FEATURE:
<223> OTHER INFORMATION: reverse primer, ZC40542

<400> SEQUENCE: 26
cccacaatgg catgtcatgt                                                               20

<210> SEQ ID NO 27

-continued

```
<211> LENGTH: 25
<212> TYPE: DNA
<213> ORGANISM: Artificial Sequence
<220> FEATURE:
<223> OTHER INFORMATION: IL-20 TaqMan? probe ZC40544

<400> SEQUENCE: 27
agaaggacct ccggctctgt catgc                                            25

<210> SEQ ID NO 28
<211> LENGTH: 57
<212> TYPE: DNA
<213> ORGANISM: Artificial Sequence
<220> FEATURE:
<223> OTHER INFORMATION: Oligonucleotide primer ZC45,593

<400> SEQUENCE: 28
caggaaatcc atgccgagtt gagacgcttc cgtagacacg ccctgagga ccctcg          57

<210> SEQ ID NO 29
<211> LENGTH: 63
<212> TYPE: DNA
<213> ORGANISM: Artificial Sequence
<220> FEATURE:
<223> OTHER INFORMATION: Oligonucleotide primer ZC45,592

<400> SEQUENCE: 29
tctgggctca ccgcttccag acccgcttcc agacccgctt cctgtccggt ctggcagtgt     60
ctt                                                                    63

<210> SEQ ID NO 30
<211> LENGTH: 63
<212> TYPE: DNA
<213> ORGANISM: Artificial Sequence
<220> FEATURE:
<223> OTHER INFORMATION: Oligonucleotide primer ZC45,591

<400> SEQUENCE: 30
gaccggacag gaagcgggtc tggaagcggg tctggaagcg gtgagcccag aggccccaca     60
atc                                                                    63

<210> SEQ ID NO 31
<211> LENGTH: 57
<212> TYPE: DNA
<213> ORGANISM: Artificial Sequence
<220> FEATURE:
<223> OTHER INFORMATION: Oligonucleotide primer ZC45,594

<400> SEQUENCE: 31
agagctgttt taaggcgcgc ctctagatta tttttattta cccggagtcc gggagaa       57

<210> SEQ ID NO 32
<211> LENGTH: 531
<212> TYPE: DNA
<213> ORGANISM: Mus musculus
<220> FEATURE:
<221> NAME/KEY: CDS
<222> LOCATION: (1)...(531)

<400> SEQUENCE: 32 atg aaa ggc ttt ggt ctt gcc ttt gga ctg ttc tcc gct gtg ggt ttt      48
Met Lys Gly Phe Gly Leu Ala Phe Gly Leu Phe Ser Ala Val Gly Phe
 1               5                  10                  15 ctt ctc tgg act cct tta act ggg ctc aag acc ctc cat ttg gga agc      96
Leu Leu Trp Thr Pro Leu Thr Gly Leu Lys Thr Leu His Leu Gly Ser
```

```
                    20                    25                    30
tgt gtg att act gca aac cta cag gca ata caa aag gaa ttt tct gag     144
Cys Val Ile Thr Ala Asn Leu Gln Ala Ile Gln Lys Glu Phe Ser Glu
         35                    40                    45 att cgg gat agt gtg caa gct gaa gat aca aat att gac atc aga att     192
Ile Arg Asp Ser Val Gln Ala Glu Asp Thr Asn Ile Asp Ile Arg Ile
 50                    55                    60 tta agg acg act gag tct ttg aaa gac ata aag tct ttg gat agg tgc     240
Leu Arg Thr Thr Glu Ser Leu Lys Asp Ile Lys Ser Leu Asp Arg Cys
 65                    70                    75                    80 tgc ttc ctt cgt cat cta gtg aga ttc tat ctg gac agg gta ttc aaa     288
Cys Phe Leu Arg His Leu Val Arg Phe Tyr Leu Asp Arg Val Phe Lys
             85                    90                    95 gtc tac cag acc cct gac cac cat acc ctg aga aag atc agc agc ctc     336
Val Tyr Gln Thr Pro Asp His His Thr Leu Arg Lys Ile Ser Ser Leu
            100                   105                   110 gcc aac tcc ttt ctt atc atc aag aag gac ctc tca gtc tgt cat tct     384
Ala Asn Ser Phe Leu Ile Ile Lys Lys Asp Leu Ser Val Cys His Ser
            115                   120                   125 cac atg gca tgt cat tgt ggg gaa gaa gca atg gag aaa tac aac caa     432
His Met Ala Cys His Cys Gly Glu Glu Ala Met Glu Lys Tyr Asn Gln
130                   135                   140 att ctg agt cac ttc ata gag ttg gaa ctt cag gca gcg gtg gta aag     480
Ile Leu Ser His Phe Ile Glu Leu Glu Leu Gln Ala Ala Val Val Lys
145                   150                   155                   160 gct ttg gga gaa cta ggc att ctt ctg aga tgg atg gag gag atg cta     528
Ala Leu Gly Glu Leu Gly Ile Leu Leu Arg Trp Met Glu Glu Met Leu
                165                   170                   175 tag                                                                 531
*

<210> SEQ ID NO 33
<211> LENGTH: 176
<212> TYPE: PRT
<213> ORGANISM: Mus musculus

<400> SEQUENCE: 33

Met Lys Gly Phe Gly Leu Ala Phe Gly Leu Phe Ser Ala Val Gly Phe
 1               5                  10                  15

Leu Leu Trp Thr Pro Leu Thr Gly Leu Lys Thr Leu His Leu Gly Ser
             20                  25                  30

Cys Val Ile Thr Ala Asn Leu Gln Ala Ile Gln Lys Glu Phe Ser Glu
         35                  40                  45

Ile Arg Asp Ser Val Gln Ala Glu Asp Thr Asn Ile Asp Ile Arg Ile
 50                  55                  60

Leu Arg Thr Thr Glu Ser Leu Lys Asp Ile Lys Ser Leu Asp Arg Cys
 65                  70                  75                  80

Cys Phe Leu Arg His Leu Val Arg Phe Tyr Leu Asp Arg Val Phe Lys
             85                  90                  95

Val Tyr Gln Thr Pro Asp His His Thr Leu Arg Lys Ile Ser Ser Leu
            100                 105                 110

Ala Asn Ser Phe Leu Ile Ile Lys Lys Asp Leu Ser Val Cys His Ser
            115                 120                 125

His Met Ala Cys His Cys Gly Glu Glu Ala Met Glu Lys Tyr Asn Gln
        130                 135                 140

Ile Leu Ser His Phe Ile Glu Leu Glu Leu Gln Ala Ala Val Val Lys
145                 150                 155                 160
```

```
Ala Leu Gly Glu Leu Gly Ile Leu Leu Arg Trp Met Glu Glu Met Leu
            165                 170                 175
```

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide primer ZC22901

<400> SEQUENCE: 34
catcaaaccg cctgatgtga c                                                    21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide primer ZC45039

<400> SEQUENCE: 35
attaggcttg ggagggaatg g                                                    21

<210> SEQ ID NO 36
<211> LENGTH: 23
<212> TYPE: DNA
<213> ORGANISM: Artificial Sequence
<220> FEATURE:
<223> OTHER INFORMATION: Oligonucleotide primer ZC38573

<400> SEQUENCE: 36
tggcgatgcc tgcttgccga ata                                                  23

<210> SEQ ID NO 37
<211> LENGTH: 22
<212> TYPE: DNA
<213> ORGANISM: Artificial Sequence
<220> FEATURE:
<223> OTHER INFORMATION: Oligonucleotide primer ZC25223

<400> SEQUENCE: 37
gtcttcctca catctgttat cg                                                   22

<210> SEQ ID NO 38
<211> LENGTH: 24
<212> TYPE: DNA
<213> ORGANISM: Artificial Sequence
<220> FEATURE:
<223> OTHER INFORMATION: Oligonucleotide primer ZC40128

<400> SEQUENCE: 38
ggcttgaact ttgagaaagg cagt                                                 24

<210> SEQ ID NO 39
<211> LENGTH: 1473
<212> TYPE: DNA
<213> ORGANISM: Artificial Sequence
<220> FEATURE:
<223> OTHER INFORMATION: IL-22RA Extracellular domain with tPA leader
      and fused to murine gamma 2a heavy chain Fc region
      (mG2a)
<220> FEATURE:
<221> NAME/KEY: CDS
<222> LOCATION: (1)...(1473)

<400> SEQUENCE: 39 atg gat gca atg aag aga ggg ctc tgc tgt gtg ctg ctg ctg tgt ggc             48

```
                Met Asp Ala Met Lys Arg Gly Leu Cys Cys Val Leu Leu Leu Cys Gly
                 1           5                  10                  15 gcc gtc ttc gtt tcg ctc agc cag gaa atc cat gcc gag ttg aga cgc         96
Ala Val Phe Val Ser Leu Ser Gln Glu Ile His Ala Glu Leu Arg Arg
                 20                  25                  30 ttc cgt aga cac gcc cct gag gac ccc tcg gat ctg ctc cag cac gtg        144
Phe Arg Arg His Ala Pro Glu Asp Pro Ser Asp Leu Leu Gln His Val
             35                  40                  45 aaa ttc cag tcc agc aac ttt gaa aac atc ctg acg tgg gac agc ggg        192
Lys Phe Gln Ser Ser Asn Phe Glu Asn Ile Leu Thr Trp Asp Ser Gly
         50                  55                  60 cca gag ggc acc cca gac acg gtc tac agc atc gag tat aag acg tac        240
Pro Glu Gly Thr Pro Asp Thr Val Tyr Ser Ile Glu Tyr Lys Thr Tyr
 65                  70                  75                  80 gga gag agg gac tgg gtg gca aag aag ggc tgt cag cgg atc acc cgg        288
Gly Glu Arg Asp Trp Val Ala Lys Lys Gly Cys Gln Arg Ile Thr Arg
                 85                  90                  95 aag tcc tgc aac ctg acg gtg gag acg ggc aac ctc acg gag ctc tac        336
Lys Ser Cys Asn Leu Thr Val Glu Thr Gly Asn Leu Thr Glu Leu Tyr
            100                 105                 110 tat gcc agg gtc acc gct gtc agt gcg gga ggc cgg tca gcc acc aag        384
Tyr Ala Arg Val Thr Ala Val Ser Ala Gly Gly Arg Ser Ala Thr Lys
        115                 120                 125 atg act gac agg ttc agc tct ctg cag cac act acc ctc aag cca cct        432
Met Thr Asp Arg Phe Ser Ser Leu Gln His Thr Thr Leu Lys Pro Pro
    130                 135                 140 gat gtg acc tgt atc tcc aaa gtg aga tcg att cag atg att gtt cat        480
Asp Val Thr Cys Ile Ser Lys Val Arg Ser Ile Gln Met Ile Val His
145                 150                 155                 160 cct acc ccc acg cca atc cgt gca ggc gat ggc cac cgg cta acc ctg        528
Pro Thr Pro Thr Pro Ile Arg Ala Gly Asp Gly His Arg Leu Thr Leu
                165                 170                 175 gaa gac atc ttc cat gac ctg ttc tac cac tta gag ctc cag gtc aac        576
Glu Asp Ile Phe His Asp Leu Phe Tyr His Leu Glu Leu Gln Val Asn
            180                 185                 190 cgc acc tac caa atg cac ctt gga ggg aag cag aga gaa tat gag ttc        624
Arg Thr Tyr Gln Met His Leu Gly Gly Lys Gln Arg Glu Tyr Glu Phe
        195                 200                 205 ttc ggc ctg acc cct gac aca gag ttc ctt ggc acc atc atg att tgc        672
Phe Gly Leu Thr Pro Asp Thr Glu Phe Leu Gly Thr Ile Met Ile Cys
    210                 215                 220 gtt ccc acc tgg gcc aag gag agt gcc ccc tac atg tgc cga gtg aag        720
Val Pro Thr Trp Ala Lys Glu Ser Ala Pro Tyr Met Cys Arg Val Lys
225                 230                 235                 240 aca ctg cca gac cgg aca gga agc ggg tct gga agc ggg tct gga agc        768
Thr Leu Pro Asp Arg Thr Gly Ser Gly Ser Gly Ser Gly Ser Gly Ser
                245                 250                 255 ggt gag ccc aga ggc ccc aca atc aag ccc tgt cct cca tgc aaa tgc        816
Gly Glu Pro Arg Gly Pro Thr Ile Lys Pro Cys Pro Pro Cys Lys Cys
            260                 265                 270 cca gca cct aac ctc ttg ggt gga cca tcc gtc ttc atc ttc cct cca        864
Pro Ala Pro Asn Leu Leu Gly Gly Pro Ser Val Phe Ile Phe Pro Pro
        275                 280                 285 aag atc aag gat gta ctc atg atc tcc ctg agc ccc ata gtc aca tgt        912
Lys Ile Lys Asp Val Leu Met Ile Ser Leu Ser Pro Ile Val Thr Cys
    290                 295                 300 gtg gtg gtg gat gtg agc gag gat gac cca gat gtc cag atc agc tgg        960
Val Val Val Asp Val Ser Glu Asp Asp Pro Asp Val Gln Ile Ser Trp
305                 310                 315                 320
```

```
ttt gtg aac aac gtg gaa gta cac aca gct cag aca caa acc cat aga      1008
Phe Val Asn Asn Val Glu Val His Thr Ala Gln Thr Gln Thr His Arg
                325                 330                 335 gag gat tac aac agt act ctc cgg gtg gtc agt gcc ctc ccc atc cag      1056
Glu Asp Tyr Asn Ser Thr Leu Arg Val Val Ser Ala Leu Pro Ile Gln
            340                 345                 350 cac cag gac tgg atg agt ggc aag gag ttc aaa tgc aag gtc aac aac      1104
His Gln Asp Trp Met Ser Gly Lys Glu Phe Lys Cys Lys Val Asn Asn
        355                 360                 365 aaa gac ctc cca gcg ccc atc gag aga acc atc tca aaa ccc aaa ggg      1152
Lys Asp Leu Pro Ala Pro Ile Glu Arg Thr Ile Ser Lys Pro Lys Gly
    370                 375                 380 tca gta aga gct cca cag gta tat gtc ttg cct cca cca gaa gaa gag      1200
Ser Val Arg Ala Pro Gln Val Tyr Val Leu Pro Pro Pro Glu Glu Glu
385                 390                 395                 400 atg act aag aaa cag gtc act ctg acc tgc atg gtc aca gac ttc atg      1248
Met Thr Lys Lys Gln Val Thr Leu Thr Cys Met Val Thr Asp Phe Met
                405                 410                 415 cct gaa gac att tac gtg gag tgg acc aac aac ggg aaa aca gag cta      1296
Pro Glu Asp Ile Tyr Val Glu Trp Thr Asn Asn Gly Lys Thr Glu Leu
            420                 425                 430 aac tac aag aac act gaa cca gtc ctg gac tct gat ggt tct tac ttc      1344
Asn Tyr Lys Asn Thr Glu Pro Val Leu Asp Ser Asp Gly Ser Tyr Phe
        435                 440                 445 atg tac agc aag ctg aga gtg gaa aag aag aac tgg gtg gaa aga aat      1392
Met Tyr Ser Lys Leu Arg Val Glu Lys Lys Asn Trp Val Glu Arg Asn
    450                 455                 460 agc tac tcc tgt tca gtg gtc cac gag ggt ctg cac aat cac cac acg      1440
Ser Tyr Ser Cys Ser Val Val His Glu Gly Leu His Asn His His Thr
465                 470                 475                 480 act aag agc ttc tcc cgg act ccg ggt aaa taa                          1473
Thr Lys Ser Phe Ser Arg Thr Pro Gly Lys *
                485                 490

<210> SEQ ID NO 40
<211> LENGTH: 490
<212> TYPE: PRT
<213> ORGANISM: Artificial Sequence
<220> FEATURE:
<223> OTHER INFORMATION: IL-22RA Extracellular domain with tPA leader
      and fused to murine gamma 2a heavy chain Fc region
      (mG2a)

<400> SEQUENCE: 40

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg His Ala Pro Glu Asp Pro Ser Asp Leu Leu Gln His Val
        35                  40                  45

Lys Phe Gln Ser Ser Asn Phe Glu Asn Ile Leu Thr Trp Asp Ser Gly
    50                  55                  60

Pro Glu Gly Thr Pro Asp Thr Val Tyr Ser Ile Glu Tyr Lys Thr Tyr
65                  70                  75                  80

Gly Glu Arg Asp Trp Val Ala Lys Lys Gly Cys Gln Arg Ile Thr Arg
                85                  90                  95

Lys Ser Cys Asn Leu Thr Val Glu Thr Gly Asn Leu Thr Glu Leu Tyr
            100                 105                 110

Tyr Ala Arg Val Thr Ala Val Ser Ala Gly Gly Arg Ser Ala Thr Lys
        115                 120                 125
```

```
Met Thr Asp Arg Phe Ser Ser Leu Gln His Thr Thr Leu Lys Pro Pro
    130                 135                 140

Asp Val Thr Cys Ile Ser Lys Val Arg Ser Ile Gln Met Ile Val His
145                 150                 155                 160

Pro Thr Pro Thr Pro Ile Arg Ala Gly Asp Gly His Arg Leu Thr Leu
                165                 170                 175

Glu Asp Ile Phe His Asp Leu Phe Tyr His Leu Glu Leu Gln Val Asn
            180                 185                 190

Arg Thr Tyr Gln Met His Leu Gly Gly Lys Gln Arg Glu Tyr Glu Phe
        195                 200                 205

Phe Gly Leu Thr Pro Asp Thr Glu Phe Leu Gly Thr Ile Met Ile Cys
    210                 215                 220

Val Pro Thr Trp Ala Lys Glu Ser Ala Pro Tyr Met Cys Arg Val Lys
225                 230                 235                 240

Thr Leu Pro Asp Arg Thr Gly Ser Gly Ser Gly Ser Gly Ser Gly Ser
                245                 250                 255

Gly Glu Pro Arg Gly Pro Thr Ile Lys Pro Cys Pro Pro Cys Lys Cys
            260                 265                 270

Pro Ala Pro Asn Leu Leu Gly Gly Pro Ser Val Phe Ile Phe Pro Pro
        275                 280                 285

Lys Ile Lys Asp Val Leu Met Ile Ser Leu Ser Pro Ile Val Thr Cys
    290                 295                 300

Val Val Val Asp Val Ser Glu Asp Asp Pro Asp Val Gln Ile Ser Trp
305                 310                 315                 320

Phe Val Asn Asn Val Glu Val His Thr Ala Gln Thr Gln Thr His Arg
                325                 330                 335

Glu Asp Tyr Asn Ser Thr Leu Arg Val Val Ser Ala Leu Pro Ile Gln
            340                 345                 350

His Gln Asp Trp Met Ser Gly Lys Glu Phe Lys Cys Lys Val Asn Asn
        355                 360                 365

Lys Asp Leu Pro Ala Pro Ile Glu Arg Thr Ile Ser Lys Pro Lys Gly
    370                 375                 380

Ser Val Arg Ala Pro Gln Val Tyr Val Leu Pro Pro Pro Glu Glu Glu
385                 390                 395                 400

Met Thr Lys Lys Gln Val Thr Leu Thr Cys Met Val Thr Asp Phe Met
                405                 410                 415

Pro Glu Asp Ile Tyr Val Glu Trp Thr Asn Asn Gly Lys Thr Glu Leu
            420                 425                 430

Asn Tyr Lys Asn Thr Glu Pro Val Leu Asp Ser Asp Gly Ser Tyr Phe
        435                 440                 445

Met Tyr Ser Lys Leu Arg Val Glu Lys Lys Asn Trp Val Glu Arg Asn
    450                 455                 460

Ser Tyr Ser Cys Ser Val Val His Glu Gly Leu His Asn His His Thr
465                 470                 475                 480

Thr Lys Ser Phe Ser Arg Thr Pro Gly Lys
                485                 490

<210> SEQ ID NO 41
<211> LENGTH: 1834
<212> TYPE: DNA
<213> ORGANISM: Mus musculus
<220> FEATURE:
<221> NAME/KEY: CDS
<222> LOCATION: (43)...(1788)
```

<400> SEQUENCE: 41

```
ttggtccaga gccgaggccc gaaggggccc tggagggacc ca atg aag aca cta              54
                                              Met Lys Thr Leu
                                                1 ctg acc atc ctg acg gtg gga tcc ctg gcc gct cac acc act gtg gac            102
Leu Thr Ile Leu Thr Val Gly Ser Leu Ala Ala His Thr Thr Val Asp
  5              10                  15                  20 aca tcc ggt ctc ctt caa cac gtg aaa ttc cag tcc agc aac ttt gag            150
Thr Ser Gly Leu Leu Gln His Val Lys Phe Gln Ser Ser Asn Phe Glu
             25                  30                  35 aac atc ttg acg tgg gat ggt ggg ccc gct agc acc tct gac acc gtc            198
Asn Ile Leu Thr Trp Asp Gly Gly Pro Ala Ser Thr Ser Asp Thr Val
         40                  45                  50 tac agt gtg gaa tat aag aaa tac gga gag aga aag tgg ctg gcc aag            246
Tyr Ser Val Glu Tyr Lys Lys Tyr Gly Glu Arg Lys Trp Leu Ala Lys
     55                  60                  65 gcg ggc tgc cag cgg atc acc cag aag ttc tgc aac ctg act atg gag            294
Ala Gly Cys Gln Arg Ile Thr Gln Lys Phe Cys Asn Leu Thr Met Glu
 70                  75                  80 acc cgc aac cac act gag ttt tac tac gcc aag gtc acg gca gtc agc            342
Thr Arg Asn His Thr Glu Phe Tyr Tyr Ala Lys Val Thr Ala Val Ser
 85                  90                  95                 100 gca gga ggc cca cca gtc aca aag atg act gat cgt ttc agc tcg ctg            390
Ala Gly Gly Pro Pro Val Thr Lys Met Thr Asp Arg Phe Ser Ser Leu
                105                 110                 115 cag cac act acc atc aaa ccg cct gat gtg acc tgt atc ccc aaa gtg            438
Gln His Thr Thr Ile Lys Pro Pro Asp Val Thr Cys Ile Pro Lys Val
             120                 125                 130 agg tcc att cag atg ctg gtc cac ccc aca ctc aca ccg gtc ctc tcg            486
Arg Ser Ile Gln Met Leu Val His Pro Thr Leu Thr Pro Val Leu Ser
         135                 140                 145 gaa gat ggc cac cag cta acc ctg gag gag att ttc cat gac ctg ttc            534
Glu Asp Gly His Gln Leu Thr Leu Glu Glu Ile Phe His Asp Leu Phe
     150                 155                 160 tac cgc tta gag ctc cac gtc aac cac acc tac cag atg cac ctt gaa            582
Tyr Arg Leu Glu Leu His Val Asn His Thr Tyr Gln Met His Leu Glu
165                 170                 175                 180 ggc aaa cag aga gaa tac gag ttc ctt ggc ctg act ccc gac aca gag            630
Gly Lys Gln Arg Glu Tyr Glu Phe Leu Gly Leu Thr Pro Asp Thr Glu
                185                 190                 195 ttc ctc ggc tcc atc aca att ttg act ccg ata ttg tcc aag gaa agt            678
Phe Leu Gly Ser Ile Thr Ile Leu Thr Pro Ile Leu Ser Lys Glu Ser
             200                 205                 210 gcc ccc tac gtg tgc cga gtg aag acg ctg ccc gat cgg acg tgg gcc            726
Ala Pro Tyr Val Cys Arg Val Lys Thr Leu Pro Asp Arg Thr Trp Ala
         215                 220                 225 tac tcc ttc tcg ggc gcc gtg ctc ttt tcc atg ggt ttc ctc gtc ggc            774
Tyr Ser Phe Ser Gly Ala Val Leu Phe Ser Met Gly Phe Leu Val Gly
     230                 235                 240 ttg ctc tgt tat ctg ggc tac aaa tac atc acc aag cca cct gta cct            822
Leu Leu Cys Tyr Leu Gly Tyr Lys Tyr Ile Thr Lys Pro Pro Val Pro
245                 250                 255                 260 cct aac tcc ctg aac gtc caa cgt gtc ctg acc ttt caa ccc cta cgc            870
Pro Asn Ser Leu Asn Val Gln Arg Val Leu Thr Phe Gln Pro Leu Arg
                265                 270                 275 ttc atc caa gaa cac gta ctg atc cct gtc ttg gac ctc agt ggc ccc            918
Phe Ile Gln Glu His Val Leu Ile Pro Val Leu Asp Leu Ser Gly Pro
             280                 285                 290 agc agt ctg cct cag ccc atc cag tac tcc caa gtg gtg gtg tct ggg            966
Ser Ser Leu Pro Gln Pro Ile Gln Tyr Ser Gln Val Val Val Ser Gly
```

|                                                                                          |      |
|------------------------------------------------------------------------------------------|------|
| Ser Ser Leu Pro Gln Pro Ile Gln Tyr Ser Gln Val Val Ser Gly<br>    295             300             305                |      |
| ccc agg gag cct cct gga gct gtg tgg cgg cag agc ctg tct gac ctc<br>Pro Arg Glu Pro Pro Gly Ala Val Trp Arg Gln Ser Leu Ser Asp Leu<br>    310             315             320 | 1014 |
| acc tac gta ggg cag tca gat gtc tcc atc ctg caa cct acc aac gtg<br>Thr Tyr Val Gly Gln Ser Asp Val Ser Ile Leu Gln Pro Thr Asn Val<br>325             330             335             340 | 1062 |
| cca gct cag cag aca ctg tcc cca cca tcc tac gcg ccg aag gct gtc<br>Pro Ala Gln Gln Thr Leu Ser Pro Pro Ser Tyr Ala Pro Lys Ala Val<br>                345             350             355 | 1110 |
| cct gag gtc cag ccc cct tcc tat gcg cct cag gta gcc tcg gat gcc<br>Pro Glu Val Gln Pro Pro Ser Tyr Ala Pro Gln Val Ala Ser Asp Ala<br>        360             365             370 | 1158 |
| aaa gct ctg ttc tac tca cca caa cag ggg atg aag acc agg cct gcc<br>Lys Ala Leu Phe Tyr Ser Pro Gln Gln Gly Met Lys Thr Arg Pro Ala<br>    375             380             385 | 1206 |
| acc tat gac ccg cag gac att ctg gac agc tgc cct gct tct tat gct<br>Thr Tyr Asp Pro Gln Asp Ile Leu Asp Ser Cys Pro Ala Ser Tyr Ala<br>    390             395             400 | 1254 |
| gtg tgt gtg gaa gac tct ggc aaa gac tct acc cca ggc atc ctc tcc<br>Val Cys Val Glu Asp Ser Gly Lys Asp Ser Thr Pro Gly Ile Leu Ser<br>405             410             415             420 | 1302 |
| act ccc aaa tac ctc aag aca aaa ggt cag ctc cag gaa gac aca ctt<br>Thr Pro Lys Tyr Leu Lys Thr Lys Gly Gln Leu Gln Glu Asp Thr Leu<br>                425             430             435 | 1350 |
| gtt aga agc tgt ctc cca ggg gac ctt tct cta cag aaa gtc acc tcc<br>Val Arg Ser Cys Leu Pro Gly Asp Leu Ser Leu Gln Lys Val Thr Ser<br>        440             445             450 | 1398 |
| tta ggt gaa ggg gag aca cag aga cca aaa tca ctc ccc tca cct ctg<br>Leu Gly Glu Gly Glu Thr Gln Arg Pro Lys Ser Leu Pro Ser Pro Leu<br>    455             460             465 | 1446 |
| gga ttt tgc aca gac aga gga cct gac ctt cac aca ctg cgc agt gag<br>Gly Phe Cys Thr Asp Arg Gly Pro Asp Leu His Thr Leu Arg Ser Glu<br>    470             475             480 | 1494 |
| gaa cca gag aca cca cgg tac ctg aag ggg gcg ctg tct ctc ctg tcc<br>Glu Pro Glu Thr Pro Arg Tyr Leu Lys Gly Ala Leu Ser Leu Leu Ser<br>485             490             495             500 | 1542 |
| tct gtg cag atc gag ggc cac cct gtc tcc ctc cct ttg cac gtc cat<br>Ser Val Gln Ile Glu Gly His Pro Val Ser Leu Pro Leu His Val His<br>                505             510             515 | 1590 |
| tct gtc tca tgt tcc ccc tca gac gag gga cca agt ccc tgg ggc ctg<br>Ser Val Ser Cys Ser Pro Ser Asp Glu Gly Pro Ser Pro Trp Gly Leu<br>        520             525             530 | 1638 |
| ctg gac tcc ctt gtg tgt cca aag gat gag ggt ccc gcg gtt gag act<br>Leu Asp Ser Leu Val Cys Pro Lys Asp Glu Gly Pro Ala Val Glu Thr<br>    535             540             545 | 1686 |
| gag gcc atg tgc ccc agt gct gca gcc tct gag ctg gag cag tcc aca<br>Glu Ala Met Cys Pro Ser Ala Ala Ala Ser Glu Leu Glu Gln Ser Thr<br>    550             555             560 | 1734 |
| gaa ctg gac tct ctt ttc aaa ggc ttg gcc ctg act gtg cag tgg gaa<br>Glu Leu Asp Ser Leu Phe Lys Gly Leu Ala Leu Thr Val Gln Trp Glu<br>565             570             575             580 | 1782 |
| tcc tga agggagatcg gagcaagcag gcctaagttt cctcccgccc caccta<br>Ser  *                                                                  | 1834 |

<210> SEQ ID NO 42
<211> LENGTH: 581
<212> TYPE: PRT
<213> ORGANISM: Mus musculus

<400> SEQUENCE: 42

```
Met Lys Thr Leu Leu Thr Ile Leu Thr Val Gly Ser Leu Ala Ala His
1               5                   10                  15

Thr Thr Val Asp Thr Ser Gly Leu Leu Gln His Val Lys Phe Gln Ser
            20                  25                  30

Ser Asn Phe Glu Asn Ile Leu Thr Trp Asp Gly Gly Pro Ala Ser Thr
        35                  40                  45

Ser Asp Thr Val Tyr Ser Val Glu Tyr Lys Lys Tyr Gly Glu Arg Lys
    50                  55                  60

Trp Leu Ala Lys Ala Gly Cys Gln Arg Ile Thr Gln Lys Phe Cys Asn
65                  70                  75                  80

Leu Thr Met Glu Thr Arg Asn His Thr Glu Phe Tyr Tyr Ala Lys Val
                85                  90                  95

Thr Ala Val Ser Ala Gly Gly Pro Pro Val Thr Lys Met Thr Asp Arg
            100                 105                 110

Phe Ser Ser Leu Gln His Thr Thr Ile Lys Pro Pro Asp Val Thr Cys
        115                 120                 125

Ile Pro Lys Val Arg Ser Ile Gln Met Leu Val His Pro Thr Leu Thr
    130                 135                 140

Pro Val Leu Ser Glu Asp Gly His Gln Leu Thr Leu Glu Glu Ile Phe
145                 150                 155                 160

His Asp Leu Phe Tyr Arg Leu Glu Leu His Val Asn His Thr Tyr Gln
                165                 170                 175

Met His Leu Glu Gly Lys Gln Arg Glu Tyr Glu Phe Leu Gly Leu Thr
            180                 185                 190

Pro Asp Thr Glu Phe Leu Gly Ser Ile Thr Ile Leu Thr Pro Ile Leu
        195                 200                 205

Ser Lys Glu Ser Ala Pro Tyr Val Cys Arg Val Lys Thr Leu Pro Asp
    210                 215                 220

Arg Thr Trp Ala Tyr Ser Phe Ser Gly Ala Val Leu Phe Ser Met Gly
225                 230                 235                 240

Phe Leu Val Gly Leu Leu Cys Tyr Leu Gly Tyr Lys Tyr Ile Thr Lys
                245                 250                 255

Pro Pro Val Pro Pro Asn Ser Leu Asn Val Gln Arg Val Leu Thr Phe
            260                 265                 270

Gln Pro Leu Arg Phe Ile Gln Glu His Val Leu Ile Pro Val Leu Asp
        275                 280                 285

Leu Ser Gly Pro Ser Ser Leu Pro Gln Pro Ile Gln Tyr Ser Gln Val
    290                 295                 300

Val Val Ser Gly Pro Arg Glu Pro Pro Gly Ala Val Trp Arg Gln Ser
305                 310                 315                 320

Leu Ser Asp Leu Thr Tyr Val Gly Gln Ser Asp Val Ser Ile Leu Gln
                325                 330                 335

Pro Thr Asn Val Pro Ala Gln Gln Thr Leu Ser Pro Ser Tyr Ala
            340                 345                 350

Pro Lys Ala Val Pro Glu Val Gln Pro Ser Tyr Ala Pro Gln Val
        355                 360                 365

Ala Ser Asp Ala Lys Ala Leu Phe Tyr Ser Pro Gln Gln Gly Met Lys
    370                 375                 380

Thr Arg Pro Ala Thr Tyr Asp Pro Gln Asp Ile Leu Asp Ser Cys Pro
385                 390                 395                 400

Ala Ser Tyr Ala Val Cys Val Glu Asp Ser Gly Lys Asp Ser Thr Pro
```

```
                        405                 410                 415
Gly Ile Leu Ser Thr Pro Lys Tyr Leu Lys Thr Lys Gly Gln Leu Gln
            420                 425                 430

Glu Asp Thr Leu Val Arg Ser Cys Leu Pro Gly Asp Leu Ser Leu Gln
            435                 440                 445

Lys Val Thr Ser Leu Gly Glu Gly Glu Thr Gln Arg Pro Lys Ser Leu
            450                 455                 460

Pro Ser Pro Leu Gly Phe Cys Thr Asp Arg Gly Pro Asp Leu His Thr
465                 470                 475                 480

Leu Arg Ser Glu Glu Pro Glu Thr Pro Arg Tyr Leu Lys Gly Ala Leu
            485                 490                 495

Ser Leu Leu Ser Ser Val Gln Ile Glu Gly His Pro Val Ser Leu Pro
            500                 505                 510

Leu His Val His Ser Val Ser Cys Ser Pro Ser Asp Glu Gly Pro Ser
            515                 520                 525

Pro Trp Gly Leu Leu Asp Ser Leu Val Cys Pro Lys Asp Glu Gly Pro
            530                 535                 540

Ala Val Glu Thr Glu Ala Met Cys Pro Ser Ala Ala Ala Ser Glu Leu
545                 550                 555                 560

Glu Gln Ser Thr Glu Leu Asp Ser Leu Phe Lys Gly Leu Ala Leu Thr
            565                 570                 575

Val Gln Trp Glu Ser
            580

<210> SEQ ID NO 43
<211> LENGTH: 660
<212> TYPE: DNA
<213> ORGANISM: Homo Sapiens
<220> FEATURE:
<221> NAME/KEY: CDS
<222> LOCATION: (1)...(660)

<400> SEQUENCE: 43 atg gcg tgg agt ctt ggg agc tgg ctg ggt ggc tgc ctg ctg gtg tca      48
Met Ala Trp Ser Leu Gly Ser Trp Leu Gly Gly Cys Leu Leu Val Ser
1               5                   10                  15 gca ttg gga atg gta cca cct ccc gaa aat gtc aga atg aat tct gtt      96
Ala Leu Gly Met Val Pro Pro Pro Glu Asn Val Arg Met Asn Ser Val
                20                  25                  30 aat ttc aag aac att cta cag tgg gag tca cct gct ttt gcc aaa ggg     144
Asn Phe Lys Asn Ile Leu Gln Trp Glu Ser Pro Ala Phe Ala Lys Gly
            35                  40                  45 aac ctg act ttc aca gct cag tac cta agt tat agg ata ttc caa gat     192
Asn Leu Thr Phe Thr Ala Gln Tyr Leu Ser Tyr Arg Ile Phe Gln Asp
        50                  55                  60 aaa tgc atg aat act acc ttg acg gaa tgt gat ttc tca agt ctt tcc     240
Lys Cys Met Asn Thr Thr Leu Thr Glu Cys Asp Phe Ser Ser Leu Ser
65                  70                  75                  80 aag tat ggt gac cac acc ttg aga gtc agg gct gaa ttt gca gat gag     288
Lys Tyr Gly Asp His Thr Leu Arg Val Arg Ala Glu Phe Ala Asp Glu
                85                  90                  95 cat tca gac tgg gta aac atc acc ttc tgt cct gtg gat gac acc att     336
His Ser Asp Trp Val Asn Ile Thr Phe Cys Pro Val Asp Asp Thr Ile
            100                 105                 110 att gga ccc cct gga atg caa gta gaa gta ctt gat gat tct tta cat     384
Ile Gly Pro Pro Gly Met Gln Val Glu Val Leu Asp Asp Ser Leu His
        115                 120                 125 atg cgt ttc tta gcc cct aaa att gag aat gaa tac gaa act tgg act     432
```

```
Met Arg Phe Leu Ala Pro Lys Ile Glu Asn Glu Tyr Glu Thr Trp Thr
            130                 135                 140 atg aag aat gtg tat aac tca tgg act tat aat gtg caa tac tgg aaa       480
Met Lys Asn Val Tyr Asn Ser Trp Thr Tyr Asn Val Gln Tyr Trp Lys
145                 150                 155                 160 aac ggt act gat gaa aag ttt caa att act ccc cag tat gac ttt gag       528
Asn Gly Thr Asp Glu Lys Phe Gln Ile Thr Pro Gln Tyr Asp Phe Glu
                165                 170                 175 gtc ctc aga aac ctg gag cca tgg aca act tat tgt gtt caa gtt cga       576
Val Leu Arg Asn Leu Glu Pro Trp Thr Thr Tyr Cys Val Gln Val Arg
            180                 185                 190 ggg ttt ctt cct gat cgg aac aaa gct ggg gaa tgg agt gag cct gtc       624
Gly Phe Leu Pro Asp Arg Asn Lys Ala Gly Glu Trp Ser Glu Pro Val
        195                 200                 205 tgt gag caa aca acc cat gac gaa acg gtc ccc tcc                       660
Cys Glu Gln Thr Thr His Asp Glu Thr Val Pro Ser
210                 215                 220
```

<210> SEQ ID NO 44
<211> LENGTH: 220
<212> TYPE: PRT
<213> ORGANISM: Homo Sapiens

<400> SEQUENCE: 44

```
Met Ala Trp Ser Leu Gly Ser Trp Leu Gly Gly Cys Leu Leu Val Ser
1               5                   10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Asp Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser
    210                 215                 220
```

<210> SEQ ID NO 45
<211> LENGTH: 199
<212> TYPE: PRT
<213> ORGANISM: homo sapiens

```
<400> SEQUENCE: 45

Met Val Pro Pro Glu Asn Val Arg Met Asn Ser Val Asn Phe Lys
1               5                   10                  15

Asn Ile Leu Gln Trp Glu Ser Pro Ala Phe Ala Lys Gly Asn Leu Thr
            20                  25                  30

Phe Thr Ala Gln Tyr Leu Ser Tyr Arg Ile Phe Gln Asp Lys Cys Met
            35                  40                  45

Asn Thr Thr Leu Thr Glu Cys Asp Phe Ser Ser Leu Ser Lys Tyr Gly
            50              55                  60

Asp His Thr Leu Arg Val Arg Ala Glu Phe Ala Asp Glu His Ser Asp
65                  70                  75                  80

Trp Val Asn Ile Thr Phe Cys Pro Val Asp Asp Thr Ile Ile Gly Pro
                85                  90                  95

Pro Gly Met Gln Val Glu Val Leu Ala Asp Ser Leu His Met Arg Phe
            100                 105                 110

Leu Ala Pro Lys Ile Glu Asn Glu Tyr Glu Thr Trp Thr Met Lys Asn
            115                 120                 125

Val Tyr Asn Ser Trp Thr Tyr Asn Val Gln Tyr Trp Lys Asn Gly Thr
130                 135                 140

Asp Glu Lys Phe Gln Ile Thr Pro Gln Tyr Asp Phe Glu Val Leu Arg
145                 150                 155                 160

Asn Leu Glu Pro Trp Thr Thr Tyr Cys Val Gln Val Arg Gly Phe Leu
                165                 170                 175

Pro Asp Arg Asn Lys Ala Gly Glu Trp Ser Pro Val Cys Glu Gln
            180                 185                 190

Thr Thr His Asp Glu Thr Val
            195

<210> SEQ ID NO 46
<211> LENGTH: 211
<212> TYPE: PRT
<213> ORGANISM: Homo sapiens

<400> SEQUENCE: 46

Ser Asp Ala His Gly Thr Glu Leu Pro Ser Pro Pro Ser Val Trp Phe
1               5                   10                  15

Glu Ala Glu Phe Phe His His Ile Leu His Trp Thr Pro Ile Pro Asn
            20                  25                  30

Gln Ser Glu Ser Thr Cys Tyr Glu Val Ala Leu Leu Arg Tyr Gly Ile
            35                  40                  45

Glu Ser Trp Asn Ser Ile Ser Asn Cys Ser Gln Thr Leu Ser Tyr Asp
            50                  55                  60

Leu Thr Ala Val Thr Leu Asp Leu Tyr His Ser Asn Gly Tyr Arg Ala
65                  70                  75                  80

Arg Val Arg Ala Val Asp Gly Ser Arg His Ser Asn Trp Thr Val Thr
                85                  90                  95

Asn Thr Arg Phe Ser Val Asp Glu Val Thr Leu Thr Val Gly Ser Val
            100                 105                 110

Asn Leu Glu Ile His Asn Gly Phe Ile Leu Gly Lys Ile Gln Leu Pro
            115                 120                 125

Arg Pro Lys Met Ala Pro Ala Asn Asp Thr Tyr Glu Ser Ile Phe Ser
130                 135                 140

His Phe Arg Glu Tyr Glu Ile Ala Ile Arg Lys Val Pro Gly Asn Phe
145                 150                 155                 160
```

```
Thr Phe Thr His Lys Lys Val Lys His Glu Asn Phe Ser Leu Leu Thr
                165                 170                 175

Ser Gly Glu Val Gly Glu Phe Cys Val Gln Val Lys Pro Ser Val Ala
            180                 185                 190

Ser Arg Ser Asn Lys Gly Met Trp Ser Lys Glu Glu Cys Ile Ser Leu
        195                 200                 205

Thr Arg Gln
    210

<210> SEQ ID NO 47
<211> LENGTH: 201
<212> TYPE: PRT
<213> ORGANISM: homo sapiens

<400> SEQUENCE: 47

Asp Glu Val Ala Ile Leu Pro Ala Pro Gln Asn Leu Ser Val Leu Ser
  1               5                  10                  15

Thr Asn Met Lys His Leu Leu Met Trp Ser Pro Val Ile Ala Pro Gly
                 20                  25                  30

Glu Thr Val Tyr Tyr Ser Val Glu Tyr Gln Gly Glu Tyr Glu Ser Leu
             35                  40                  45

Tyr Thr Ser His Ile Trp Ile Pro Ser Ser Trp Cys Ser Leu Thr Glu
     50                  55                  60

Gly Pro Glu Cys Asp Val Thr Asp Asp Ile Thr Ala Thr Val Pro Tyr
 65                  70                  75                  80

Asn Leu Arg Val Arg Ala Thr Leu Gly Ser Gln Thr Ser Ala Trp Ser
                 85                  90                  95

Ile Leu Lys His Pro Phe Asn Arg Asn Ser Thr Ile Leu Thr Arg Pro
            100                 105                 110

Gly Met Glu Ile Thr Lys Asp Gly Phe His Leu Val Ile Glu Leu Glu
        115                 120                 125

Asp Leu Gly Pro Gln Phe Glu Phe Leu Val Ala Tyr Trp Arg Arg Glu
    130                 135                 140

Pro Gly Ala Glu Glu His Val Lys Met Val Arg Ser Gly Gly Ile Pro
145                 150                 155                 160

Val His Leu Glu Thr Met Glu Pro Gly Ala Ala Tyr Cys Val Lys Ala
                165                 170                 175

Gln Thr Phe Val Lys Ala Ile Gly Arg Tyr Ser Ala Phe Ser Gln Thr
            180                 185                 190

Glu Cys Val Glu Val Gln Gly Glu Ala
        195                 200

<210> SEQ ID NO 48
<211> LENGTH: 68
<212> TYPE: PRT
<213> ORGANISM: Mus musculus

<400> SEQUENCE: 48

His Thr Thr Val Asp Thr Ser Gly Leu Leu Gln His Val Lys Phe Gln
  1               5                  10                  15

Ser Ser Asn Phe Glu Asn Ile Leu Thr Trp Asp Gly Gly Pro Ala Ser
                 20                  25                  30

Thr Ser Asp Thr Val Tyr Ser Val Glu Tyr Lys Lys Tyr Gly Glu Arg
             35                  40                  45

Lys Trp Leu Ala Lys Ala Gly Cys Gln Arg Ile Thr Gln Lys Phe Cys
     50                  55                  60
```

-continued

```
Asn Leu Thr Met
 65

<210> SEQ ID NO 49
<211> LENGTH: 26
<212> TYPE: PRT
<213> ORGANISM: mus musculus

<400> SEQUENCE: 49

Glu Thr Arg Asn His Thr Glu Phe Tyr Tyr Ala Lys Val Thr Ala Val
 1               5                  10                  15

Ser Ala Gly Gly Pro Pro Val Thr Lys Met
            20                  25

<210> SEQ ID NO 50
<211> LENGTH: 28
<212> TYPE: PRT
<213> ORGANISM: mus musculus

<400> SEQUENCE: 50

Thr Asp Arg Phe Ser Ser Leu Gln His Thr Thr Ile Lys Pro Pro Asp
 1               5                  10                  15

Val Thr Cys Ile Pro Lys Val Arg Ser Ile Gln Met
            20                  25

<210> SEQ ID NO 51
<211> LENGTH: 40
<212> TYPE: PRT
<213> ORGANISM: Mus musculus

<400> SEQUENCE: 51

Leu Val His Pro Thr Leu Thr Pro Val Leu Ser Glu Asp Gly His Gln
 1               5                  10                  15

Leu Thr Leu Glu Glu Ile Phe His Asp Leu Phe Tyr Arg Leu Glu Leu
            20                  25                  30

His Val Asn His Thr Tyr Gln Met
        35                  40

<210> SEQ ID NO 52
<211> LENGTH: 50
<212> TYPE: PRT
<213> ORGANISM: Mus musculus

<400> SEQUENCE: 52

His Leu Glu Gly Lys Gln Arg Glu Tyr Glu Phe Leu Gly Leu Thr Pro
 1               5                  10                  15

Asp Thr Glu Phe Leu Gly Ser Ile Thr Ile Leu Thr Pro Ile Leu Ser
            20                  25                  30

Lys Glu Ser Ala Pro Tyr Val Cys Arg Val Lys Thr Leu Pro Leu Val
        35                  40                  45

Pro Arg
    50

<210> SEQ ID NO 53
<211> LENGTH: 70
<212> TYPE: PRT
<213> ORGANISM: Mus musculus

<400> SEQUENCE: 53

His Leu Glu Gly Lys Gln Arg Glu Tyr Glu Phe Leu Gly Leu Thr Pro
 1               5                  10                  15
```

-continued

```
Asp Thr Glu Phe His Leu Glu Gly Lys Gln Arg Glu Tyr Glu Phe Leu
            20                  25                  30

Gly Leu Thr Pro Asp Thr Glu Phe Leu Gly Ser Ile Thr Ile Leu Thr
        35                  40                  45

Pro Ile Leu Ser Lys Glu Ser Ala Pro Tyr Val Cys Arg Val Lys Thr
50                  55                  60

Leu Pro Leu Val Pro Arg
65                  70

<210> SEQ ID NO 54
<211> LENGTH: 46
<212> TYPE: PRT
<213> ORGANISM: Mus musculus

<400> SEQUENCE: 54

Glu Thr Arg Asn His Thr Glu Phe Tyr Tyr Ala Lys Val Thr Ala Val
1               5                   10                  15

Ser Ala Gly Gly Glu Thr Arg Asn His Thr Glu Phe Tyr Tyr Ala Lys
            20                  25                  30

Val Thr Ala Val Ser Ala Gly Gly Pro Pro Val Thr Lys Met
        35                  40                  45

<210> SEQ ID NO 55
<211> LENGTH: 48
<212> TYPE: PRT
<213> ORGANISM: mus musculus
<220> FEATURE:
<221> NAME/KEY: VARIANT
<222> LOCATION: 6, 11, 13,
<223> OTHER INFORMATION: Xaa = Any Amino Acid

<400> SEQUENCE: 55

Thr Asp Arg Phe Ser Xaa Leu Gln His Thr Xaa Ile Xaa Pro Xaa Asp
1               5                   10                  15

Xaa Xaa Xaa Ile Thr Asp Arg Phe Ser Ser Leu Gln His Thr Thr Ile
            20                  25                  30

Lys Pro Pro Asp Val Thr Cys Ile Pro Lys Val Arg Ser Ile Gln Met
        35                  40                  45

<210> SEQ ID NO 56
<211> LENGTH: 92
<212> TYPE: PRT
<213> ORGANISM: homo sapiens

<400> SEQUENCE: 56

Pro Glu Asp Pro Ser Asp Leu Leu Gln His Val Lys Phe Gln Ser Ser
1               5                   10                  15

Asn Phe Glu Asn Ile Leu Thr Trp Asp Ser Gly Pro Glu Gly Thr Pro
            20                  25                  30

Asp Thr Val Tyr Ser Ile Glu Tyr Lys Thr Tyr Gly Glu Arg Asp Trp
        35                  40                  45

Val Ala Lys Lys Gly Cys Gln Arg Ile Thr Arg Lys Ser Cys Asn Leu
50                  55                  60

Thr Val Glu Thr Gly Asn Leu Thr Glu Leu Tyr Tyr Ala Arg Val Thr
65                  70                  75                  80

Ala Val Ser Ala Gly Gly Arg Ser Ala Thr Lys Met
            85                  90

<210> SEQ ID NO 57
<211> LENGTH: 28
```

```
<212> TYPE: PRT
<213> ORGANISM: Homo sapiens

<400> SEQUENCE: 57

Thr Asp Arg Phe Ser Ser Leu Gln His Thr Thr Leu Lys Pro Pro Asp
  1               5                  10                  15

Val Thr Cys Ile Ser Lys Val Arg Ser Ile Gln Met
             20                  25

<210> SEQ ID NO 58
<211> LENGTH: 40
<212> TYPE: PRT
<213> ORGANISM: Homo sapiens

<400> SEQUENCE: 58

Ile Val His Pro Thr Pro Thr Pro Ile Arg Ala Gly Asp Gly His Arg
  1               5                  10                  15

Leu Thr Leu Glu Asp Ile Phe His Asp Leu Phe Tyr His Leu Glu Leu
             20                  25                  30

Gln Val Asn Arg Thr Tyr Gln Met
         35                  40

<210> SEQ ID NO 59
<211> LENGTH: 25
<212> TYPE: PRT
<213> ORGANISM: Homo sapiens

<400> SEQUENCE: 59

His Leu Gly Gly Lys Gln Arg Glu Tyr Glu Phe Phe Gly Leu Thr Pro
  1               5                  10                  15

Asp Thr Glu Phe Leu Gly Thr Ile Met
             20                  25

<210> SEQ ID NO 60
<211> LENGTH: 14
<212> TYPE: PRT
<213> ORGANISM: Homo sapiens

<400> SEQUENCE: 60

Ile Cys Val Pro Thr Trp Ala Lys Glu Ser Ala Pro Tyr Met
  1               5                  10

<210> SEQ ID NO 61
<211> LENGTH: 12
<212> TYPE: PRT
<213> ORGANISM: Homo sapiens

<400> SEQUENCE: 61

Cys Arg Val Lys Thr Leu Pro Asp Arg Thr Trp Thr
  1               5                  10

<210> SEQ ID NO 62
<211> LENGTH: 212
<212> TYPE: PRT
<213> ORGANISM: Artificial Sequence
<220> FEATURE:
<223> OTHER INFORMATION: A murine IL-22RA soluble receptor with cleavage
      site (Leu Val Pro Arg) remaining on C-Terminus

<400> SEQUENCE: 62

His Thr Thr Val Asp Thr Ser Gly Leu Leu Gln His Val Lys Phe Gln
  1               5                  10                  15

Ser Ser Asn Phe Glu Asn Ile Leu Thr Trp Asp Gly Gly Pro Ala Ser
```

```
                    20                  25                  30
Thr Ser Asp Thr Val Tyr Ser Val Glu Tyr Lys Tyr Gly Glu Arg
        35                  40                  45

Lys Trp Leu Ala Lys Ala Gly Cys Gln Arg Ile Thr Gln Lys Phe Cys
    50                  55                  60

Asn Leu Thr Met Glu Thr Arg Asn His Thr Glu Phe Tyr Tyr Ala Lys
65                  70                  75                  80

Val Thr Ala Val Ser Ala Gly Gly Pro Pro Val Thr Lys Met Thr Asp
                85                  90                  95

Arg Phe Ser Ser Leu Gln His Thr Thr Ile Lys Pro Pro Asp Val Thr
            100                 105                 110

Cys Ile Pro Lys Val Arg Ser Ile Gln Met Leu Val His Pro Thr Leu
        115                 120                 125

Thr Pro Val Leu Ser Glu Asp Gly His Gln Leu Thr Leu Glu Glu Ile
    130                 135                 140

Phe His Asp Leu Phe Tyr Arg Leu Glu Leu His Val Asn His Thr Tyr
145                 150                 155                 160

Gln Met His Leu Glu Gly Lys Gln Arg Glu Tyr Glu Phe Leu Gly Leu
                165                 170                 175

Thr Pro Asp Thr Glu Phe Leu Gly Ser Ile Thr Ile Leu Thr Pro Ile
            180                 185                 190

Leu Ser Lys Glu Ser Ala Pro Tyr Val Cys Arg Val Lys Thr Leu Pro
        195                 200                 205

Leu Val Pro Arg
    210
```